(12) United States Patent
Tremblay et al.

(10) Patent No.: US 11,162,103 B2
(45) Date of Patent: Nov. 2, 2021

(54) APOLIPOPROTEIN C3 (APOC3) IRNA COMPOSITIONS AND METHODS OF USE THEREOF

(71) Applicant: Alnylam Pharmaceuticals, Inc., Cambridge, MA (US)

(72) Inventors: Frederic Tremblay, Boston, MA (US); Lucas D. BonDurant, Brookline, MA (US); James D. McIninch, Burlington, MA (US); Adam Castoreno, Framingham, MA (US); Mark K. Schlegel, Boston, MA (US); Charalambos Kaittanis, Cambridge, MA (US)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 17/180,997

(22) Filed: Feb. 22, 2021

(65) Prior Publication Data

US 2021/0292756 A1    Sep. 23, 2021

Related U.S. Application Data

(63) Continuation of application No. PCT/US2021/017826, filed on Feb. 12, 2021.

(60) Provisional application No. 63/144,516, filed on Feb. 2, 2021, provisional application No. 62/977,875, filed on Feb. 18, 2020.

(51) Int. Cl.
    *C12N 15/113* (2010.01)

(52) U.S. Cl.
    CPC ...... *C12N 15/113* (2013.01); *C12N 2310/315* (2013.01); *C12N 2310/321* (2013.01); *C12N 2310/322* (2013.01); *C12N 2310/351* (2013.01)

(58) Field of Classification Search
    None
    See application file for complete search history.

(56) References Cited

U.S. PATENT DOCUMENTS

| 9,796,974 | B2 | 10/2017 | Rajeev et al. |
| 9,988,627 | B2 | 6/2018 | Baryza et al. |
| 10,240,153 | B2 | 3/2019 | Weiler et al. |
| 10,407,679 | B2 | 9/2019 | Fitzgerald et al. |
| 2012/0184595 | A1 | 7/2012 | MacDonald et al. |
| 2013/0317085 | A1 | 11/2013 | Crooke et al. |
| 2017/0260527 | A1* | 9/2017 | Fitzgerald ............ C12N 15/113 |
| 2018/0008724 | A1 | 1/2018 | Rajeev et al. |

FOREIGN PATENT DOCUMENTS

| WO | WO-2009/073809 A2 | 6/2009 |
| WO | WO-2010/083615 A1 | 7/2010 |
| WO | WO-2012/177947 A2 | 12/2012 |
| WO | WO-2013/074974 A2 | 5/2013 |
| WO | WO-2013/165816 A2 | 11/2013 |
| WO | WO-2014/179626 A2 | 11/2014 |
| WO | WO-2016/011123 A1 | 1/2016 |
| WO | WO-2019/051402 A1 | 3/2019 |

OTHER PUBLICATIONS

International Search Report and Written Opinion from PCT/US2015/061065, dated May 2, 2016.
Reynolds et al., "Rational siRNA design for RNA interference," Nature Biotechnology, vol. 22, pp. 326-330, 2004.
Holmberg et al., "Lowering apolipoprotein CIII delays onset of type 1 diabetes", PNAS,108 (26), pp. 10685-10689, Jun. 28, 2011.
Petersen et al., :"Apolipoprotein C3 Gene Variants in Nonalcoholic Fatty Liver Disease", N Engl J Med 2010; 362:1082-1089.
Krawczyk et al. "Nonalcoholic fatty liver disease", Best Practice & Research Clinical Gastroenterology 24 (2010) 695-708.
Jian et al. "Relative Quantitation of Glycoisoforms of Intact Apolipoprotein C3 in Human Plasma by Liquid Chromatography-High-Resolution Mass Spectrometry", Anal. Chem. 2013, 85, 5, 2867-2874.

* cited by examiner

*Primary Examiner* — Tracy Vivlemore
(74) *Attorney, Agent, or Firm* — McCarter & English, LLP; Maria Laccotripe Zacharakis; Deborah L. Nagle

(57) ABSTRACT

The present invention relates to RNAi agents, e.g., double stranded RNA (dsRNA) agents, targeting the apolipoprotein C3 gene (APOC3). The invention also relates to methods of using such RNAi agents to inhibit expression of an APOC3 gene and to methods of preventing and treating an APOC3-associated disorder, e.g., hypertriglyceridemia, non-alcoholic fatty liver disease, non-alcoholic steatohepatitis, polycystic ovary syndrome, kidney disease, obesity, type 2 diabetes mellitus (insulin resistance), hypertension, arthero-sclerosis and pancreatitis.

23 Claims, 3 Drawing Sheets

Specification includes a Sequence Listing.

SEQUENCE LISTING

```
<160> NUMBER OF SEQ ID NOS: 916

<210> SEQ ID NO 1
<211> LENGTH: 535
<212> TYPE: DNA
<213> ORGANISM: Homo sapiens

<400> SEQUENCE: 1
ctgctcagtt catccctaga ggcagctgct ccaggaacag aggtgccatg cagccccggg      60
tactccttgt tgttgccctc ctggcgctcc tggcctctgc ccgagcttca gaggccgagg     120
atgcctccct tctcagcttc atgcagggtt acatgaagca cgccaccaag accgccaagg     180
atgcactgag cagcgtgcag gagtcccagg tggcccagca ggccaggggc tgggtgaccg     240
```

```
atggcttcag ttccctgaaa gactactgga gcaccgttaa ggacaagttc tctgagttct    300
gggatttgga ccctgaggtc agaccaactt cagccgtggc tgcctgagac ctcaataccc    360
caagtccacc tgcctatcca tcctgcgagc tccttgggtc ctgcaatctc cagggctgcc    420
cctgtaggtt gcttaaaagg gacagtattc tcagtgctct cctacccac ctcatgcctg     480 gccccctcc aggcatgctg gcctcccaat aaagctggac aagaagctgc tatga          535
```

<210> SEQ ID NO 2
<211> LENGTH: 535
<212> TYPE: DNA
<213> ORGANISM: Homo sapiens

<400> SEQUENCE: 2

```
tcatagcagc ttcttgtcca gctttattgg gaggccagca tgcctggagg ggggccaggc     60
atgaggtggg gtaggagagc actgagaata ctgtcccttt taagcaacct acaggggcag    120
ccctggagat tgcaggaccc aaggagctcg caggatggat aggcaggtgg acttggggta    180
ttgaggtctc aggcagccac ggctgaagtt ggtctgacct cagggtccaa atcccagaac    240
tcagagaact tgtccttaac ggtgctccag tagtctttca gggaactgaa gccatcggtc    300
acccagcccc tggcctgctg gccacctgg gactcctgca cgctgctcag tgcatccttg     360
gcggtcttgg tggcgtgctt catgtaaccc tgcatgaagc tgagaaggga ggcatcctcg    420
gcctctgaag ctcgggcaga ggccaggagc gccaggaggg caacaacaag gagtacccgg    480
ggctgcatgg cacctctgtt cctggagcag ctgcctctag ggatgaactg agcag          535
```

<210> SEQ ID NO 3
<211> LENGTH: 567
<212> TYPE: DNA
<213> ORGANISM: Macaca fascicularis

<400> SEQUENCE: 3

```
aatataaaac aggtcagaac cctcctgcct gcctgctctg ttcatcccta gaggcagctg     60
ctccaggaac agaggcgcca tgcagccccg ggtactcctt gttgctgccc tgctgtcact    120
cctggcctct gccagagctt cagaggccga ggacacctcc cttcttggct tcatgcaggg    180
ctacatgcag catgccacca agaccgccaa ggatgcactg accagcgtcc aggagtccca    240 ggtgcccag caggccagag ctgggtgac cgatggcttc agttccctga agactactg       300 gagcaccgtt aaggacaagt tatctgggtt ctgggatttg aaccctgagg ccaaacccac    360
tctggctgag gctgcctgag acctcaatac cccaagtcca cctgcctgtc catcctgcca    420
gctccttggg tcctgcagcc tccagggctg ccctgtaggt tgcttaaaa gggacagtat     480 tctcagtgcc ctcctaccgc acctcatgcc tggcccccct ccaggcaggg tgtcctccca    540
ataaagctgg acaagaagct gctatga                                         567
```

<210> SEQ ID NO 4
<211> LENGTH: 567
<212> TYPE: DNA
<213> ORGANISM: Macaca fascicularis

<400> SEQUENCE: 4

```
tcatagcagc ttcttgtcca gctttattgg gaggacaccc tgcctggagg ggggccaggc     60
atgaggtgcg gtaggagggc actgagaata ctgtcccttt taagcaacct acaggggcag    120
ccctggaggc tgcaggaccc aaggagctgg caggatggac aggcaggtgg acttggggta    180
```

```
ttgaggtctc aggcagcctc agccagagtg ggtttggcct cagggttcaa atcccagaac    240
ccagataact tgtccttaac ggtgctccag tagtctttca gggaactgaa gccatcggtc    300
acccagcctc tggcctgctg ggccacctgg gactcctgga cgctggtcag tgcatccttg    360
gcggtcttgg tggcatgctg catgtagccc tgcatgaagc caagaaggga ggtgtcctcg    420
gcctctgaag ctctggcaga ggccaggagt gacagcaggg cagcaacaag gagtacccgg    480
ggctgcatgg cgcctctgtt cctggagcag ctgcctctag ggatgaacag agcaggcagg    540
caggagggtt ctgacctgtt ttatatt                                        567

<210> SEQ ID NO 5
<211> LENGTH: 547
<212> TYPE: DNA
<213> ORGANISM: Macaca mulatta

<400> SEQUENCE: 5
cctcctgcct gcctgctctg ttcatcccta gaggcagctg ctccaggaac agaggcgcca     60
tgcagccccg ggtactcctt gttgctgccg tgctgtcact cctggcctct gccagagctt    120
cagaggccga ggacacctcc cttcttggct tcatgcagga ctacatgcag catgccacca    180
agaccgccaa ggatgcactg accagcgtcc aggagtccca ggtggcccag caggccagag    240
gctgggtgac cgatggcttc agttccctga agactactg gagcaccgtt aaggacaagt     300
tatctgggtt ctgggatttg aaccctgagg ccaaacccac tctggctgag ctgcctgag    360 acctcaatac cccaagtcca cctgcctgtc catcctgcca gctccttggg tcctgcagcc    420
tccagggctg cccctgtagg ttgcttaaaa gggacagtat tctcagtgcc ctcctaccgc    480
acctcatgcc tggccccct ccaggcaggg tgtcctccca ataaagctgg acaagaagct    540
gctatga                                                              547

<210> SEQ ID NO 6
<211> LENGTH: 547
<212> TYPE: DNA
<213> ORGANISM: Macaca mulatta

<400> SEQUENCE: 6
tcatagcagc ttcttgtcca gctttattgg gaggacaccc tgcctggagg ggggccaggc     60
atgaggtgcg gtaggagggc actgagaata ctgtcccttt taagcaacct acaggggcag    120
ccctggaggc tgcaggaccc aaggagctgg caggatggac aggcaggtgg acttggggta    180
ttgaggtctc aggcagcctc agccagagtg ggtttggcct cagggttcaa atcccagaac    240
ccagataact tgtccttaac ggtgctccag tagtctttca gggaactgaa gccatcggtc    300
acccagcctc tggcctgctg ggccacctgg gactcctgga cgctggtcag tgcatccttg    360
gcggtcttgg tggcatgctg catgtagtcc tgcatgaagc caagaaggga ggtgtcctcg    420
gcctctgaag ctctggcaga ggccaggagt gacagcacgg cagcaacaag gagtacccgg    480
ggctgcatgg cgcctctgtt cctggagcag ctgcctctag ggatgaacag agcaggcagg    540
caggagg                                                              547

<210> SEQ ID NO 7
<211> LENGTH: 527
<212> TYPE: DNA
<213> ORGANISM: Mus musculus

<400> SEQUENCE: 7
gcctgctcag ttttatccct agaagcagct agctactcca ggtacgtagg tgccatgcag     60
```

```
cccccggacgc tcctcactgt ggccctcttg gctctcctgg catctgcccg agctgaagag    120
gtagagggat ccttgctgct gggctctgta cagggctaca tggaacaagc ctccaagacg    180
gtccaggatg cgctaagtag cgtgcaggag tccgatatag ctgtggtggc cagggctgg     240 atggacaatc acttcagatc cctgaaaggc tactggagca agtttactga caagttcacc    300
ggcttctggg attctaaccc tgaggaccaa ccaactccag ctattgagtc gtgagacttc    360
tgtgttgcag atgtgcctgt tcctccatcc tgctgccccc ctccaggcct gccaggtggc    420
ccctgaaggt tgctttaagg ggaaagtatg ttctcatgtc ttcaccctc cctagatctc     480 acctaaacat gctgtcccta ataaagctgg ataagaagct gctgtta                  527
```

<210> SEQ ID NO 8
<211> LENGTH: 527
<212> TYPE: DNA
<213> ORGANISM: Mus musculus

<400> SEQUENCE: 8

```
taacagcagc ttcttatcca gctttattag ggacagcatg tttaggtgag atctagggag    60
gggtgaagac atgagaacat actttcccct taaagcaacc ttcaggggcc acctggcagg    120
cctggagggg ggcagcagga tggaggaaca ggcacatctg caacacagaa gtctcacgac    180
tcaatagctg gagttggttg gtcctcaggg ttagaatccc agaagccggt gaacttgtca    240
gtaaacttgc tccagtagcc tttcagggat ctgaagtgat tgtccatcca gcccctggcc    300
accacagcta tatcggactc ctgcacgcta cttagcgcat cctggaccgt cttggaggct    360
tgttccatgt agccctgtac agagcccagc agcaaggatc cctctacctc ttcagctcgg    420
gcagatgcca ggagagccaa gagggccaca gtgaggagcg tccggggctg catggcacct    480
acgtacctgg agtagctagc tgcttctagg gataaaactg agcaggc                  527
```

<210> SEQ ID NO 9
<211> LENGTH: 536
<212> TYPE: DNA
<213> ORGANISM: Rattus norvegicus

<400> SEQUENCE: 9

```
aatataaaac agatcagagg cctcccggct tgcctgccca gttttatccc tagaagcagc    60
tagctactcc aggtgcacag gtgccatgca gccccgaatg ctcctcatcg tggccctcgt    120
ggctctcctg gcctctgccc gagctgatga gggagaggga tccttgctgc tgggctctat    180
gcagggctac atggaacaag cctccaagac ggtccaggat gcactaagca gcatgcagga    240
gtctgatata gctgtggtgg ccaggggctg gatggacaat cgcttcaaat ccctgaaagg    300
ctactggagc aagttcactg ataagttcac tggcctctgg gagtctggcc ctgaggacca    360
actaacaaca ccaactcttg agccgtgaga cctccatgtt ccagatgtgt ctggccatct    420
atcctgctgc ctccgaaggt tgctctaagg ggaaagtata ttctcatgcc tttatccctc    480
cccagacctc acctaaacat gctgtcccta ataaagctgg acacgaagct gccatg        536
```

<210> SEQ ID NO 10
<211> LENGTH: 536
<212> TYPE: DNA
<213> ORGANISM: Rattus norvegicus

<400> SEQUENCE: 10

```
catggcagct tcgtgtccag ctttattagg gacagcatgt ttaggtgagg tctggggagg    60
```

```
gataaaggca tgagaatata ctttcccctt agagcaacct tcggaggcag caggatagat      120
ggccagacac atctggaaca tggaggtctc acggctcaag agttggtgtt gttagttggt      180
cctcagggcc agactcccag aggccagtga acttatcagt gaacttgctc cagtagcctt      240
tcagggattt gaagcgattg tccatccagc ccctggccac cacagctata tcagactcct      300
gcatgctgct tagtgcatcc tggaccgtct tggaggcttg ttccatgtag ccctgcatag      360
agcccagcag caaggatccc tctccctcat cagctcgggc agaggccagg agagccacga      420
gggccacgat gaggagcatt cggggctgca tgcacctgt gcacctggag tagctagctg       480
cttctaggga taaaactggg caggcaagcc gggaggcctc tgatctgttt tatatt          536
```

<210> SEQ ID NO 11
<211> LENGTH: 615
<212> TYPE: DNA
<213> ORGANISM: Oryctolagus cuniculus

<400> SEQUENCE: 11

```
cccgctgtcc tggggcagta taaaaacagg ccggcagcct cttgctgggc ttctactcag      60
ttcatcccca gaagcagtgg ctccaggaac agaggtgccg ccatgcgtcc ctggctgctc      120
ctggttgtca ccctcctggc gctcctggcc tctgcccgag caatggaggc cgaggacccc      180
aaggacgcct cccttctcag cgtcatgcag ggctatgtgc aacacgccac caagacggcc      240
catgacgcgc tgagcagcat gcaggagtcc caaatggccc agcaggccag gggctgggtg      300
gacgctggca tcagctccct gaaaggctac ttgagcacgt tgcggacaa gttctctggg       360 ttctgggacc tgagccctga ggccagtccg acccaggcgc tgaggctgt ctgagacctc       420 agcacccgca gtctgcctgc ccatccgtcc cgccgttgcc ctggctcccg tgggctccag      480
agctgtcccc acgcgtggct tgaagggaca gtaacctcag tgcccctcg ccccccccc        540 ccgacctggc tcacttccaa gcatactgcc tcccaataaa gctggacgag aagccgcgga      600
gagcgggatg tccca                                                      615
```

<210> SEQ ID NO 12
<211> LENGTH: 615
<212> TYPE: DNA
<213> ORGANISM: Oryctolagus cuniculus

<400> SEQUENCE: 12

```
tgggacatcc cgctctccgc ggcttctcgt ccagctttat tgggaggcag tatgcttgga      60
agtgagccag gtcgggggggg gggggcgagg gggcactgag gttactgtcc cttcaagcca    120
cgcgtgggga cagctctgga gcccacggga gccagggcaa cggcgggacg gatgggcagg      180
cagactgcgg gtgctgaggt ctcagacagc ctcagacgcc tgggtcggac tggcctcagg      240
gctcaggtcc cagaacccag agaacttgtc cgcaaacgtg ctcaagtagc ctttcaggga     300
gctgatgcca gcgtccaccc agccctggcc ctgctgggcc atttgggact cctgcatgct      360
gctcagcgcg tcatgggccg tcttggtggc gtgttgcaca tagccctgca tgacgctgag      420
aagggaggcg tccttggggt cctcggcctc cattgctcgg gcagaggcca ggagcgccag      480
gagggtgaca accaggagca gccagggacg catggcggca cctctgttcc tggagccact      540
gcttctgggg atgaactgag tagaagccca gcaagaggct gccggcctgt ttttatactg      600
ccccaggaca gcggg                                                     615
```

<210> SEQ ID NO 13
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
cuuaaaaggg acaguauucu a                                              21

<210> SEQ ID NO 14
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
uagaauacug ucccuuuuaa gcc                                            23

<210> SEQ ID NO 15
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
cuuaaaaggg acaguauucu a                                              21

<210> SEQ ID NO 16
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
uagaauacug ucccuuuuaa gcc                                            23

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
cuuaaaaggg acaguauucu a                                              21

<210> SEQ ID NO 18
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      RFGF peptide"

<400> SEQUENCE: 18
```

```
Ala Ala Val Ala Leu Leu Pro Ala Val Leu Leu Ala Leu Leu Ala Pro
1               5                   10                  15

<210> SEQ ID NO 19
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide"

<400> SEQUENCE: 19

Ala Ala Leu Leu Pro Val Leu Leu Ala Ala Pro
1               5                   10

<210> SEQ ID NO 20
<211> LENGTH: 13
<212> TYPE: PRT
<213> ORGANISM: Human immunodeficiency virus

<400> SEQUENCE: 20

Gly Arg Lys Lys Arg Arg Gln Arg Arg Arg Pro Pro Gln
1               5                   10

<210> SEQ ID NO 21
<211> LENGTH: 16
<212> TYPE: PRT
<213> ORGANISM: Drosophila sp.

<400> SEQUENCE: 21

Arg Gln Ile Lys Ile Trp Phe Gln Asn Arg Arg Met Lys Trp Lys Lys
1               5                   10                  15

<210> SEQ ID NO 22
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
cuuacgcuga guacuucgat t                                              21

<210> SEQ ID NO 23
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 23
ucgaaguacu cagcguaagt t                                              21

<210> SEQ ID NO 24
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
cuucaguucc cugaaagacu u                                              21

<210> SEQ ID NO 25
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
aagucuuuca gggaacugaa gcc                                            23

<210> SEQ ID NO 26
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uucaguuccc ugaaagacua u                                              21

<210> SEQ ID NO 27
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
auagucuuuc agggaacuga agc                                            23

<210> SEQ ID NO 28
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ccaauaaagc uggacaagaa u                                              21

<210> SEQ ID NO 29
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
```
auucuugucc agcuuuauug gga                                                    23

<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
aaaagggaca guauucucag u                                                      21

<210> SEQ ID NO 31
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
acugagaaua cugucccuuu uaa                                                    23

<210> SEQ ID NO 32
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
auggcuucag uucccugaaa u                                                      21

<210> SEQ ID NO 33
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
auuucaggga acugaagcca ucg                                                    23

<210> SEQ ID NO 34
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
agcaccguua aggacaaguu u                                                      21

<210> SEQ ID NO 35
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 35
aaacuugucc uuaacggugc ucc                                             23

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
uaaaagggac aguauucuca u                                               21

<210> SEQ ID NO 37
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
augagaauac ugucccuuuu aag                                             23

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
accgauggcu ucaguucccu u                                               21

<210> SEQ ID NO 39
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
aagggaacug aagccaucgg uca                                             23

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
uuaaaaggga caguauucuc u                                               21

<210> SEQ ID NO 41
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
agagaauacu gucccuuuua agc                                              23

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
gcuucaguuc ccugaaagac u                                                21

<210> SEQ ID NO 43
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
agucuuucag ggaacugaag cca                                              23

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
gauggcuuca guucccugaa u                                                21

<210> SEQ ID NO 45
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
auucagggaa cugaagccau cgg                                              23

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
```
aagggacagu auucucagug u    21

<210> SEQ ID NO 47
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
acacugagaa uacugucccu uuu    23

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48 cuuaaaggg acaguauucu u    21

<210> SEQ ID NO 49
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
aagaauacug ucccuuuuaa gca    23

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
cucccaauaa agcuggacaa u    21

<210> SEQ ID NO 51
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
auuguccagc uuuauuggga ggc    23

<210> SEQ ID NO 52
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 52
ugcuuaaaag ggacaguauu u                                              21

<210> SEQ ID NO 53
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
aaauacuguc ccuuuuaagc aac                                            23

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ccucccaaua aagcuggaca u                                              21

<210> SEQ ID NO 55
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
auguccagcu uuauugggag gcc                                            23

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
gcuuaaaagg gacaguauuc u                                              21

<210> SEQ ID NO 57
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
agaauacugu cccuuuuaag caa                                            23
```

```
<210> SEQ ID NO 58
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
uagaauacug ucccuuuuaa gca                                              23

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
cccaauaaag cuggacaaga u                                                21

<210> SEQ ID NO 60
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
aucuugucca gcuuuauugg gag                                              23

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
cuggagcacc guuaaggaca u                                                21

<210> SEQ ID NO 62
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
auguccuuaa cggugcucca gua                                              23

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 63
aaagggacag uauucucagu u                                              21

<210> SEQ ID NO 64
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
aacugagaau acugucccuu uua                                            23

<210> SEQ ID NO 65
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
gugaccgaug gcuucaguuc u                                              21

<210> SEQ ID NO 66
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
agaacugaag ccaucgguca ccc                                            23

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
ucccaauaaa gcuggacaag u                                              21

<210> SEQ ID NO 68
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
acuuguccag cuuuauuggg agg                                            23

<210> SEQ ID NO 69
<211> LENGTH: 21
<212> TYPE: RNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 69
gguugcuuaa aagggacagu u                                              21

<210> SEQ ID NO 70
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
aacugucccu uuuaagcaac cua                                            23

<210> SEQ ID NO 71
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ucaguucccu gaaagacuac u                                              21

<210> SEQ ID NO 72
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
aguagucuuu cagggaacug aag                                            23

<210> SEQ ID NO 73
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
agacuacugg agcaccguua u                                              21

<210> SEQ ID NO 74
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
auaacggugc uccaguaguc uuu                                            23
```

<210> SEQ ID NO 75
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
ccaccaagac cgccaaggau u                                           21

<210> SEQ ID NO 76
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
aauccuuggc ggucuuggug gcg                                         23

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
ugaccgaugg cuucaguucc u                                           21

<210> SEQ ID NO 78
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
aggaacugaa gccaucgguc acc                                         23

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
cugggugacc gauggcuuca u                                           21

<210> SEQ ID NO 80
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 80
augaagccau cggucaccca gcc                                          23

<210> SEQ ID NO 81
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
caauaaagcu ggacaagaag u                                            21

<210> SEQ ID NO 82
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
acuucuuguc cagcuuuauu ggg                                          23

<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
cgauggcuuc aguucccuga u                                            21

<210> SEQ ID NO 84
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
aucagggaac ugaagccauc ggu                                          23

<210> SEQ ID NO 85
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
agggacagua uucucagugc u                                            21

<210> SEQ ID NO 86
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
agcacugaga auacugaccc uuu                                              23

<210> SEQ ID NO 87
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
cugaaagacu acuggagcac u                                                21

<210> SEQ ID NO 88
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
agugcuccag uagucuuuca ggg                                              23

<210> SEQ ID NO 89
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
auaaagcugg acaagaagcu u                                                21

<210> SEQ ID NO 90
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
aagcuucuug uccagcuuua uug                                              23

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
aagacuacug gagcaccguu u                                                21
```

-continued

```
<210> SEQ ID NO 92
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
aaacggugcu ccaguagucu uuc                                              23

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
uggcuucagu ucccugaaag u                                                21

<210> SEQ ID NO 94
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
acuuucaggg aacugaagcc auc                                              23

<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gccucccaau aaagcuggac u                                                21

<210> SEQ ID NO 96
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
aguccagcuu uauugggagg cca                                              23

<210> SEQ ID NO 97
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 97
aguucccuga aagacuacug u                                              21

<210> SEQ ID NO 98
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
acaguagucu uucagggaac uga                                            23

<210> SEQ ID NO 99
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
aagcuggaca agaagcugcu u                                              21

<210> SEQ ID NO 100
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
aagcagcuuc uuguccagcu uua                                            23

<210> SEQ ID NO 101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
gcuggacaag aagcugcuau a                                              21

<210> SEQ ID NO 102
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
uauagcagcu ucuuguccag cuu                                            23

<210> SEQ ID NO 103
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
cccugaaaga cuacuggagc u                                              21

<210> SEQ ID NO 104
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
agcuccagua gucuuucagg gaa                                            23

<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
aauaaagcug gacaagaagc u                                              21

<210> SEQ ID NO 106
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
agcuucuugu ccagcuuuau ugg                                            23

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
ggcuggguga ccgauggcuu u                                              21

<210> SEQ ID NO 108
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
```
aaagccaucg gucacccagc ccc                                    23

<210> SEQ ID NO 109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
caguucccug aaagacuacu u                                      21

<210> SEQ ID NO 110
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
aaguagucuu ucagggaacu gaa                                    23

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
ccugaaagac uacuggagca u                                      21

<210> SEQ ID NO 112
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
augcuccagu agucuuucag gga                                    23

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
caucccuaga ggcagcugcu u                                      21

<210> SEQ ID NO 114
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 114
aagcagcugc cucuagggau gaa                                               23

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
cugccugaga ccucaauacc u                                                 21

<210> SEQ ID NO 116
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
agguauugag gucucaggca gcc                                               23

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
aaagcuggac aagaagcugc u                                                 21

<210> SEQ ID NO 118
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
agcagcuucu uguccagcuu uau                                               23

<210> SEQ ID NO 119
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
uucccugaaa gacuacugga u                                                 21

<210> SEQ ID NO 120
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
auccaguagu cuuucaggga acu                                              23

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
uagguugcuu aaaagggaca u                                                21

<210> SEQ ID NO 122
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122 augcccuuu uaagcaaccu aca                                               23

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
caccaagacc gccaaggaug u                                                21

<210> SEQ ID NO 124
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
acauccuugg cggucuuggu ggc                                              23

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
```
agguugcuua aaagggacag u                                    21

<210> SEQ ID NO 126
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
acugucccuu uuaagcaacc uac                                  23

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
agcuggacaa gaagcugcua u                                    21

<210> SEQ ID NO 128
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
auagcagcuu cuuguccagc uuu                                  23

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
cccuagaggc agcugcucca u                                    21

<210> SEQ ID NO 130
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
auggagcagc ugccucuagg gau                                  23

<210> SEQ ID NO 131
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 131
uggagcaccg uuaaggacaa u                                              21

<210> SEQ ID NO 132
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
auuguccuua acggugcucc agu                                            23

<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
gaccgccaag gaugcacuga u                                              21

<210> SEQ ID NO 134
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
aucagugcau ccuuggcggu cuu                                            23

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
uaaagcugga caagaagcug u                                              21

<210> SEQ ID NO 136
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
acagcuucuu guccagcuuu auu                                            23
```

```
<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
ucccugaaag acuacuggag u                                              21

<210> SEQ ID NO 138
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
acuccaguag ucuuucaggg aac                                            23

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
gaccgauggc uucaguuccc u                                              21

<210> SEQ ID NO 140
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
agggaacuga agccaucggu cac                                            23

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
ucccuagagg cagcugcucc u                                              21

<210> SEQ ID NO 142
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 142
aggagcagcu gccucuaggg aug                                          23

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
ccgauggcuu caguucccug u                                            21

<210> SEQ ID NO 144
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
acagggaacu gaagccaucg guc                                          23

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
guagguugcu uaaaagggac u                                            21

<210> SEQ ID NO 146
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
agucccuuuu aagcaaccua cag                                          23

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
ccuagaggca gcugcuccag u                                            21

<210> SEQ ID NO 148
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 148
acuggagcag cugccucuag gga                                              23

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
uguagguugc uuaaaaggga u                                                21

<210> SEQ ID NO 150
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
aucccuuuua agcaaccuac agg                                              23

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
aaagacuacu ggagcaccgu u                                                21

<210> SEQ ID NO 152
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
aacggugcuc caguagucuu uca                                              23

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
aggcagcugc uccaggaaca u                                                21
```

<210> SEQ ID NO 154
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
auguuccugg agcagcugcc ucu                                            23

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
gcagcugcuc caggaacaga u                                              21

<210> SEQ ID NO 156
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
aucuguuccu ggagcagcug ccu                                            23

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
cgccaccaag accgccaagg u                                              21

<210> SEQ ID NO 158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
accuuggcgg ucuugguggc gug                                            23

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
cuacuggagc accguuaagg u                                       21

<210> SEQ ID NO 160
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
accuuaacgg ugcuccagua guc                                     23

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
uggcugccug agaccucaau u                                       21

<210> SEQ ID NO 162
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
aauugagguc ucaggcagcc acg                                     23

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
ggcuucaguu cccugaaaga u                                       21

<210> SEQ ID NO 164
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
aucuuucagg gaacugaagc cau                                     23

<210> SEQ ID NO 165
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
aucccuagag gcagcugcuc u                                           21

<210> SEQ ID NO 166
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
agagcagcug ccucuaggga uga                                         23

<210> SEQ ID NO 167
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
ugaaagacua cuggagcacc u                                           21

<210> SEQ ID NO 168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
aggugcucca guagucuuuc agg                                         23

<210> SEQ ID NO 169
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
aagaccgcca aggaugcacu u                                           21

<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
aagugcaucc uuggcggucu ugg                                         23
```

<210> SEQ ID NO 171
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
gcugccugag accucaauac u                                                 21

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
aguauugagg ucucaggcag cca                                               23

<210> SEQ ID NO 173
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
ggccucccaa uaaagcugga u                                                 21

<210> SEQ ID NO 174
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
auccagcuuu auugggaggc cag                                               23

<210> SEQ ID NO 175
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
caguucaucc cuagaggcag u                                                 21

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 176
acugccucua gggaugaacu gag                                    23

<210> SEQ ID NO 177
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
ggcugccuga gaccucaaua u                                      21

<210> SEQ ID NO 178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
auauugaggu cucaggcagc cac                                    23

<210> SEQ ID NO 179
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
gaaagacuac uggagcaccg u                                      21

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
acggugcucc aguagucuuu cag                                    23

<210> SEQ ID NO 181
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gaggcagcug cuccaggaac u                                      21

<210> SEQ ID NO 182
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
aguuccugga gcagcugccu cua                                        23

<210> SEQ ID NO 183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
guggcugccu gagaccucaa u                                          21

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
auugaggucu caggcagcca cgg                                        23

<210> SEQ ID NO 185
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
gcugggugac cgauggcuuc u                                          21

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
agaagccauc ggucacccag ccc                                        23

<210> SEQ ID NO 187
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
```

```
ggagcaccgu uaaggacaag u                                              21
```

<210> SEQ ID NO 188
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188

```
acuuguccuu aacggugcuc cag                                            23
```

<210> SEQ ID NO 189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189

```
cuguagguug cuuaaaaggg u                                              21
```

<210> SEQ ID NO 190
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190

```
acccuuuuaa gcaaccuaca ggg                                            23
```

<210> SEQ ID NO 191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191

```
guucccugaa agacuacugg u                                              21
```

<210> SEQ ID NO 192
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192

```
accaguaguc uuucagggaa cug                                            23
```

<210> SEQ ID NO 193
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 193
gggcugggug accgauggcu u                                              21

<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
aagccaucgg ucacccagcc ccu                                            23

<210> SEQ ID NO 195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
gccaccaaga ccgccaagga u                                              21

<210> SEQ ID NO 196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
auccuuggcg gucuuggugg cgu                                            23

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
agaggcagcu gcuccaggaa u                                              21

<210> SEQ ID NO 198
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
auuccuggag cagcugccuc uag                                            23

<210> SEQ ID NO 199
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ucaucccuag aggcagcugc u                                              21

<210> SEQ ID NO 200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
agcagcugcc ucuagggaug aac                                            23

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
uucaucccua gaggcagcug u                                              21

<210> SEQ ID NO 202
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
acagcugccu cuagggauga acu                                            23

<210> SEQ ID NO 203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
cgagcuccuu ggguccugca u                                              21

<210> SEQ ID NO 204
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
```
augcaggacc caaggagcuc gca                                          23

<210> SEQ ID NO 205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
ggcagcugcu ccaggaacag u                                            21

<210> SEQ ID NO 206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
acuguuccug gagcagcugc cuc                                          23

<210> SEQ ID NO 207
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
ccaagaccgc caaggaugca u                                            21

<210> SEQ ID NO 208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
augcauccuu ggcggucuug gug                                          23

<210> SEQ ID NO 209
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
gacuacugga gcaccguuaa u                                            21

<210> SEQ ID NO 210
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 210
auuaacggug cuccaguagu cuu                                             23

<210> SEQ ID NO 211
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
aguucauccc uagaggcagc u                                               21

<210> SEQ ID NO 212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
agcugccucu agggaugaac uga                                             23

<210> SEQ ID NO 213
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
acuggagcac cguuaaggac u                                               21

<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
aguccuuaac ggugcuccag uag                                             23

<210> SEQ ID NO 215
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
ugggugaccg auggcuucag u                                               21
```

```
<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
acugaagcca ucggucaccc agc                                           23

<210> SEQ ID NO 217
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
ccgagcuuca gaggccgagg u                                             21

<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
accucggccu cugaagcucg ggc                                           23

<210> SEQ ID NO 219
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
accaagaccg ccaaggaugc u                                             21

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
agcauccuug gcggucuugg ugg                                           23

<210> SEQ ID NO 221
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 221
uagaggcagc ugcuccagga u                                              21

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
auccuggagc agcugccucu agg                                            23

<210> SEQ ID NO 223
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
gggugaccga uggcuucagu u                                              21

<210> SEQ ID NO 224
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
aacugaagcc aucggucacc cag                                            23

<210> SEQ ID NO 225
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
guucaucccu agaggcagcu u                                              21

<210> SEQ ID NO 226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
aagcugccuc uagggaugaa cug                                            23

<210> SEQ ID NO 227
<211> LENGTH: 21
<212> TYPE: RNA
<213> ORGANISM: Artificial Sequence
```

-continued

<220> FEATURE:
<221> NAME/KEY: source
<223> OTHER INFORMATION: /note="Description of Artificial Sequence:
      Synthetic oligonucleotide"

<400> SEQUENCE: 227
acuacuggag caccguuaag u                                              21

<210> SEQ ID NO 228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
acuuaacggu gcuccaguag ucu                                            23

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
cagcugcucc aggaacagag u                                              21

<210> SEQ ID NO 230
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
acucguuucc uggagcagcu gcc                                            23

<210> SEQ ID NO 231
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
cgagcuucag aggccgagga u                                              21

<210> SEQ ID NO 232
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
auccucggcc ucugaagcuc ggg                                            23

```
<210> SEQ ID NO 233
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
cuagaggcag cugcuccagg u                                           21

<210> SEQ ID NO 234
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
accuggagca gcugccucua ggg                                         23

<210> SEQ ID NO 235
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
gagucccagg uggcccagca u                                           21

<210> SEQ ID NO 236
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
augcugggcc accugggacu ccu                                         23

<210> SEQ ID NO 237
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
agaccgccaa ggaugcacug u                                           21

<210> SEQ ID NO 238
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 238
acagugcauc cuuggcgguc uug                                    23

<210> SEQ ID NO 239
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
ccagguggcc cagcaggcca u                                      21

<210> SEQ ID NO 240
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
auggccugcu gggccaccug gga                                    23

<210> SEQ ID NO 241
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
acgccaccaa gaccgccaag u                                      21

<210> SEQ ID NO 242
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
acuuggcggu cuugguggcg ugc                                    23

<210> SEQ ID NO 243
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
ggugaccgau ggcuucaguu u                                      21

<210> SEQ ID NO 244
<211> LENGTH: 23
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
aaacugaagc caucggucac cca                                              23

<210> SEQ ID NO 245
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
uacuggagca ccguuaagga u                                                21

<210> SEQ ID NO 246
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
auccuuaacg gugcuccagu agu                                              23

<210> SEQ ID NO 247
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ggagucccag guggcccagc u                                                21

<210> SEQ ID NO 248
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
agcugggcca ccugggacuc cug                                              23

<210> SEQ ID NO 249
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
gcaggagucc cagguggccc u                                                21
```

```
<210> SEQ ID NO 250
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
agggccaccu gggacuccug cac                                               23

<210> SEQ ID NO 251
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
ugcaggaguc caggugggcc u                                                 21

<210> SEQ ID NO 252
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
aggccaccug ggacuccugc acg                                               23

<210> SEQ ID NO 253
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
caggagaccc aggugggcca u                                                 21

<210> SEQ ID NO 254
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
augggccacc ugggacuccu gca                                               23

<210> SEQ ID NO 255
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 255
agcugcucca ggaacagagg u                                        21

<210> SEQ ID NO 256
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
accucuguuc cuggagcagc ugc                                      23

<210> SEQ ID NO 257
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
agucccaggu ggcccagcag u                                        21

<210> SEQ ID NO 258
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
acugcugggc caccugggac ucc                                      23

<210> SEQ ID NO 259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
aggaguccca gguggcccag u                                        21

<210> SEQ ID NO 260
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
acugggccac cugggacucc ugc                                      23

<210> SEQ ID NO 261
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 261
aagucutuca gggaacugaa gcc                                              23

<210> SEQ ID NO 262
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 262
agucuutcag ggaacugaag cca                                              23

<210> SEQ ID NO 263
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
guugcuuaaa agggacagua u                                                21

<210> SEQ ID NO 264
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 264
auacugtccc uuuuaagcaa ccu                                              23

<210> SEQ ID NO 265
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 265
aucuugtcca gcuuuauugg gag                                          23

<210> SEQ ID NO 266
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 266
auagucuuuc agggaacuga agc                                          23

<210> SEQ ID NO 267
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 267 auguccuaa cggugcucca gua                                           23

<210> SEQ ID NO 268
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 268
aggaactgaa gccaucgguc acc                                          23

<210> SEQ ID NO 269
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 269 agcuucugu ccagcuuuau ugg                                           23

<210> SEQ ID NO 270
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
gagcaccguu aaggacaagu u                                              21

<210> SEQ ID NO 271
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 271
aacuugtccu uaacggugcu cca                                            23

<210> SEQ ID NO 272
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 272
acuucutguc cagcuuuauu ggg                                            23

<210> SEQ ID NO 273
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 273
agcagctucu uguccagcuu uau                                            23

<210> SEQ ID NO 274
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 274
acugccucua gggaugaacu gag					23

<210> SEQ ID NO 275
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 275
acagcutcuu guccagcuuu auu					23

<210> SEQ ID NO 276
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 276
aaauactguc ccuuuuaagc aac					23

<210> SEQ ID NO 277
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 277
aggugcucca guagucuuuc agg					23

<210> SEQ ID NO 278
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 278
agguautgag gucucaggca gcc					23

<210> SEQ ID NO 279
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 279
aauccutggc ggucuuggug gcg                                           23

<210> SEQ ID NO 280
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 280
aaguagtcuu ucagggaacu gaa                                           23

<210> SEQ ID NO 281
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 281
aucccutuua agcaaccuac agg                                           23

<210> SEQ ID NO 282
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 282
aaacggtgcu ccaguagucu uuc                                           23

<210> SEQ ID NO 283
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 283
aguucctgga gcagcugccu cua                                              23

<210> SEQ ID NO 284
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
caagaccgcc aaggaugcac u                                                21

<210> SEQ ID NO 285
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 285
agugcatccu uggcggucuu ggu                                              23

<210> SEQ ID NO 286
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 286
acaucctugg cggucuuggu ggc                                              23

<210> SEQ ID NO 287
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 287
aucugutccu ggagcagcug ccu                                              23

<210> SEQ ID NO 288
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 288
agcagctgcc ucuagggaug aac                                         23

<210> SEQ ID NO 289
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 289
auccagtagu cuuucaggga acu                                         23

<210> SEQ ID NO 290
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 290
agagaatacu gucccuuuua agc                                         23

<210> SEQ ID NO 291
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 291
acccuutuaa gcaaccuaca ggg                                         23

<210> SEQ ID NO 292
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 292
aguccutaac ggugcuccag uag                                             23

<210> SEQ ID NO 293
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 293
aguccctuuu aagcaaccua cag                                             23

<210> SEQ ID NO 294
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 294
acucugtucc uggagcagcu gcc                                             23

<210> SEQ ID NO 295
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
uugcuuaaaa gggacaguau u                                               21

<210> SEQ ID NO 296
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
aauacugucc cuuuuaagca acc                                             23

<210> SEQ ID NO 297
<211> LENGTH: 23
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 297
auggcctgcu gggccaccug gga                                          23

<210> SEQ ID NO 298
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 298
aagccatcgg ucacccagcc ccu                                          23

<210> SEQ ID NO 299
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
uaaaagggac aguauucua                                               19

<210> SEQ ID NO 300
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
uagaauacug ucccuuuuaa g                                            21

<210> SEQ ID NO 301
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 301
agaatacugu cccuuuuaag caa                                          23

<210> SEQ ID NO 302
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
agaauacugu cccuuuuaag cgc                                          23

<210> SEQ ID NO 303
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 303
agaatacugu cccuuuuaag cgc                                          23

<210> SEQ ID NO 304
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
uuaaaaggga caguauucu                                               19

<210> SEQ ID NO 305
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
agaauacugu cccuuuuaag c                                            21

<210> SEQ ID NO 306
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 306
agaatacugu cccuuuuaag c                                            21

<210> SEQ ID NO 307
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 307
uaaaagggac aguauuuuca u                                              21

<210> SEQ ID NO 308
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
augaaaauac ugucccuuuu aag                                            23

<210> SEQ ID NO 309
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
augagaauac ugucccuuuu acc                                            23

<210> SEQ ID NO 310
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
aaagggacag uauucucau                                                 19

<210> SEQ ID NO 311
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
augagaauac ugucccuuuu g                                              21

<210> SEQ ID NO 312
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
aaaaagggac aguauucuca u                                              21
```

<210> SEQ ID NO 313
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
augagaauac ugucccuuuu gcc                                                23

<210> SEQ ID NO 314
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 314
uaaaagggac agtauucuca u                                                  21

<210> SEQ ID NO 315
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
aagaauacug ucccuuuuaa gcc                                                23

<210> SEQ ID NO 316
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
uaaaagggac aguauucuu                                                     19

<210> SEQ ID NO 317
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
aagaauacug ucccuuuuaa g                                                  21

<210> SEQ ID NO 318
<211> LENGTH: 23
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 318
acugagaaua cugucccuuu ugc                                              23

<210> SEQ ID NO 319
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
acugagaaua cugucccuuu ucc                                              23

<210> SEQ ID NO 320
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
aagggacagu auucucagu                                                   19

<210> SEQ ID NO 321
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
acugagaaua cugucccuuu u                                                21

<210> SEQ ID NO 322
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
aaaagggaca guauuuucag u                                                21

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
acugaaaaua cugucccuuu ugc                                              23
```

<210> SEQ ID NO 324
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 324
ccaauaaagc uggauaagaa u                                              21

<210> SEQ ID NO 325
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 325
auucuuaucc agcuuuauug gga                                            23

<210> SEQ ID NO 326
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 326 auuctgucc agcuuuauug gga                                             23

<210> SEQ ID NO 327
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 327 auuctgucc agcuuuauug ggc                                             23

<210> SEQ ID NO 328
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 328
aauaaagcug gacaagaau                                                 19

```
<210> SEQ ID NO 329
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 329 auucugucc agcuuuauug g                                              21

<210> SEQ ID NO 330
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 330 auucugucc agcuuuauuc c                                              21

<210> SEQ ID NO 331
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
aagcagcuuc uuguccagcu uuc                                           23

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
aagcagcuuc uuguccagcu ucc                                           23

<210> SEQ ID NO 333
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
gcuggacaag aagcugcuu                                                19

<210> SEQ ID NO 334
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
aagcagcuuc uuguccagcu u                                          21

<210> SEQ ID NO 335
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
aagcuggaca agaagcuacu u                                          21

<210> SEQ ID NO 336
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
aaguagcuuc uuguccagcu ucc                                        23

<210> SEQ ID NO 337
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
aagcuggaca agaaguugcu u                                          21

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
aagcaacuuc uuguccagcu ucc                                        23

<210> SEQ ID NO 339
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
```

```
acgggacagu auucucagua                                             20
```

<210> SEQ ID NO 340
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340

```
ucacugagaa uacugucccg u                                           21
```

<210> SEQ ID NO 341
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341

```
cuucaguucc cugaaagacu u                                           21
```

<210> SEQ ID NO 342
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342

```
aagucuuuca gggaacugaa gcc                                         23
```

<210> SEQ ID NO 343
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 343

```
ggcuucaguu cccugaaaga cua                                         23
```

<210> SEQ ID NO 344
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344

```
uucaguuccc ugaaagacua u                                           21
```

<210> SEQ ID NO 345
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 345
auagucuuuc agggaacuga agc                                           23

<210> SEQ ID NO 346
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 346
gcuucaguuc ccugaaagac uac                                           23

<210> SEQ ID NO 347
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
ccaauaaagc uggacaagaa u                                             21

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
auucuugucc agcuuuauug gga                                           23

<210> SEQ ID NO 349
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 349
ucccaauaaa gcuggacaag aag                                           23

<210> SEQ ID NO 350
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
aaaagggaca guauucucag u                                             21
```

```
<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
acugagaaua cugucccuuu uaa                                              23

<210> SEQ ID NO 352
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 352
uuaaaaggga caguauucuc agu                                              23

<210> SEQ ID NO 353
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
auggcuucag uucccugaaa u                                                21

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
auuucaggga acugaagcca ucg                                              23

<210> SEQ ID NO 355
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 355
cgauggcuuc aguucccuga aag                                              23

<210> SEQ ID NO 356
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 356
agcaccguua aggacaaguu u                                            21

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
aaacuugucc uuaacggugc ucc                                          23

<210> SEQ ID NO 358
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 358
ggagcaccgu uaaggacaag uuc                                          23

<210> SEQ ID NO 359
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
uaaaagggac aguauucuca u                                            21

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
augagaauac ugucccuuuu aag                                          23

<210> SEQ ID NO 361
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 361 cuuaaaggg acaguauucu cag                                           23

<210> SEQ ID NO 362
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 362
accgauggcu ucaguccccu u                                              21

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
aagggaacug aagccaucgg uca                                            23

<210> SEQ ID NO 364
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 364
ugaccgaugg cuucaguucc cug                                            23

<210> SEQ ID NO 365
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
uuaaaaggga caguauucuc u                                              21

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
agagaauacu gucccuuuua agc                                            23

<210> SEQ ID NO 367
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 367
gcuuaaaagg gacaguauuc uca                                            23
```

<210> SEQ ID NO 368
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
gcuucaguuc ccugaaagac u                                              21

<210> SEQ ID NO 369
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
agucuuucag ggaacugaag cca                                            23

<210> SEQ ID NO 370
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 370
uggcuucagu ucccugaaag acu                                            23

<210> SEQ ID NO 371
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
gauggcuuca guucccugaa u                                              21

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
auucagggaa cugaagccau cgg                                            23

<210> SEQ ID NO 373
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

-continued

<400> SEQUENCE: 373
ccgauggcuu caguucccug aaa                                          23

<210> SEQ ID NO 374
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
aagggacagu auucucagug u                                            21

<210> SEQ ID NO 375
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
acacugagaa uacugucccu uuu                                          23

<210> SEQ ID NO 376
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 376
aaaagggaca guauucucag ugc                                          23

<210> SEQ ID NO 377
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
cuuaaaaggg acaguauucu u                                            21

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
aagaauacug ucccuuuuaa gca                                          23

<210> SEQ ID NO 379
<211> LENGTH: 23
<212> TYPE: RNA

-continued

```
<213> ORGANISM: Unknown
<220> FEATURE:
<221> NAME/KEY: source
<223> OTHER INFORMATION: /note="Description of Unknown:
      target sequence"

<400> SEQUENCE: 379
ugcuuaaaag ggacaguauu cuc                                              23

<210> SEQ ID NO 380
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
cucccaauaa agcuggacaa u                                                21

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
auuguccagc uuuauuggga ggc                                              23

<210> SEQ ID NO 382
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 382
gccucccaau aaagcuggac aag                                              23

<210> SEQ ID NO 383
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
ugcuuaaaag ggacaguauu u                                                21

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
aaauacuguc ccuuuaagc aac                                               23
```

<210> SEQ ID NO 385
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 385
guugcuuaaa agggacagua uuc                                              23

<210> SEQ ID NO 386
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
ccucccaaua aagcuggaca u                                                21

<210> SEQ ID NO 387
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
auguccagcu uuauugggag gcc                                              23

<210> SEQ ID NO 388
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 388
ggccucccaa uaaagcugga caa                                              23

<210> SEQ ID NO 389
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
gcuuaaaagg gacaguauuc u                                                21

<210> SEQ ID NO 390
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 390
agaauacugu cccuuuuaag caa                          23

<210> SEQ ID NO 391
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 391
uugcuuaaaa gggacaguau ucu                          23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
uagaauacug ucccuuuuaa gca                          23

<210> SEQ ID NO 393
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 393
cuuaaaaggg acaguauucu a                            21

<210> SEQ ID NO 394
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
cccaauaaag cuggacaaga u                            21

<210> SEQ ID NO 395
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
aucuugucca gcuuuauugg gag                          23

<210> SEQ ID NO 396
<211> LENGTH: 23

```
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 396
cucccaauaa agcuggacaa gaa                                           23

<210> SEQ ID NO 397
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
cuggagcacc guuaaggaca u                                             21

<210> SEQ ID NO 398
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
auguccuuaa cggugcucca gua                                           23

<210> SEQ ID NO 399
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 399
uacuggagca ccguuaagga caa                                           23

<210> SEQ ID NO 400
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
aaagggacag uauucucagu u                                             21

<210> SEQ ID NO 401
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
```

-continued

```
aacugagaau acugucccuu uua                                        23

<210> SEQ ID NO 402
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 402
uaaaagggac aguauucuca gug                                        23

<210> SEQ ID NO 403
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
gugaccgaug gcuucaguuc u                                          21

<210> SEQ ID NO 404
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
agaacugaag ccaucgguca ccc                                        23

<210> SEQ ID NO 405
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 405
gggugaccga uggcuucagu ucc                                        23

<210> SEQ ID NO 406
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
ucccaauaaa gcuggacaag u                                          21

<210> SEQ ID NO 407
<211> LENGTH: 23
<212> TYPE: RNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"

<400> SEQUENCE: 407
acuuguccag cuuuauuggg agg                                              23

<210> SEQ ID NO 408
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 408
ccucccaaua aagcuggaca aga                                              23

<210> SEQ ID NO 409
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
gguugcuuaa aagggacagu u                                                21

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
aacugucccu uuuaagcaac cua                                              23

<210> SEQ ID NO 411
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 411
uagguugcuu aaaagggaca gua                                              23

<210> SEQ ID NO 412
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
ucaguucccu gaaagacuac u                                                21

<210> SEQ ID NO 413
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
aguagucuuu cagggaacug aag                                            23

<210> SEQ ID NO 414
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 414
cuucaguucc cugaaagacu acu                                            23

<210> SEQ ID NO 415
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
agacuacugg agcaccguua u                                              21

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
auaacggugc uccaguaguc uuu                                            23

<210> SEQ ID NO 417
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 417
aaagacuacu ggagcaccgu uaa                                            23

<210> SEQ ID NO 418
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
```

```
ccaccaagac cgccaaggau u                                              21

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
aauccuuggc ggucuuggug gcg                                            23

<210> SEQ ID NO 420
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 420
cgccaccaag accgccaagg aug                                            23

<210> SEQ ID NO 421
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
ugaccgaugg cuucaguucc u                                              21

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
aggaacugaa gccaucgguc acc                                            23

<210> SEQ ID NO 423
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 423
ggugaccgau ggcuucaguu ccc                                            23

<210> SEQ ID NO 424
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 424
cugggugacc gauggcuuca u                                              21

<210> SEQ ID NO 425
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
augaagccau cggucaccca gcc                                            23

<210> SEQ ID NO 426
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 426
ggcuggguga ccgauggcuu cag                                            23

<210> SEQ ID NO 427
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
caauaaagcu ggacaagaag u                                              21

<210> SEQ ID NO 428
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
acuucuuguc cagcuuuauu ggg                                            23

<210> SEQ ID NO 429
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 429
cccaauaaag cuggacaaga agc                                            23
```

```
<210> SEQ ID NO 430
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
cgauggcuuc aguucccuga u                                           21

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
aucagggaac ugaagccauc ggu                                         23

<210> SEQ ID NO 432
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 432
accgauggcu ucaguocccu gaa                                         23

<210> SEQ ID NO 433
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
agggacagua uucucagugc u                                           21

<210> SEQ ID NO 434
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
agcacugaga auacuguccc uuu                                         23

<210> SEQ ID NO 435
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"
```

```
<400> SEQUENCE: 435
aaagggacag uauucucagu gcu                                              23

<210> SEQ ID NO 436
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
cugaaagacu acuggagcac u                                                21

<210> SEQ ID NO 437
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
agugcuccag uagucuuuca ggg                                              23

<210> SEQ ID NO 438
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 438
cccugaaaga cuacuggagc acc                                              23

<210> SEQ ID NO 439
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
auaaagcugg acaagaagcu u                                                21

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
aagcuucuug uccagcuuua uug                                              23

<210> SEQ ID NO 441
<211> LENGTH: 23
<212> TYPE: RNA
<213> ORGANISM: Unknown
```

```
<220> FEATURE:
<221> NAME/KEY: source
<223> OTHER INFORMATION: /note="Description of Unknown:
      target sequence"

<400> SEQUENCE: 441
caauaaagcu ggacaagaag cug                                          23

<210> SEQ ID NO 442
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
aagacuacug gagcaccguu u                                            21

<210> SEQ ID NO 443
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
aaacggugcu ccaguagucu uuc                                          23

<210> SEQ ID NO 444
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 444
gaaagacuac uggagcaccg uua                                          23

<210> SEQ ID NO 445
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
uggcuucagu ucccugaaag u                                            21

<210> SEQ ID NO 446
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
acuuucaggg aacugaagcc auc                                          23
```

-continued

<210> SEQ ID NO 447
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 447
gauggcuuca guucccugaa aga                                           23

<210> SEQ ID NO 448
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
gccucccaau aaagcuggac u                                             21

<210> SEQ ID NO 449
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
aguccagcuu uauugggagg cca                                           23

<210> SEQ ID NO 450
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 450
uggccuccca auaaagcugg aca                                           23

<210> SEQ ID NO 451
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
aguucccuga aagacuacug u                                             21

<210> SEQ ID NO 452
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

```
<400> SEQUENCE: 452
acaguagucu uucagggaac uga                                              23

<210> SEQ ID NO 453
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 453
ucaguvcccu gaaagacuac ugg                                              23

<210> SEQ ID NO 454
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
aagcuggaca agaagcugcu u                                                21

<210> SEQ ID NO 455
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
aagcagcuuc uuguccagcu uua                                              23

<210> SEQ ID NO 456
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 456
uaaagcugga caagaagcug cua                                              23

<210> SEQ ID NO 457
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
gcuggacaag aagcugcuau a                                                21

<210> SEQ ID NO 458
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
uauagcagcu ucuuguccag cuu                                            23

<210> SEQ ID NO 459
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 459
gcuggacaag aagcugcuau aua                                            23

<210> SEQ ID NO 460
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
cccugaaaga cuacuggagc u                                              21

<210> SEQ ID NO 461
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
agcuccagua gucuuucagg gaa                                            23

<210> SEQ ID NO 462
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 462
uucccugaaa gacuacugga gca                                            23

<210> SEQ ID NO 463
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
aauaaagcug gacaagaagc u                                              21
```

<210> SEQ ID NO 464
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
agcuucuugu ccagcuuuau ugg                                           23

<210> SEQ ID NO 465
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 465
ccaauaaagc uggacaagaa gcu                                           23

<210> SEQ ID NO 466
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
ggcuggguga ccgauggcuu u                                             21

<210> SEQ ID NO 467
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
aaagccaucg gucacccagc ccc                                           23

<210> SEQ ID NO 468
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 468
ggggcugggu gaccgauggc uuc                                           23

<210> SEQ ID NO 469
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

```
                          -continued
      Synthetic oligonucleotide"

<400> SEQUENCE: 469
caguucccug aaagacuacu u                                          21

<210> SEQ ID NO 470
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
aaguagucuu ucagggaacu gaa                                        23

<210> SEQ ID NO 471
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 471
uucaguuccc ugaaagacua cug                                        23

<210> SEQ ID NO 472
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
ccugaaagac uacuggagca u                                          21

<210> SEQ ID NO 473
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
augcuccagu agucuuucag gga                                        23

<210> SEQ ID NO 474
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 474
ucccugaaag acuacuggag cac                                        23

<210> SEQ ID NO 475
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
caucccuaga ggcagcugcu u                                              21

<210> SEQ ID NO 476
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
aagcagcugc cucuagggau gaa                                            23

<210> SEQ ID NO 477
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 477
uucaucccua gaggcagcug cuc                                            23

<210> SEQ ID NO 478
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
cugccugaga ccucaauacc u                                              21

<210> SEQ ID NO 479
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
agguauugag gucucaggca gcc                                            23

<210> SEQ ID NO 480
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 480
```

```
ggcugccuga gaccucaaua ccc                                           23

<210> SEQ ID NO 481
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
aaagcuggac aagaagcugc u                                             21

<210> SEQ ID NO 482
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
agcagcuucu uguccagcuu uau                                           23

<210> SEQ ID NO 483
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 483
auaaagcugg acaagaagcu gcu                                           23

<210> SEQ ID NO 484
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
uucccugaaa gacuacugga u                                             21

<210> SEQ ID NO 485
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
auccaguagu cuuucaggga acu                                           23

<210> SEQ ID NO 486
<211> LENGTH: 23
<212> TYPE: RNA
<213> ORGANISM: Unknown
<220> FEATURE:
<221> NAME/KEY: source
```

```
-continued

<223> OTHER INFORMATION: /note="Description of Unknown:
      target sequence"

<400> SEQUENCE: 486
aguucccuga aagacuacug gag                                          23

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
uagguugcuu aaaagggaca u                                            21

<210> SEQ ID NO 488
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
augucccuuu uaagcaaccu aca                                          23

<210> SEQ ID NO 489
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 489
uguagguugc uuaaaaggga cag                                          23

<210> SEQ ID NO 490
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
caccaagacc gccaaggaug u                                            21

<210> SEQ ID NO 491
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
acauccuugg cggucuuggu ggc                                          23

<210> SEQ ID NO 492
```

```
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 492
gccaccaaga ccgccaagga ugc                                             23

<210> SEQ ID NO 493
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
agguugcuua aaagggacag u                                               21

<210> SEQ ID NO 494
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
acugucccuu uuaagcaacc uac                                             23

<210> SEQ ID NO 495
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 495
guagguugcu uaaaagggac agu                                             23

<210> SEQ ID NO 496
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
agcuggacaa gaagcugcua u                                               21

<210> SEQ ID NO 497
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
```

```
auagcagcuu cuuguccagc uuu                                               23

<210> SEQ ID NO 498
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 498
aaagcuggac aagaagcugc uau                                               23

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
cccuagaggc agcugcucca u                                                 21

<210> SEQ ID NO 500
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
auggagcagc ugccucuagg gau                                               23

<210> SEQ ID NO 501
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 501
aucccuagag gcagcugcuc cag                                               23

<210> SEQ ID NO 502
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
uggagcaccg uuaaggacaa u                                                 21

<210> SEQ ID NO 503
<211> LENGTH: 23
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 503
auuguccuua acggugcucc agu                                              23

<210> SEQ ID NO 504
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 504
acuggagcac cguuaaggac aag                                              23

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
gaccgccaag gaugcacuga u                                                21

<210> SEQ ID NO 506
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
aucagugcau ccuuggcggu cuu                                              23

<210> SEQ ID NO 507
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 507
aagaccgcca aggaugcacu gag                                              23

<210> SEQ ID NO 508
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
uaaagcugga caagaagcug u                                                21
```

```
<210> SEQ ID NO 509
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
acagcuucuu guccagcuuu auu                                              23

<210> SEQ ID NO 510
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 510
aauaaagcug gacaagaagc ugc                                              23

<210> SEQ ID NO 511
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
ucccugaaag acuacuggag u                                                21

<210> SEQ ID NO 512
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
acuccaguag ucuuucaggg aac                                              23

<210> SEQ ID NO 513
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 513
guucccugaa agacuacugg agc                                              23

<210> SEQ ID NO 514
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 514
gaccgauggc uucaguuccc u                                               21

<210> SEQ ID NO 515
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
agggaacuga agccaucggu cac                                             23

<210> SEQ ID NO 516
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 516
gugaccgaug gcuucaguuc ccu                                             23

<210> SEQ ID NO 517
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
ucccuagagg cagcugcucc u                                               21

<210> SEQ ID NO 518
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
aggagcagcu gccucuaggg aug                                             23

<210> SEQ ID NO 519
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 519
caucccuaga ggcagcugcu cca                                             23

<210> SEQ ID NO 520
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 520
ccgauggcuu caguucccug u                                                    21

<210> SEQ ID NO 521
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
acagggaacu gaagccaucg guc                                                  23

<210> SEQ ID NO 522
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 522
gaccgauggc uucaguuccc uga                                                  23

<210> SEQ ID NO 523
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
guagguugcu uaaaagggac u                                                    21

<210> SEQ ID NO 524
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
agucccuuuu aagcaaccua cag                                                  23

<210> SEQ ID NO 525
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 525
cuguagguug cuuaaaaggg aca                                                  23
```

```
<210> SEQ ID NO 526
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
ccuagaggca gcugcuccag u                                            21

<210> SEQ ID NO 527
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
acuggagcag cugccucuag gga                                          23

<210> SEQ ID NO 528
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 528
ucccuagagg cagcugcucc agg                                          23

<210> SEQ ID NO 529
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
uguagguugc uuaaaaggga u                                            21

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
aucccuuuua agcaaccuac agg                                          23

<210> SEQ ID NO 531
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"
```

-continued

<400> SEQUENCE: 531
ccuguagguu gcuuaaaagg gac                                           23

<210> SEQ ID NO 532
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
aaagacuacu ggagcaccgu u                                             21

<210> SEQ ID NO 533
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
aacggugcuc caguagucuu uca                                           23

<210> SEQ ID NO 534
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 534
ugaaagacua cuggagcacc guu                                           23

<210> SEQ ID NO 535
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
aggcagcugc uccaggaaca u                                             21

<210> SEQ ID NO 536
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
auguuccugg agcagcugcc ucu                                           23

<210> SEQ ID NO 537
<211> LENGTH: 23
<212> TYPE: RNA

```
<213> ORGANISM: Unknown
<220> FEATURE:
<221> NAME/KEY: source
<223> OTHER INFORMATION: /note="Description of Unknown:
      target sequence"

<400> SEQUENCE: 537
agaggcagcu gcuccaggaa cag                                            23

<210> SEQ ID NO 538
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
gcagcugcuc caggaacaga u                                              21

<210> SEQ ID NO 539
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
aucuguuccu ggagcagcug ccu                                            23

<210> SEQ ID NO 540
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 540
aggcagcugc uccaggaaca gag                                            23

<210> SEQ ID NO 541
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
cgccaccaag accgccaagg u                                              21

<210> SEQ ID NO 542
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
accuuggcgg ucuuggugge gug                                            23
```

```
<210> SEQ ID NO 543
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 543
cacgccacca agaccgccaa gga                                           23

<210> SEQ ID NO 544
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
cuacuggagc accguuaagg u                                             21

<210> SEQ ID NO 545
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
accuuaacgg ugcuccagua guc                                           23

<210> SEQ ID NO 546
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 546
gacuacugga gcaccguuaa gga                                           23

<210> SEQ ID NO 547
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
uggcugccug agaccucaau u                                             21

<210> SEQ ID NO 548
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 548
aauugagguc ucaggcagcc acg        23

<210> SEQ ID NO 549
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 549
cguggcugcc ugagaccuca aua        23

<210> SEQ ID NO 550
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
ggcuucaguu cccugaaaga u        21

<210> SEQ ID NO 551
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
aucuuucagg gaacugaagc cau        23

<210> SEQ ID NO 552
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 552
auggcuucag uucccugaaa gac        23

<210> SEQ ID NO 553
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
aucccuagag gcagcugcuc u        21

<210> SEQ ID NO 554
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
agagcagcug ccucuaggga uga                                              23

<210> SEQ ID NO 555
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 555
ucaucccuag aggcagcugc ucc                                              23

<210> SEQ ID NO 556
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
ugaaagacua cuggagcacc u                                                21

<210> SEQ ID NO 557
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
aggugcucca guagucuuuc agg                                              23

<210> SEQ ID NO 558
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 558
ccugaaagac uacuggagca ccg                                              23

<210> SEQ ID NO 559
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
```
aagaccgcca aggaugcacu u                                               21

<210> SEQ ID NO 560
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
aagugcaucc uuggcggucu ugg                                             23

<210> SEQ ID NO 561
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 561
ccaagaccgc caaggaugca cug                                             23

<210> SEQ ID NO 562
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
gcugccugag accucaauac u                                               21

<210> SEQ ID NO 563
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
aguauugagg ucucaggcag cca                                             23

<210> SEQ ID NO 564
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 564
uggcugccug agaccucaau acc                                             23

<210> SEQ ID NO 565
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 565
ggccucccaa uaaagcugga u                                              21

<210> SEQ ID NO 566
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
auccagcuuu auugggaggc cag                                            23

<210> SEQ ID NO 567
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 567
cuggccuccc aauaaagcug gac                                            23

<210> SEQ ID NO 568
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
caguucaucc cuagaggcag u                                              21

<210> SEQ ID NO 569
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
acugccucua gggaugaacu gag                                            23

<210> SEQ ID NO 570
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 570
cucaguucau cccuagaggc agc                                            23

<210> SEQ ID NO 571
```

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
ggcugccuga gaccucaaua u                                              21

<210> SEQ ID NO 572
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
auauugaggu cucaggcagc cac                                            23

<210> SEQ ID NO 573
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 573
guggcugccu gagaccucaa uac                                            23

<210> SEQ ID NO 574
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
gaaagacuac uggagcaccg u                                              21

<210> SEQ ID NO 575
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
acggugcucc aguagucuuu cag                                            23

<210> SEQ ID NO 576
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 576

-continued cugaaagacu acuggagcac cgu                                    23

<210> SEQ ID NO 577
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
gaggcagcug cuccaggaac u                                      21

<210> SEQ ID NO 578
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
aguuccugga gcagcugccu cua                                    23

<210> SEQ ID NO 579
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 579
uagaggcagc ugcuccagga aca                                    23

<210> SEQ ID NO 580
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
guggcugccu gagaccucaa u                                      21

<210> SEQ ID NO 581
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
auugaggucu caggcagcca cgg                                    23

<210> SEQ ID NO 582
<211> LENGTH: 23
<212> TYPE: RNA
<213> ORGANISM: Unknown
<220> FEATURE:

```
<221> NAME/KEY: source
<223> OTHER INFORMATION: /note="Description of Unknown:
      target sequence"

<400> SEQUENCE: 582
ccguggcugc cugagaccuc aau                                          23

<210> SEQ ID NO 583
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
gcugggugac cgauggcuuc u                                            21

<210> SEQ ID NO 584
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
agaagccauc ggucacccag ccc                                          23

<210> SEQ ID NO 585
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 585
gggcugggug accgauggcu uca                                          23

<210> SEQ ID NO 586
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
ggagcaccgu uaaggacaag u                                            21

<210> SEQ ID NO 587
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
acuuguccuu aacggugcuc cag                                          23
```

```
<210> SEQ ID NO 588
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 588
cuggagcacc guuaaggaca agu                                              23

<210> SEQ ID NO 589
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
cuguagguug cuuaaaaggg u                                                21

<210> SEQ ID NO 590
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
acccuuuuaa gcaaccuaca ggg                                              23

<210> SEQ ID NO 591
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 591
cccuguaggu ugcuuaaaag gga                                              23

<210> SEQ ID NO 592
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
guucccugaa agacuacugg u                                                21

<210> SEQ ID NO 593
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 593
accaguaguc uuucagggaa cug                                            23

<210> SEQ ID NO 594
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 594
caguucccug aaagacuacu gga                                            23

<210> SEQ ID NO 595
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
gggcugggug accgauggcu u                                              21

<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
aagccaucgg ucacccagcc ccu                                            23

<210> SEQ ID NO 597
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 597
aggggcuggg ugaccgaugg cuu                                            23

<210> SEQ ID NO 598
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
gccaccaaga ccgccaagga u                                              21

<210> SEQ ID NO 599
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 599
auccuuggcg gucuuggugg cgu                                              23

<210> SEQ ID NO 600
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 600
acgccaccaa gaccgccaag gau                                              23

<210> SEQ ID NO 601
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
agaggcagcu gcuccaggaa u                                                21

<210> SEQ ID NO 602
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
auuccuggag cagcugccuc uag                                              23

<210> SEQ ID NO 603
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 603
cuagaggcag cugcuccagg aac                                              23

<210> SEQ ID NO 604
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial
      Sequence: Synthetic oligonucleotide"

<400> SEQUENCE: 604
ucaucccuag aggcagcugc u                                                21
```

<210> SEQ ID NO 605
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
agcagcugcc ucuagggaug aac                                           23

<210> SEQ ID NO 606
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 606
guucaucccu agaggcagcu gcu                                           23

<210> SEQ ID NO 607
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
uucaucccua gaggcagcug u                                             21

<210> SEQ ID NO 608
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
acagcugccu cuagggauga acu                                           23

<210> SEQ ID NO 609
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 609
aguucauccc uagaggcagc ugc                                           23

<210> SEQ ID NO 610
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 610
cgagcuccuu ggguccugca u                                              21

<210> SEQ ID NO 611
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
augcaggacc caaggagcuc gca                                            23

<210> SEQ ID NO 612
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 612
ugcgagcucc uuggguccug caa                                            23

<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
ggcagcugcu ccaggaacag u                                              21

<210> SEQ ID NO 614
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
acuguuccug gagcagcugc cuc                                            23

<210> SEQ ID NO 615
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 615
gaggcagcug cuccaggaac aga                                            23

<210> SEQ ID NO 616
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
ccaagaccgc caaggaugca u                                              21

<210> SEQ ID NO 617
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
augcauccuu ggcggucuug gug                                            23

<210> SEQ ID NO 618
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 618
caccaagacc gccaaggaug cac                                            23

<210> SEQ ID NO 619
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
gacuacugga gcaccguuaa u                                              21

<210> SEQ ID NO 620
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
auuaacggug cuccaguagu cuu                                            23

<210> SEQ ID NO 621
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 621
aagacuacug gagcaccguu aag                                            23
```

<210> SEQ ID NO 622
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 622
aguucauccc uagaggcagc u                                              21

<210> SEQ ID NO 623
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 623
agcugccucu agggaugaac uga                                            23

<210> SEQ ID NO 624
<211> LENGTH: 23
<212> TYPE: RNA
<213> ORGANISM: Unknown
<220> FEATURE:
<221> NAME/KEY: source
<223> OTHER INFORMATION: /note="Description of Unknown:
    target sequence"

<400> SEQUENCE: 624
ucaguucauc ccuagaggca gcu                                            23

<210> SEQ ID NO 625
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 625
acuggagcac cguuaaggac u                                              21

<210> SEQ ID NO 626
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 626
aguccuuaac ggugcuccag uag                                            23

<210> SEQ ID NO 627
<211> LENGTH: 23
<212> TYPE: RNA
<213> ORGANISM: Unknown
<220> FEATURE:
<221> NAME/KEY: source
<223> OTHER INFORMATION: /note="Description of Unknown:

-continued target sequence"

<400> SEQUENCE: 627
cuacuggagc accguuaagg aca                                          23

<210> SEQ ID NO 628
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
ugggugaccg auggcuucag u                                            21

<210> SEQ ID NO 629
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
acugaagcca ucggcaccc agc                                           23

<210> SEQ ID NO 630
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 630
gcugggugac cgauggcuuc agu                                          23

<210> SEQ ID NO 631
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
ccgagcuuca gaggccgagg u                                            21

<210> SEQ ID NO 632
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
accucggccu cugaagcucg ggc                                          23

<210> SEQ ID NO 633
<211> LENGTH: 23

```
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 633
gcccgagcuu cagaggccga gga                                              23

<210> SEQ ID NO 634
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
accaagaccg ccaaggaugc u                                                21

<210> SEQ ID NO 635
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
agcauccuug gcggucuugg ugg                                              23

<210> SEQ ID NO 636
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 636
ccaccaagac cgccaaggau gca                                              23

<210> SEQ ID NO 637
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
uagaggcagc ugcuccagga u                                                21

<210> SEQ ID NO 638
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
```

```
auccuggagc agcugccucu agg                                          23
```

<210> SEQ ID NO 639
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 639

```
ccuagaggca gcugcuccag gaa                                          23
```

<210> SEQ ID NO 640
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640

```
gggugaccga uggcuucagu u                                            21
```

<210> SEQ ID NO 641
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641

```
aacugaagcc aucggucacc cag                                          23
```

<210> SEQ ID NO 642
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 642

```
cugggugacc gauggcuuca guu                                          23
```

<210> SEQ ID NO 643
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643

```
guucaucccu agaggcagcu u                                            21
```

<210> SEQ ID NO 644
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 644
aagcugccuc uagggaugaa cug                                        23

<210> SEQ ID NO 645
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 645
caguucaucc cuagaggcag cug                                        23

<210> SEQ ID NO 646
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
acuacuggag caccguuaag u                                          21

<210> SEQ ID NO 647
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
acuuaacggu gcuccaguag ucu                                        23

<210> SEQ ID NO 648
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 648
agacuacugg agcaccguua agg                                        23

<210> SEQ ID NO 649
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
cagcugcucc aggaacagag u                                          21

<210> SEQ ID NO 650
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
acucuguucc uggagcagcu gcc                                              23

<210> SEQ ID NO 651
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 651
ggcagcugcu ccaggaacag agg                                              23

<210> SEQ ID NO 652
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
cgagcuucag aggccgagga u                                                21

<210> SEQ ID NO 653
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
auccucggcc ucugaagcuc ggg                                              23

<210> SEQ ID NO 654
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 654
cccgagcuuc agaggccgag gau                                              23

<210> SEQ ID NO 655
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
```

```
cuagaggcag cugcuccagg u                                    21

<210> SEQ ID NO 656
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
accuggagca gcugccucua ggg                                  23

<210> SEQ ID NO 657
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 657
cccuagaggc agcugcucca gga                                  23

<210> SEQ ID NO 658
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
gagucccagg uggcccagca u                                    21

<210> SEQ ID NO 659
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
augcugggcc accugggacu ccu                                  23

<210> SEQ ID NO 660
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 660
aggaguccca gguggcccag cag                                  23

<210> SEQ ID NO 661
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 661
agaccgccaa ggaugcacug u                                              21

<210> SEQ ID NO 662
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
acagugcauc cuuggcgguc uug                                            23

<210> SEQ ID NO 663
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 663
caagaccgcc aaggaugcac uga                                            23

<210> SEQ ID NO 664
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
ccagguggcc cagcaggcca u                                              21

<210> SEQ ID NO 665
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
auggccugcu gggccaccug gga                                            23

<210> SEQ ID NO 666
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 666
ucccaggugg cccagcaggc cag                                            23
```

```
<210> SEQ ID NO 667
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
acgccaccaa gaccgccaag u                                              21

<210> SEQ ID NO 668
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
acuuggcggu cuugguggcg ugc                                            23

<210> SEQ ID NO 669
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 669
gcacgccacc aagaccgcca agg                                            23

<210> SEQ ID NO 670
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
ggugaccgau ggcuucaguu u                                              21

<210> SEQ ID NO 671
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
aaacugaagc caucggucac cca                                            23

<210> SEQ ID NO 672
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"
```

```
<400> SEQUENCE: 672
ugggugaccg auggcuucag uuc                                              23

<210> SEQ ID NO 673
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
uacuggagca ccguuaagga u                                                21

<210> SEQ ID NO 674
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
auccuuaacg gugcuccagu agu                                              23

<210> SEQ ID NO 675
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 675
acuacuggag caccguuaag gac                                              23

<210> SEQ ID NO 676
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
ggagucccag guggcccagc u                                                21

<210> SEQ ID NO 677
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
agcugggcca ccugggacuc cug                                              23

<210> SEQ ID NO 678
<211> LENGTH: 23
<212> TYPE: RNA
<213> ORGANISM: Unknown
```

```
<220> FEATURE:
<221> NAME/KEY: source
<223> OTHER INFORMATION: /note="Description of Unknown:
      target sequence"

<400> SEQUENCE: 678
caggaguccc agguggccca gca                                            23

<210> SEQ ID NO 679
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
gcaggagucc cagguggccc u                                              21

<210> SEQ ID NO 680
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
agggccaccu gggacuccug cac                                            23

<210> SEQ ID NO 681
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 681
gugcaggagu cccaggugcc cca                                            23

<210> SEQ ID NO 682
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
ugcaggaguc ccagguggcc u                                              21

<210> SEQ ID NO 683
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
aggccaccug ggacuccugc acg                                            23
```

<210> SEQ ID NO 684
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 684
cgugcaggag ucccaggugg ccc                                              23

<210> SEQ ID NO 685
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
caggagsccc agguggccca u                                                21

<210> SEQ ID NO 686
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
augggccacc uggacuccu gca                                               23

<210> SEQ ID NO 687
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 687
ugcaggaguc ccagguggcc cag                                              23

<210> SEQ ID NO 688
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
agcugcucca ggaacagagg u                                                21

<210> SEQ ID NO 689
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 689
accucuguuc cuggagcagc ugc                                          23

<210> SEQ ID NO 690
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 690
gcagcugcuc caggaacaga ggu                                          23

<210> SEQ ID NO 691
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
agucccaggu ggcccagcag u                                            21

<210> SEQ ID NO 692
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
acugcugggc caccugggac ucc                                          23

<210> SEQ ID NO 693
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 693
ggagucccag guggcccagc agg                                          23

<210> SEQ ID NO 694
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
aggaguccca gguggcccag u                                            21

<210> SEQ ID NO 695
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
acugggccac cugggacucc ugc                                              23

<210> SEQ ID NO 696
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 696
gcaggagucc cagguggccc agc                                              23

<210> SEQ ID NO 697
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 697
aagucutuca gggaacugaa gcc                                              23

<210> SEQ ID NO 698
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
auucagggaa cugaagccau cgg                                              23

<210> SEQ ID NO 699
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
acacugagaa uacugucccu uuu                                              23

<210> SEQ ID NO 700
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<220> FEATURE:
<221> NAME/KEY: source
<223> OTHER INFORMATION: /note="Description of Combined DNA/RNA
      Molecule: Synthetic oligonucleotide"

<400> SEQUENCE: 700
agucuutcag ggaacugaag cca                                         23

<210> SEQ ID NO 701
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
auucuugucc agcuuuauug gga                                         23

<210> SEQ ID NO 702
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
augagaauac ugucccuuuu aag                                         23

<210> SEQ ID NO 703
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
aguccagcuu uauugggagg cca                                         23

<210> SEQ ID NO 704
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 704
auacugtccc uuuuaagcaa ccu                                         23

<210> SEQ ID NO 705
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"
```

```
<400> SEQUENCE: 705
agguugcuua aaagggacag uau                                           23

<210> SEQ ID NO 706
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
agcacugaga auacuguccc uuu                                           23

<210> SEQ ID NO 707
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 707
aucuugtcca gcuuuauugg gag                                           23

<210> SEQ ID NO 708
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 708
auaguctuuc agggaacuga agc                                           23

<210> SEQ ID NO 709
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
auguccagcu uuauugggag gcc                                           23

<210> SEQ ID NO 710
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 710 auguccuaa cggugcucca gua                                              23

<210> SEQ ID NO 711
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
acugagaaua cugucccuuu uaa                                             23

<210> SEQ ID NO 712
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
agaacugaag ccaucgguca ccc                                             23

<210> SEQ ID NO 713
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 713
aggaactgaa gccaucgguc acc                                             23

<210> SEQ ID NO 714
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 714
uagaauacug ucccuuuuaa gca                                             23

<210> SEQ ID NO 715
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715
```
aguagucuuu cagggaacug aag                                          23

<210> SEQ ID NO 716
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
aagcuucuug uccagcuuua uug                                          23

<210> SEQ ID NO 717
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
auuucaggga acugaagcca ucg                                          23

<210> SEQ ID NO 718
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
aagcagcuuc uuguccagcu uua                                          23

<210> SEQ ID NO 719
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
aaacuugucc uuaacggugc ucc                                          23

<210> SEQ ID NO 720
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
acaguagucu uucagggaac uga                                          23

<210> SEQ ID NO 721
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 721
agcuuctugu ccagcuuuau ugg                                            23

<210> SEQ ID NO 722
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
guugcuuaaa agggacagua u                                              21

<210> SEQ ID NO 723
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 723
aacuugtccu uaacggugcu cca                                            23

<210> SEQ ID NO 724
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 724
uggagcaccg uuaaggacaa guu                                            23

<210> SEQ ID NO 725
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 725
acuucutguc cagcuuuauu ggg                                            23

<210> SEQ ID NO 726
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
aucagugcau ccuuggcggu cuu                                              23

<210> SEQ ID NO 727
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 727
agcagctucu uguccagcuu uau                                              23

<210> SEQ ID NO 728
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
auagcagcuu cuuguccagc uuu                                              23

<210> SEQ ID NO 729
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 729
uauagcagcu ucuuguccag cuu                                              23

<210> SEQ ID NO 730
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 730
acugccucua gggaugaacu gag                                              23

<210> SEQ ID NO 731
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 731
auaacggugc uccaguaguc uuu                                             23

<210> SEQ ID NO 732
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732 auguccugg agcagcugcc ucu                                              23

<210> SEQ ID NO 733
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
aucagggaac ugaagccauc ggu                                             23

<210> SEQ ID NO 734
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
acuuguccag cuuuauuggg agg                                             23

<210> SEQ ID NO 735
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 735
acagcutcuu guccagcuuu auu                                             23

<210> SEQ ID NO 736
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 736
augaagccau cggucaccca gcc                                              23

<210> SEQ ID NO 737
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
agagcagcug ccucuaggga uga                                              23

<210> SEQ ID NO 738
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
auuguccagc uuuauuggga ggc                                              23

<210> SEQ ID NO 739
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
aacugagaau acugucccuu uua                                              23

<210> SEQ ID NO 740
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
agugcuccag uagucuuuca ggg                                              23

<210> SEQ ID NO 741
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
gagcaccguu aaggacaagu u                                                21

<210> SEQ ID NO 742
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 742
aaauactguc ccuuuuaagc aac                                              23

<210> SEQ ID NO 743
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
acuuucaggg aacugaagcc auc                                              23

<210> SEQ ID NO 744
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 744
aggugctcca guagucuuuc agg                                              23

<210> SEQ ID NO 745
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 745
agguautgag gucucaggca gcc                                              23

<210> SEQ ID NO 746
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
auccuuggcg gucuuggugg cgu                                              23

<210> SEQ ID NO 747
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 747
aauccutggc ggucuuggug gcg                                             23

<210> SEQ ID NO 748
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
aggagcagcu gccucuaggg aug                                             23

<210> SEQ ID NO 749
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 749
aaguagtcuu ucagggaacu gaa                                             23

<210> SEQ ID NO 750
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 750
aucccutuua agcaaccuac agg                                             23

<210> SEQ ID NO 751
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
acuuguccuu aacggugcuc cag                                             23
```

<210> SEQ ID NO 752
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 752
aaacggtgcu ccaguagucu uuc                                          23

<210> SEQ ID NO 753
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 753
aguucctgga gcagcugccu cua                                          23

<210> SEQ ID NO 754
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 754
agugcatccu uggcggucuu ggu                                          23

<210> SEQ ID NO 755
<211> LENGTH: 23
<212> TYPE: RNA
<213> ORGANISM: Unknown
<220> FEATURE:
<221> NAME/KEY: source
<223> OTHER INFORMATION: /note="Description of Unknown:
    target sequence"

<400> SEQUENCE: 755
accaagaccg ccaaggaugc acu                                          23

<210> SEQ ID NO 756
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

```
<400> SEQUENCE: 756
agcuccagua gucuuucagg gaa                                              23

<210> SEQ ID NO 757
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 757
acaucctugg cggucuuggu ggc                                              23

<210> SEQ ID NO 758
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 758
aucugutccu ggagcagcug ccu                                              23

<210> SEQ ID NO 759
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
acuccaguag ucuuucaggg aac                                              23

<210> SEQ ID NO 760
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
aagggaacug aagccaucgg uca                                              23

<210> SEQ ID NO 761
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
```
auccagcuuu auugggaggc cag                                              23

<210> SEQ ID NO 762
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
aguauugagg ucucaggcag cca                                              23

<210> SEQ ID NO 763
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
auugaggucu caggcagcca cgg                                              23

<210> SEQ ID NO 764
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
aagcugccuc uagggaugaa cug                                              23

<210> SEQ ID NO 765
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
aagcagcugc cucuagggau gaa                                              23

<210> SEQ ID NO 766
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
auauugaggu cucaggcagc cac                                              23

<210> SEQ ID NO 767
<211> LENGTH: 23
<212> TYPE: RNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 767
augcuccagu agucuuucag gga                                              23

<210> SEQ ID NO 768
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
auccuggagc agcugccucu agg                                              23

<210> SEQ ID NO 769
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 769
agcagctgcc ucuagggaug aac                                              23

<210> SEQ ID NO 770
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 770
auccagtagu cuuucaggga acu                                              23

<210> SEQ ID NO 771
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
auggagcagc ugccucuagg gau                                              23

<210> SEQ ID NO 772
<211> LENGTH: 21
<212> TYPE: RNA
<213> ORGANISM: Artificial Sequence
<220> FEATURE:
<221> NAME/KEY: source
```

-continued

<223> OTHER INFORMATION: /note="Description of Artificial Sequence:
     Synthetic oligonucleotide"

<400> SEQUENCE: 772
caagaccgcc aaggaugcac u                                              21

<210> SEQ ID NO 773
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 773
agaauacugu cccuuuuaag caa                                            23

<210> SEQ ID NO 774
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 774
agagaatacu gucccuuuua agc                                            23

<210> SEQ ID NO 775
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 775
accuuggcgg ucuugguggc gug                                            23

<210> SEQ ID NO 776
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 776
aaagccaucg gucacccagc ccc                                            23

<210> SEQ ID NO 777
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 777
aacugucccu uuuaagcaac cua                                              23

<210> SEQ ID NO 778
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
aacggugcuc caguagucuu uca                                              23

<210> SEQ ID NO 779
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
accucggccu cugaagcucg ggc                                              23

<210> SEQ ID NO 780
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
aauugagguc ucaggcagcc acg                                              23

<210> SEQ ID NO 781
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
acagcugccu cuagggauga acu                                              23

<210> SEQ ID NO 782
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
acuggagcag cugccucuag gga                                              23

<210> SEQ ID NO 783
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
acugucccuu uuaagcaacc uac                                           23

<210> SEQ ID NO 784
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 784
acccuutuaa gcaaccuaca ggg                                           23

<210> SEQ ID NO 785
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
acggugcucc aguagucuuu cag                                           23

<210> SEQ ID NO 786
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
acugaagcca ucggucaccc agc                                           23

<210> SEQ ID NO 787
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
accaguaguc uuucagggaa cug                                           23

<210> SEQ ID NO 788
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788

```
agggaacuga agccaucggu cac                              23
```

<210> SEQ ID NO 789
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 789

```
aguccutaac ggugcuccag uag                              23
```

<210> SEQ ID NO 790
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 790

```
aguccctuuu aagcaaccua cag                              23
```

<210> SEQ ID NO 791
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 791

```
acucugtucc uggagcagcu gcc                              23
```

<210> SEQ ID NO 792
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792

```
auuccuggag cagcugccuc uag                              23
```

<210> SEQ ID NO 793
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 793
aauacugucc cuuuuaagca acc                                             23

<210> SEQ ID NO 794
<211> LENGTH: 23
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 794
gguugcuuaa aagggacagu auu                                             23

<210> SEQ ID NO 795
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
auuguccuua acggugcucc agu                                             23

<210> SEQ ID NO 796
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
accuggagca gcugccucua ggg                                             23

<210> SEQ ID NO 797
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797
accuuaacgg ugcuccagua guc                                             23

<210> SEQ ID NO 798
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
augcugggcc accuggacu ccu                                              23

<210> SEQ ID NO 799
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
augcaggacc caaggagcuc gca                                          23

<210> SEQ ID NO 800
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
acagugcauc cuuggcgguc uug                                          23

<210> SEQ ID NO 801
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
acagggaacu gaagccaucg guc                                          23

<210> SEQ ID NO 802
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
aaacugaagc caucggucac cca                                          23

<210> SEQ ID NO 803
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
agaagccauc ggucacccag ccc                                          23

<210> SEQ ID NO 804
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 804
auggccugcu gggccaccug gga                                          23

<210> SEQ ID NO 805
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
agcugccucu agggaugaac uga                                          23

<210> SEQ ID NO 806
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
aagugcaucc uuggcggucu ugg                                          23

<210> SEQ ID NO 807
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
acuguuccug gagcagcugc cuc                                          23

<210> SEQ ID NO 808
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
aucuuucagg gaacugaagc cau                                          23

<210> SEQ ID NO 809
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
accucuguuc cuggagcagc ugc                                          23

<210> SEQ ID NO 810
<211> LENGTH: 23
<212> TYPE: RNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
acuuggcggu cuugguggcg ugc                                           23

<210> SEQ ID NO 811
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
uugcuuaaaa gggacaguau u                                             21

<210> SEQ ID NO 812
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 812
aagccatcgg ucacccagcc ccu                                           23

<210> SEQ ID NO 813
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
auccucggcc ucugaagcuc ggg                                           23

<210> SEQ ID NO 814
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
agcugggcca ccugggacuc cug                                           23

<210> SEQ ID NO 815
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 815
augucccuuu uaagcaaccu aca                                         23

<210> SEQ ID NO 816
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
aggccaccug ggacuccugc acg                                         23

<210> SEQ ID NO 817
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
agcauccuug gcggucuugg ugg                                         23

<210> SEQ ID NO 818
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
acuuaacggu gcuccaguag ucu                                         23

<210> SEQ ID NO 819
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
auccuuaacg gugcuccagu agu                                         23

<210> SEQ ID NO 820
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
auuaacggug cuccaguagu cuu                                         23

<210> SEQ ID NO 821
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
aagaauacug ucccuuuuaa gca                                           23

<210> SEQ ID NO 822
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
augcauccuu ggcggucuug gug                                           23

<210> SEQ ID NO 823
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
agggccaccu gggacuccug cac                                           23

<210> SEQ ID NO 824
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
augggccacc ugggacuccu gca                                           23

<210> SEQ ID NO 825
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
aacugaagcc aucggucacc cag                                           23

<210> SEQ ID NO 826
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
acugggccac cugggacucc ugc                                           23
```

```
<210> SEQ ID NO 827
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
acugcugggc caccugggac ucc                                           23

<210> SEQ ID NO 828
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 828
cuuaaaaggg acaguauucu c                                             21

<210> SEQ ID NO 829
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
uagaauacug ucccuuuuaa gca                                           23

<210> SEQ ID NO 830
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
uagaauacug ucccuuuuaa gca                                           23

<210> SEQ ID NO 831
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
uagaauacug ucccuuuuaa gcc                                           23

<210> SEQ ID NO 832
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 832
uaaaagggac aguauucua                                        19

<210> SEQ ID NO 833
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
uagaauacug ucccuuuuaa g                                     21

<210> SEQ ID NO 834
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
uagaauacug ucccuuuuaa g                                     21

<210> SEQ ID NO 835
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
cuuaaaaggg acaguauucu a                                     21

<210> SEQ ID NO 836
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
cuuaaaaggg acaguauucu a                                     21

<210> SEQ ID NO 837
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837
agaauacugu cccuuuuaag caa                                   23

<210> SEQ ID NO 838
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
agaauacugu cccuuuuaag caa                                            23

<210> SEQ ID NO 839
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 839
agaatacugu cccuuuuaag caa                                            23

<210> SEQ ID NO 840
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
agaauacugu cccuuuuaag cgc                                            23

<210> SEQ ID NO 841
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 841
agaatacugu cccuuuuaag cgc                                            23

<210> SEQ ID NO 842
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
uuaaaaggga caguauucu                                                 19

<210> SEQ ID NO 843
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
agaauacugu cccuuuuaag c                                              21

<210> SEQ ID NO 844
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 844
gcuuaaaagg gacaguauuc u                                              21

<210> SEQ ID NO 845
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 845
agaatacugu cccuuuuaag c                                              21

<210> SEQ ID NO 846
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
gcuuaaaagg gacaguauuc u                                              21

<210> SEQ ID NO 847
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
gcuuaaaagg gacaguauuc u                                              21

<210> SEQ ID NO 848
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 848
uaaaagggac aguauuuuca u                                              21

<210> SEQ ID NO 849
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
augaaaauac ugucccuuuu aag                                            23

<210> SEQ ID NO 850
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
augagaauac ugucccuuuu aag                                            23

<210> SEQ ID NO 851
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 851
augagaauac ugucccuuuu aag                                            23

<210> SEQ ID NO 852
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
augagaauac ugucccuuuu acc                                            23

<210> SEQ ID NO 853
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
augagaauac ugucccuuuu acc                                            23

<210> SEQ ID NO 854
<211> LENGTH: 19
<212> TYPE: RNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
aaagggacag uauucucau                                                        19

<210> SEQ ID NO 855
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
augagaauac ugucccuuuu g                                                     21

<210> SEQ ID NO 856
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 856
uaaaagggac aguauucuca g                                                     21

<210> SEQ ID NO 857
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
augagaauac ugucccuuuu g                                                     21

<210> SEQ ID NO 858
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
uaaaagggac aguauucuca u                                                     21

<210> SEQ ID NO 859
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
aaaaagggac aguauucuca u                                                     21
```

<210> SEQ ID NO 860
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
augagaauac ugucccuuuu gcc                                              23

<210> SEQ ID NO 861
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 861
uaaaagggac agtauucuca u                                                21

<210> SEQ ID NO 862
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
augagaauac ugucccuuuu aag                                              23

<210> SEQ ID NO 863
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
aagaauacug ucccuuuuaa gca                                              23

<210> SEQ ID NO 864
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
aagaauacug ucccuuuuaa gca                                              23

<210> SEQ ID NO 865
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
aagaauacug ucccuuuuaa gcc                                            23

<210> SEQ ID NO 866
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
aagaauacug ucccuuuuaa gcc                                            23

<210> SEQ ID NO 867
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 867
uaaaagggac aguauucuu                                                 19

<210> SEQ ID NO 868
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 868
aagaauacug ucccuuuuaa g                                              21

<210> SEQ ID NO 869
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
aagaauacug ucccuuuuaa g                                              21

<210> SEQ ID NO 870
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 870
cuuaaaaggg acaguauucu u                                              21
```

```
<210> SEQ ID NO 871
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
cuuaaaaggg acaguauucu u                                              21

<210> SEQ ID NO 872
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
acugagaaua cugucccuuu uaa                                            23

<210> SEQ ID NO 873
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
acugagaaua cugucccuuu uaa                                            23

<210> SEQ ID NO 874
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
acugagaaua cugucccuuu ugc                                            23

<210> SEQ ID NO 875
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
acugagaaua cugucccuuu ucc                                            23

<210> SEQ ID NO 876
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 876
aagggacagu auucucagu                                                 19

<210> SEQ ID NO 877
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
acugagaaua cugucccuuu u                                              21

<210> SEQ ID NO 878
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 878
aaaagggaca guauucucag u                                              21

<210> SEQ ID NO 879
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
aaaagggaca guauucucag u                                              21

<210> SEQ ID NO 880
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
aaaagggaca guauuuucag u                                              21

<210> SEQ ID NO 881
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
acugaaaaua cugucccuuu ugc                                            23

<210> SEQ ID NO 882
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
aaaagggaca guauucucag u                                                 21

<210> SEQ ID NO 883
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
aaaagggaca guauucucag u                                                 21

<210> SEQ ID NO 884
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
ccaauaaagc uggauaagaa u                                                 21

<210> SEQ ID NO 885
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
auucuuaucc agcuuuauug gga                                               23

<210> SEQ ID NO 886
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 886
auuctugucc agcuuuauug gga                                               23

<210> SEQ ID NO 887
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 887
auucuguccc agcuuuauug ggc                                          23

<210> SEQ ID NO 888
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
aauaaagcug gacaagaau                                               19

<210> SEQ ID NO 889
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 889
auucuguccc agcuuuauug g                                            21

<210> SEQ ID NO 890
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 890
ccaauaaagc uggacaagaa g                                            21

<210> SEQ ID NO 891
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 891
auucuguccc agcuuuauuc c                                            21

<210> SEQ ID NO 892
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 892
ccaauaaagc uggacaagaa u                                              21

<210> SEQ ID NO 893
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
ccaauaaagc uggacaagaa u                                              21

<210> SEQ ID NO 894
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
auucuugucc agcuuuauug gga                                            23

<210> SEQ ID NO 895
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 895
aagcagcuuc uuguccagcu uua                                            23

<210> SEQ ID NO 896
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
aagcagcuuc uuguccagcu uua                                            23

<210> SEQ ID NO 897
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
aagcagcuuc uuguccagcu uua                                            23
```

<210> SEQ ID NO 898
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 898
aagcagcuuc uuguccagcu uuc                                              23

<210> SEQ ID NO 899
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 899
aagcagcuuc uuguccagcu uuc                                              23

<210> SEQ ID NO 900
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 900
aagcagcuuc uuguccagcu ucc                                              23

<210> SEQ ID NO 901
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 901
aagcagcuuc uuguccagcu ucc                                              23

<210> SEQ ID NO 902
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 902
gcuggacaag aagcugcuu                                                   19

<210> SEQ ID NO 903
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 903
aagcagcuuc uuguccagcu u                                               21

<210> SEQ ID NO 904
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 904
aagcuggaca agaagcugcu a                                               21

<210> SEQ ID NO 905
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
aagcagcuuc uuguccagcu u                                               21

<210> SEQ ID NO 906
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
aagcuggaca agaagcugcu u                                               21

<210> SEQ ID NO 907
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
aagcuggaca agaagcugcu u                                               21

<210> SEQ ID NO 908
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
aagcuggaca agaagcuacu u                                               21

<210> SEQ ID NO 909
<211> LENGTH: 23
<212> TYPE: RNA
```

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 909
aaguagcuuc uuguccagcu ucc    23

<210> SEQ ID NO 910
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 910
aagcuggaca agaaguugcu u    21

<210> SEQ ID NO 911
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 911
aagcaacuuc uuguccagcu ucc    23

<210> SEQ ID NO 912
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 912
aagcuggaca agaagcugcu u    21

<210> SEQ ID NO 913
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 913
gcuggacaag aagcugcuu    19

<210> SEQ ID NO 914
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

```
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (23)..(23)
<223> OTHER INFORMATION: 2-hydroxymethyl-tetrahydrofurane-5-phosphate

<400> SEQUENCE: 914
nacgggacag uauucucagu nan                                            23

<210> SEQ ID NO 915
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
ucacugagaa uacugucccg u                                              21

<210> SEQ ID NO 916
<211> LENGTH: 21
<212> TYPE: RNA
<213> ORGANISM: Unknown
<220> FEATURE:
<221> NAME/KEY: source
<223> OTHER INFORMATION: /note="Description of Unknown:
      target sequence"

<400> SEQUENCE: 916
aagggacagu auucucagug c                                              21
```

APOLIPOPROTEIN C3 (APOC3) IRNA COMPOSITIONS AND METHODS OF USE THEREOF

RELATED APPLICATIONS

This application is a 35 § U.S.C. 111(a) continuation application which claims the benefit of priority to PCT/US2021/017826, filed on Feb. 12, 2021, which, in turn, claims the benefit of priority to U.S. Provisional Application No. 63/144,516, filed on Feb. 2, 2021, and U.S. Provisional Application No. 62/977,875, filed on Feb. 18, 2020. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Feb. 11, 2021, is named 121301_10420_SL.TXT and is 249,455 bytes in size.

BACKGROUND OF THE INVENTION

Apolipoprotein C3 (APOC3) is a very low density lipoprotein (VLDL) and an important regulator of lipoprotein metabolism. In humans, APOC3 is encoded by the APOC3 gene that is located in a gene cluster together with the APOA1 and APOA4 genes on the long arm of chromosome 11. APOC3 is expressed in the liver and, to a lesser extent, in the intestines, as a small 99-amino acid protein. Following removal of the 20-amino-acid signal peptide in the endoplasmic reticulum, a mature ApoC3 protein of 79 amino acids is formed, which may be present as a non-glycosylated or a glycosylated isoform.

The primary role of APOC3 is as a regulator of lipolysis through non-competitive inhibition of endothelial bound lipoprotein lipase (LPL). LPL hydrolyses triacylglycerols in triacylglycerol (triglyceride)-rich lipoproteins (TRLs), releasing fatty acids into the plasma and transforming large triacylglycerol-rich particles into smaller triacylglycerol-depleted remnant lipoproteins. Individuals lacking APOC3 have low TRL levels, coupled with highly efficient lipolysis of triacylglycerols. Furthermore, mice in which the APOC3 gene has been genetically deleted were shown to have low plasma triacylglycerol levels and efficient TRL catabolism. APOC3 also inhibits hepatic lipase (HL), a lipolytic enzyme with triacylglycerol lipase and phospholipase A1 activity that is synthesized in the liver. The inhibitory effect of APOC3 on HL further reduces the lipolysis and uptake of TRL remnants by the liver. APOC3 has also been shown to stimulate synthesis of very low density lipoproteins (VLDLs). It is believed that the underlying mechanisms associated with this effect of APOC3 may relate to the inhibition of proteasome mediated degradation of APOB, resulting in increased APOB synthesis and secretion, and increased synthesis of VLDL triacylglycerols. APOC3 may, therefore, play a key role in regulating VLDL output by the liver.

Cellular studies report that APOC3 may interfere with TRL and remnant binding to hepatic lipoprotein receptors. APOC3 can abolish APOB- and ApoE-mediated binding of lipoproteins to low density lipoprotein receptor (LDLR), either by masking or altering the conformation of APOB and APOE. The binding of chylomicrons and VLDL particles to the lipolysis-stimulated receptor (LSR) is also significantly inhibited by APOC3.

An increase in APOC3 levels induces the development of hypertriglyceridemia, or high (hyper-) blood levels (-emia) of triglycerides. Elevated levels of triglycerides are associated with a variety of diseases, including cardiovascular disease, atherosclerosis, non-alcoholic fatty liver disease, non-alcoholic steatohepatitis, polycystic ovary syndrome, kidney disease, obesity, type 2 diabetes mellitus (insulin resistance), hypertension and skin lesions (xanthomas). Very high triglyceride levels also increase the risk of acute pancreatitis. Therefore, regulating APOC3 metabolism is an important therapeutic approach to managing hypertriglyceridemia and the associated diseases.

Accordingly, there is a need in the art for regulators of APOC3 expression for treating apolipoprotein C3-associated disorders, such as hypertriglyceridemia.

SUMMARY OF THE INVENTION

The present invention provides iRNA compositions which affect the RNA-induced silencing complex (RISC)-mediated cleavage of RNA transcripts of a gene encoding apolipoprotein C3 (APOC3). The apolipoprotein C3 (APOC3) may be within a cell, e.g., a cell within a subject, such as a human subject.

In an aspect, the invention provides a double stranded ribonucleic acid (dsRNA) agent for inhibiting expression of apolipoprotein C3 in a cell, wherein the dsRNA agent comprises a sense strand and an antisense strand forming a double stranded region, wherein the sense strand comprises at least 15 contiguous nucleotides differing by no more than 0, 1, 2, or 3 nucleotides from the nucleotide sequence of SEQ ID NO:1 and the antisense strand comprises at least 15 contiguous nucleotides differing by no more than 1, 2, or 3 nucleotides from the nucleotide sequence of SEQ ID NO:2. In one embodiment, the dsRNA agent comprises at least one thermally destabilizing nucleotide modification, e.g., an abasic modification; a mismatch with the opposing nucleotide in the duplex; and destabilizing sugar modification, a 2'-deoxy modification, an acyclic nucleotide, an unlocked nucleic acids (UNA), or a glycerol nucleic acid (GNA), e.g., the antisense strand comprises at least one thermally destabilizing nucleotide modification.

In another aspect, the present invention provides a double stranded ribonucleic acid (dsRNA) for inhibiting expression of apolipoprotein C3 in a cell, wherein said dsRNA comprises a sense strand and an antisense strand forming a double stranded region, wherein the antisense strand comprises a region of complementarity to an mRNA encoding apolipoprotein C3, and wherein the region of complementarity comprises at least 15 contiguous nucleotides differing by no more than 0, 1, 2, or 3 nucleotides from any one of the antisense nucleotide sequences in any one of Tables 2-5, 14, and 15.

In one aspect, the present invention provides a double stranded ribonucleic acid (dsRNA) for inhibiting expression of apolipoprotein C3 in a cell, wherein said dsRNA comprises a sense strand and an antisense strand forming a double stranded region, wherein the sense strand comprises at least 15 contiguous nucleotides differing by no more than 0, 1, 2, or 3 nucleotides from any one of the nucleotide sequence of nucleotides; 232-254; 233-255; 238-260; 239-261; 242-264; 243-265; 244-266; 264-286; 268-290; 426-448; 431-453; 432-454; 433-455; 435-457; 436-458; 499-521; 500-522; 503-525; 504-526; 507-529; 510-532; or 511-533 of the nucleotide sequence of SEQ ID NO:1, and the antisense strand comprises at least 19 contiguous nucleotides from the corresponding nucleotide sequence of SEQ ID NO:2.

In one embodiment, the antisense strand comprises at least 15 contiguous nucleotides differing by nor more than 0, 1, 2, or 3 nucleotides from any one of the antisense strand nucleotide sequences of a duplex selected from the group consisting of AD-959917.1; AD-959918.1; AD-960096.1; AD-960064.1; AD-959914.1; AD-959941.1; AD-960031.1; AD-960063.1; AD-960293.1; AD-960288.1; AD-960445.1; AD-960292.1; AD-960475.1; AD-960442.1; AD-960470.1; AD-960436.1; AD-960446.1; AD-960474.1; AD-960294.1; AD-960471.1; AD-960314.1; AD-960443.1; AD-960282.1; AD-960283.1; AD-80794.7; AD-960478.1; AD-960481.1; and AD-960482.1.

In another aspect, the present invention provides a double stranded ribonucleic acid (dsRNA) for inhibiting expression of apolipoprotein C3 in a cell, wherein the dsRNA comprises a sense strand and an antisense strand forming a double stranded region, wherein the sense strand comprises at least 15 contiguous nucleotides differing by no more than 0, 1, 2, or 3 nucleotides from any one of the nucleotide sequence of nucleotides 235-257; 238-260; 242-264; 243-265; 244-266; 426-448; 430-450; 431-453; 432-454; 433-455; 435-457; 436-458; 499-521; 503-525; and 504-526 of the nucleotide sequence of SEQ ID NO:1, and the antisense strand comprises at least 19 contiguous nucleotides from the corresponding nucleotide sequence of SEQ ID NO:2.

In one embodiment, the antisense strand comprises at least 15 contiguous nucleotides differing by not more than 0, 1, 2, or 3 nucleotides from any one of the antisense strand nucleotide sequences of a duplex selected from the group consisting of AD-959917.1; AD-960064.1; AD-960031.1; AD-960063.1; AD-960293.1; AD-960288.1; AD-960445.1; AD-960292.1; AD-960475.1; AD-960442.1; AD-960470.1; AD-960436.1; AD-960446.1; AD-960474.1; AD-960294.1; AD-960443.1; AD-80794.7; and AD-959910.1.

In another aspect, the present invention provides a double stranded ribonucleic acid (dsRNA) for inhibiting expression of apolipoprotein C3 in a cell, wherein the dsRNA comprises a sense strand and an antisense strand forming a double stranded region, wherein the sense strand comprises at least 15 contiguous nucleotides differing by no more than 0, 1, 2, or 3 nucleotides from any one of the nucleotide sequence of nucleotides 232-254; 239-261; 242-264; 244-266; 258-280; 264-286; 268-290; 429-451; 430-450; 430-452; 433-455; 434-456; 435-457; 500-522; 503-525; 507-529; and 510-532 of the nucleotide sequence of SEQ ID NO:1, and the antisense strand comprises at least 19 contiguous nucleotides from the corresponding nucleotide sequence of SEQ ID NO:2.

In one embodiment, the antisense strand comprises at least 15 contiguous nucleotides differing by not more than 0, 1, 2, or 3 nucleotides from any one of the antisense strand nucleotide sequences of a duplex selected from the group consisting of AD-80794.8; AD-959907.2; AD-959914.2; AD-959916.2; AD-959932.2; AD-960314.2; AD-959941.2; AD-960030.2; AD-960062.2; AD-960064.2; AD-960065.2; AD-960066.2; AD-960294.2; AD-960471.2; AD-960474.2; AD-960478.2; and AD-960481.2.

In one aspect, the present invention provides a double stranded ribonucleic acid (dsRNA) for inhibiting expression of apolipoprotein C3 in a cell, wherein the dsRNA comprises a sense strand and an antisense strand forming a double stranded region, wherein the sense strand comprises at least 15 contiguous nucleotides differing by no more than 0, 1, 2, or 3 nucleotides from any one of the nucleotide sequence of nucleotides 429-455 or 504-532 of the nucleotide sequence of SEQ ID NO:1, and the antisense strand comprises at least 19 contiguous nucleotides from the corresponding nucleotide sequence of SEQ ID NO:2.

In another aspect, the present invention provides a double stranded ribonucleic acid (dsRNA) for inhibiting expression of apolipoprotein C3 in a cell, wherein the dsRNA comprises a sense strand and an antisense strand forming a double stranded region, wherein the sense strand comprises at least 15 contiguous nucleotides differing by no more than 0, 1, 2, or 3 nucleotides from any one of the nucleotide sequence of nucleotides 429-451; 430-452; 431-451; 432-452; 433-455; 434-452; 504-526; and 506-526 of the nucleotide sequence of SEQ ID NO:1, and the antisense strand comprises at least 19 contiguous nucleotides from the corresponding nucleotide sequence of SEQ ID NO:2.

In one embodiment, the antisense strand comprises at least 15 contiguous nucleotides differing by not more than 0, 1, 2, or 3 nucleotides from any one of the antisense strand nucleotide sequences of a duplex selected from the group consisting of AD-960030; AD-960064; AD-1143243; AD-1143245; AD-1143247; AD-1143249; AD-1143256; AD-1143260; AD-1143278; AD-1143287; AD-1143295; AD-1143299; AD-1143302; and AD-1143305.

In one embodiment, the antisense strand comprises at least 15 contiguous nucleotides differing by not more than 0, 1, 2, or 3 nucleotides from the antisense strand nucleotide sequence of duplex AD-1143278 or AD-960064.

In one embodiment, the antisense strand comprises at least 15 contiguous nucleotides differing by not more than 0, 1, 2, or 3 nucleotides from the nucleotide sequence of nucleotides 429-456 of SEQ ID NO:1.

In one embodiment, the sense strand comprises at least 15 contiguous nucleotides differing by not more than 0, 1, 2, or 3 nucleotides from the nucleotide sequence of nucleotides 433-455 of SEQ ID NO:1.

In one embodiment, the sense strand comprises at least 15 contiguous nucleotides differing by not more than 0, 1, 2, or 3 nucleotides from the nucleotide sequence of nucleotides 434-452 of SEQ ID NO:1.

In one embodiment, the antisense strand comprises at least 15 contiguous nucleotides differing by not more than 0, 1, 2, or 3 nucleotides from the antisense strand nucleotide sequence of duplex AD-1143243.

In one embodiment, the dsRNA agent comprises at least one modified nucleotide.

In one embodiment, substantially all of the nucleotides of the sense strand; substantially all of the nucleotides of the antisense strand comprise a modification; or substantially all of the nucleotides of the sense strand and substantially all of the nucleotides of the antisense strand comprise a modification.

In one embodiment, all of the nucleotides of the sense strand comprise a modification; all of the nucleotides of the antisense strand comprise a modification; or all of the nucleotides of the sense strand and all of the nucleotides of the antisense strand comprise a modification.

In one embodiment, at least one of the modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, a nucleotide comprising a 5'-phosphate mimic, a thermally destabilizing nucleotide, a glycol modified nucleotide (GNA), and a 2-O—(N-methylacetamide) modified nucleotide; and combinations thereof.

In one embodiment, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and glycol; and combinations thereof.

In one embodiment, at least one of the modified nucleotides is selected from the group consisting of a deoxy-nucleotide, a 2'-O-methyl modified nucleotide, a 2'-fluoro modified nucleotide, a 2'-deoxy-modified nucleotide, a glycol modified nucleotide (GNA), e.g., Ggn, Cgn, Tgn, or Agn, and, a vinyl-phosphonate nucleotide; and combinations thereof.

In another embodiment, at least one of the modifications on the nucleotides is a thermally destabilizing nucleotide modification.

In one embodiment, the thermally destabilizing nucleotide modification is selected from the group consisting of an abasic modification; a mismatch with the opposing nucleotide in the duplex; and destabilizing sugar modification, a 2'-deoxy modification, an acyclic nucleotide, an unlocked nucleic acids (UNA), and a glycerol nucleic acid (GNA).

The double stranded region may be 19-30 nucleotide pairs in length; 19-25 nucleotide pairs in length; 19-23 nucleotide pairs in length; 23-27 nucleotide pairs in length; or 21-23 nucleotide pairs in length.

In one embodiment, each strand is independently no more than 30 nucleotides in length.

In one embodiment, the sense strand is 21 nucleotides in length and the antisense strand is 23 nucleotides in length.

The region of complementarity may be at least 17 nucleotides in length; between 19 and 23 nucleotides in length; or 19 nucleotides in length.

In one embodiment, at least one strand comprises a 3' overhang of at least 1 nucleotide. In another embodiment, at least one strand comprises a 3' overhang of at least 2 nucleotides.

In one embodiment, the dsRNA agent further comprises a ligand.

In one embodiment, the ligand is conjugated to the 3' end of the sense strand of the dsRNA agent.

In one embodiment, the ligand is an N-acetylgalactosamine (GalNAc) derivative.

In one embodiment, the ligand is one or more GalNAc derivatives attached through a monovalent, bivalent, or trivalent branched linker.

In one embodiment, the ligand is

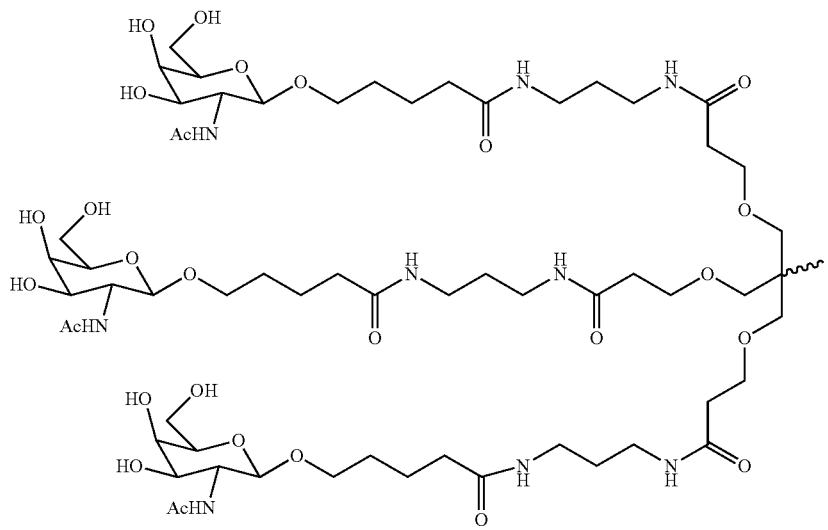 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA agent is conjugated to the ligand as shown in the following schematic

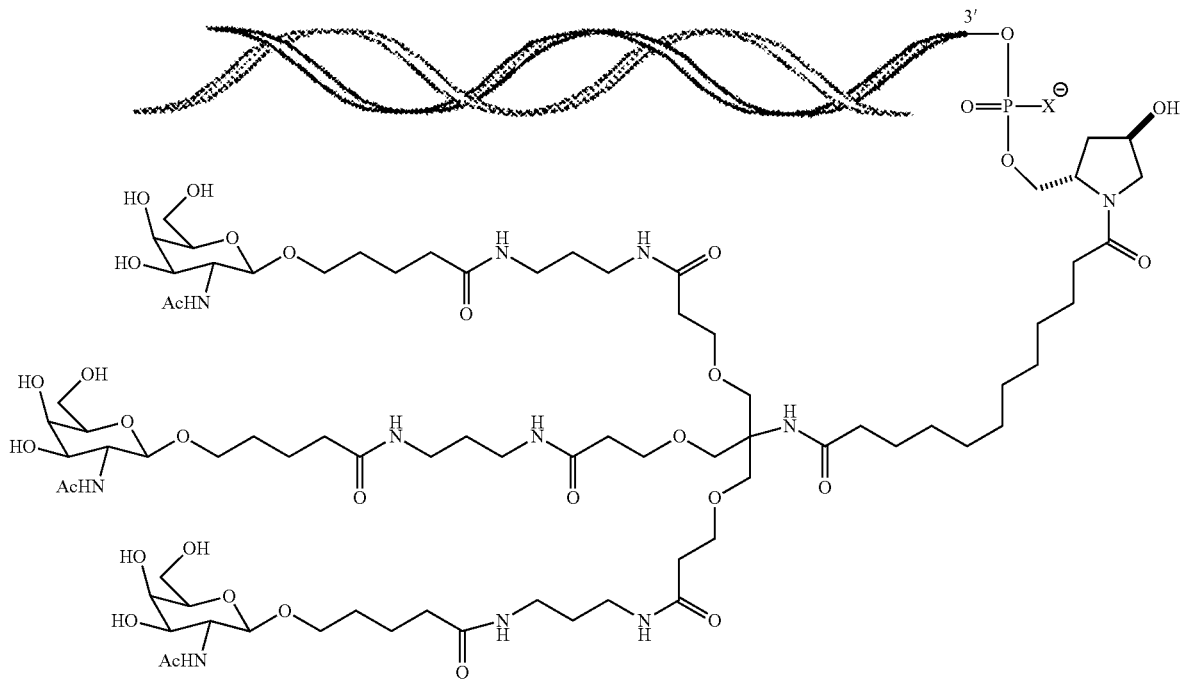

and, wherein X is O or S.

In one embodiment, the X is O.

In one embodiment, the dsRNA agent further comprises at least one phosphorothioate or methylphosphonate internucleotide linkage.

In one embodiment, the phosphorothioate or methylphosphonate internucleotide linkage is at the 3'-terminus of one strand, e.g., the antisense strand or the sense strand.

In another embodiment, the phosphorothioate or methylphosphonate internucleotide linkage is at the 5'-terminus of one strand, e.g., the antisense strand or the sense strand.

In one embodiment, the phosphorothioate or methylphosphonate internucleotide linkage is at the both the 5'- and 3'-terminus of one strand. In one embodiment, the strand is the antisense strand.

In one embodiment, the base pair at the 1 position of the 5'-end of the antisense strand of the duplex is an AU base pair.

In one aspect, the present invention provides a double stranded ribonucleic acid (dsRNA) for inhibiting expression of apolipoprotein C3 in a cell, wherein the dsRNA comprises a sense strand and an antisense strand forming a double stranded region, wherein the sense strand comprises at least 15, contiguous nucleotides differing by no more than 0, 1, 2, or 3 nucleotides from the nucleotide sequence of nucleotides 434-452 of the nucleotide sequence of SEQ ID NO:1, and the antisense strand comprises at least 19 contiguous nucleotides from the corresponding nucleotide sequence of SEQ ID NO:2, wherein substantially all of the nucleotides of the sense strand and substantially all of the nucleotides of the antisense strand comprise a modification selected from the group consisting of a 2'-O-methyl modification, a 2'-fluoro modification, and a deoxy-modification, wherein both the sense strand and the antisense strand independently further comprise at least one phosphorothioate or methylphosphonate internucleotide linkage, and wherein at least one strand is conjugated to a ligand.

In one embodiment, all of the nucleotides of the sense strand and all of the nucleotides of the antisense strand comprise a modification selected from the group consisting of a 2'-O-methyl modification, a 2'-fluoro modification, and a 2'-deoxy-modification.

In one embodiment, the sense strand comprises 2-6, e.g., 2, 3, 4, 5, or 6, 2'-fluoro modified nucleotides. In another embodiment, the sense strand comprises no more than 6, e.g., 0, 1, 2, 3, 4, 5, or 6, 2'-fluoro modified nucleotides.

In one embodiment, the sense strand comprises no more than 2, e.g., 0, 1, or 2, 2'-deoxy-modified nucleotides.

In one embodiment, the antisense strand comprises no more than 4, e.g., 0, 1, 2, 3, or 4, 2'-fluoro modified nucleotides.

In one embodiment, the antisense strand comprises no more than 5, e.g., 0, 1, 2, 3, 4, or 5, 2'-deoxy-modified nucleotides. In another embodiment, the antisense strand comprises 1-5, e.g., 1, 2, 3, 4, or 5, deoxy-nucleotides.

In one embodiment, the sense strand comprises 4 2'-fluoro modified nucleotides, e.g., nucleotides 7 and 9-11, counting from the 5'-end, and the antisense strand comprises 2 2'-fluoro modified nucleotides, e.g., nucleotides 14 and 16, counting from the 5'-end, and 3 2'-deoxy-modified nucleotides, e.g., nucleotides 2, 5, and 7, counting from the 5'-end.

In one embodiment, the phosphorothioate or methylphosphonate internucleotide linkage is at the 3'-terminus of one strand, e.g., the antisense strand or the sense strand.

In another embodiment, the phosphorothioate or methylphosphonate internucleotide linkage is at the 5'-terminus of one strand, e.g., the antisense strand or the sense strand.

In one embodiment, the phosphorothioate or methylphosphonate internucleotide linkage is at both the 5'- and 3'-terminus of one strand. In one embodiment, the strand is the antisense strand.

In one embodiment, the sense strand comprises two phosphorothioate or methylphosphonate internucleotide linkages at the 5'-terminus.

In one embodiment, the antisense strand comprises two phosphorothioate or methylphosphonate internucleotide linkages at the 5'-terminus.

In another embodiment, the antisense strand comprises two phosphorothioate or methylphosphonate internucleotide linkages at both the 5'- and 3'-terminus.

In one embodiment, the sense strand comprises two phosphorothioate or methylphosphonate internucleotide linkages at the 5'-terminus and the antisense strand comprises two phosphorothioate or methylphosphonate internucleotide linkages at both the 5'- and 3'-terminus.

In one embodiment, the ligand is conjugated to the senese strand.

In one embodiment the ligand is conjugated to the 3'-end of the sense strand.

In one embodiment, the ligand is n N-acetylgalactosamine (GalNAc) derivative.

In one embodiment, the ligand is one or more GalNAc derivatives attached through a monovalent, bivalent, or trivalent branched linker.

In one embodiment, the ligand is

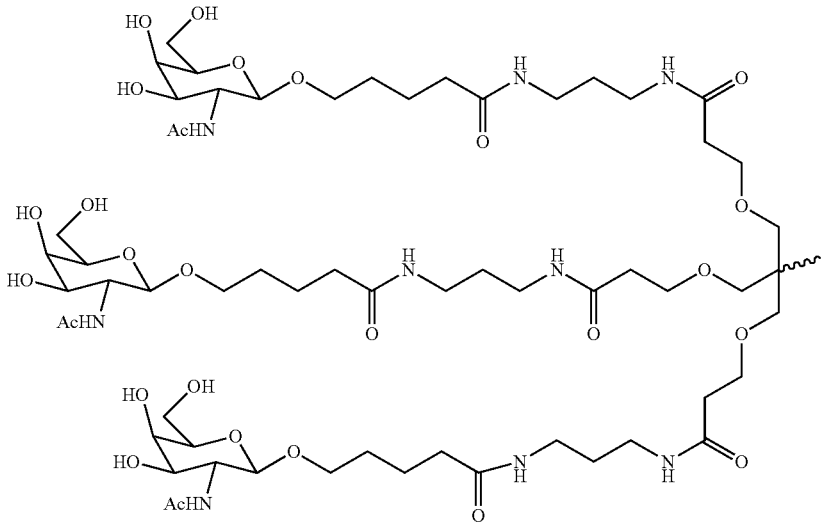 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA agent is conjugated to the ligand as shown in the following schematic

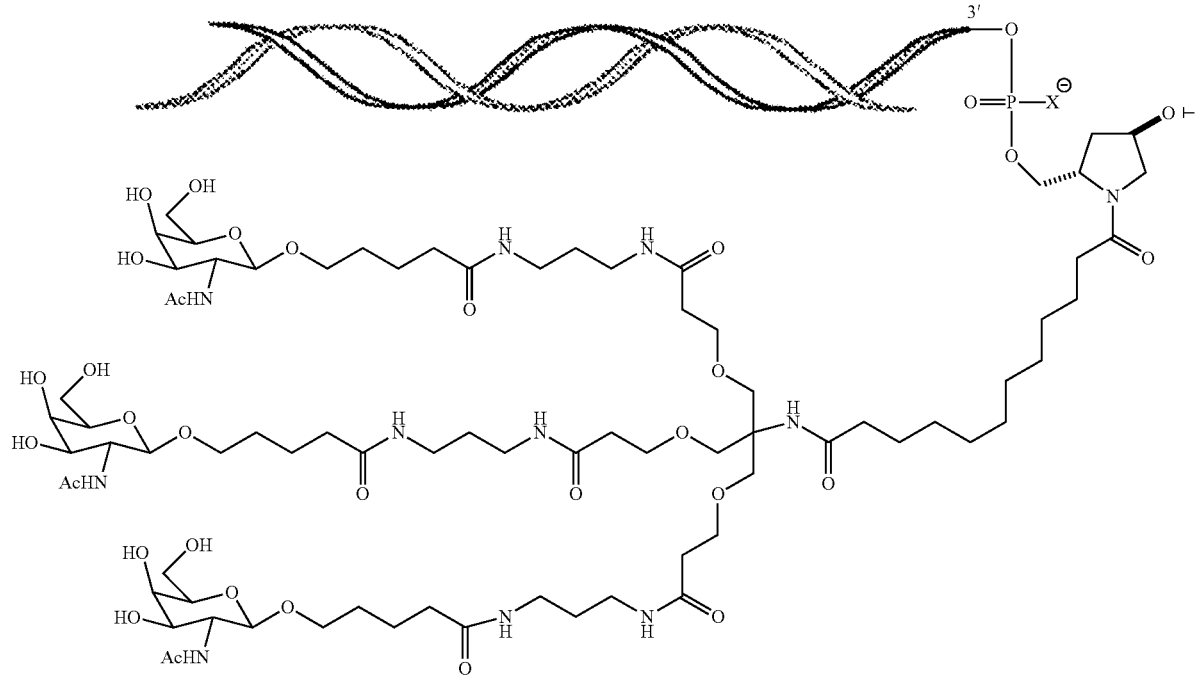

and, wherein X is O or S.

In one embodiment, the X is O.

In one embodiment, the sense strand comprises at least 17, contiguous nucleotides differing by no more than 0, 1, 2, or 3 nucleotides from the nucleotide sequence of 5'-CUUAAAAGGGACAGUAUUCUA-3'(SEQ ID NO: 13).

In one embodiment, the sense strand comprises at least 19, contiguous nucleotides differing by no more than 0, 1, 2, or 3 nucleotides from the nucleotide sequence of 5'-CUUAAAAGGGACAGUAUUCUA-3'(SEQ ID NO: 13).

In one embodiment, the sense strand comprises the nucleotide sequence of 5'-CUUAAAAGGGAC-AGUAUUCUA-3'(SEQ ID NO: 13).

In one embodiment, the antisense strand comprises at least 17, contiguous nucleotides differing by no more than 0, 1, 2, or 3 nucleotides from the nucleotide sequence of 5'-UAGAAUACUGUCCCUUUUAAGCC-3' (SEQ ID NO: 14).

In one embodiment, the antisense strand comprises at least 19, contiguous nucleotides differing by no more than 0, 1, 2, or 3 nucleotides from the nucleotide sequence of 5'-UAGAAUACUGUCCCUUUUAAGCC-3' (SEQ ID NO: 14).

In one embodiment, the antisense strand comprises at least 21, contiguous nucleotides differing by no more than 0, 1, 2, or 3 nucleotides from the nucleotide sequence of 5'-UAGAAUACUGUCCCUUUUAAGCC-3'(SEQ ID NO: 14).

In one embodiment, the antisense strand comprises the nucleotide sequence of 5'-UAGAAUACUGUCCC-UUUUAAGCC-3'(SEQ ID NO: 14).

In one embodiment, the sense strand comprises the nucleotide sequence of 5'-CUUAAAAGGGAC-AGUAUUCUA-3' (SEQ ID NO: 13) and the antisense strand comprises the nucleotide sequence of 5'-UAGAAUA-CUGUCCCUUUUAAGCC-3'(SEQ ID NO: 14).

In one embodiment, the sense strand differs by no more than 3, e.g., 0, 1, 2, or 3, modified nucleotides from the nucleotide sequence of 5'-csusuaaaAfgGfGfAfcaguauucua-3' (SEQ ID NO: 15) wherein a, g, c and u are 2'-O-methyl (2'-OMe) A, G, C, and U respectively; Af, Gf, Cf and Uf are 2'-fluoro A, G, C and U respectively; and s is a phosphorothioate linkage.

In one embodiment, the antisense strand differs by no more than 3, e.g., 0, 1, 2, or 3, modified nucleotides from the nucleotide sequence of of 5'-usdAsgadAudAcuguccCfuU-fuuaagscsc-3' (SEQ ID NO: 16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

In one embodiment, the sense strand comprises the nucleotide sequence of 5'-csusuaaaAfgGfGfAfcaguauucua-3' (SEQ ID NO: 15) and the antisense strand comprises the nucleotide sequence of 5'-usdAsgadAudAcuguccCfuU-fuuaagscsc-3' (SEQ ID NO: 16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

In one embodiment, the sense strand comprises the nucleotide sequence of 5'-csusuaaaAfgGfGfAfcaguauuc-uaL96-3' (SEQ ID NO: 17) and the antisense strand comprises the nucleotide sequence of 5'-usdAsgadAudAcugu-ccCfuUfuuaagscsc-3' (SEQ ID NO: 16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; s is a phosphorothioate linkage, and L96 is N-[tris(GalNAc-alkyl)-amidodecanoyl)]-4-hydroxyprolinol.

In one embodiment, the sense strand comprises the nucleotide sequence of 5'-csusuaaaAfgGfGfAfcaguauucua-3' (SEQ ID NO: 15) and the antisense strand comprises the nucleotide sequence of 5'-usdAsgadAudAcuguccCfuU-fuuaagscsc-3' (SEQ ID NO: 16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage, wherein the 3'-end of the sense strand is conjugated to the ligand as shown in the following schematic:

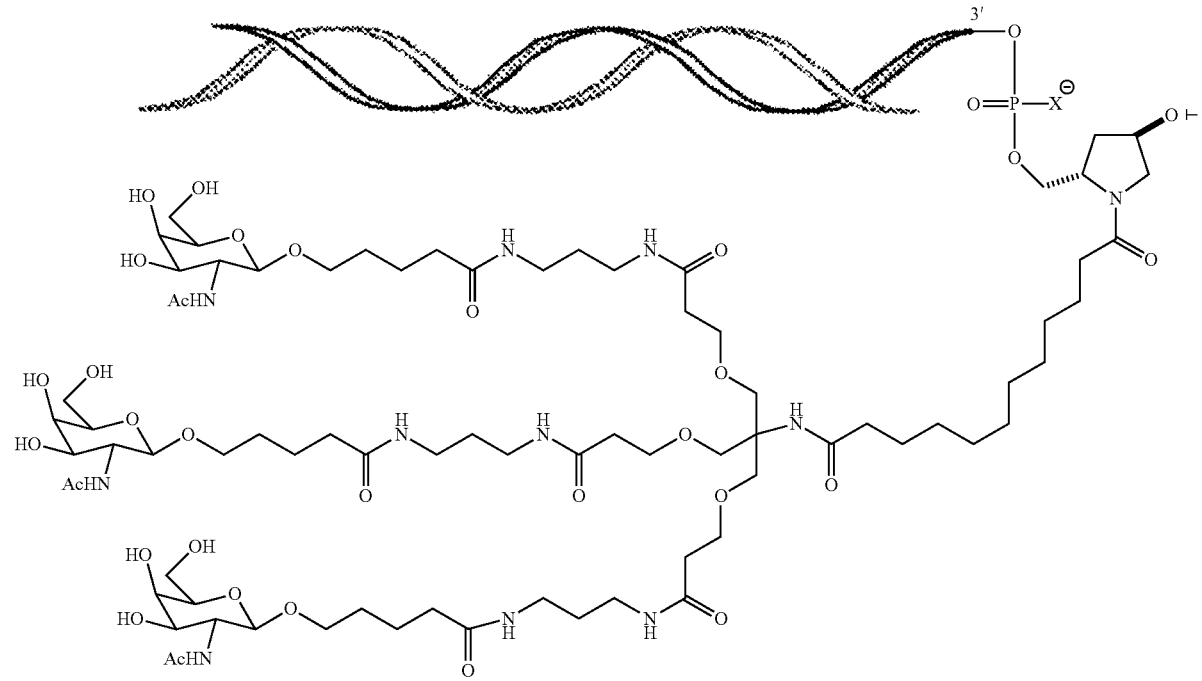

and, wherein X is O.

In one embodiment, the sense strand comprises at least 17, contiguous nucleotides differing by no more than 0, 1, 2, or 3 nucleotides from the nucleotide sequence of 5'-CUUAAAAGGGACAGUAUUCUU-3'(SEQ ID NO: 48).

In one embodiment, the sense strand comprises at least 19, contiguous nucleotides differing by no more than 0, 1, 2, or 3 nucleotides from the nucleotide sequence of 5'-CUUAAAAGGGACAGUAUUCUU-3'(SEQ ID NO: 48).

In one embodiment, the sense strand comprises the nucleotide sequence of 5'-CUUAAAAGGGAC-AGUAUUCUU-3'(SEQ ID NO: 48).

In one embodiment, the antisense strand comprises at least 17, contiguous nucleotides differing by no more than 0, 1, 2, or 3 nucleotides from the nucleotide sequence of 5'-AAGAAUACUGUCCCUUUUAAGCC-3' (SEQ ID NO: 315).

In one embodiment, the antisense strand comprises at least 19, contiguous nucleotides differing by no more than 0, 1, 2, or 3 nucleotides from the nucleotide sequence of 5'-AAGAAUACUGUCCCUUUUAAGCC-3' (SEQ ID NO: 315).

In one embodiment, the antisense strand comprises at least 21, contiguous nucleotides differing by no more than 0, 1, 2, or 3 nucleotides from the nucleotide sequence of 5'-AAGAAUACUGUCCCUUUUAAGCC-3' (SEQ ID NO: 315).

In one embodiment, the antisense strand comprises the nucleotide sequence of 5'-AAGAAUACUGUCCC-UUUUAAGCC-3' (SEQ ID NO: 315).

In one embodiment, the sense strand comprises the nucleotide sequence of 5'-CUUAAAAGGGACAGUAUUCUU-3' (SEQ ID NO: 48) and the antisense strand comprises the nucleotide sequence of 5'-AAGAAUACUGUCCC-UUUUAAGCC-3' (SEQ ID NO: 315).

In one embodiment, the sense strand differs by no more than 3, e.g., 0, 1, 2, or 3, modified nucleotides from the nucleotide sequence of 5'-csusuaaaAfgGfGfAfcaguauucuu-3' (SEQ ID NO: 377) wherein a, g, c and u are 2'-O-methyl (2'-OMe) A, G, C, and U respectively; Af, Gf, Cf and Uf are 2'-fluoro A, G, C and U respectively; and s is a phosphorothioate linkage.

In one embodiment, the antisense strand differs by no more than 3, e.g., 0, 1, 2, or 3, modified nucleotides from the nucleotide sequence of 5'-asdAsgadAudAcuguccCfuUfuuaagscsc-3' (SEQ ID NO: 866), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

In one embodiment, the sense strand comprises the nucleotide sequence of 5'-csusuaaaAfgGfGfAfcaguauucuu-3' (SEQ ID NO: 377) and the antisense strand comprises the nucleotide sequence of 5'-asdAsgadAudAcuguccCfuUfuuaagscsc-3' (SEQ ID NO: 866), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

In one embodiment, the sense strand comprises the nucleotide sequence of 5'-csusuaaaAfgGfGfAfcaguauucuuL96-3' (SEQ ID NO: 377) and the antisense strand comprises the nucleotide sequence of 5'-asdAsgadAudAcuguccCfuUfuuaagscsc-3' (SEQ ID NO: 866), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; s is a phosphorothioate linkage, and L96 is N-[tris(GalNAc-alkyl)-amidodecanoyl)]-4-hydroxyprolinol.

In one embodiment, the sense strand comprises the nucleotide sequence of 5'-csusuaaaAfgGfGfAfcaguauucuu-3' (SEQ ID NO: 377) and the antisense strand comprises the nucleotide sequence of 5'-asdAsgadAudAcuguccCfuUfuuaagscsc-3' (SEQ ID NO: 866), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage, wherein the 3'-end of the sense strand is conjugated to the ligand as shown in the following schematic:

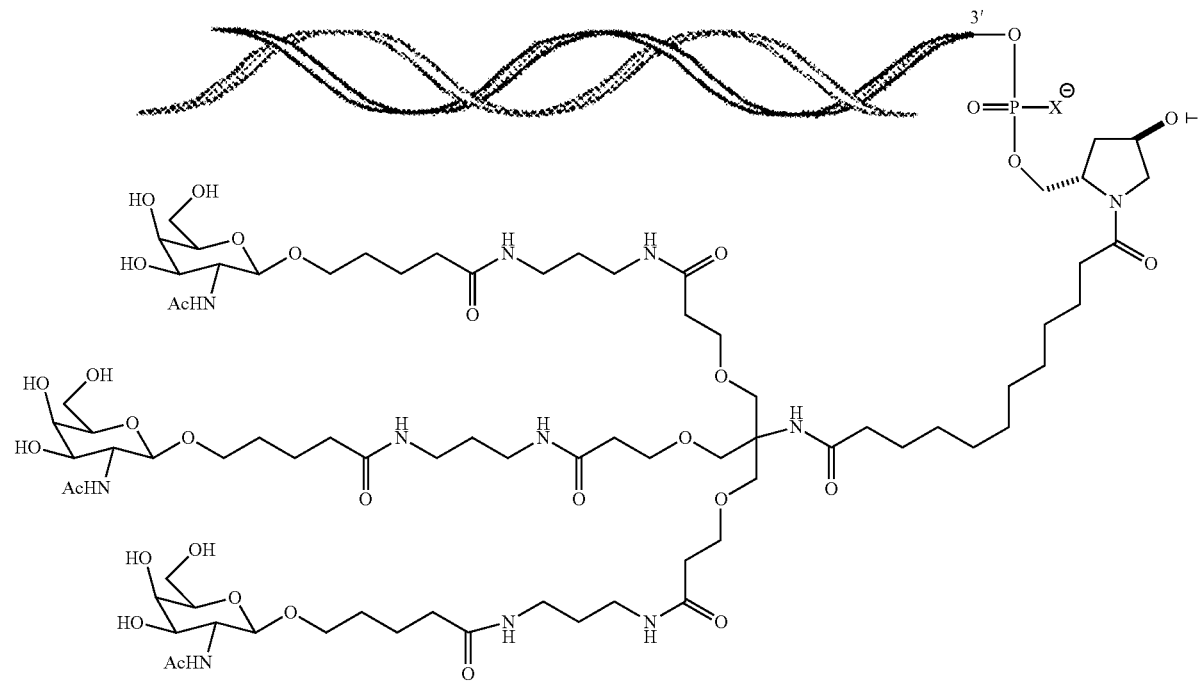

and, wherein X is O.

In one embodiment, the sense strand comprises at least 17, contiguous nucleotides differing by no more than 0, 1, 2, or 3 nucleotides from the nucleotide sequence of 5'-AAAAGGGACAGUAUUCUCAGU-3'(SEQ ID NO: 30).

In one embodiment, the sense strand comprises at least 19, contiguous nucleotides differing by no more than 0, 1, 2, or 3 nucleotides from the nucleotide sequence of 5'-AAAAGGGACAGUAUUCUCAGU-3'(SEQ ID NO: 30).

In one embodiment, the sense strand comprises the nucleotide sequence of 5'-AAAAGGGACAGUAUUCUCAGU-3'(SEQ ID NO: 30).

In one embodiment, the antisense strand comprises at least 17, contiguous nucleotides differing by no more than 0, 1, 2, or 3 nucleotides from the nucleotide sequence of 5'-ACUGAGAAUACUGUCCCUUUUAA-3' (SEQ ID NO: 31).

In one embodiment, the antisense strand comprises at least 19, contiguous nucleotides differing by no more than 0, 1, 2, or 3 nucleotides from the nucleotide sequence of 5'-ACUGAGAAUACUGUCCCUUUUAA-3' (SEQ ID NO: 31).

In one embodiment, the antisense strand comprises at least 21, contiguous nucleotides differing by no more than 0, 1, 2, or 3 nucleotides from the nucleotide sequence of 5'-ACUGAGAAUACUGUCCCUUUUAA-3' (SEQ ID NO: 31).

In one embodiment, the antisense strand comprises the nucleotide sequence of 5'-ACUGAGAAUACUGUCCCUUUUAA-3' (SEQ ID NO: 31).

In one embodiment, the sense strand comprises the nucleotide sequence of 5'-AAAAGGGACAGUAUUCUCAGU-3'(SEQ ID NO: 30) and the antisense strand comprises the nucleotide sequence of 5'-ACUGAGAAUACUGUCCCUUUUAA-3' (SEQ ID NO: 31).

In one embodiment, the sense strand differs by no more than 3, e.g., 0, 1, 2, or 3, modified nucleotides from the nucleotide sequence of 5'-asasaaggGfaCfAfGfuauucucagu-3' (SEQ ID NO: 350) wherein a, g, c and u are 2'-O-methyl (2'-OMe) A, G, C, and U respectively; Af, Gf, Cf and Uf are 2'-fluoro A, G, C and U respectively; and s is a phosphorothioate linkage.

In one embodiment, the antisense strand differs by no more than 3, e.g., 0, 1, 2, or 3, modified nucleotides from the nucleotide sequence of 5'-asCfsugaGfaAfUfacugUfcCfcuuuusasa-3' (SEQ ID NO: 351), wherein a, g, c and u are 2'-O-methyl (2'-OMe) A, G, C, and U respectively; Af, Gf, Cf and Uf are 2'-fluoro A, G, C and U respectively; and s is a phosphorothioate linkage.

In one embodiment, the sense strand comprises the nucleotide sequence of 5'-asasaaggGfaCfAfGfuauucucagu-3' (SEQ ID NO: 350) and the antisense strand comprises the nucleotide sequence of 5'-asCfsugaGfaAfUfacugUfcCfcuuuusasa-3' (SEQ ID NO: 351), wherein a, g, c and u are 2'-O-methyl (2'-OMe) A, G, C, and U respectively; Af, Gf, Cf and Uf are 2'-fluoro A, G, C and U respectively; and s is a phosphorothioate linkage.

In one embodiment, the sense strand comprises the nucleotide sequence of 5'-asasaaggGfaCfAfGfuauucucaguL96-3' (SEQ ID NO: 350) and the antisense strand comprises the nucleotide sequence of 5'-asCfsugaGfaAfUfacugUfcCfcuuuusasa-3' (SEQ ID NO: 351), wherein a, g, c and u are 2'-O-methyl (2'-OMe) A, G, C, and U respectively; Af, Gf, Cf and Uf are 2'-fluoro A, G, C and U respectively; s is a phosphorothioate linkage, and L96 is N-[tris(GalNAc-alkyl)-amidodecanoyl)]-4-hydroxyprolinol.

In one embodiment, the sense strand comprises the nucleotide sequence of 5'-asasaaggGfaCfAfGfuauucucagu-3' (SEQ ID NO: 350) and the antisense strand comprises the nucleotide sequence of 5'-asCfsugaGfaAfUfacugUfcCfcuuuusasa-3' (SEQ ID NO: 351), wherein a, g, c and u are 2'-O-methyl (2'-OMe) A, G, C, and U respectively; Af, Gf, Cf and Uf are 2'-fluoro A, G, C and U respectively; and s is a phosphorothioate linkage, wherein the 3'-end of the sense strand is conjugated to the ligand as shown in the following schematic:

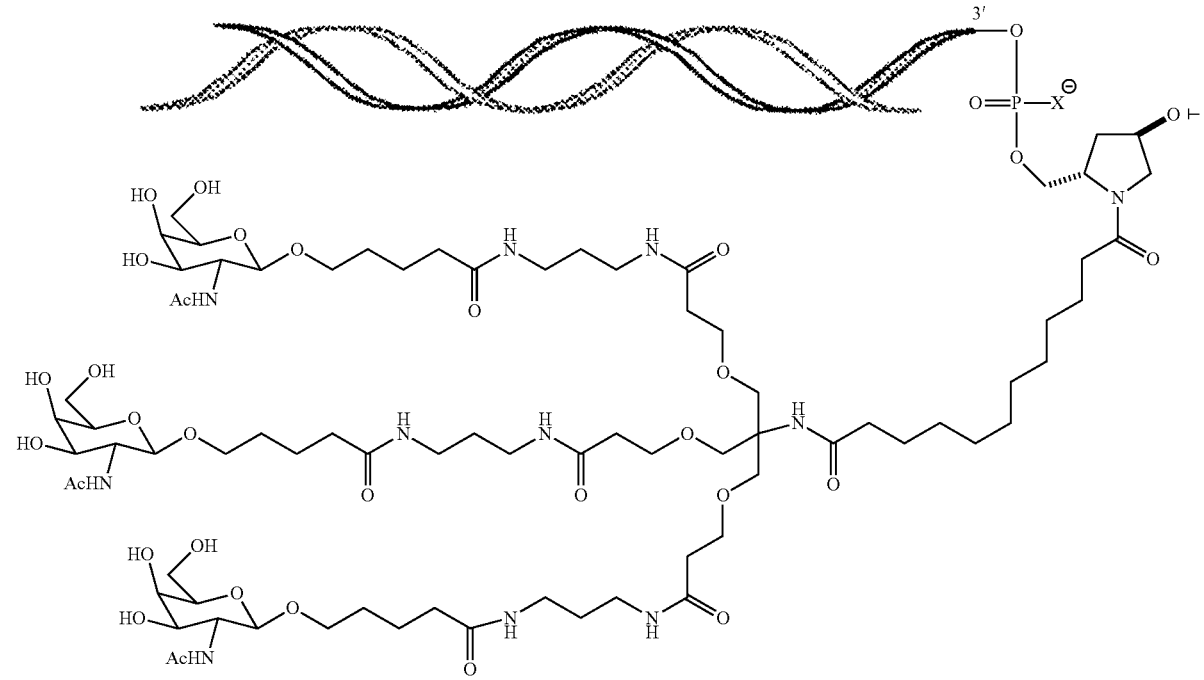

and, wherein X is O.

In one aspect, the present invention provides a double stranded ribonucleic acid (dsRNA) for inhibiting expression of apolipoprotein C3 in a cell, wherein the dsRNA comprises a sense strand and an antisense strand forming a double stranded region, wherein the sense strand comprises at least 15, contiguous nucleotides differing by no more than 0, 1, 2, or 3 nucleotides from the nucleotide sequence of nucleotides 429-456 of the nucleotide sequence of SEQ ID NO:1, and the antisense strand comprises at least 19 contiguous nucleotides from the corresponding nucleotide sequence of SEQ ID NO:2, wherein substantially all of the nucleotides of the sense strand and substantially all of the nucleotides of the antisense strand comprise a modification selected from the group consisting of a 2'-O-methyl modification, a 2'-fluoro modification, and a deoxy-modification, wherein both the sense strand and the antisense strand independently further comprise at least one phosphorothioate or methylphosphonate internucleotide linkage, and wherein at least one strand is conjugated to a ligand.

In one embodiment, the sense strand comprises 2-6 2'-fluoro modified nucleotides.

In one embodiment, the antisense strand comprises no more than 4 2'-fluoro modified nucleotides.

In one embodiment, the antisense strand comprises 1-5 deoxy-modified nucleotides.

In one aspect, the present invention provides a double stranded ribonucleic acid (dsRNA) agent for inhibiting expression of apolipoprotein C3 in a cell, wherein the dsRNA agent comprises a sense strand and an antisense strand forming a double stranded region, wherein the sense strand comprises at least 15 contiguous nucleotides differing by no more than 3 nucleotides from the nucleotide sequence of nucleotides 429-456 of the nucleotide sequence of SEQ ID NO:1, and the antisense strand comprises at least 19 contiguous nucleotides from the corresponding nucleotide sequence of SEQ ID NO:2, wherein all of the nucleotides of the sense strand and all of the nucleotides of the antisense strand comprise a modification selected from the group consisting of a 2'-O-methyl modification, a 2'-fluoro modification, and a deoxy-modification, wherein both the sense strand and the antisense strand independently further comprise at least one phosphorothioate or methylphosphonate internucleotide linkage, and wherein at least one strand is conjugated to a ligand.

In one embodiment, the sense strand comprises 2-6 2'-fluoro modified nucleotides.

In one embodiment, the sense strand comprises 4 2'-fluoro modified nucleotides.

In one embodiment, the antisense strand comprises 2-4 2'-fluoro modified nucleotides.

In one embodiment, the antisense strand comprises 2 2'-fluoro modified nucleotides.

In one embodiment, the antisense strand comprises 1-5 2'-deoxy-modified nucleotides.

In one embodiment, the antisense strand comprises 3 2'-deoxy-modified nucleotides.

In one embodiment, the sense strand comprises 4 2'-fluoro modified nucleotides at nucleotides 7 and 9-11, counting from the 5'-end, and the antisense strand comprises 2 2'-fluoro modified nucleotides at nucleotides 14 and 16, counting from the 5'-end, and 3 2'-deoxy-modified nucleotides at nucleotides 2, 5, and 7, counting from the 5'-end.

In one embodiment, the sense strand comprises two phosphorothioate or methylphosphonate internucleotide linkages at the 5'-terminus.

In one embodiment, the antisense strand comprises two phosphorothioate or methylphosphonate internucleotide linkages at both the 5'- and the 3'-terminus.

In one embodiment, the sense strand comprises two phosphorothioate or methylphosphonate internucleotide linkages at the 5'-terminus and the antisense strand comprises two phosphorothioate or methylphosphonate internucleotide linkages at both the 5'- and the 3'-terminus.

In one embodiment, the ligand is conjugated to the 3'-end of the sense strand.

In one embodiment, the ligand is an N-acetylgalactosamine (GalNAc) derivative.

In one embodiment, the ligand is one or more GalNAc derivatives attached through a monovalent, bivalent, or trivalent branched linker.

In one embodiment, the ligand is

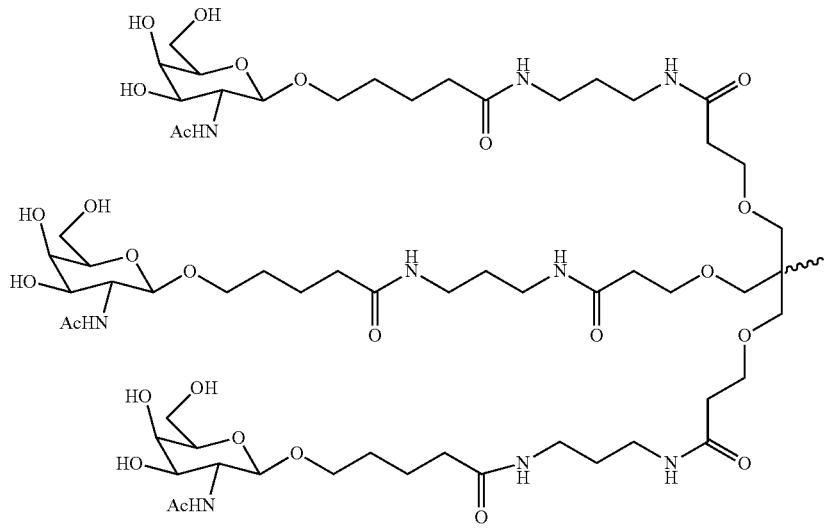 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA agent is conjugated to the ligand as shown in the following schematic

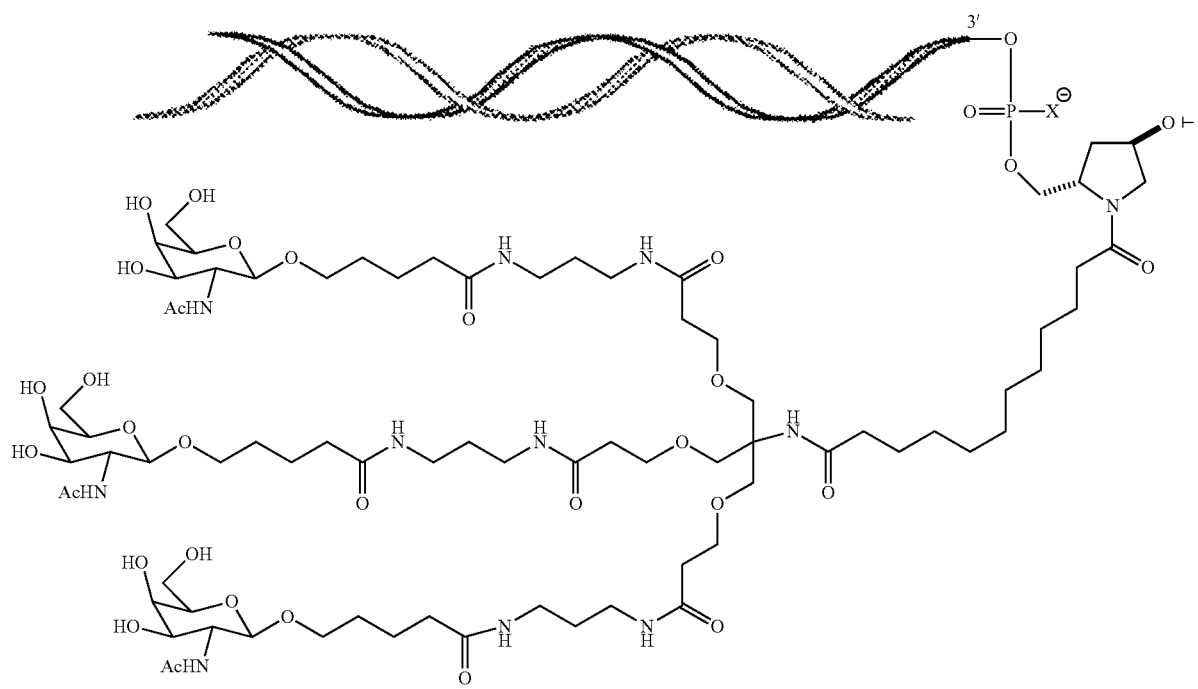

and, wherein X is O.

In one aspect, the present invention provides a double stranded ribonucleic acid (dsRNA) agent for inhibiting expression of apolipoprotein C3 in a cell, wherein the dsRNA agent comprises a sense strand and an antisense strand forming a double stranded region, wherein the sense strand differs by no more than 3 modified nucleotides from the nucleotide sequence of 5'-csusuaaaAfgGfGfAfcaguauucua-3' (SEQ ID NO:15) and wherein the antisense strand differs by no more than 3 modified nucleotides from the nucleotide sequence of 5'-usdAsgadAudAcuguccCfuUfuuaagscsc-3' (SEQ ID NO:16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

In one embodiment, the sense strand differs by no more than 2 modified nucleotides from the nucleotide sequence of 5'-csusuaaaAfgGfGfAfcaguauucua-3' (SEQ ID NO:15) and wherein the antisense strand differs by no more than 2 modified nucleotides from the nucleotide sequence of 5'-usdAsgadAudAcuguccCfuUfuuaagscsc-3' (SEQ ID NO:16).

In one embodiment, the sense strand differs by no more than 1 modified nucleotide from the nucleotide sequence of 5'-csusuaaaAfgGfGfAfcaguauucua-3' (SEQ ID NO:15) and wherein the antisense strand differs by no more than 1 modified nucleotides from the nucleotide sequence of 5'-usdAsgadAudAcuguccCfuUfuuaagscsc-3' (SEQ ID NO:16).

In one embodiment, the dsRNA agent is conjugated to the ligand as shown in the following schematic

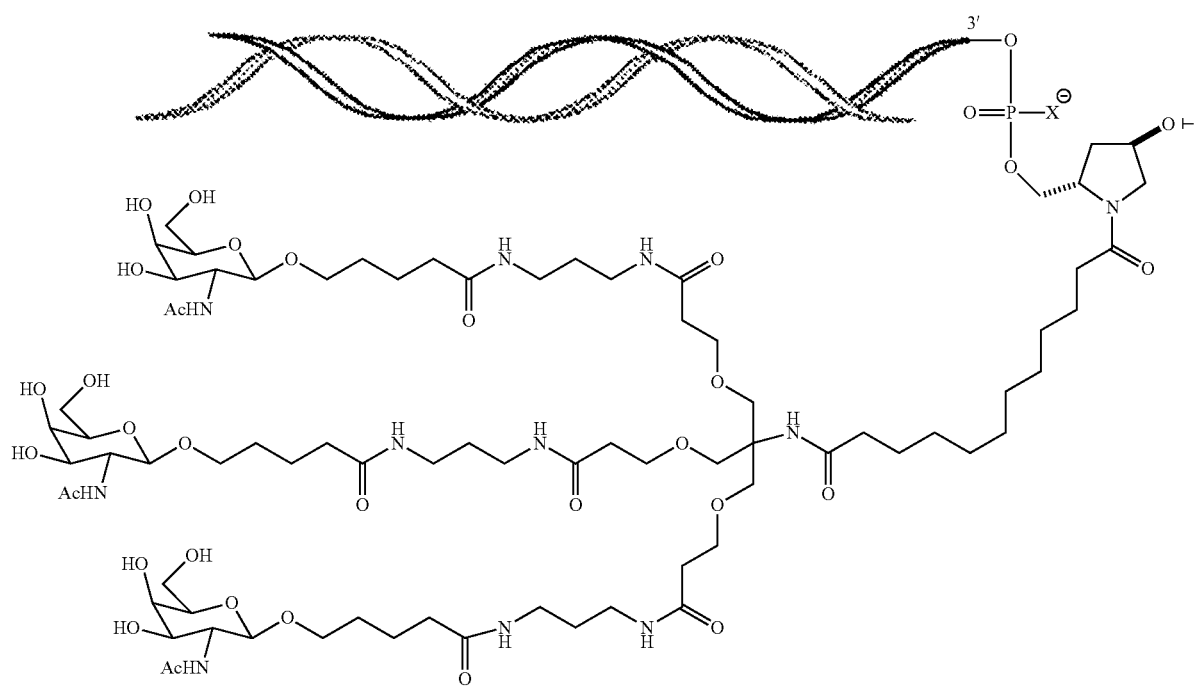

and, wherein X is O.

In one aspect, the present invention provides a double stranded ribonucleic acid (dsRNA) agent for inhibiting expression of apolipoprotein C3 in a cell, wherein the dsRNA agent comprises a sense strand and an antisense strand forming a double stranded region, wherein the sense strand comprises the nucleotide sequence of 5'-csusuaaaAf-gGfGfAfcaguauucua-3' (SEQ ID NO:15) and the antisense strand comprises the nucleotide sequence of 5'-us-dAsgadAudAcuguccCfuUfuuaagscsc-3' *SEQ ID NO:16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

In one aspect, the present invention provides a double stranded ribonucleic acid (dsRNA) agent for inhibiting expression of apolipoprotein C3 in a cell, wherein the dsRNA agent comprises a sense strand and an antisense strand forming a double stranded region, wherein the sense strand comprises the nucleotide sequence of 5'-csusuaaaAf-gGfGfAfcaguauucuaL96-3' (SEQ ID NO:17) and the antisense strand comprises the nucleotide sequence of 5'-us-dAsgadAudAcuguccCfuUfuuaagscsc-3' (SEQ ID NO:16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; s is a phosphorothioate linkage, and L96 is N-[tris(GalNAc-alkyl)-amidodecanoyl)]-4-hydroxyprolinol.

In another aspect, the present invention provides a double stranded ribonucleic acid (dsRNA) agent for inhibiting expression of apolipoprotein C3 in a cell, wherein the dsRNA agent comprises a sense strand and an antisense strand forming a double stranded region, wherein the sense strand comprises the nucleotide sequence of 5'-csusuaaaAf-gGfGfAfcaguauucua-3' (SEQ ID NO:15) and the antisense strand comprises the nucleotide sequence of 5'-us-dAsgadAudAcuguccCfuUfuuaagscsc-3' (SEQ ID NO:16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage; and wherein the 3'-end of the sense strand is conjugated to a ligand as shown in the following schematic:

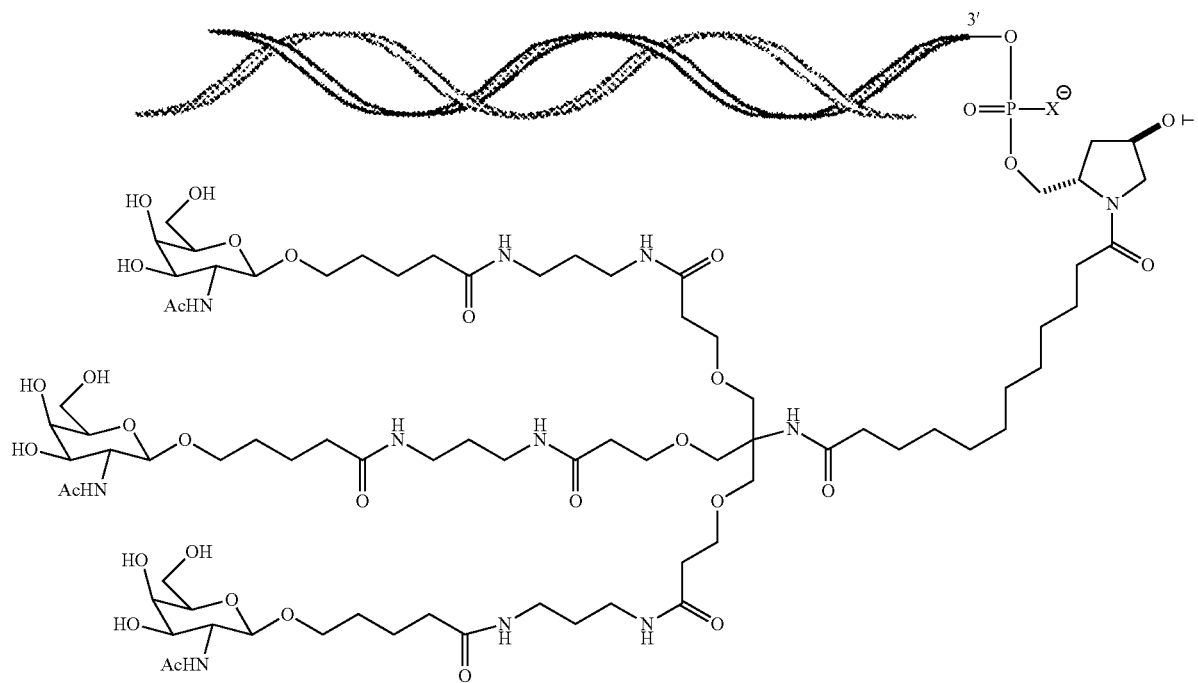

wherein X is O.

In one aspect, the present invention provides a double stranded ribonucleic acid (dsRNA) agent for inhibiting expression of apolipoprotein C3 in a cell, wherein the dsRNA agent comprises a sense strand and an antisense strand forming a double stranded region, wherein the sense strand consists of the nucleotide sequence of 5'-csusuaaaAfgGfGfAfcaguauucua-3' (SEQ ID NO:15) and the antisense strand consists of the nucleotide sequence of 5'-usdAsgadAudAcuguccCfuUfuuaagscsc-3' (SEQ ID NO:16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage; and wherein the 3'-end of the sense strand is conjugated to a ligand as shown in the following schematic:

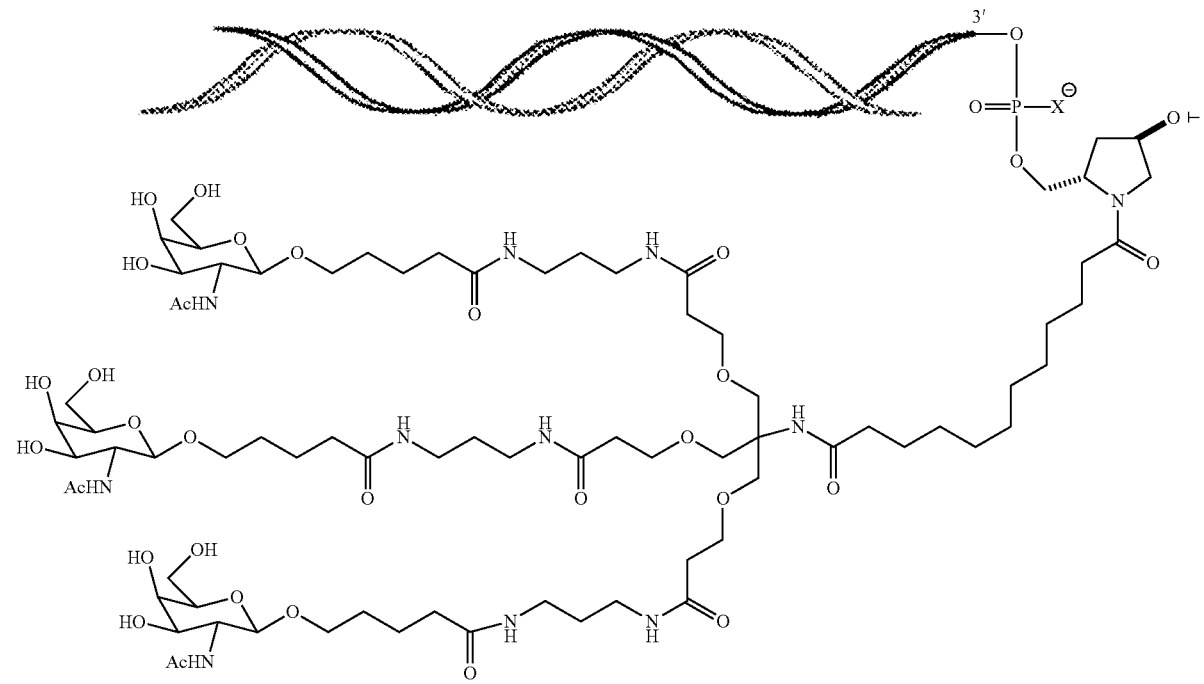

wherein X is O.

The present invention also provides cells containing any of the dsRNA agents of the invention and pharmaceutical compositions comprising any of the dsRNA agents of the invention.

The pharmaceutical composition of the invention may include dsRNA agent in an unbuffered solution, e.g., saline or water, or the pharmaceutical composition of the invention may include the dsRNA agent is in a buffer solution, e.g., a buffer solution comprising acetate, citrate, prolamine, carbonate, or phosphate or any combination thereof; or phosphate buffered saline (PBS).

In one aspect, the present invention provides a method of inhibiting expression of an apolipoprotein C3 (APOC3) gene in a cell. The method includes contacting the cell with any of the dsRNAs of the invention or any of the pharmaceutical compositions of the invention, thereby inhibiting expression of the APOC3 gene in the cell.

In one embodiment, the cell is within a subject, e.g., a human subject, e.g., a subject having an apolipoprotein C3-associated disorder, such as an apolipoprotein C3-associated disorder selected from the group consisting of hypertriglyceridemia, non-alcoholic fatty liver disease, non-alcoholic steatohepatitis, polycystic ovary syndrome, kidney disease, obesity, type 2 diabetes mellitus (insulin resistance), hypertension, artherosclerosis and pancreatitis.

In one embodiment, contacting the cell with the dsRNA agent inhibits the expression of APOC3 by at least 50%, 60%, 70%, 80%, 90%, or 95%.

In one embodiment, inhibiting expression of apolipoprotein C3 decreases APOC3 protein level in serum of the subject by at least 50%, 60%, 70%, 80%, 90%, or 95%.

In one aspect, the present invention provides a method of treating a subject having a disorder that would benefit from reduction in apolipoprotein C3 (APOC3) expression. The method includes administering to the subject a therapeutically effective amount of any of the dsRNAs of the invention or any of the pharmaceutical compositions of the invention, thereby treating the subject having the disorder that would benefit from reduction in APOC3 expression.

In another aspect, the present invention provides a method of preventing at least one symptom in a subject having a disorder that would benefit from reduction in apolipoprotein C3 (APOC3) expression. The method includes administering to the subject a prophylactically effective amount of any of the dsRNAs of the invention or any of the pharmaceutical compositions of the invention, thereby preventing at least one symptom in the subject having the disorder that would benefit from reduction in APOC3 expression.

In one embodiment, the disorder is am apolipoprotein C3-associated disorder, e.g., an apolipoprotein C3-associated disorder is selected from the group consisting of hypertriglyceridemia, non-alcoholic fatty liver disease, non-alcoholic steatohepatitis, polycystic ovary syndrome, kidney disease, obesity, type 2 diabetes mellitus (insulin resistance), hypertension, artherosclerosis and pancreatitis.

In one embodiment, the apolipoprotein C3-associated disorder is hypertriglyceridemia.

In one embodiment, the subject is human.

In one embodiment, the dsRNA agent is administered to the subject at a dose of about 0.01 mg/kg to about 50 mg/kg.

In one embodiment, the dsRNA agent is administered to the subject subcutaneously.

In one embodiment, the methods of the invention include further determining the level of apolipoprotein C3 in a sample(s) from the subject.

In one embodiment, the level of apolipoprotein C3 in the subject sample(s) is an apolipoprotein C3 protein level in a blood or serum sample(s).

In certain embodiments, the methods of the invention further comprise administering to the subject an additional therapeutic agent. In one embodiment, the additional thereapeutic is a dsRNA agent targeting PCSK9, e.g., Inclisiran. In one embodiment, the additional therapeutic is a PCSK9 inhibitor. In one embodiment, the PCSK9 inhibitor is an anti-PCSK9 monoclonal antibody, e.g., evolocumab (Repatha®) and alirocumab (Praluent®). In another embodiment, the PCSK9 inhibitor is a dsRNA agent targeting PCSK9, e.g., Inclisiran. In a further embodiment, the additional therapeutic agent is selected from the group consisting of an HMG-CoA reductase inhibitor, a fibrate, a bile acid sequestrant, niacin, an antiplatelet agent, an angiotensin converting enzyme inhibitor, an angiotensin II receptor antagonist, an acylCoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR) agonist, a gene-based therapy, a composite vascular protectant, a glycoprotein IIb/IIIa inhibitor, aspirin or an aspirin-like compound, an IBAT inhibitor, a squalene synthase inhibitor, a monocyte chemoattractant protein (MCP)-I inhibitor, or fish oil.

The present invention also provides kits comprising any of the dsRNAs of the invention or any of the pharmaceutical compositions of the invention, and optionally, instructions for use.

DETAILED DESCRIPTION OF THE INVENTION

Figure 1:
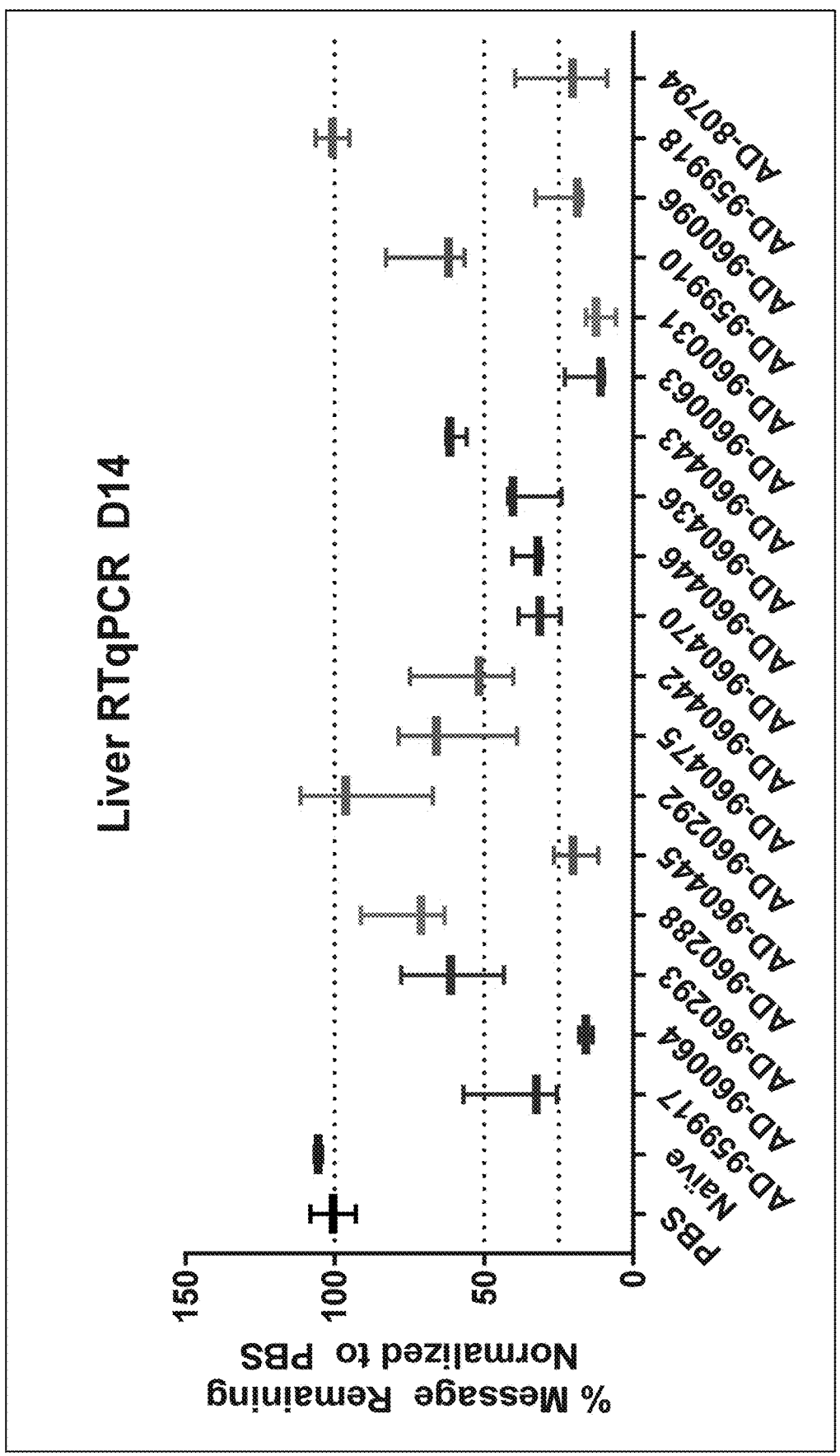
FIG. 1 is a graph showing human APOC3 mRNA levels in mice (n=3 per group) subcutaneously administered a single 3 mg/kg dose of the indicated dsRNA duplexes, on day14 post-dose. Human APOC3 mRNA levels are shown relative to control levels detected with PBS treatment.

The present invention provides iRNA compositions which effect the RNA-induced silencing complex (RISC)-mediated cleavage of RNA transcripts of an apolipoprotein C3 (APO3) gene. The gene may be within a cell, e.g., a cell within a subject, such as a human. The use of these iRNAs enables the targeted degradation of mRNAs of the corresponding gene (apolipoprotein C3 gene) in mammals.

The iRNAs of the invention have been designed to target the human apolipoprotein C3 gene, including portions of the gene that are conserved in the apolipoprotein C3 orthologs of other mammalian species. Without intending to be limited by theory, it is believed that a combination or sub-combination of the foregoing properties and the specific target sites or the specific modifications in these iRNAs confer to the iRNAs of the invention improved efficacy, stability, potency, durability, and safety.

Accordingly, the present invention provides methods for treating and preventing an apolipoprotein C3-associated disorder, e.g., hypertriglyceridemia, non-alcoholic fatty liver disease, non-alcoholic steatohepatitis, polycystic ovary syndrome, kidney disease, obesity, type 2 diabetes mellitus (insulin resistance), hypertension, artherosclerosis and pancreatitis, using iRNA compositions which effect the RNA-induced silencing complex (RISC)-mediated cleavage of RNA transcripts of a apolipoprotein C3 gene.

The iRNAs of the invention include an RNA strand (the antisense strand) having a region which is up to about 30 nucleotides or less in length, e.g., 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an APOC3 gene.

In certain embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of an APOC3 gene. In some embodiments, such iRNA agents having longer length antisense strands preferably may include a second RNA strand (the sense strand) of 20-60 nucleotides in length wherein the sense and antisense strands form a duplex of 18-30 contiguous nucleotides.

The use of iRNAs of the invention enables the targeted degradation of mRNAs of the corresponding gene (apolipoprotein C3 gene) in mammals. Using in vitro assays, the present inventors have demonstrated that iRNAs targeting an APOC3 gene can potently mediate RNAi, resulting in significant inhibition of expression of an APOC3 gene. Thus, methods and compositions including these iRNAs are useful for treating a subject having an apolipoprotein C3-associated disorder, e.g., hypertriglyceridemia, non-alcoholic fatty liver disease, non-alcoholic steatohepatitis, polycystic ovary syndrome, kidney disease, obesity, type 2 diabetes mellitus (insulin resistance), hypertension, artherosclerosis and pancreatitis.

Accordingly, the present invention provides methods and combination therapies for treating a subject having a disorder that would benefit from inhibiting or reducing the expression of an APOC3 gene, e.g., an apolipoprotein C3-associated disease, such as hypertriglyceridemia, non-alcoholic fatty liver disease, non-alcoholic steatohepatitis, polycystic ovary syndrome, kidney disease, obesity, type 2 diabetes mellitus (insulin resistance), hypertension, artherosclerosis and pancreatitis, using iRNA compositions which effect the RNA-induced silencing complex (RISC)-mediated cleavage of RNA transcripts of an APOC3 gene.

The present invention also provides methods for preventing at least one symptom in a subject having a disorder that would benefit from inhibiting or reducing the expression of an APOC3 gene, e.g., hypertriglyceridemia, non-alcoholic fatty liver disease, non-alcoholic steatohepatitis, polycystic ovary syndrome, kidney disease, obesity, type 2 diabetes mellitus (insulin resistance), hypertension, artherosclerosis and pancreatitis. For example, in a subject having hypertriglyceridemia, the methods of the present invention may reduce at least one symptom in the subject, e.g., lower triglyceride levels.

The following detailed description discloses how to make and use compositions containing iRNAs to inhibit the expression of an APOC3 gene as well as compositions, uses, and methods for treating subjects that would benefit from inhibition and/or reduction of the expression of an APOC3 gene, e.g., subjects susceptible to or diagnosed with an apolipoprotein C3-associated disorder.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 19 nucleotides of a 21 nucleotide nucleic acid molecule" means that 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range. As used herein, ranges include both the upper and lower limit.

As used herein, methods of detection can include determination that the amount of analyte present is below the level of detection of the method.

In the event of a conflict between an indicated target site and the nucleotide sequence for a sense or antisense strand, the indicated sequence takes precedence.

In the event of a conflict between a sequence and its indicated site on a transcript or other sequence, the nucleotide sequence recited in the specification takes precedence.

As used herein, the term "APOC3" refers to the well-known gene that encodes apolipoprotein C3, as well as to its protein product, also known in the art as HALP2 or APOCIII.

The term "APOC3" includes human APOC3, the amino acid and complete coding sequence of which may be found in for example, GenBank Accession No. GI:4557322 (NM_000040.3; SEQ ID NO:1; reverse complement, SEQ ID NO:2); *Macaca fascicularis* APOC3, the amino acid and complete coding sequence of which may be found in for example, GenBank Accession No. GI:544489959 (XM_05579730.1, SEQ ID NO:3; reverse complement, SEQ ID NO:4); *Macaca mulatta* APOC3, the amino acid and complete coding sequence of which may be found in for example, GenBank Accession No. GI:297269260 (XM_001090312.4; SEQ ID NO: 5; reverse complement, SEQ ID NO:6); mouse (*Mus musculus*) APOC3, the amino acid and complete coding sequence of which may be found in for example, GenBank Accession No. GI:577019555 (NM_023114.4, SEQ ID NO:7; reverse complement, SEQ ID NO:8); rat (*Rattus norvegicus*) APOC3, the amino acid and complete coding sequence of which may be found in for example, GenBank Accession No. GI:402534545 (NM_012501.2, SEQ ID NO:9; reverse complement, SEQ ID NO:2-10); and rabbit (*Oryctolagus cuniculus*), GenBank Accession No.GI:655601498 (XM_002708371.3, SEQ ID NO:11; reverse complement, SEQ ID NO:12).

Further information on APOC3 can be found, for example, at www.ncbi.nlm.nih.gov/gene/345.

Additional examples of APOC3 mRNA sequences are readily available through publicly available databases, e.g., GenBank, UniProt, OMIM, and the *Macaca* genome project web site.

The term"APOC3," as used herein, also refers to naturally occurring DNA sequence variations of the APOC3 gene, such as a single nucleotide polymorphism (SNP) in the APOC3 gene. Exemplary SNPs in the APOC3 DNA sequence may be found through the dbSNP database available at www.ncbi.nlm.nih.gov/projects/SNP/. Non-limiting examples of sequence variations within the APOC3 gene include, for example, the two variations rs2854116 and rs2854117, described in Petersen, K. F. et al., (2010), *N. Engl. J. Med.* 362(12):1082-1089, the entire contents of which are incorporated herein by reference.

Exemplary APOC3 nucleotide sequences may also be found in SEQ ID NOs:1-12. SEQ ID NOs:2, 4, 6, 8, 10, and 12 are the reverse complement sequences of SEQ ID NOs:1, 3, 5, 7, 9, and 11, respectively.

The entire contents of each of the foregoing GenBank Accession numbers and the Gene database numbers are incorporated herein by reference as of the date of filing this application. As used herein, "target sequence" refers to a contiguous portion of the nucleotide sequence of an mRNA molecule formed during the transcription of an apolipoprotein C3 gene, including mRNA that is a product of RNA processing of a primary transcription product. The target portion of the sequence will be at least long enough to serve as a substrate for iRNA-directed cleavage at or near that portion of the nucleotide sequence of an mRNA molecule formed during the transcription of an APOC3 gene. In one embodiment, the target sequence is within the protein coding region of APOC3.

The target sequence may be from about 19-36 nucleotides in length, preferably about 19-30 nucleotides in length. For example, the target sequence can be about 19-30 nucleotides, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. In certain embodiments, the target sequence is 19-23 nucleotides in length, optionally 21-23 nucleotides in length. Ranges and lengths intermediate to the above recited ranges and lengths are also contemplated to be part of the disclosure.

As used herein, the term "strand comprising a sequence" refers to an oligonucleotide comprising a chain of nucleotides that is described by the sequence referred to using the standard nucleotide nomenclature.

"G," "C," "A," "T," and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of an apolipoprotein C3 gene in a cell, e.g., a cell within a subject, such as a mammalian subject.

In one embodiment, an RNAi agent of the invention includes a single stranded RNA that interacts with a target RNA sequence, e.g., an apolipoprotein C3 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107: 309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., an apolipoprotein C3 (APOC3) gene. Accordingly, the term "siRNA" is also used herein to refer to an iRNA as described above.

In certain embodiments, the RNAi agent may be a single-stranded siRNA (ssRNAi) that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) Cell 150:883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150:883-894.

In certain embodiments, an "iRNA" for use in the compositions, uses, and methods of the invention is a double stranded RNA and is referred to herein as a "double stranded RNA agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an apolipoprotein C3 (APOC3) gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide or a modified nucleotide. In addition, as used in this specification, an "iRNA" may include ribonucleotides with chemical modifications; an iRNA may include substantial modifications at multiple nucleotides. As used herein, the term "modified nucleotide" refers to a nucleotide having, independently, a modified sugar moiety, a modified internucleotide linkage, or modified nucleobase, or any combination thereof. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "iRNA" or "RNAi agent" for the purposes of this specification and claims.

In certain embodiments of the instant disclosure, inclusion of a deoxy-nucleotide if present within an RNAi agent can be considered to constitute a modified nucleotide.

The duplex region may be of any length that permits specific degradation of a desired target RNA through a RISC pathway, and may range from about 19 to 36 base pairs in length, e.g., about 19-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. In certain embodiments, the duplex region is 19-21 base pairs in length, e.g., 21 base pairs in length. Ranges and lengths intermediate to the above recited ranges and lengths are also contemplated to be part of the disclosure.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, 3, 4, 5, 6, 7, 8, 9, 10, 20, 23 or more unpaired nucleotides. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not be, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs. In one embodiment of the RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, an iRNA agent of the invention is a dsRNA, each strand of which comprises 19-23 nucleotides, that interacts with a target RNA sequence, e.g., an apolipoprotein C3 (APOC3) gene, to direct cleavage of the target RNA.

In some embodiments, an iRNA of the invention is a dsRNA of 24-30 nucleotides that interacts with a target RNA sequence, e.g., an APOC3 target mRNA sequence, to direct the cleavage of the target RNA.

As used herein, the term "nucleotide overhang" refers to at least one unpaired nucleotide that protrudes from the duplex structure of a double stranded iRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the antisense strand of a dsRNA has a 1-10 nucleotides, e.g., a 1, 2, 3, 4, 5, 6, 7, 8, 9, or 10 nucleotide, overhang at the 3'-end or the 5'-end. In certain embodiments, the overhang on the sense strand or the antisense strand, or both, can include extended lengths longer than 10 nucleotides, e.g., 1-30 nucleotides, 2-30 nucleotides, 10-30 nucleotides, 10-25 nucleotides, 10-20 nucleotides, or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5' end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the extended overhang is replaced with a nucleoside thiophosphate. In certain embodiments, the overhang includes a self-complementary portion such that the overhang is capable of forming a hairpin structure that is stable under physiological conditions.

"Blunt" or "blunt end" means that there are no unpaired nucleotides at that end of the double stranded RNA agent, i.e., no nucleotide overhang. A "blunt ended" double stranded RNA agent is double stranded over its entire length, i.e., no nucleotide overhang at either end of the molecule. The RNAi agents of the invention include RNAi agents with no nucleotide overhang at one end (i.e., agents with one overhang and one blunt end) or with no nucleotide overhangs at either end. Most often such a molecule will be double-stranded over its entire length.

The term "antisense strand" or "guide strand" refers to the strand of an iRNA, e.g., a dsRNA, which includes a region that is substantially complementary to a target sequence, e.g., an APOC3 mRNA.

As used herein, the term "region of complementarity" refers to the region on the antisense strand that is substantially complementary to a sequence, for example a target sequence, e.g., an apolipoprotein C3 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, or 3 nucleotides of the 5'- or 3'-end of the iRNA. In some embodiments, a double stranded RNA agent of the invention includes a nucleotide mismatch in the antisense strand. In some embodiments, the antisense strand of the double stranded RNA agent of the invention includes no more than 4 mismatches with the target mRNA, e.g., the antisense strand includes 4, 3, 2, 1, or 0 mismatches with the target mRNA. In some embodiments, the antisense strand of the double stranded RNA agent of the invention includes no more than 4 mismatches with the sense strand, e.g., the antisense strand includes 4, 3, 2, 1, or 0 mismatches with the sense strand. In some embodiments, a double stranded RNA agent of the invention includes a nucleotide mismatch in the sense strand. In some embodiments, the sense strand of the double stranded RNA agent of the invention includes no more than 4 mismatches with the antisense strand, e.g., the sense strand includes 4, 3, 2, 1, or 0 mismatches with the antisense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA agent. In some embodiments, the mismatch(s) is not in the seed region.

Thus, an RNAi agent as described herein can contain one or more mismatches to the target sequence. In one embodiment, a RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, if the antisense strand of the RNAi agent contains mismatches to the target sequence, the mismatch can optionally be restricted to be within the last 5 nucleotides from either the 5'- or 3'-end of the region of complementarity. For example, in such embodiments, for a 23 nucleotide RNAi agent, the strand which is complementary to a region of an APOC3 gene, generally does not contain any mismatch within the central 13 nucleotides. The methods described herein or methods known in the art can be used to determine whether an RNAi agent containing a mismatch to a target sequence is effective in inhibiting the expression of an APOC3 gene. Consideration of the efficacy of RNAi agents with mismatches in inhibiting expression of an APOC3 gene is important, especially if the particular region of complementarity in an APOC3 gene is known to have polymorphic sequence variation within the population.

The term "sense strand" or "passenger strand" as used herein, refers to the strand of an iRNA that includes a region that is substantially complementary to a region of the antisense strand as that term is defined herein.

As used herein, "substantially all of the nucleotides are modified" are largely but not wholly modified and can include not more than 5, 4, 3, 2, or 1 unmodified nucleotides.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of a double stranded RNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding an apolipoprotein C3 gene). For example, a polynucleotide is complementary to at least a part of an apolipoprotein C3 mRNA if the sequence is substantially complementary to a non-interrupted portion of an mRNA encoding an apolipoprotein C3 gene.

Accordingly, in some embodiments, the antisense polynucleotides disclosed herein are fully complementary to the target APOC3 sequence. In other embodiments, the antisense polynucleotides disclosed herein are substantially complementary to the target APOC3 sequence and comprise a contiguous nucleotide sequence which is at least 80% complementary over its entire length to the equivalent region of the nucleotide sequence of any one of SEQ ID NOs:1, 3, 5, 7, 9, or 11, or a fragment of any one of SEQ ID NOs:1-1, 3, 5, 7, 9, or 11, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target APOC3 sequence and comprise a contiguous nucleotide sequence which is at least 80% complementary over its entire length to a fragment of SEQ ID NO: 1 selected from the group of nucleotides; 232-254; 233-255; 238-260; 239-261; 242-264; 243-265; 244-266; 264-286; 268-290; 426-448; 431-453; 432-454; 433-455; 435-457; 436-458; 499-521; 500-522; 503-525; 504-526; 507-529; 510-532; and 511-533 of SEQ ID NO: 1, such as about 85%, about 90%, about 91%, about 92%, about 93%, about 94%, about 95%, about 96%, about 97%, about 98%, or about 99% complementary.

In other embodiments, the antisense polynucleotides disclosed herein are substantially complementary to a fragment of a target APOC3 sequence and comprise a contiguous nucleotide sequence which is at least 80% complementary over its entire length to a fragment of SEQ ID NO: 1 selected from the group of nucleotides 235-257; 238-260; 242-264; 243-265; 244-266; 426-448; 430-450; 431-453; 432-454; 433-455; 435-457; 436-458; 499-521; 503-525; and 504-526 of SEQ ID NO: 1, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target APOC3 sequence and comprise a contiguous nucleotide sequence which is at least 80% complementary over its entire length to a fragment of SEQ ID NO: 1 selected from the group of nucleotides 232-254; 239-261; 242-264; 244-266; 258-280; 264-286; 268-290; 429-451; 430-450; 430-452; 433-455; 434-456; 435-457; 500-522; 503-525; 507-529; and 510-532; and 504-526 of SEQ ID NO: 1, such as about 85%, about 90%, about 91%, about 92%, about 93%, about 94%, about 95%, about 96%, about 97%, about 98%, or about 99% complementary.

In other embodiments, the antisense polynucleotides disclosed herein are substantially complementary to a fragment of a target APOC3 sequence and comprise a contiguous nucleotide sequence which is at least 80% complementary over its entire length to a fragment of SEQ ID NO: 1 selected from the group of nucleotides 429-451; 430-452; 431-451; 432-452; 433-455; 504-526; and 506-526 of SEQ ID NO: 1, such as about 85%, about 90%, about 91%, about 92%, about 93%, about 94%, about 95%, about 96%, about 97%, about 98%, or about 99% complementary.

In other embodiments, the antisense polynucleotides disclosed herein are substantially complementary to the target APOC3 sequence and comprise a contiguous nucleotide sequence which is at least about 80% complementary over its entire length to any one of the sense strand nucleotide sequences in any one of any one of Tables 2-5, 14, and 15, or a fragment of any one of the sense strand nucleotide sequences in any one of Tables 2-5, 14, and 15, such as about 85%, about 90%, about 91%, about 92%, about 93%, about 94%, about 95%, about 96%, about 97%, about 98%, about 99%, or 100% complementary.

In one embodiment, an RNAi agent of the disclosure includes a sense strand that is substantially complementary to an antisense polynucleotide which, in turn, is the same as a target APOC3 sequence, and wherein the sense strand polynucleotide comprises a contiguous nucleotide sequence which is at least about 80% complementary over its entire length to the equivalent region of the nucleotide sequence of SEQ ID NOs: 2, 4, 6, 8, 10, or 12, or a fragment of any one of SEQ ID NOs:2, 4, 6, 8, 10, or 12, such as about 85%, about 90%, about 91%, about 92%, about 93%, about 94%, about 95%, about 96%, about 97%, about 98%, about 99%, or 100% complementary.

In some embodiments, an iRNA of the invention includes a sense strand that is substantially complementary to an antisense polynucleotide which, in turn, is complementary to a target apolipoprotein C3 sequence, and wherein the sense strand polynucleotide comprises a contiguous nucleotide sequence which is at least about 80% complementary over its entire length to any one of the antisense strand nucleotide sequences in any one of any one of Tables 2-5, 14, and 15, or a fragment of any one of the antisense strand nucleotide sequences in any one of Tables 2-5, 14, and 15, such as about 85%, about 90%, about 91%, about 92%, about 93%, about 94%, about 95%, about 96%, about 97%, about 98%, about 99%, or 100% complementary In certain embodiments, the sense and antisense strands are selected from any one of duplexes AD-959917.1; AD-959918.1; AD-960096.1; AD-960064.1; AD-959914.1; AD-959941.1; AD-960031.1; AD-960063.1; AD-960293.1; AD-960288.1; AD-960445.1; AD-960292.1; AD-960475.1; AD-960442.1; AD-960470.1; AD-960436.1; AD-960446.1; AD-960474.1; AD-960294.1; AD-960471.1; AD-960314.1; AD-960443.1; AD-960282.1; AD-960283.1; AD-80794.7; AD-960478.1; AD-960481.1; or AD-960482.1.

In other embodiments, the sense and antisense strands are selected from any one of duplexes AD-959917.1; AD-960064.1; AD-960031.1; AD-960063.1; AD-960293.1; AD-960288.1; AD-960445.1; AD-960292.1; AD-960475.1; AD-960442.1; AD-960470.1; AD-960436.1; AD-960446.1; AD-960474.1; AD-960294.1; AD-960443.1; AD-80794.7; and AD-959910.1.

In some embodiments, the sense and antisense strands are selected from any one of duplexes AD-80794.8; AD-959907.2; AD-959914.2; AD-959916.2; AD-959932.2; AD-960314.2; AD-959941.2; AD-960030.2; AD-960062.2; AD-960064.2; AD-960065.2; AD-960066.2; AD-960294.2; AD-960471.2; AD-960474.2; AD-960478.2; and AD-960481.2.

In other embodiments, the sense and antisense strands are selected from any one of duplexes AD-960030; AD-1143243; AD-1143245; AD-1143247; AD-1143249; AD-1143256; AD-1143260; AD-1143278; AD-1143287; AD-1143295; AD-1143299; AD-1143302; and AD-1143305.

In one embodiment, the sense and antisense strands are of duplex AD-1143243.

In general, an "iRNA" includes ribonucleotides with chemical modifications. Such modifications may include all types of modifications disclosed herein or known in the art. Any such modifications, as used in a dsRNA molecule, are encompassed by "iRNA" for the purposes of this specification and claims.

In certain embodiments of the instant disclosure, inclusion of a deoxy-nucleotide if present within an RNAi agent can be considered to constitute a modified nucleotide.

In an aspect of the invention, an agent for use in the methods and compositions of the invention is a single-stranded antisense oligonucleotide molecule that inhibits a target mRNA via an antisense inhibition mechanism. The single-stranded antisense oligonucleotide molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) Mol Cancer Ther 1:347-355. The single-stranded antisense oligonucleotide molecule may be about 14 to about 30 nucleotides in length and have a sequence that is complementary to a target sequence. For example, the single-stranded antisense oligonucleotide molecule may comprise a sequence that is at least about 14, 15, 16, 17, 18, 19, 20, or more contiguous nucleotides from any one of the antisense sequences described herein.

The phrase "contacting a cell with an iRNA," such as a dsRNA, as used herein, includes contacting a cell by any possible means. Contacting a cell with an iRNA includes contacting a cell in vitro with the iRNA or contacting a cell in vivo with the iRNA. The contacting may be done directly or indirectly. Thus, for example, the iRNA may be put into physical contact with the cell by the individual performing the method, or alternatively, the iRNA may be put into a situation that will permit or cause it to subsequently come into contact with the cell.

Contacting a cell in vitro may be done, for example, by incubating the cell with the iRNA. Contacting a cell in vivo may be done, for example, by injecting the iRNA into or near the tissue where the cell is located, or by injecting the iRNA into another area, e.g., the bloodstream or the subcutaneous space, such that the agent will subsequently reach the tissue where the cell to be contacted is located. For example, the iRNA may contain or be coupled to a ligand, e.g., GalNAc, that directs the iRNA to a site of interest, e.g., the liver. Combinations of in vitro and in vivo methods of contacting are also possible. For example, a cell may also be contacted in vitro with an iRNA and subsequently transplanted into a subject.

In certain embodiments, contacting a cell with an iRNA includes "introducing" or "delivering the iRNA into the cell" by facilitating or effecting uptake or absorption into the cell. Absorption or uptake of an iRNA can occur through unaided diffusion or active cellular processes, or by auxiliary agents or devices. Introducing an iRNA into a cell may be in vitro or in vivo. For example, for in vivo introduction, iRNA can be injected into a tissue site or administered systemically. In vitro introduction into a cell includes methods known in the art such as electroporation and lipofection. Further approaches are described herein below or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858, 225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a horse, a goat, a rabbit, a sheep, a hamster, a guinea pig, a cat, a dog, a rat, or a mouse), or a bird that expresses the target gene, either endogenously or heterologously. In an embodiment, the subject is a human, such as a human being treated or assessed for a disease or disorder that would benefit from reduction in APOC3 expression; a human at risk for a disease or disorder that would benefit from reduction in APOC3 expression; a human having a disease or disorder that would benefit from reduction in APOC3 expression; or human being treated for a disease or disorder that would benefit from reduction in APOC3 expression as described herein. In some embodiments, the subject is a female human.

In other embodiments, the subject is a male human. In one embodiment, the subject is an adult subject. In another embodiment, the subject is a pediatric subject.

As used herein, the terms "treating" or "treatment" refer to a beneficial or desired result, such as reducing at least one sign or symptom of an APOC3-associated disorder in a subject. Treatment also includes a reduction of one or more sign or symptoms associated with unwanted APOC3 expression; diminishing the extent of unwanted APOC3 activation or stabilization; amelioration or palliation of unwanted APOC3 activation or stabilization. "Treatment" can also mean prolonging survival as compared to expected survival in the absence of treatment. The term "lower" in the context of the level of APOC3 in a subject or a disease marker or symptom refers to a statistically significant decrease in such level. The decrease can be, for example, at least 10%, 15%, 20%, 25%, 30%, %, 40%, 45%, 50%, 55%, 60%, 65%, 70%, 75%, 80%, 85%, 90%, 95%, or more. In certain embodiments, a decrease is at least 20%. In certain embodiments, the decrease is at least 50% in a disease marker, e.g., protein or gene expression level. "Lower" in the context of the level of APOC3 in a subject is preferably down to a level accepted as within the range of normal for an individual without such disorder. In certain embodiments, "lower" is the decrease in the difference between the level of a marker or symptom for a subject suffering from a disease and a level accepted within the range of normal for an individual, e.g., the level of decrease in bodyweight between an obese individual and an individual having a weight accepted within the range of normal.

As used herein, "prevention" or "preventing," when used in reference to a disease, disorder or condition thereof, may be treated or ameliorated by a reduction in expression of an APOC3 gene, refers to a reduction in the likelihood that a subject will develop a symptom associated with such a disease, disorder, or condition, e.g., a symptom of unwanted or excessive APOC3 expression, such as hypertriglyceridemia. The likelihood of developing, e.g., hypertriglyceridemia, is reduced, for example, when an individual having one or more risk factors for hypertriglyceridemia either fails to develop hypertriglyceridemia or develops hypertriglyceridemia with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention.

As used herein, the term "apolipoprotein C3-associated disease" or "APOC3-associated disease," is a disease, disorder or a condition that is caused by, or is associated with, unwanted or excessive APOC3 expression. The term "APOC3-associated disease" includes a disease, disorder or condition that may be treated or ameliorated by a reduction in APOC3 expression. The term APOC3-associated disease" includes hypertriglyceridemia, or a high triglyceride levels.

The levels of triglycerides in a serum of a subject, e.g., a human subject, that may be indicative of hypertriglyceridemia are described in Oh, R. C. et al., (2007) *American Family Physician*, 75(9):1366-1371. Specifically, hypertriglyceridemia may be associated with "borderline-high serum triglyceride levels" (i.e., 150 to 199 mg per dL or 1.70 to 2.25 mmol per L); "high serum triglyceride levels" (i.e., 200 to 499 mg per dL or 2.26 to 5.64 mmol per L); or "very high triglyceride levels" (i.e., 500 mg per dL or higher (or 5.65 mmol per L or higher)

In one embodiment, an APOC3-associated disease is primary hypertriglyceridemia. "Primary triglyceridemia" results from environmental or genetic causes (e.g., a result of no obvious underlying medical cause). Exemplary diseases characterized as primary hypertriglyceridemias include, but are not limited to, familial chylomicronemia (hyperlipoproteinemia type I), primary mixed hyperlipidemia (type 5), familial hypertriglyceridemia (hyperlipoproteinemia type 4), familial combined hyperlipoproteinemia (type 2B) and familial dysbetalipoproteinemia (hyperlipoproteinemia type 3).

In another embodiment, an APOC3-associated disease is secondary hypertriglyceridemia. "Secondary triglyceridemia" is caused by, or be associated with, other underlying disorders and conditions. Such disorders and/or conditions include, e.g., obesity, metabolic syndrome, diabetes, fatty liver, alcohol use, renal disease, pregnancy, nonalcoholic fatty liver disorder, hypothyroidism, paraproteinemias (such as hypergammaglobulinemia in macroglobulinemia, myeloma, lymphoma and lymphocytic leukemias), autoimmune disorders (such as systemic lupus erythematosis), intake of medications (such as antiretroviral drugs, including ritonavir and lopinavir, and antipsychotic medications, including clozapine and olanzapine), see G. Yuan et al., (2007) *Canadian Medical Association Journal*, 176(8): 1113-1120.

Any disorder that may be a cause of hypertriglyceridemia (e.g., secondary hypertriglyceridemia) or that may be a consequence of hypertriglyceridemia (e.g., primary or secondary hypertriglyceridemia) is encompassed by the term "APOC3-associated disease". Non-limiting examples of APOC3-associated diseases include metabolic disorders, e.g., non-alcoholic fatty liver disease, non-alcoholic steatohepatitis, polycystic ovary syndrome, kidney disease, obesity, type 2 diabetes mellitus (insulin resistance); hypertension; cardiovascular disorders, e.g., artherosclerosis; and pancreatitis, e.g., acute pancreatitis.

"Therapeutically effective amount," as used herein, is intended to include the amount of an RNAi agent that, when administered to a subject having an APOC3-associated disease, is sufficient to effect treatment of the disease (e.g., by diminishing, ameliorating, or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an RNAi agent that, when administered to a subject having an APOC3-associated disorder, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired effect at a reasonable benefit/risk ratio applicable to any treatment. The iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition, or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Such carriers are known in the art. Pharmaceutically acceptable carriers include carriers for administration by injection.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to urine obtained from the subject. A "sample derived from a subject" can refer to blood or blood derived serum or plasma from the subject.

II. iRNAs of the Invention

The present invention provides iRNAs which inhibit the expression of an apolipoprotein C3 gene. In preferred embodiments, the iRNA includes double stranded ribonucleic acid (dsRNA) molecules for inhibiting the expression of an APOC3 gene in a cell, such as a cell within a subject, e.g., a mammal, such as a human susceptible to developing an apolipoprotein C3-associated disorder, e.g., hypertriglyceridemia. The dsRNAi agent includes an antisense strand having a region of complementarity which is complementary to at least a part of an mRNA formed in the expression of an APOC3 gene. The region of complementarity is about 19-30 nucleotides in length (e.g., about 30, 29, 28, 27, 26, 25, 24, 23, 22, 21, 20, or 19 nucleotides in length). Upon contact with a cell expressing the APOC3 gene, the iRNA inhibits the expression of the APOC3 gene (e.g., a human, a primate, a non-primate, or a rat APOC3 gene) by at least about 50% as assayed by, for example, a PCR or branched DNA (bDNA)-based method, or by a protein-based method, such as by immunofluorescence analysis, using, for example, western blotting or flow cytometric techniques. In preferred embodiments, inhibition of expression is determined by the qPCR method provided in the examples herein with the siRNA at, e.g., a 10 nM concentration, in an appropriate organism cell line provided therein. In preferred embodiments, inhibition of expression in vivo is determined by knockdown of the human gene in a rodent expressing the human gene, e.g., a mouse or an AAV-infected mouse expressing the human target gene, e.g., when administered as single dose, e.g., at 3 mg/kg at the nadir of RNA expression.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an APOC3 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 15 to 30 base pairs in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. In certain preferred embodiments, the duplex structure is 18 to 25 base pairs in length, e.g., 18-25, 18-24, 18-23, 18-22, 18-21, 18-20, 19-25, 19-24, 19-23, 19-22, 19-21, 19-20, 20-25, 20-24, 20-23, 20-22, 20-21, 21-25, 21-24, 21-23, 21-22, 22-25, 22-24, 22-23, 23-25, 23-24 or 24-25 base pairs in length, for example, 19-21 basepairs in length. Ranges and lengths intermediate to the above recited ranges and lengths are also contemplated to be part of the disclosure.

Similarly, the region of complementarity to the target sequence is 15 to 30 nucleotides in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, for example 19-23 nucleotides in length or 21-23 nucleotides in length. Ranges and lengths intermediate to the above recited ranges and lengths are also contemplated to be part of the disclosure.

In some embodiments, the duplex structure is 19 to 30 base pairs in length. Similarly, the region of complementarity to the target sequence is 19 to 30 nucleotides in length.

In some embodiments, the dsRNA is about 19 to about 23 nucleotides in length, or about 25 to about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 19 to about 30 base pairs, e.g., about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target apolipoprotein C3 gene expression is not generated in the target cell by cleavage of a larger dsRNA.

A dsRNA as described herein can further include one or more single-stranded nucleotide overhangs e.g., 1-4, 2-4, 1-3, 2-3, 1, 2, 3, or 4 nucleotides. dsRNAs having at least one nucleotide overhang can have superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In an aspect, a dsRNA of the invention includes at least two nucleotide sequences, a sense sequence and an antisense sequence. The sense strand is selected from the group of sequences provided in any one of Tables 2-5, 14, and 15, and the corresponding antisense strand of the sense strand is selected from the group of sequences of any one of Tables 2-5, 14, and 15. In this aspect, one of the two sequences is complementary to the other of the two sequences, with one of the sequences being substantially complementary to a sequence of an mRNA generated in the expression of an apolipoprotein C3 gene. As such, in this aspect, a dsRNA will include two oligonucleotides, where one oligonucleotide is described as the sense strand in any one of Tables 2-5, 14, and 15, and the second oligonucleotide is described as the corresponding antisense strand of the sense strand in any one of Tables 2-5, 14, and 15.

In certain embodiments, the substantially complementary sequences of the dsRNA are contained on separate oligonucleotides. In other embodiments, the substantially complementary sequences of the dsRNA are contained on a single oligonucleotide.

In certain embodiments, the sense or antisense strand is selected from the sense or antisense strand of any one of duplexes AD-959917.1; AD-959918.1; AD-960096.1; AD-960064.1; AD-959914.1; AD-959941.1; AD-960031.1; AD-960063.1; AD-960293.1; AD-960288.1; AD-960445.1; AD-960292.1; AD-960475.1; AD-960442.1; AD-960470.1; AD-960436.1; AD-960446.1; AD-960474.1; AD-960294.1; AD-960471.1; AD-960314.1; AD-960443.1; AD-960282.1; AD-960283.1; AD-80794.7; AD-960478.1; AD-960481.1; or AD-960482.1.

In other embodiments, the sense or antisense strand is selected from the sense or antisense strand of any one of duplexes AD-959917.1; AD-960064.1; AD-960031.1; AD-960063.1; AD-960293.1; AD-960288.1; AD-960445.1; AD-960292.1; AD-960475.1; AD-960442.1; AD-960470.1; AD-960436.1; AD-960446.1; AD-960474.1; AD-960294.1; AD-960443.1; AD-80794.7; and AD-959910.1.

In some embodiments, the sense or antisense strand is selected from the sense or antisense strand of any one of duplexes AD-80794.8; AD-959907.2; AD-959914.2; AD-959916.2; AD-959932.2; AD-960314.2; AD-959941.2; AD-960030.2; AD-960062.2; AD-960064.2; AD-960065.2; AD-960066.2; AD-960294.2; AD-960471.2; AD-960474.2; AD-960478.2; and AD-960481.2.

In some embodiments, the sense or antisense strand is selected from the sense or antisense strand of any one of duplexes AD-960030; AD-1143243; AD-1143245; AD-1143247; AD-1143249; AD-1143256; AD-1143260; AD-1143278; AD-1143287; AD-1143295; AD-1143299; AD-1143302; and AD-1143305.

In some embodiments, the sense or antisense strand is selected from the sense or antisense strand of duplex AD-1143243.

It will be understood that, although the sequences in Tables 2, 4, and 14 are not described as modified or conjugated sequences, the RNA of the iRNA of the invention e.g., a dsRNA of the invention, may comprise any one of the sequences set forth in any one of Tables 2-5, 14, and 15 that is un-modified, un-conjugated, or modified or conjugated differently than described therein. In other words, the invention encompasses dsRNA of Tables 2-5, 14, and 15 which are un-modified, un-conjugated, modified, or conjugated, as described herein.

The skilled person is well aware that dsRNAs having a duplex structure of about 20 to 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 2-5, 14, and 15, dsRNAs described herein can include at least one strand of a length of minimally 21 nucleotides. It can be reasonably expected that shorter duplexes having any one of the sequences in any one of Tables 2-5, 14, and 15 minus only a few nucleotides on one or both ends can be similarly effective as compared to the dsRNAs described above. Hence, dsRNAs having a sequence of at least 19, 20, or more contiguous nucleotides derived from any one of the sequences of any one of Tables 2-5, 14, and 15, and differing in their ability to inhibit the expression of an apolipoprotein C3 gene by not more than about 5, 10, 15, 20, 25, or 30% inhibition from a dsRNA comprising the full sequence, are contemplated to be within the scope of the present invention.

In addition, the RNAs provided in Tables 2-5, 14, and 15 identify a site(s) in a apolipoprotein C3 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 19 contiguous nucleotides from any one of the sequences provided in any one of Tables 2-5, 14, and 15 coupled to additional nucleotide sequences taken from the region contiguous to the selected sequence in an apolipoprotein C3 gene.

III. Modified iRNAs of the Invention

In certain embodiments, the RNA of the iRNA of the invention e.g., a dsRNA, is un-modified, and does not comprise, e.g., chemical modifications or conjugations known in the art and described herein. In other embodiments, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA or substantially all of the nucleotides of an iRNA are modified, i.e., not more than 5, 4, 3, 2, or 1 unmodified nucleotides are present in a strand of the iRNA.

The nucleic acids featured in the invention can be synthesized or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments of the invention, the dsRNA agents of the invention are in a free acid form. In other embodiments of the invention, the dsRNA agents of the invention are in a salt form. In one embodiment, the dsRNA agents of the invention are in a sodium salt form. In certain embodiments, when the dsRNA agents of the invention are in the sodium salt form, sodium ions are present in the agent as counterions for substantially all of the phosphodiester and/or phosphorothioate groups present in the agent. Agents in which substantially all of the phosphodiester and/or phosphorothioate linkages have a sodium counterion include not more than 5, 4, 3, 2, or 1 phosphodiester and/or phosphorothioate linkages without a sodium counterion. In some embodiments, when the dsRNA agents of the invention are in the sodium salt form, sodium ions are present in the agent as counterions for all of the phosphodiester and/or phosphorothioate groups present in the agent.

Representative U.S. Patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. Patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, the entire contents of each of which are hereby incorporated herein by reference.

Suitable RNA mimetics are contemplated for use in iRNAs provided herein, in which both the sugar and the internucleoside linkage, i.e., the backbone, of the nucleotide units are replaced with novel groups. The base units are maintained for hybridization with an appropriate nucleic acid target compound. One such oligomeric compound in which an RNA mimetic that has been shown to have excellent hybridization properties is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative US patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —CH$_2$—NH—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —N(CH$_3$)—CH$_2$—CH$_2$— [wherein the native phosphodiester backbone is represented as —O—P—O—CH$_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted C$_1$ to C$_{10}$ alkyl or C$_2$ to C$_{10}$ alkenyl and alkynyl. Exemplary suitable modifications include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. In other embodiments, dsRNAs include one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative US patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. Patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-

447; Mook, O R. et al., (2007) *Mol Canc Ther* 6(3):833-843; Grunweller, A. et al., (2003) *Nucleic Acids Research* 31(12): 3185-3193).

In some embodiments, the RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-($CH_2$)—O-2' (LNA); 4'-($CH_2$)—S-2'; 4'-($CH_2$)$_2$—O-2' (ENA); 4'-CH($CH_3$)—O-2' (also referred to as "constrained ethyl" or "cEt") and 4'-CH($CH_2OCH_3$)—O-2' (and analogs thereof; see, e.g., U.S. Pat. No. 7,399,845); 4'-C($CH_3$)($CH_3$)—O-2' (and analogs thereof; see e.g., U.S. Pat. No. 8,278,283); 4'-$CH_2$—N($OCH_3$)-2' (and analogs thereof; see e.g., U.S. Pat. No. 8,278,425); 4'-$CH_2$—O—N($CH_3$)-2' (see, e.g., U.S. Patent Publication No. 2004/0171570); 4'-$CH_2$—N(R)—O-2', wherein R is H, C1-C12 alkyl, or a protecting group (see, e.g., U.S. Pat. No. 7,427,672); 4'-$CH_2$—C(H)($CH_3$)-2' (see, e.g., Chattopadhyaya et al., *J. Org. Chem.*, 2009, 74, 118-134); and 4'-$CH_2$—C(=$CH_2$)-2' (and analogs thereof; see, e.g., U.S. Pat. No. 8,278,426). The entire contents of each of the foregoing are hereby incorporated herein by reference.

Additional representative U.S. Patents and U.S. Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH($CH_3$)—O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and -C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, U.S. Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series*, 52, 133-134 (2008) and Fluiter et al., *Mol. Biosyst.*, 2009, 10, 1039 hereby incorporated by reference).

Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an iRNA. Suitable phosphate mimics are disclosed in, for example U.S. Patent Publication No. 2012/0157511, the entire contents of which are incorporated herein by reference.

A. Modified iRNAs Comprising Motifs of the Invention

In certain aspects of the invention, the double stranded RNA agents of the invention include agents with chemical modifications as disclosed, for example, in WO2013/075035, the entire contents of each of which are incorporated herein by reference. WO2013/075035 provides motifs of three identical modifications on three consecutive nucleotides into a sense strand or antisense strand of a dsRNAi agent, particularly at or near the cleavage site. In some embodiments, the sense strand and antisense strand of the dsRNAi agent may otherwise be completely modified. The introduction of these motifs interrupts the modification pattern, if present, of the sense or antisense strand. The dsRNAi agent may be optionally conjugated with a GalNAc derivative ligand, for instance on the sense strand.

More specifically, when the sense strand and antisense strand of the double stranded RNA agent are completely modified to have one or more motifs of three identical modifications on three consecutive nucleotides at or near the cleavage site of at least one strand of a dsRNAi agent, the gene silencing activity of the dsRNAi agent was observed.

Accordingly, the invention provides double stranded RNA agents capable of inhibiting the expression of a target gene (i.e., APOC3 gene) in vivo. The RNAi agent comprises a sense strand and an antisense strand. Each strand of the RNAi agent may be, for example, 17-30 nucleotides in length, 25-30 nucleotides in length, 27-30 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as "dsRNAi agent." The duplex region of a dsRNAi agent may be, for example, the duplex region can be 27-30 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 19, 20, 21, 22, 23, 24, 25, 26, and 27 nucleotides in length.

In certain embodiments, the dsRNAi agent may contain one or more overhang regions or capping groups at the 3'-end, 5'-end, or both ends of one or both strands. The overhang can be, independently, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In certain embodiments, the overhang regions can include extended overhang regions as provided above. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In certain embodiments, the nucleotides in the overhang region of the dsRNAi agent can each independently be a modified or unmodified nucleotide including, but no limited to 2'-sugar modified, such as, 2'-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof.

For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand, or both strands of the dsRNAi agent may be phosphorylated. In some embodiments, the overhang region(s) contains two nucleotides having a phosphorothioate between the two nucleotides, where the two nucleotides can be the same or different. In some embodiments, the overhang is present at the 3'-end of the sense strand, antisense strand, or both strands. In some embodiments, this 3'-overhang is present in the antisense strand. In some embodiments, this 3'-overhang is present in the sense strand.

The dsRNAi agent may contain only a single overhang, which can strengthen the interference activity of the RNAi, without affecting its overall stability. For example, the single-stranded overhang may be located at the 3'-end of the sense strand or, alternatively, at the 3'-end of the antisense strand. The RNAi may also have a blunt end, located at the 5'-end of the antisense strand (or the 3'-end of the sense strand) or vice versa. Generally, the antisense strand of the dsRNAi agent has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In certain embodiments, the dsRNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In other embodiments, the dsRNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet other embodiments, the dsRNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In certain embodiments, the dsRNAi agent comprises a 21 nucleotide sense strand and a 23 nucleotide antisense strand, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand.

When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In certain embodiments, every nucleotide in the sense strand and the antisense strand of the dsRNAi agent, including the nucleotides that are part of the motifs are modified nucleotides. In certain embodiments each residue is independently modified with a 2'-O-methyl or 3'-fluoro, e.g., in an alternating motif. Optionally, the dsRNAi agent further comprises a ligand (preferably GalNAc$_3$).

In certain embodiments, the dsRNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In certain embodiments, the dsRNAi agent comprises sense and antisense strands, wherein the dsRNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein Dicer cleavage of the dsRNAi agent preferentially results in an siRNA comprising the 3'-end of the second strand, thereby reducing expression of the target gene in the mammal. Optionally, the dsRNAi agent further comprises a ligand.

In certain embodiments, the sense strand of the dsRNAi agent contains at least one motif of three identical modifications on three consecutive nucleotides, where one of the motifs occurs at the cleavage site in the sense strand.

In certain embodiments, the antisense strand of the dsRNAi agent can also contain at least one motif of three identical modifications on three consecutive nucleotides, where one of the motifs occurs at or near the cleavage site in the antisense strand.

For a dsRNAi agent having a duplex region of 19-23 nucleotides in length, the cleavage site of the antisense strand is typically around the 10, 11, and 12 positions from the 5'-end. Thus the motifs of three identical modifications may occur at the 9, 10, 11 positions; the 10, 11, 12 positions; the 11, 12, 13 positions; the 12, 13, 14 positions; or the 13, 14, 15 positions of the antisense strand, the count starting from the first nucleotide from the 5'-end of the antisense strand, or, the count starting from the first paired nucleotide within the duplex region from the 5'-end of the antisense strand. The cleavage site in the antisense strand may also change according to the length of the duplex region of the dsRNAi agent from the 5'-end.

The sense strand of the dsRNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In some embodiments, the sense strand of the dsRNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistries of the motifs are distinct from each other, and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the dsRNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In some embodiments, the wing modification on the sense strand or antisense strand of the dsRNAi agent typically does not include the first one or two terminal nucleotides at the 3'-end, 5'-end, or both ends of the strand.

In other embodiments, the wing modification on the sense strand or antisense strand of the dsRNAi agent typically does not include the first one or two paired nucleotides within the duplex region at the 3'-end, 5'-end, or both ends of the strand.

When the sense strand and the antisense strand of the dsRNAi agent each contain at least one wing modification, the wing modifications may fall on the same end of the duplex region, and have an overlap of one, two, or three nucleotides.

When the sense strand and the antisense strand of the dsRNAi agent each contain at least two wing modifications, the sense strand and the antisense strand can be so aligned that two modifications each from one strand fall on one end of the duplex region, having an overlap of one, two, or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In some embodiments, every nucleotide in the sense strand and antisense strand of the dsRNAi agent, including the nucleotides that are part of the motifs, may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2'-hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3'- or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5'-end or ends can be phosphorylated.

It may be possible, e.g., to enhance stability, to include particular bases in overhangs, or to include modified nucleotides or nucleotide surrogates, in single strand overhangs, e.g., in a 5'- or 3'-overhang, or in both. For example, it can be desirable to include purine nucleotides in overhangs. In some embodiments all or some of the bases in a 3'- or 5'-overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In certain embodiments, the $N_a$ or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAA-BAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "ACACAC . . . " "BDBDBD . . . " or "CDCDCD . . . ," etc.

In some embodiments, the dsRNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5' to 3' of the strand and the alternating motif in the antisense strand may start with "BABABA" from 5' to 3' of the strand within the duplex region. As another example, the alternating motif in the sense strand may start with "AABBAABB" from 5' to 3' of the strand and the alternating motif in the antisense strand may start with "BBAABBAA" from 5' to 3' of the strand within the duplex region, so that there is a complete or partial shift of the modification patterns between the sense strand and the antisense strand.

In some embodiments, the dsRNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand or antisense strand interrupts the initial modification pattern present in the sense strand or antisense strand. This interruption of the modification pattern of the sense or antisense strand by introducing one or more motifs of three identical modifications on three consecutive nucleotides to the sense or antisense strand may enhance the gene silencing activity against the target gene.

In some embodiments, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ or $N_b$ may be present or absent when there is a wing modification present.

The iRNA may further comprise at least one phosphorothioate or methylphosphonate internucleotide linkage. The phosphorothioate or methylphosphonate internucleotide linkage modification may occur on any nucleotide of the sense strand, antisense strand, or both strands in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In some embodiments, the antisense strand comprises two phosphorothioate internucleotide linkages at the 5'-end and two phosphorothioate internucleotide linkages at the 3'-end, and the sense strand comprises at least two phosphorothioate internucleotide linkages at either the 5'-end or the 3'-end.

In some embodiments, the dsRNAi agent comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, or the 5' end of the antisense strand.

In some embodiments, the 2-nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the dsRNAi agent may additionally have two phosphorothioate internucleotide linkages between the terminal three nucleotides at both the 5'-end of the sense strand and at the 5'-end of the antisense strand.

In one embodiment, the dsRNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In certain embodiments, the dsRNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In certain embodiments, the nucleotide at the 1 position within the duplex region from the 5'-end in the antisense strand is selected from A, dA, dU, U, and dT. Alternatively, at least one of the first 1, 2, or 3 base pair within the duplex region from the 5'-end of the antisense strand is an AU base pair. For example, the first base pair within the duplex region from the 5'-end of the antisense strand is an AU base pair.

In other embodiments, the nucleotide at the 3'-end of the sense strand is deoxy-thymine (dT) or the nucleotide at the 3'-end of the antisense strand is deoxy-thymine (dT). For example, there is a short sequence of deoxy-thymine nucleotides, for example, two dT nucleotides on the 3'-end of the sense, antisense strand, or both strands.

In certain embodiments, the sense strand sequence may be represented by formula (I):

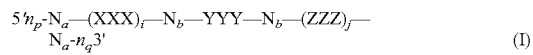

(I)

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;
each $N_b$ independently represents an oligonucleotide sequence comprising 0-10 modified nucleotides;
each $n_p$ and $n_q$ independently represent an overhang nucleotide;
wherein Nb and Y do not have the same modification; and
XXX, YYY, and ZZZ each independently represent one motif of three identical modifications on three consecutive nucleotides. Preferably YYY is all 2'-F modified nucleotides.

In some embodiments, the $N_a$ or $N_b$ comprises modifications of alternating pattern.

In some embodiments, the YYY motif occurs at or near the cleavage site of the sense strand. For example, when the dsRNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11, 12; or 11, 12, 13) of the sense strand, the count starting from the first nucleotide, from the 5'-end; or optionally, the count starting at the first paired nucleotide within the duplex region, from the 5'-end.

In one embodiment, i is 1 and j is 0, or i is 0 and j is 1, or both i and j are 1. The sense strand can therefore be represented by the following formulas:

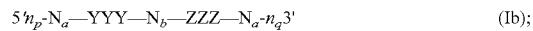

(Ib);

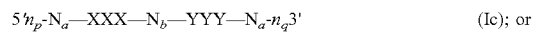

(Ic); or

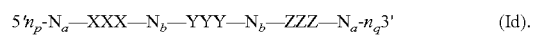

(Id).

When the sense strand is represented by formula (Ib), $N_b$ represents an oligonucleotide sequence comprising 0-10, 0-7, 0-5, 0-4, 0-2, or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2, or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2, or 0 modified nucleotides. Preferably, $N_b$ is 0, 1, 2, 3, 4, 5, or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

  (Ia).

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

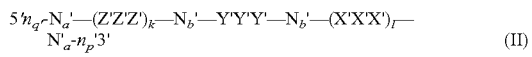  (II)

wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;
each $n_p'$ and $n_q'$ independently represent an overhang nucleotide;
wherein $N_b'$ and Y' do not have the same modification; and
X'X'X', Y'Y'Y', and Z'Z'Z' each independently represent one motif of three identical modifications on three consecutive nucleotides.

In some embodiments, the $N_a'$ or $N_b'$ comprises modifications of alternating pattern.

The Y'Y'Y' motif occurs at or near the cleavage site of the antisense strand. For example, when the dsRNAi agent has a duplex region of 17-23 nucleotides in length, the Y'Y'Y' motif can occur at positions 9, 10, 11; 10, 11, 12; 11, 12, 13; 12, 13, 14; or 13, 14, 15 of the antisense strand, with the count starting from the first nucleotide, from the 5'-end; or optionally, the count starting at the first paired nucleotide within the duplex region, from the 5'-end. Preferably, the Y'Y'Y' motif occurs at positions 11, 12, 13.

In certain embodiments, Y'Y'Y' motif is all 2'-OMe modified nucleotides.

In certain embodiments, k is 1 and l is 0, or k is 0 and l is 1, or both k and l are 1.

The antisense strand can therefore be represented by the following formulas:

  (IIb);

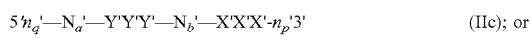  (IIc); or

  (IId).

When the antisense strand is represented by formula (IIb), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5, or 6.

In other embodiments, k is 0 and l is 0 and the antisense strand may be represented by the formula:

  (Ia).

When the antisense strand is represented as formula (IIa), each $N_a'$ independently represents an oligonucleotide sequence comprising 2-20, 2-15, or 2-10 modified nucleotides. Each of X', Y' and Z' may be the same or different from each other.

Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y', and Z', in particular, may represent a 2'-O-methyl modification or a 2'-fluoro modification.

In some embodiments, the sense strand of the dsRNAi agent may contain YYY motif occurring at 9, 10, and 11 positions of the strand when the duplex region is 21 nt, the count starting from the first nucleotide from the 5'-end, or optionally, the count starting at the first paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In some embodiments the antisense strand may contain Y'Y'Y' motif occurring at positions 11, 12, 13 of the strand, the count starting from the first nucleotide from the 5'-end, or optionally, the count starting at the first paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with an antisense strand being represented by any one of formulas (IIa), (IIb), (IIc), and (IId), respectively.

Accordingly, the dsRNAi agents for use in the methods of the invention may comprise a sense strand and an antisense strand, each strand having 14 to 30 nucleotides, the iRNA duplex represented by formula (III):

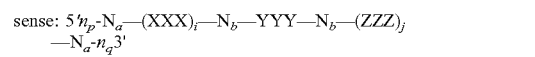

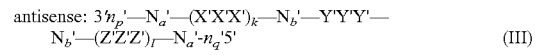  (III)

wherein:
j, k, and l are each independently 0 or 1;
p, p', q, and q' are each independently 0-6;
each $N_a$ and $N_a'$ independently represents an oligonucleotide sequence comprising 0-25 modified nucleotides, each sequence comprising at least two differently modified nucleotides;

each $N_b$ and $N_b'$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming an iRNA duplex include the formulas below:

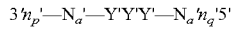 (IIIa)

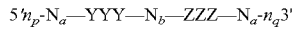

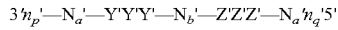 (IIIb)

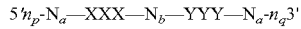

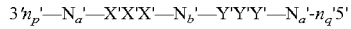 (IIIc)

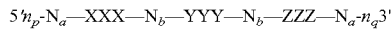

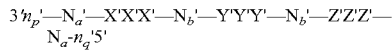 (IIId)

When the dsRNAi agent is represented by formula (IIIa), each $N_a$ independently represents an oligonucleotide sequence comprising 2-20, 2-15, or 2-10 modified nucleotides.

When the dsRNAi agent is represented by formula (IIIb), each $N_b$ independently represents an oligonucleotide sequence comprising 1-10, 1-7, 1-5, or 1-4 modified nucleotides. Each $N_a$ independently represents an oligonucleotide sequence comprising 2-20, 2-15, or 2-10 modified nucleotides.

When the dsRNAi agent is represented as formula (IIIc), each $N_b$, $N_b'$ independently represents an oligonucleotide sequence comprising 0-10, 0-7, 0-10, 0-7, 0-5, 0-4, 0-2, or 0 modified nucleotides. Each $N_a$ independently represents an oligonucleotide sequence comprising 2-20, 2-15, or 2-10 modified nucleotides.

When the dsRNAi agent is represented as formula (IIId), each $N_b$, $N_b'$ independently represents an oligonucleotide sequence comprising 0-10, 0-7, 0-10, 0-7, 0-5, 0-4, 0-2, or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$, and $N_b'$ independently comprises modifications of alternating pattern.

Each of X, Y, and Z in formulas (III), (IIIa), (IIIb), (IIIc), and (IIId) may be the same or different from each other.

When the dsRNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the dsRNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the dsRNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In certain embodiments, the modification on the Y nucleotide is different than the modification on the Y' nucleotide, the modification on the Z nucleotide is different than the modification on the Z' nucleotide, or the modification on the X nucleotide is different than the modification on the X' nucleotide.

In certain embodiments, when the dsRNAi agent is represented by formula (IIId), the $N_a$ modifications are 2'-O-methyl or 2'-fluoro modifications. In other embodiments, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet other embodiments, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker (described below). In other embodiments, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, when the dsRNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, the dsRNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In some embodiments, the dsRNAi agent is a multimer containing three, four, five, six, or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two dsRNAi agents represented by at least one of formulas (III), (IIIa), (IIIb), (IIIc), and (IIId) are linked to each other at the 5' end, and one or both of the 3' ends, and are optionally conjugated to a ligand. Each of the agents can target the same gene or two different genes; or each of the agents can target same gene at two different target sites.

In certain embodiments, an RNAi agent of the invention may contain a low number of nucleotides containing a 2'-fluoro modification, e.g., 10 or fewer nucleotides with 2'-fluoro modification. For example, the RNAi agent may contain 10, 9, 8, 7, 6, 5, 4, 3, 2, 1 or 0 nucleotides with a 2'-fluoro modification. In a specific embodiment, the RNAi agent of the invention contains 10 nucleotides with a 2'-fluoro modification, e.g., 4 nucleotides with a 2'-fluoro modification in the sense strand and 6 nucleotides with a 2'-fluoro modification in the antisense strand. In another specific embodiment, the RNAi agent of the invention contains 6 nucleotides with a 2'-fluoro modification, e.g., 4 nucleotides with a 2'-fluoro modification in the sense strand and 2 nucleotides with a 2'-fluoro modification in the antisense strand.

In other embodiments, an RNAi agent of the invention may contain an ultra low number of nucleotides containing a 2'-fluoro modification, e.g., 2 or fewer nucleotides containing a 2'-fluoro modification. For example, the RNAi agent may contain 2, 1 of 0 nucleotides with a 2'-fluoro modification. In a specific embodiment, the RNAi agent may contain 2 nucleotides with a 2'-fluoro modification, e.g., 0 nucleotides with a 2-fluoro modification in the sense strand and 2 nucleotides with a 2'-fluoro modification in the antisense strand.

Various publications describe multimeric iRNAs that can be used in the methods of the invention. Such publications include WO2007/091269, U.S. Pat. No. 7,858,769, WO2010/141511, WO2007/117686, WO2009/014887, and WO2011/031520 the entire contents of each of which are hereby incorporated herein by reference.

In certain embodiments, the compositions and methods of the disclosure include a vinyl phosphonate (VP) modification of an RNAi agent as described herein. In exemplary embodiments, a vinyl phosphonate of the disclosure has the following structure:

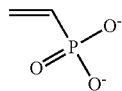

A vinyl phosphonate of the instant disclosure may be attached to either the antisense or the sense strand of a dsRNA of the disclosure. In certain preferred embodiments, a vinyl phosphonate of the instant disclosure is attached to the antisense strand of a dsRNA, optionally at the 5' end of the antisense strand of the dsRNA.

Vinyl phosphate modifications are also contemplated for the compositions and methods of the instant disclosure. An exemplary vinyl phosphate structure is:

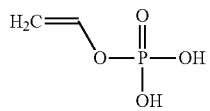

As described in more detail below, the iRNA that contains conjugations of one or more carbohydrate moieties to an iRNA can optimize one or more properties of the iRNA. In many cases, the carbohydrate moiety will be attached to a modified subunit of the iRNA. For example, the ribose sugar of one or more ribonucleotide subunits of a iRNA can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide, or polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The iRNA may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl, and decalin; preferably, the acyclic group is a serinol backbone or diethanolamine backbone.

i. Thermally Destabilizing Modifications

In certain embodiments, a dsRNA molecule can be optimized for RNA interference by incorporating thermally destabilizing modifications in the seed region of the antisense strand (i.e., at positions 2-9 of the 5'-end of the antisense strand) to reduce or inhibit off-target gene silencing. It has been discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, one or more thermally destabilizing modification(s) of the duplex is/are located in positions 2-9, or preferably positions 4-8, from the 5'-end of the antisense strand. In some further embodiments, the thermally destabilizing modification(s) of the duplex is/are located at position 6, 7 or 8 from the 5'-end of the antisense strand. In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s). In some embodiments, the thermally destabilizing modification of the duplex is located at position 2, 3, 4, 5 or 9 from the 5'-end of the antisense strand.

An iRNA agent comprises a sense strand and an antisense strand, each strand having 14 to 40 nucleotides. The RNAi agent may be represented by formula (L):

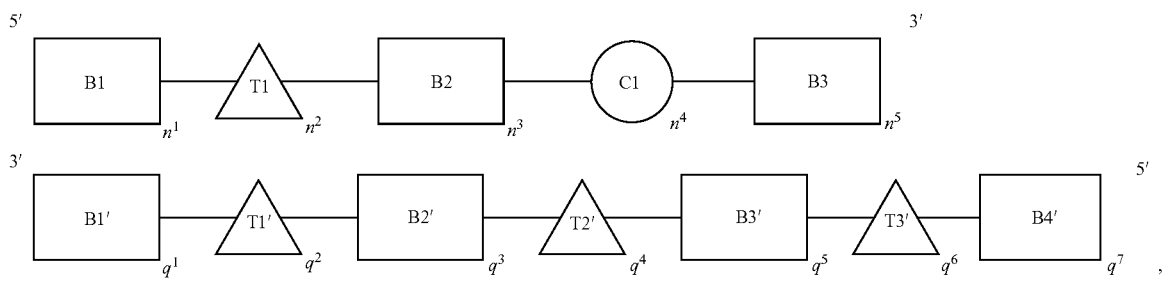

In formula (L), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In one embodiment, B1, B2, B3, B1', B2', B3', and B4' each contain 2'-OMe modifications. In one embodiment, B1, B2, B3, B1', B2', B3', and B4' each contain 2'-OMe or 2'-F modifications. In one embodiment, at least one of B1, B2, B3, B1', B2', B3', and B4' contain 2'-O—N-methylacetamido (2'-O-NMA) modification.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. In one example, C1 is at position 15 from the 5'-end of the sense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In one embodiment, C1 has thermally destabilizing modification selected from the group consisting of: i) mismatch with the opposing nucleotide in the antisense strand; ii) abasic modification selected from the group consisting of:

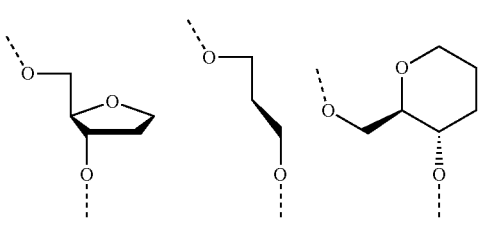

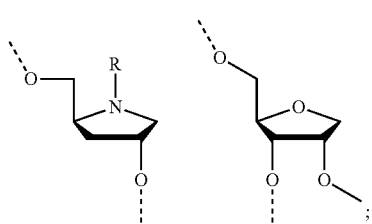

and iii) sugar modification selected from the group consisting of:

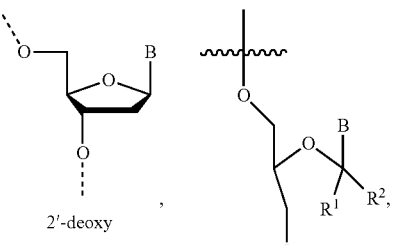

2'-deoxy

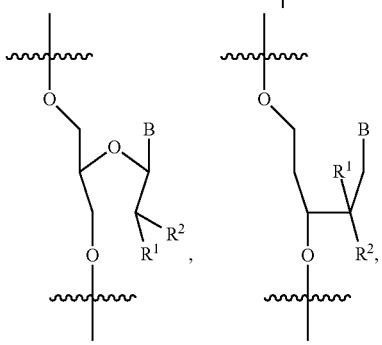

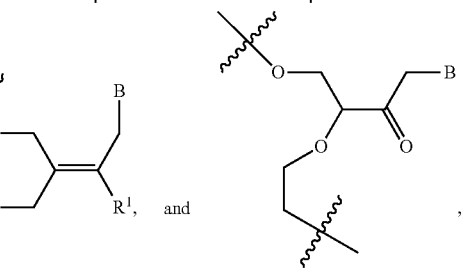

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In one embodiment, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

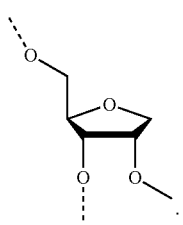

T1, T1', T2', and T3' each independently represent a nucleotide comprising a modification providing the nucleotide a steric bulk that is less or equal to the steric bulk of a 2'-OMe modification. A steric bulk refers to the sum of steric effects of a modification. Methods for determining steric effects of a modification of a nucleotide are known to one skilled in the art. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In one embodiment, T1 is DNA. In one embodiment, T1' is DNA, RNA or LNA. In one embodiment, T2' is DNA or RNA. In one embodiment, T3' is DNA or RNA.

$n^1$, $n^3$, and $q^1$ are independently 4 to 15 nucleotides in length.

$n^5$, $q^3$, and $q^7$ are independently 1-6 nucleotide(s) in length.

$n^4$, $q^2$, and $q^6$ are independently 1-3 nucleotide(s) in length; alternatively, $n^4$ is 0.

$q^5$ is independently 0-10 nucleotide(s) in length.

$n^2$ and $q^4$ are independently 0-3 nucleotide(s) in length.

Alternatively, $n^4$ is 0-3 nucleotide(s) in length.

In one embodiment, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$, $q^2$, and $q^6$ are each 1.

In one embodiment, $n^2$, $n^4$, $q^2$, $q^4$, and $q^6$ are each 1.

In one embodiment, C1 is at position 14-17 of the 5'-end of the sense strand, when the sense strand is 19-22 nucleotides in length, and $n^4$ is 1. In one embodiment, C1 is at position 15 of the 5'-end of the sense strand In one embodiment, T3' starts at position 2 from the 5' end of the antisense strand. In one example, T3' is at position 2 from the 5' end of the antisense strand and $q^6$ is equal to 1.

In one embodiment, T1' starts at position 14 from the 5' end of the antisense strand. In one example, T1' is at position 14 from the 5' end of the antisense strand and $q^2$ is equal to 1.

In an exemplary embodiment, T3' starts from position 2 from the 5' end of the antisense strand and T1' starts from position 14 from the 5' end of the antisense strand. In one example, T3' starts from position 2 from the 5' end of the antisense strand and $q^6$ is equal to 1 and T1' starts from position 14 from the 5' end of the antisense strand and $q^2$ is equal to 1.

In one embodiment, T1' and T3' are separated by 11 nucleotides in length (i.e. not counting the T1' and T3' nucleotides).

In one embodiment, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In one embodiment, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In one embodiment, T1 is at the cleavage site of the sense strand. In one example, T1 is at position 11 from the 5' end of the sense strand, when the sense strand is 19-22 nucleotides in length, and $n^2$ is 1. In an exemplary embodiment, T1 is at the cleavage site of the sense strand at position 11 from the 5' end of the sense strand, when the sense strand is 19-22 nucleotides in length, and $n^2$ is 1, In one embodiment, T2' starts at position 6 from the 5' end of the antisense strand. In one example, T2' is at positions 6-10 from the 5' end of the antisense strand, and $q^4$ is 1.

In an exemplary embodiment, T1 is at the cleavage site of the sense strand, for instance, at position 11 from the 5' end of the sense strand, when the sense strand is 19-22 nucleotides in length, and $n^2$ is 1; T1' is at position 14 from the 5' end of the antisense strand, and $q^2$ is equal to 1, and the modification to T1' is at the 2' position of a ribose sugar or at positions in a non-ribose, acyclic or backbone that provide less steric bulk than a 2'-OMe ribose; T2' is at positions 6-10 from the 5' end of the antisense strand, and $q^4$ is 1; and T3' is at position 2 from the 5' end of the antisense strand, and $q^6$ is equal to 1, and the modification to T3' is at the 2' position or at positions in a non-ribose, acyclic or backbone that provide less than or equal to steric bulk than a 2'-OMe ribose.

In one embodiment, T2' starts at position 8 from the 5' end of the antisense strand. In one example, T2' starts at position 8 from the 5' end of the antisense strand, and $q^4$ is 2.

In one embodiment, T2' starts at position 9 from the 5' end of the antisense strand. In one example, T2' is at position 9 from the 5' end of the antisense strand, and $q^4$ is 1.

In one embodiment, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 7, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within positions 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

The RNAi agent can comprise a phosphorus-containing group at the 5'-end of the sense strand or antisense strand. The 5'-end phosphorus-containing group can be 5'-end phosphate (5'-P), 5'-end phosphorothioate (5'-PS), 5'-end phosphorodithioate (5'-$PS_2$), 5'-end vinylphosphonate (5'-VP), 5'-end methylphosphonate (MePhos), or 5'-deoxy-5'-C-malonyl

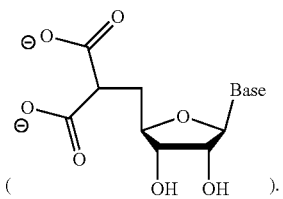

When the 5'-end phosphorus-containing group is 5'-end vinylphosphonate (5'-VP), the 5'-VP can be either 5'-E-VP isomer (i.e., trans-vinylphosphate,

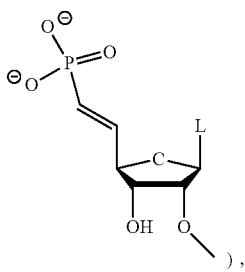

5'-Z—VP isomer (i.e., cis-vinylphosphate,

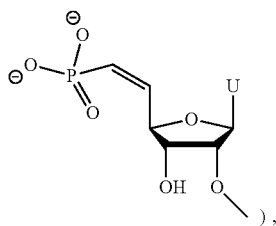

or mixtures thereof.

In one embodiment, the RNAi agent comprises a phosphorus-containing group at the 5'-end of the sense strand. In one embodiment, the RNAi agent comprises a phosphorus-containing group at the 5'-end of the antisense strand.

In one embodiment, the RNAi agent comprises a 5'-P. In one embodiment, the RNAi agent comprises a 5'-P in the antisense strand.

In one embodiment, the RNAi agent comprises a 5'-PS. In one embodiment, the RNAi agent comprises a 5'-PS in the antisense strand.

In one embodiment, the RNAi agent comprises a 5'-VP. In one embodiment, the RNAi agent comprises a 5'-VP in the antisense strand. In one embodiment, the RNAi agent comprises a 5'-E-VP in the antisense strand. In one embodiment, the RNAi agent comprises a 5'-Z—VP in the antisense strand.

In one embodiment, the RNAi agent comprises a 5'-$PS_2$. In one embodiment, the RNAi agent comprises a 5'-$PS_2$ in the antisense strand.

In one embodiment, the RNAi agent comprises a 5'-$PS_2$. In one embodiment, the RNAi agent comprises a 5'-deoxy-5'-C-malonyl in the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-VP. The 5'-VP may be 5'-E-VP, 5'-Z—VP, or combination thereof. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNAi RNA agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS$_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof), and a targeting ligand.

In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS$_2$ and a targeting ligand. In one embodiment, the 5'-PS$_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'- F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In a particular embodiment, an RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker; and
(iii) 2'-F modifications at positions 1, 3, 5, 7, 9 to 11, 13, 17, 19, and 21, and 2'-OMe modifications at positions 2, 4, 6, 8, 12, 14 to 16, 18, and 20 (counting from the 5' end); and
(b) an antisense strand having:
(i) a length of 23 nucleotides;
(ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
(iii) phosphorothioate internucleotide linkages between nucleotide positions 21 and 22, and between nucleotide positions 22 and 23 (counting from the 5' end);
wherein the dsRNA agents have a two nucleotide overhang at the 3'-end of the antisense strand, and a blunt end at the 5'-end of the antisense strand.

In another particular embodiment, an RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 1, 3, 5, 7, 9 to 11, 13, 15, 17, 19, and 21, and 2'-OMe modifications at positions 2, 4, 6, 8, 12, 14, 16, 18, and 20 (counting from the 5' end); and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, and 12 to 21, 2'-F modifications at positions 7, and 9, and a deoxy-nucleotide (e.g. dT) at position 11 (counting from the 5' end); and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end);
and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, 12, 14, and 16 to 21, and 2'-F modifications at positions 7, 9, 11, 13, and 15; and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 9, and 12 to 21, and 2'-F modifications at positions 10, and 11; and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 1, 3, 5, 7, 9 to 11, and 13, and 2'-OMe modifications at positions 2, 4, 6, 8, 12, and 14 to 21; and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and
(iv) phosphorothioate internucleotide linkages between nucleotide positions 1 and 2, and between nucleotide positions 2 and 3 (counting from the 5' end);

and
(b) an antisense strand having:
(i) a length of 25 nucleotides;
(ii) 2'-OMe modifications at positions 1, 4, 6, 7, 9, 11 to 13, 15, 17, and 19 to 23, 2'-F modifications at positions 2, 3, 5, 8, 10, 14, 16, and 18, and desoxy-nucleotides (e.g. dT) at positions 24 and 25 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a four nucleotide overhang at the 3'-end of the antisense strand, and a blunt end at the 5'-end of the antisense strand.

In another particular embodiment, a RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, and 12 to 21, and 2'-F modifications at positions 7, and 9 to 11; and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-OMe modifications at positions 1, 3 to 5, 7, 8, 10 to 13, 15, and 17 to 23, and 2'-F modifications at positions 2, 6, 9, 14, and 16 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, and 12 to 21, and 2'-F modifications at positions 7, and 9 to 11; and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-OMe modifications at positions 1, 3 to 5, 7, 10 to 13, 15, and 17 to 23, and 2'-F modifications at positions 2, 6, 8, 9, 14, and 16 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
wherein the RNAi agents have a two nucleotide overhang at the 3'-end of the antisense strand, and a blunt end at the 5'-end of the antisense strand.

In another particular embodiment, a RNAi agent of the present invention comprises:
(a) a sense strand having:
(i) a length of 19 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 4, 6, and 10 to 19, and 2'-F modifications at positions 5, and 7 to 9; and
(iv) phosphorothioate internucleotide linkages between nucleotide positions 1 and 2, and between nucleotide positions 2 and 3 (counting from the 5' end);
and
(b) an antisense strand having:
(i) a length of 21 nucleotides;
(ii) 2'-OMe modifications at positions 1, 3 to 5, 7, 10 to 13, 15, and 17 to 21, and 2'-F modifications at positions 2, 6, 8, 9, 14, and 16 (counting from the 5' end); and
(iii) phosphorothioate internucleotide linkages between nucleotide positions 1 and 2, between nucleotide positions 2 and 3, between nucleotide positions 19 and 20, and between nucleotide positions 20 and 21 (counting from the 5' end);
wherein the RNAi agents have a two nucleotide overhang at the 3'-end of the antisense strand, and a blunt end at the 5'-end of the antisense strand.

In certain embodiments, the iRNA for use in the methods of the invention is an agent selected from agents listed in any one of Tables 2-5, 14, and 15. These agents may further comprise a ligand.

III. iRNAs Conjugated to Ligands

Another modification of the RNA of an iRNA of the invention involves chemically linking to the iRNA one or more ligands, moieties or conjugates that enhance the activity, cellular distribution, or cellular uptake of the iRNA e.g., into a cell. Such moieties include but are not limited to lipid moieties such as a cholesterol moiety (Letsinger et al., *Proc. Natl. Acid. Sci. USA,* 1989, 86: 6553-6556). In other embodiments, the ligand is cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylaminocarbonyloxycholesterol moiety (Crooke et al., *J. Pharmacol. Exp. Ther.,* 1996, 277:923-937).

In certain embodiments, a ligand alters the distribution, targeting, or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands do not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, the ligand is a multivalent galactose, e.g., an N-acetylgalactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxol, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins, etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other methods for such synthesis known in the art may additionally or alternatively be employed. It is also known to use similar techniques to prepare other oligonucleotides, such as the phosphorothioates and alkylated derivatives.

In the ligand-conjugated iRNAs and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In other embodiments, the lipid based ligand binds HSA weakly or not at all, such that the conjugate will be preferably distributed to the kidney. Other moieties that target to kidney cells can also be used in place of, or in addition to, the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 18). An RFGF analogue (e.g., amino acid sequence AALLPVL-LAAP (SEQ ID NO:19) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:20) and the *Drosophila* Antennapedia protein (RQIKIWFQNRRMKWKK (SEQ ID NO:21) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA further comprises a carbohydrate. The carbohydrate conjugated iRNA is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri-, and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In certain embodiments, a carbohydrate conjugate for use in the compositions and methods of the invention is a monosaccharide.

In certain embodiments, the monosaccharide is an N-acetylgalactosamine (GalNAc). GalNAc conjugates, which comprise one or more N-acetylgalactosamine (GalNAc) derivatives, are described, for example, in U.S. Pat. No. 8,106,022, the entire content of which is hereby incorporated herein by reference. In some embodiments, the GalNAc conjugate serves as a ligand that targets the iRNA to particular cells. In some embodiments, the GalNAc conjugate targets the iRNA to liver cells, e.g., by serving as a ligand for the asialoglycoprotein receptor of liver cells (e.g., hepatocytes).

In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc conjugate is conjugated to the iRNA agent (e.g., to the 3' end of the sense strand) via a linker, e.g., a linker as described herein. In some embodiments the GalNAc conjugate is conjugated to the 5' end of the sense strand. In some embodiments, the GalNAc conjugate is conjugated to the iRNA agent (e.g., to the 5' end of the sense strand) via a linker, e.g., a linker as described herein.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker. In other embodiments of the invention, the GalNAc or GalNAc derivative is attached to an iRNA agent of the invention via a tetravalent linker.

In certain embodiments, the double stranded RNAi agents of the invention comprise one GalNAc or GalNAc derivative attached to the iRNA agent. In certain embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In one embodiment, a carbohydrate conjugate for use in the compositions and methods of the invention is selected from the group consisting of:

Formula II

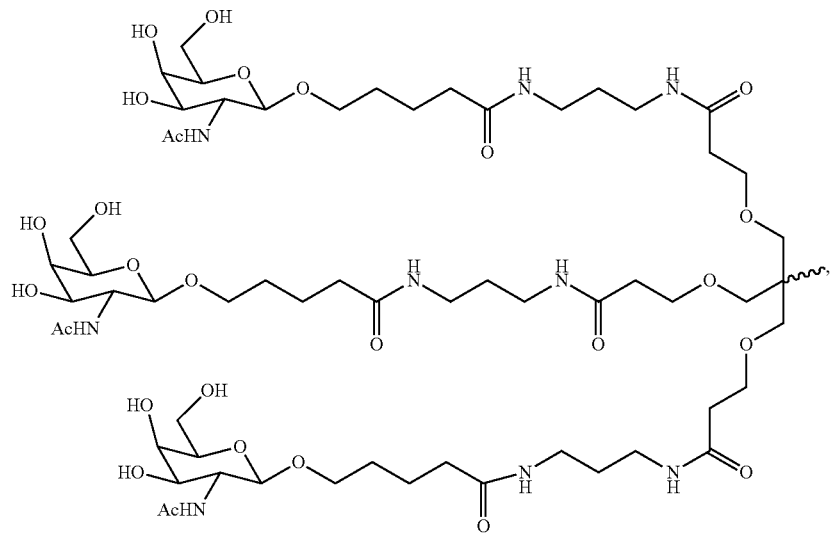

-continued
Formula III
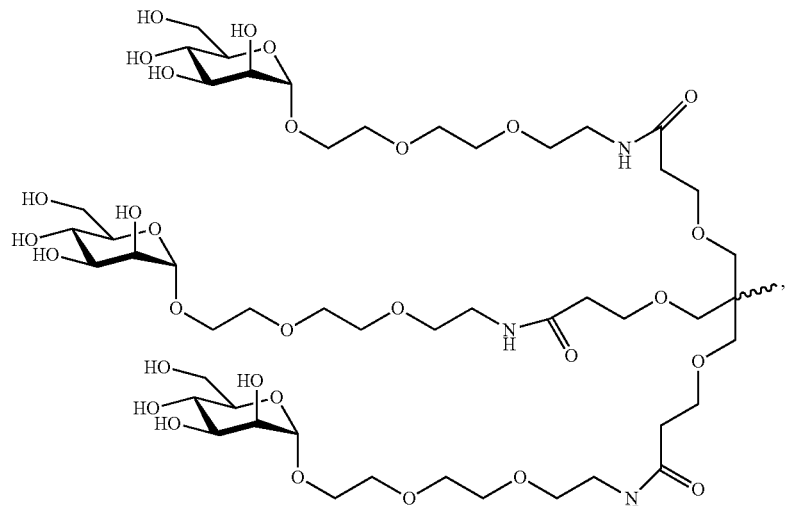
Formula IV
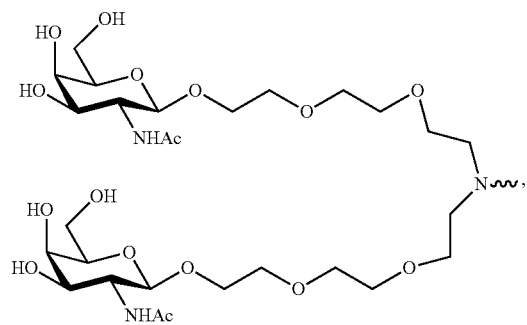
Formula V
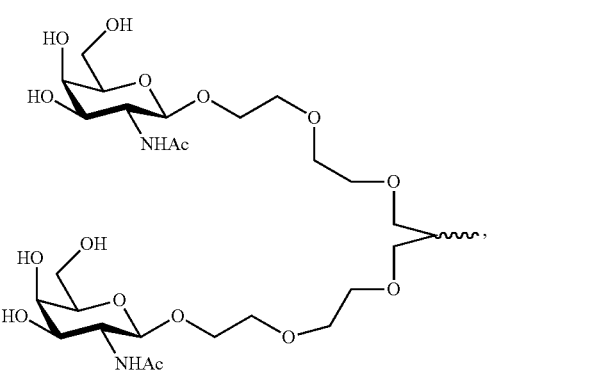
Formula VI
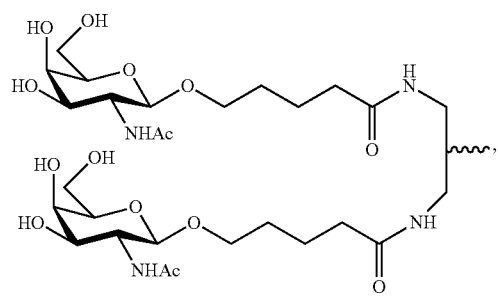
Formula VII
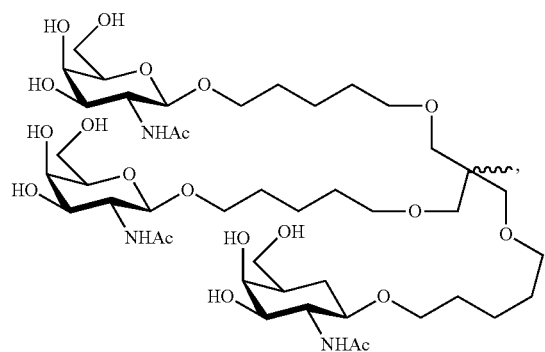
Formula VIII
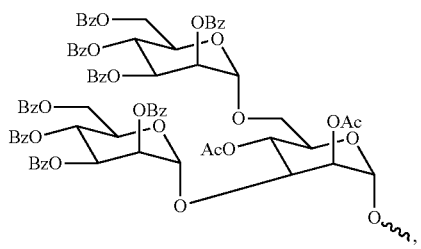

Formula IX
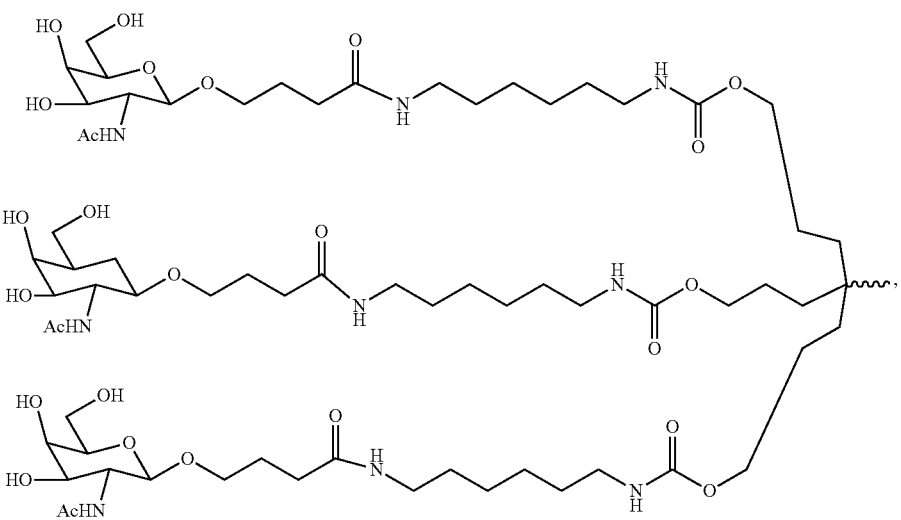
Formula X
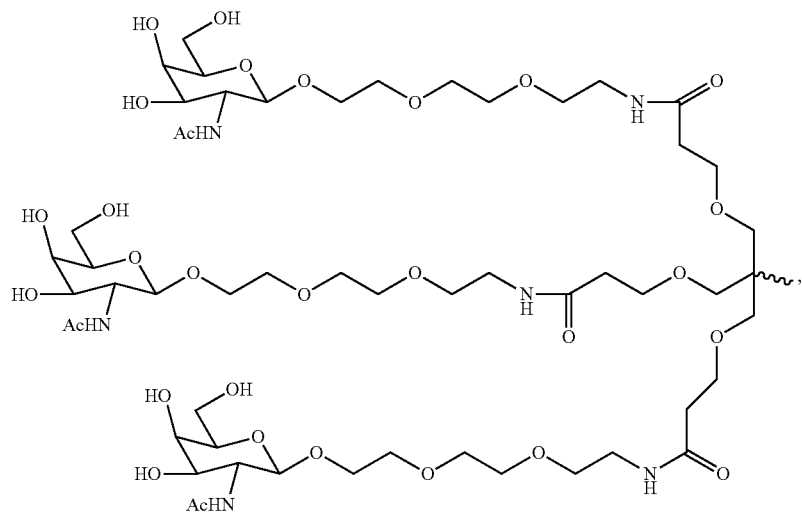
Formula XI
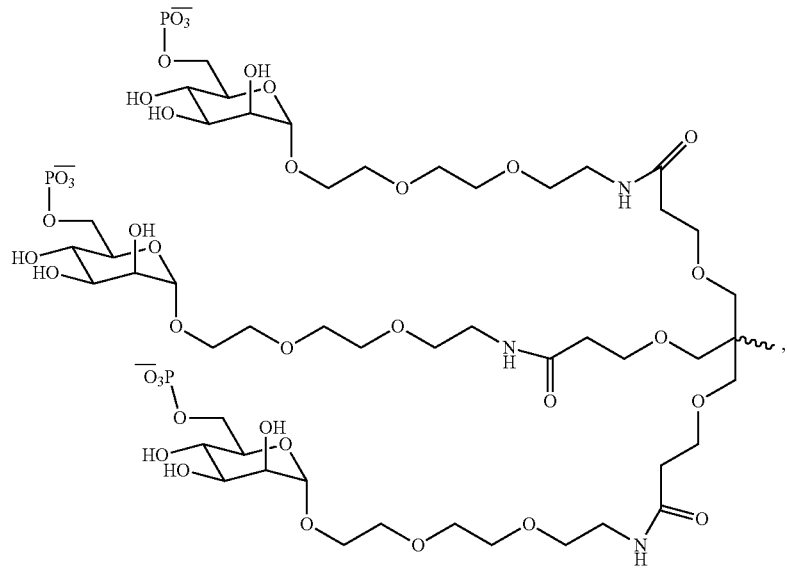

-continued
Formula XII
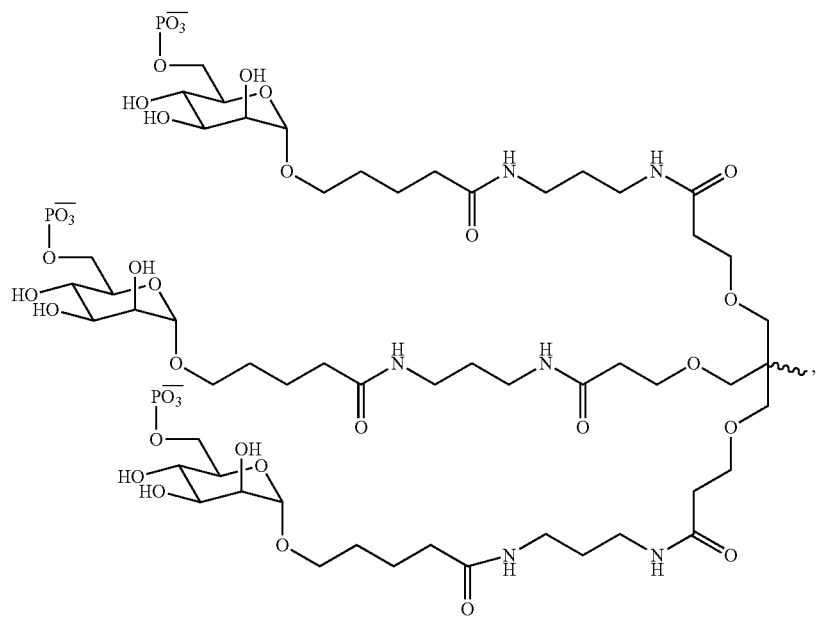
Formula XIII
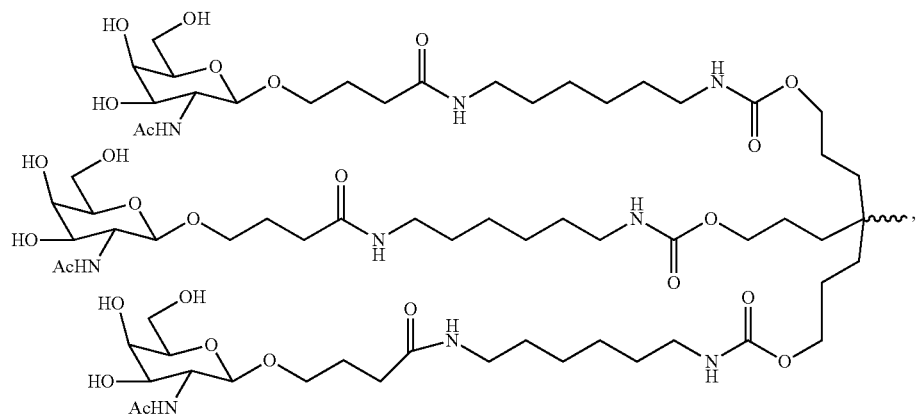
Formula XIV
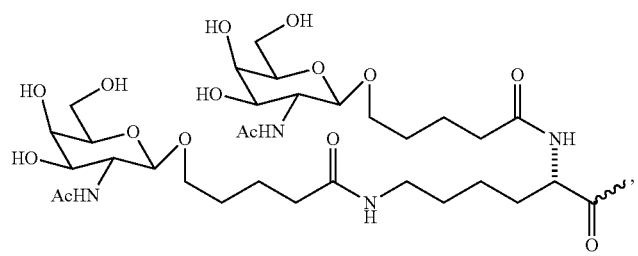
Formula XV
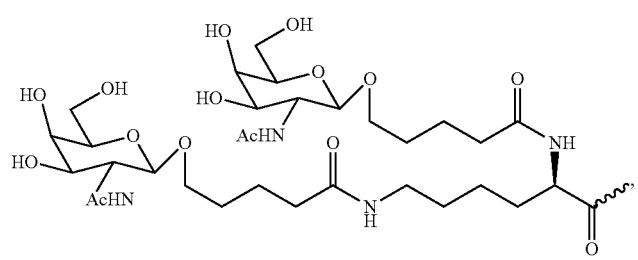

-continued
Formula XVI
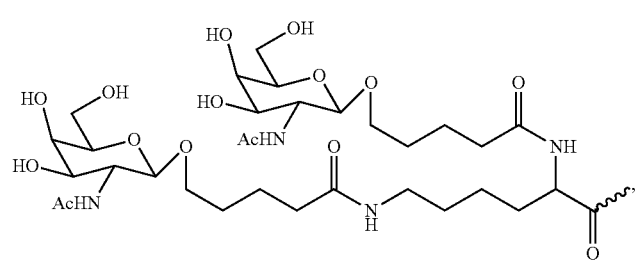
Formula XVII
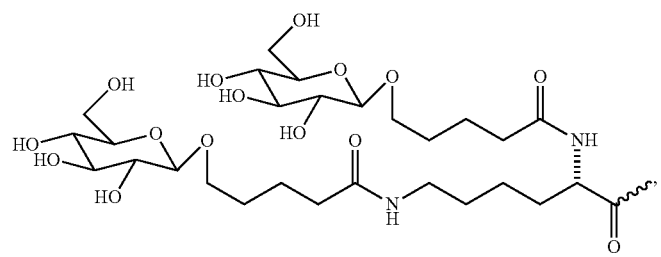
Formula XVIII
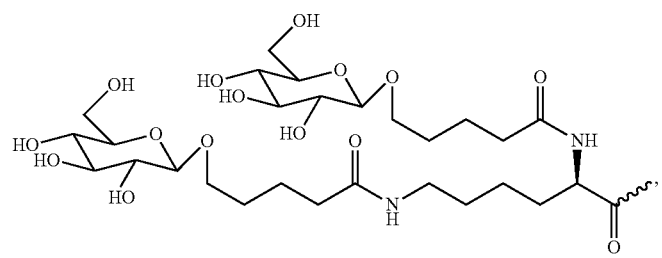
Formula XIX
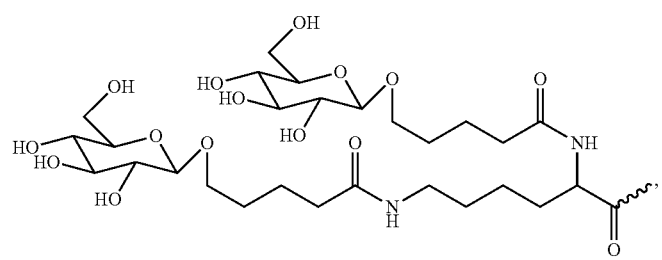
Formula XX
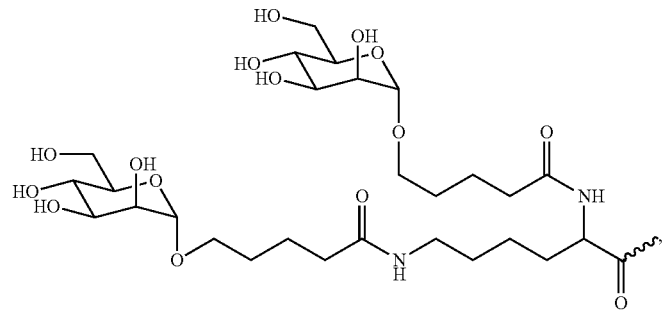

-continued
Formula XXI
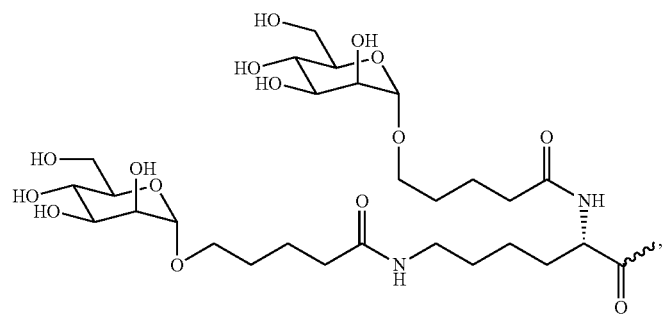
Formula XXII
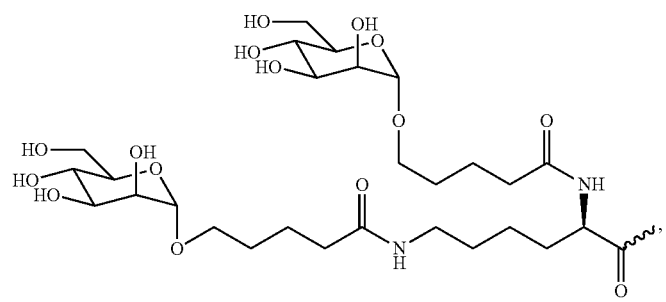
Formula XXIII
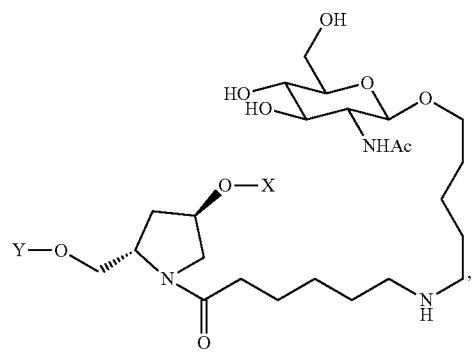
(Formula XXIV)
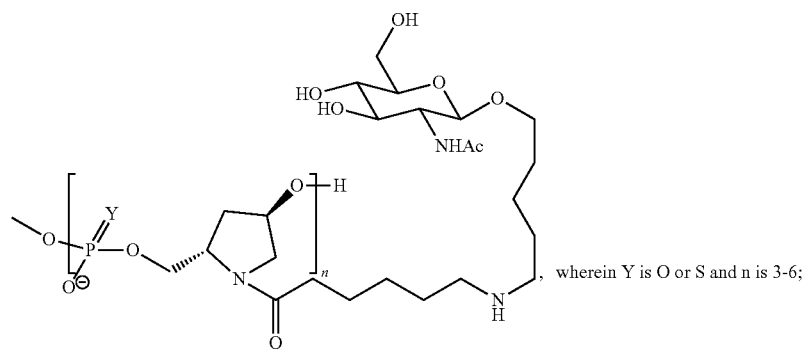, wherein Y is O or S and n is 3-6;

-continued
(Formula XXV)
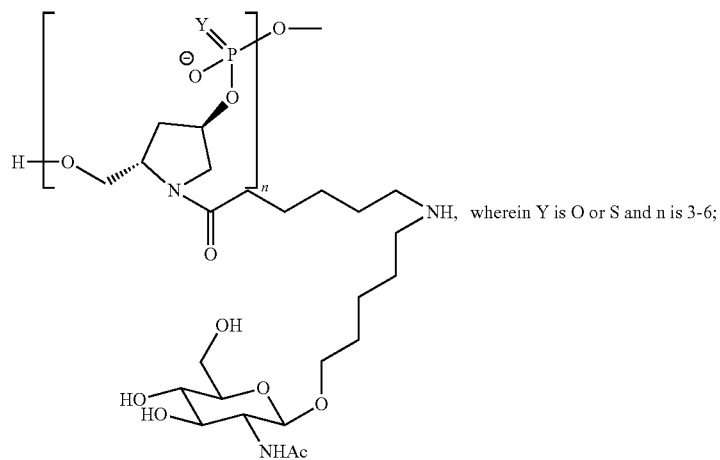
wherein Y is O or S and n is 3-6;
Formula XXVI
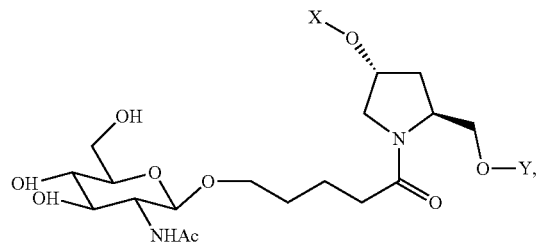
Formula XXVII
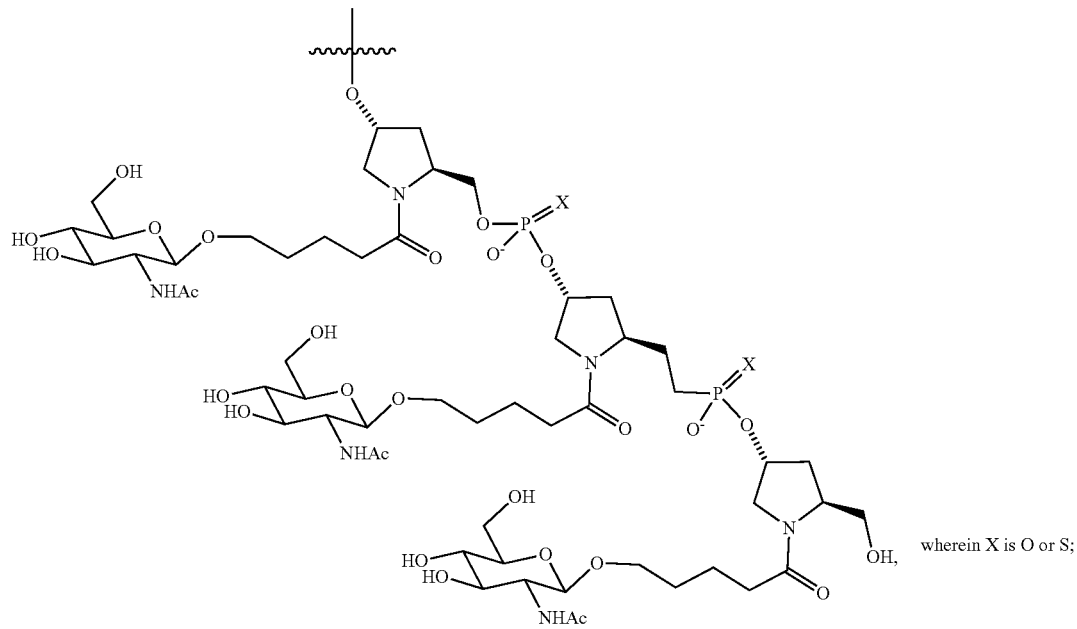
wherein X is O or S;

(Formula XXVII)
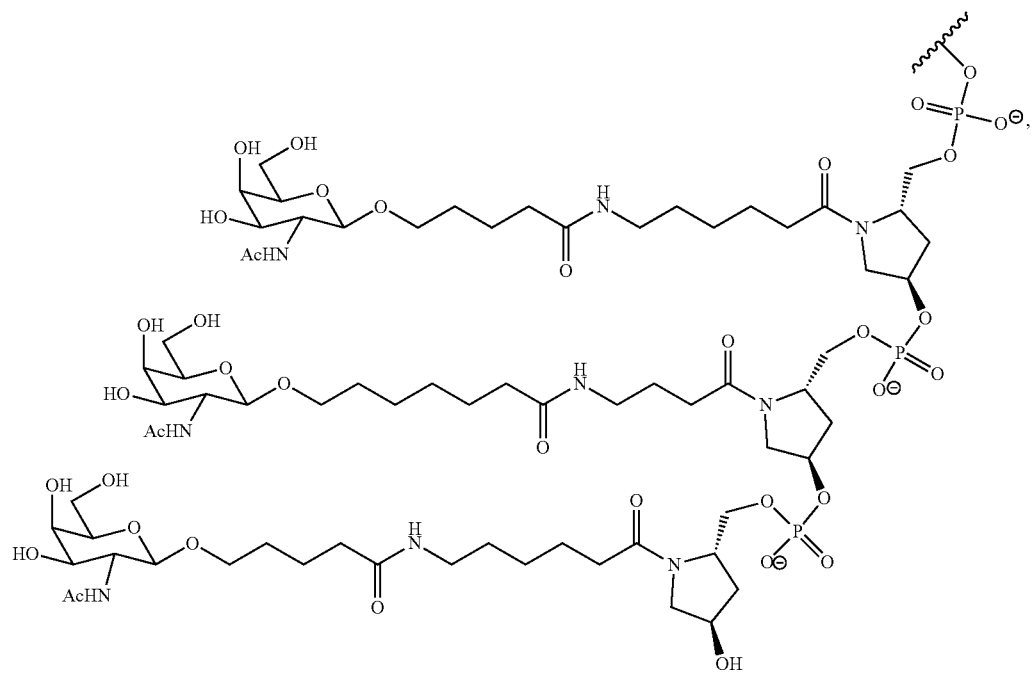
Formula XXIX
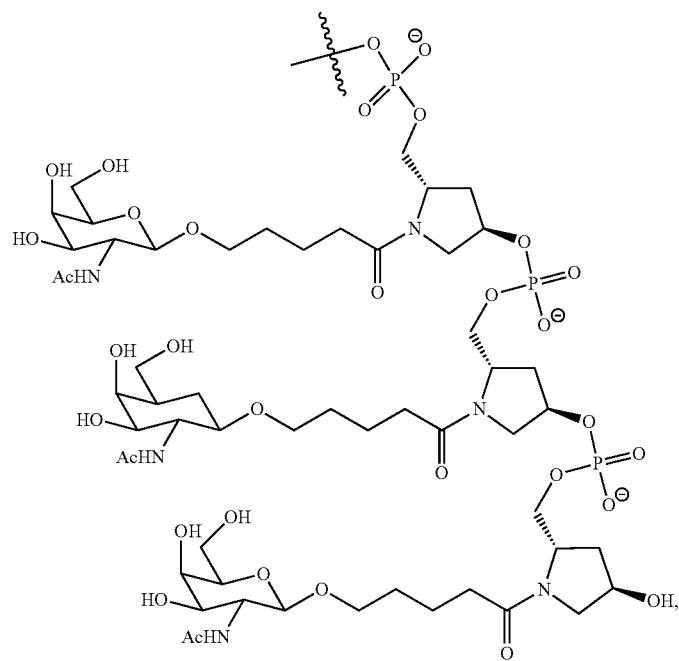

-continued
Formula XXX
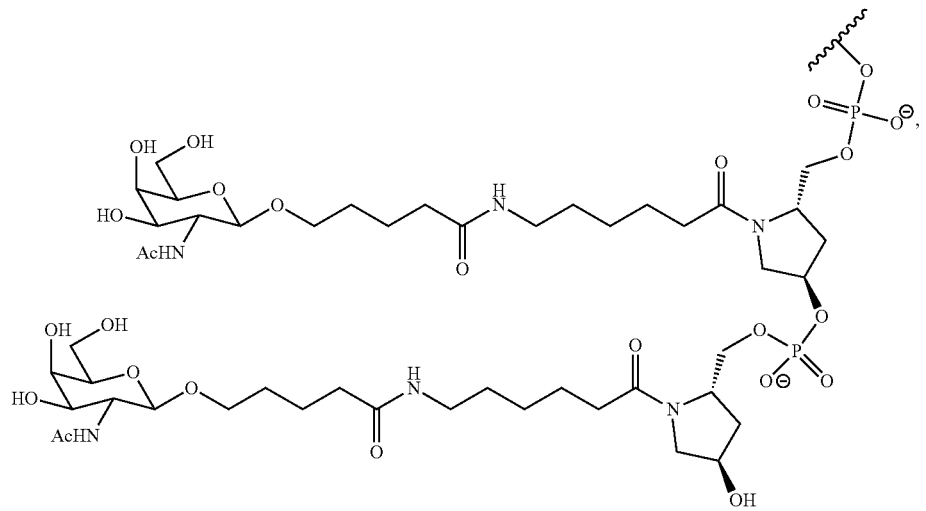
Formula XXXI
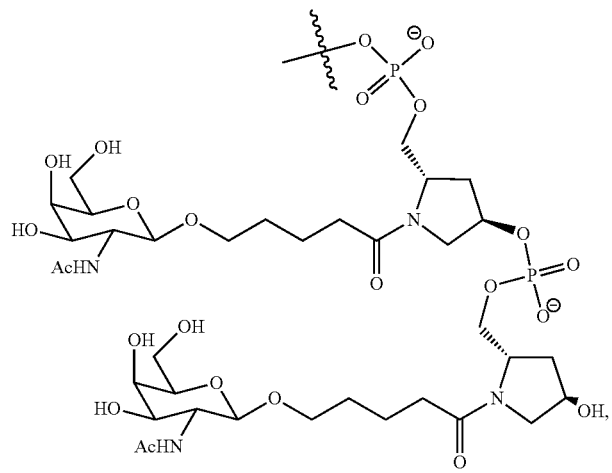
Formula XXXII
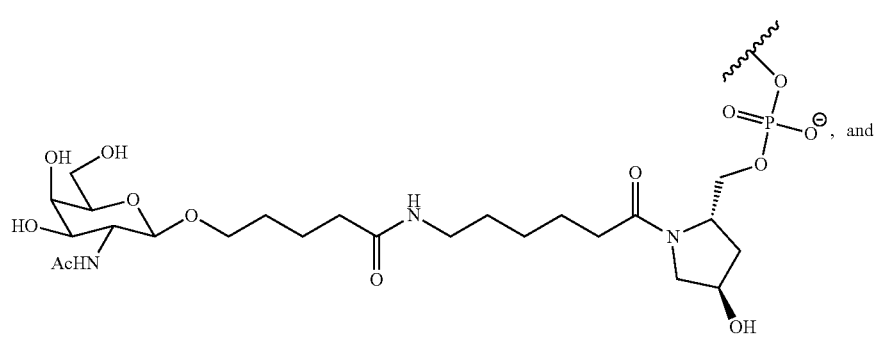
Formula XXXIII
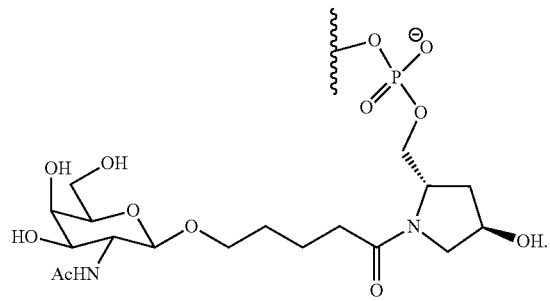

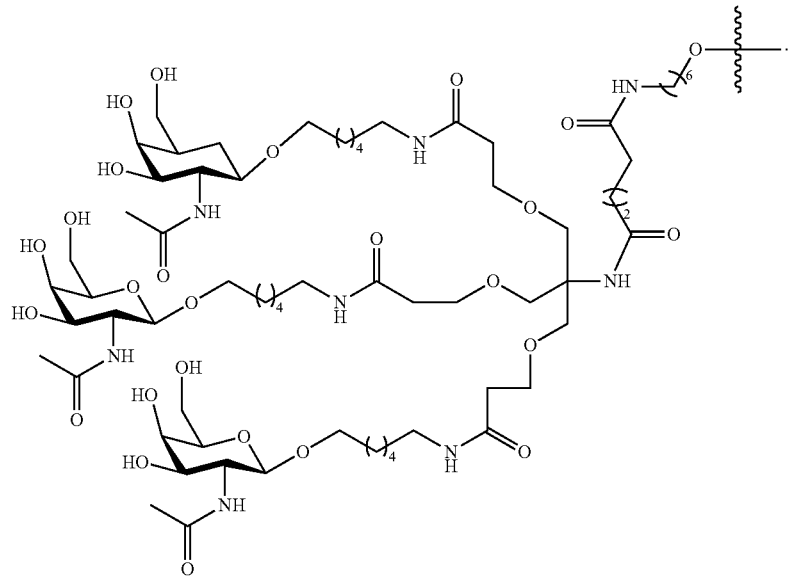
XXXIV
In another embodiment, a carbohydrate conjugate for use in the compositions and methods of the invention is a monosaccharide. In one embodiment, the monosaccharide is an N-acetylgalactosamine, such as
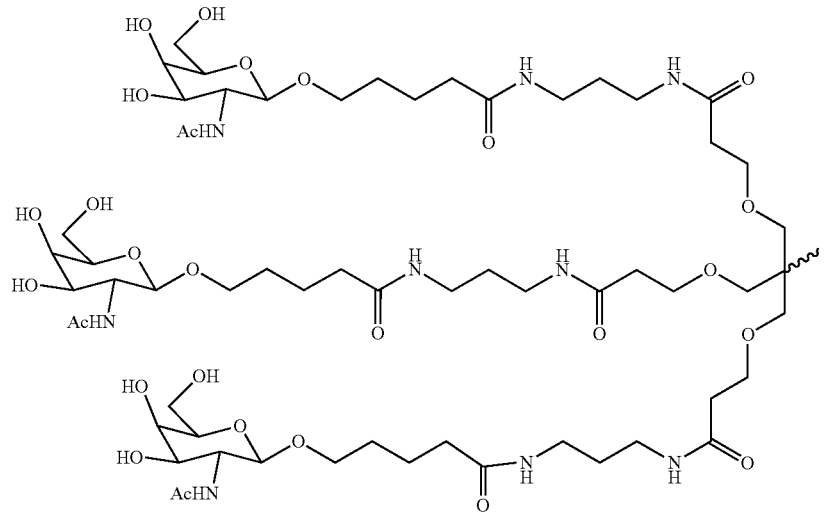
Formula II In some embodiments, the RNAi agent is attached to the carbohydrate conjugate via a linker as shown in the following schematic, wherein X is O or S
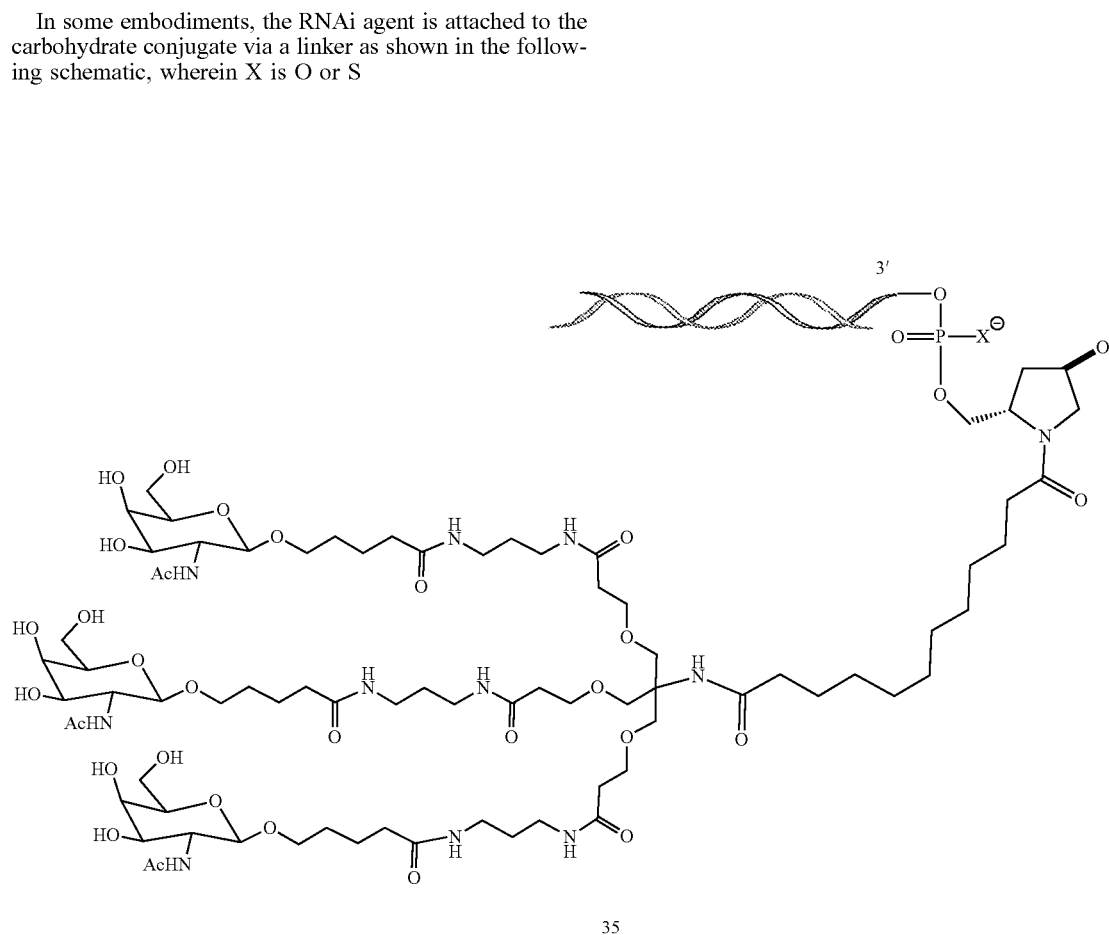
35
In some embodiments, the RNAi agent is conjugated to L96 as defined in Table 1 and shown below:
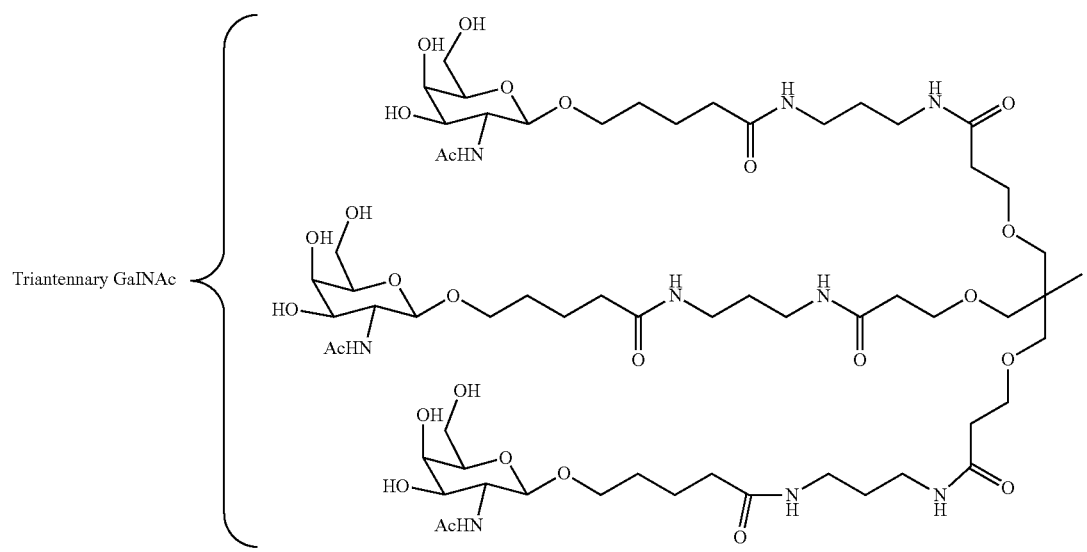

-continued
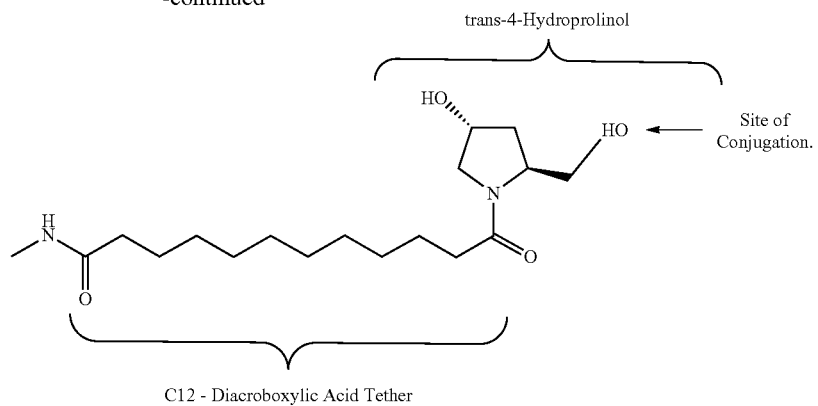
Another representative carbohydrate conjugate for use in the embodiments described herein includes, but is not limited to,

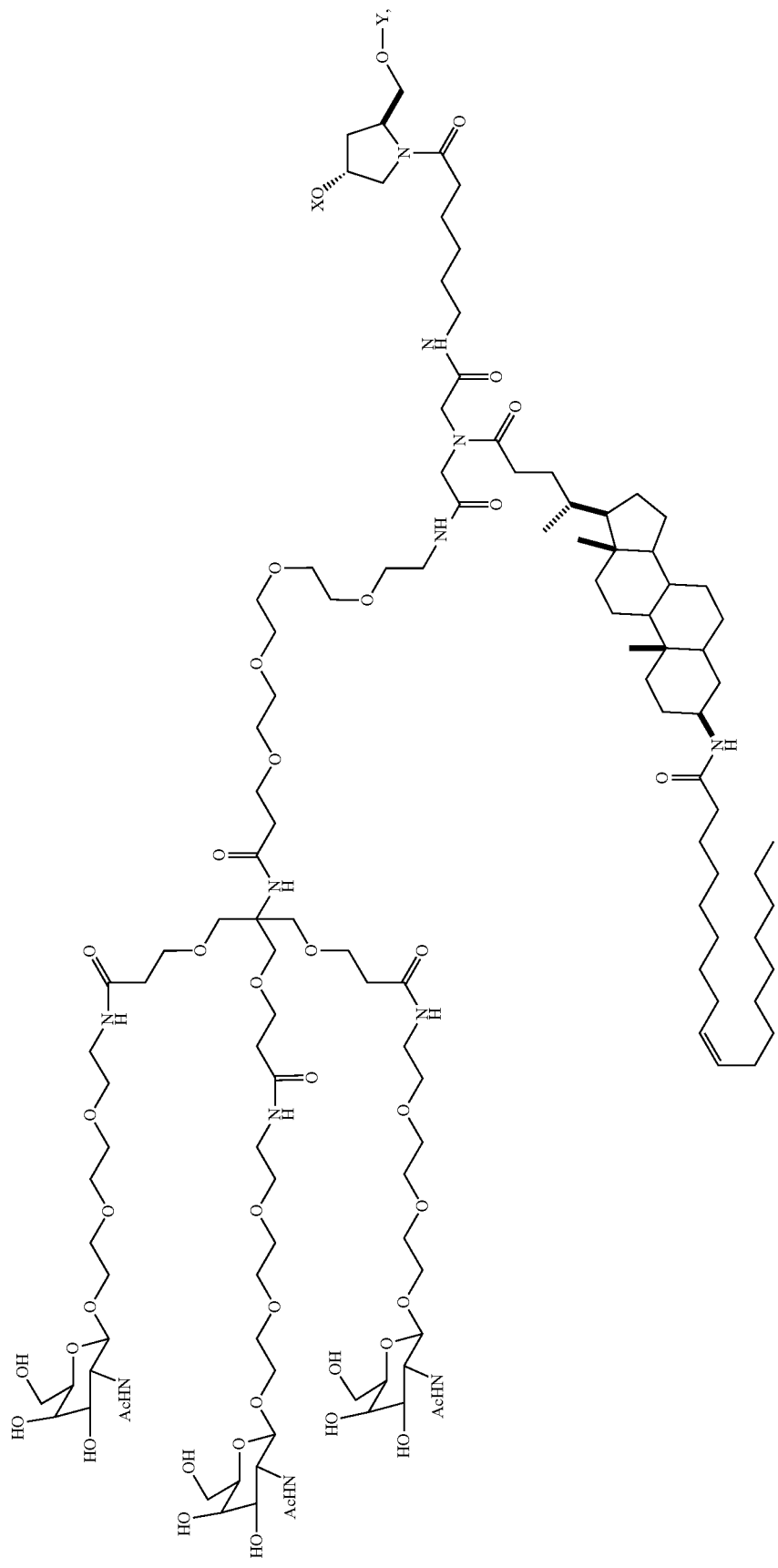
(Formula XXXVI)

when one of X or Y is an oligonucleotide, the other is a hydrogen.

In some embodiments, a suitable ligand is a ligand disclosed in WO 2019/055633, the entire contents of which are incorporated herein by reference. In one embodiment the ligand comprises the structure below:

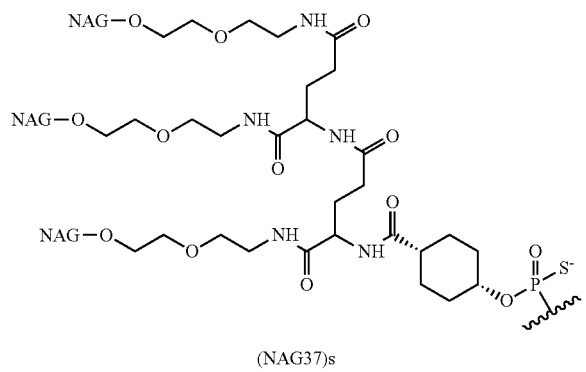

(NAG37)s

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one or more GalNAc or GalNAc derivative attached to the iRNA agent. The GalNAc may be attached to any nucleotide via a linker on the sense strand or antsisense strand. The GalNac may be attached to the 5'-end of the sense strand, the 3' end of the sense strand, the 5'-end of the antisense strand, or the 3'-end of the antisense strand. In one embodiment, the GalNAc is attached to the 3' end of the sense strand, e.g., via a trivalent linker.

In other embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of linkers, e.g., monovalent linkers.

In some embodiments, for example, when the two strands of an iRNA agent of the invention is part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NRB, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, or substituted or unsubstituted heterocyclic; where R8 is hydrogen, acyl, aliphatic, or substituted aliphatic. In one embodiment, the linker is about 1-24 atoms, 2-24, 3-24, 4-24, 5-24, 6-24, 6-18, 7-18, 8-18, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times, or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In other embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, and —O—P(S)(H)—S—. A preferred embodiment is —O—P(O)(OH)—O—. These candidates can be evaluated using methods analogous to those described above.

iii. Acid Cleavable Linking Groups

In other embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In other embodiments, a cleavable linker comprises an ester-based cleavable linking group. An ester-based cleavable linking group is cleaved by enzymes such as esterases and amidases in cells. Examples of ester-based cleavable linking groups include, but are not limited to, esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet other embodiments, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to,
(Formula XXXVII)
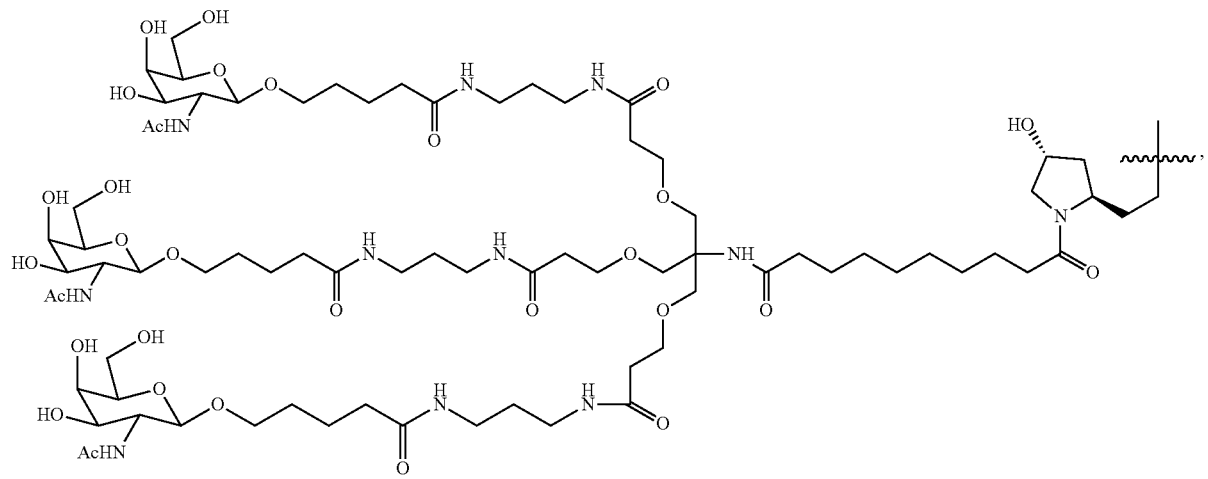
(Formula XXXVIII)
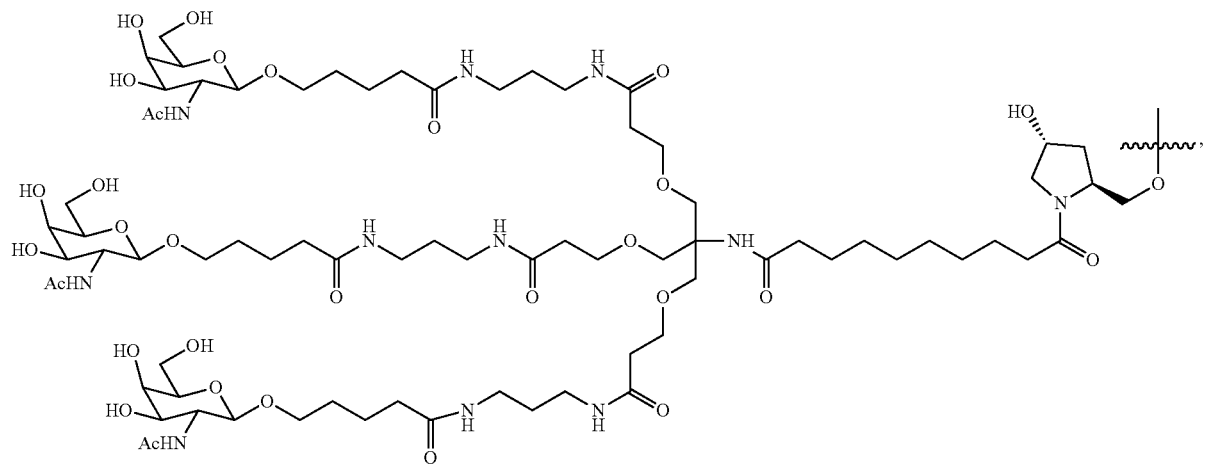
(Formula XXXIX)
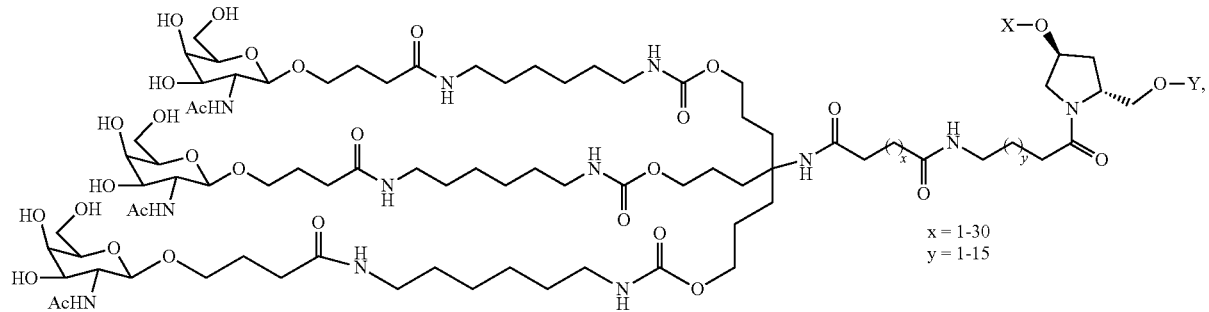
x = 1-30
y = 1-15

(Formula XL)
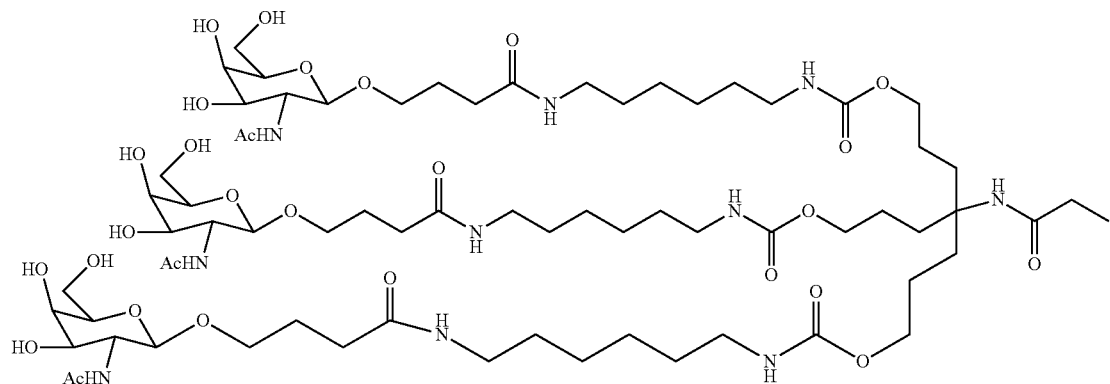
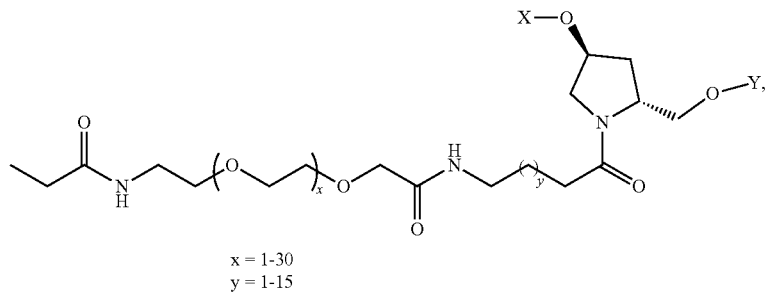
x = 1-30
y = 1-15
(Formula XLI)
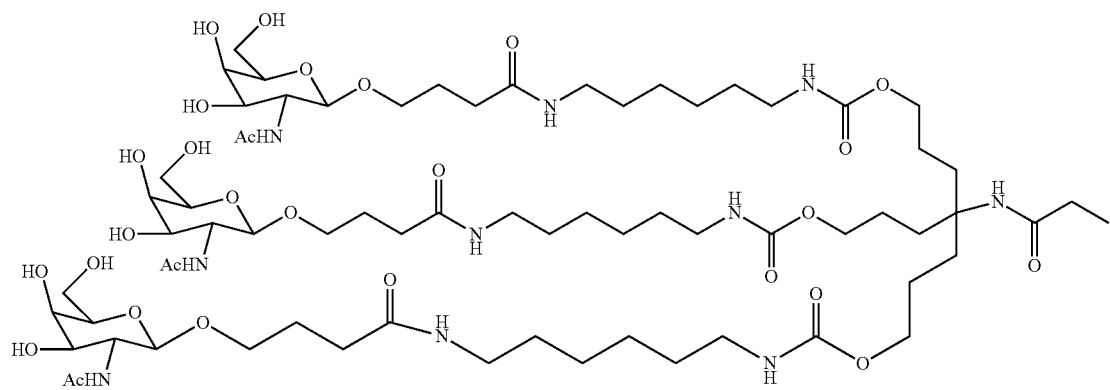
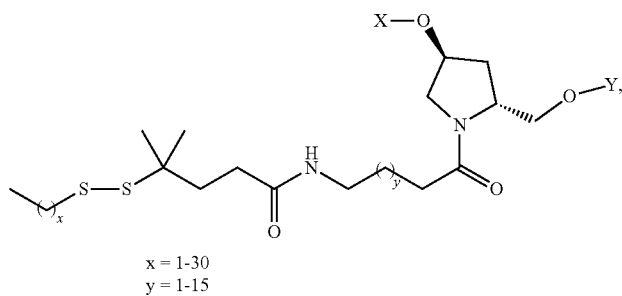
x = 1-30
y = 1-15

(Formula XLII)
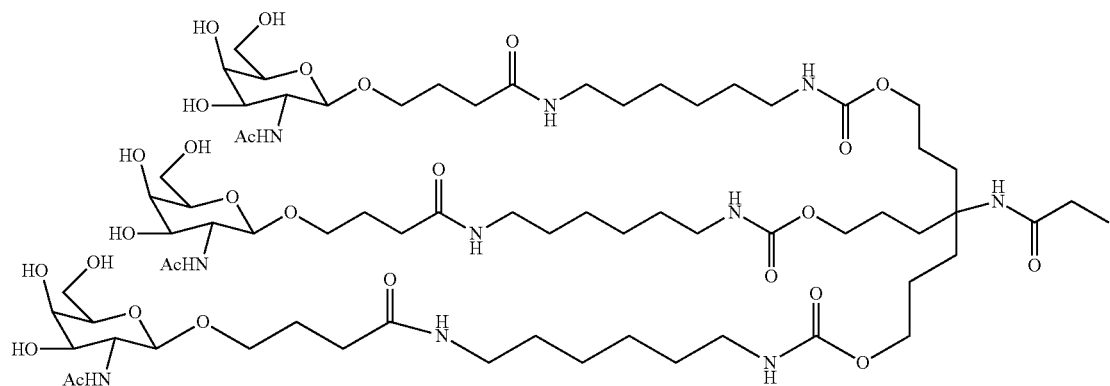
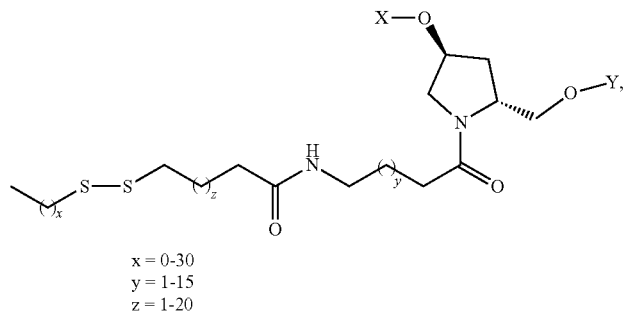
x = 0-30
y = 1-15
z = 1-20
(Formula XLIII)
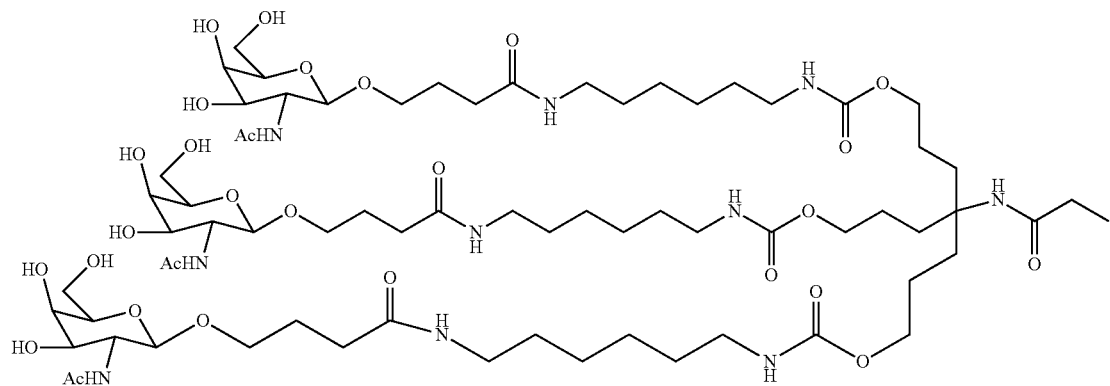
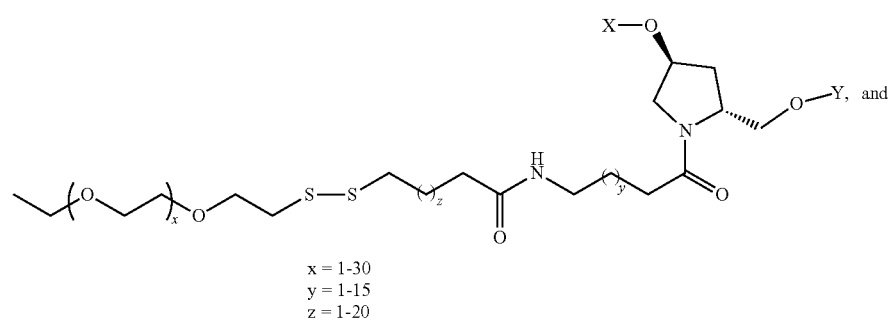
x = 1-30
y = 1-15
z = 1-20

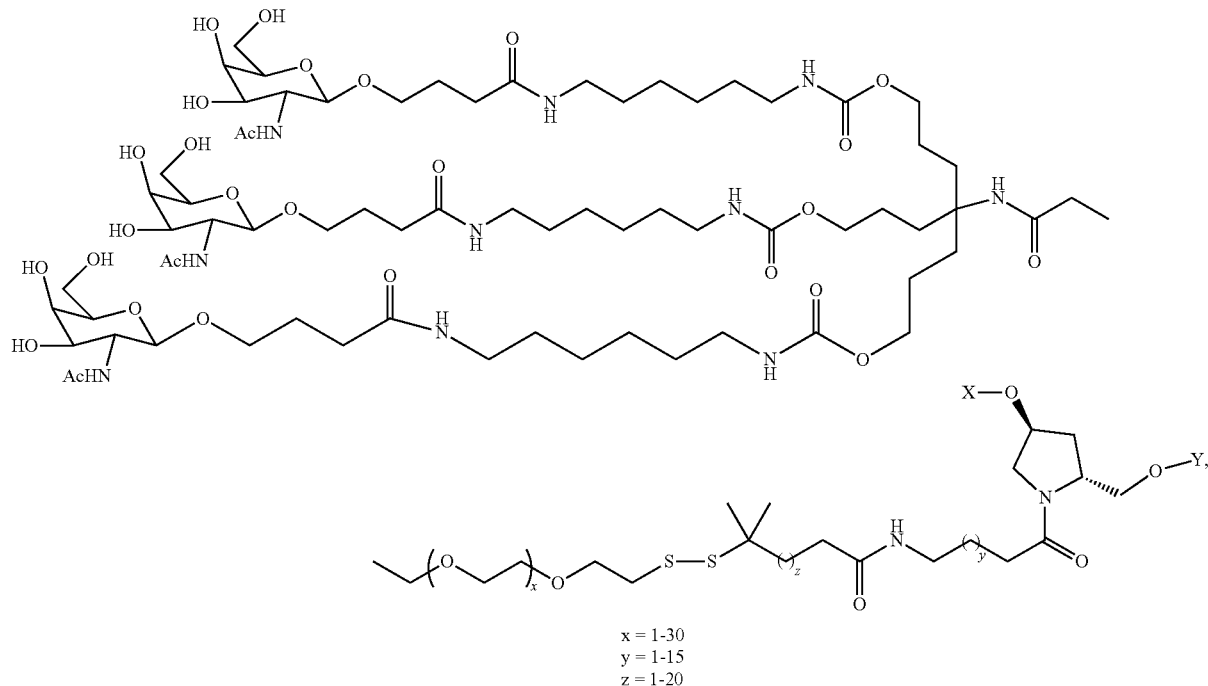

(Formula XLIV)

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XLV)-(XLVI):

Formula XXXXV

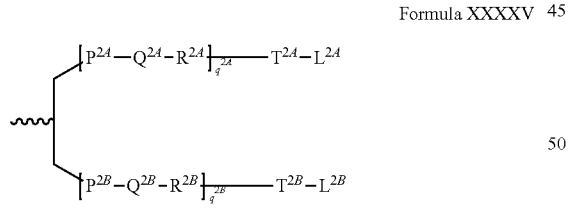

Formula XLVI

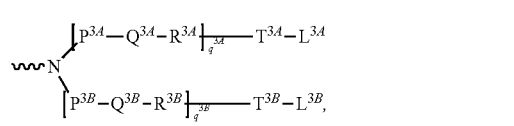

Formula XLVII

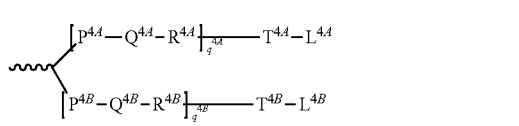

Formula XLVIII

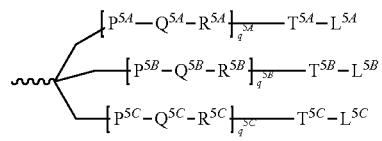

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, $C(R')=C(R'')$, $C \equiv C$ or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—$CH(R^a)$—NH—, CO, CH=N—O.

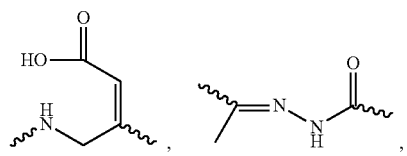

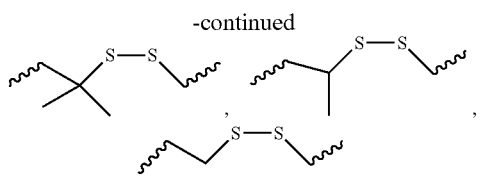

or heterocyclyl;
$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

Formula (VI]

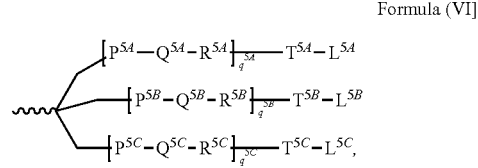

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAi agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject susceptible to or diagnosed with an apolipoprotein C3-associated disorder, e.g., hypertriglyceridemia) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602). Modification of the RNA or the pharmaceutical carrier can also permit targeting of the iRNA to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178).

In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H, et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R, et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N, et al (2003), supra), "solid nucleic acid lipid particles" (Zimmermann, T S, et al (2006) *Nature* 441:111-114), cardiolipin (Chien, P Y, et al (2005) *Cancer Gene Ther.* 12:321-328; Pal, A, et al (2005) *Int J. Oncol.* 26:1087-1091), polyethyleneimine (Bonnet M E, et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A, et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the apolipoprotein C3 gene can be expressed from transcription units inserted into DNA or RNA vectors (see, e.g., Couture, A, et al., TIG. (1996), 12:5-10; Skillern, A, et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for preventing or treating an apolipoprotein C3-associated disorder, e.g., hypertriglyceridemia. Such pharmaceutical compositions are formulated based on the mode of delivery. One example is compositions that are formulated for systemic administration via parenteral delivery, e.g., by subcutaneous (SC), intramuscular (IM), or intravenous (IV) delivery. The pharmaceutical compositions of the invention may be administered in dosages sufficient to inhibit expression of an apolipoprotein C3 gene.

In some embodiments, the pharmaceutical compositions of the invention are sterile. In another embodiment, the pharmaceutical compositions of the invention are pyrogen free.

The pharmaceutical compositions of the invention may be administered in dosages sufficient to inhibit expression of an apolipoprotein C3 gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg. A repeat-dose regimen may include administration of a therapeutic amount of iRNA on a regular basis, such as every month, once every 3-6 months, or once a year. In certain embodiments, the iRNA is administered about once per month to about once per six months.

After an initial treatment regimen, the treatments can be administered on a less frequent basis. Duration of treatment can be determined based on the severity of disease.

In other embodiments, a single dose of the pharmaceutical compositions can be long lasting, such that doses are administered at not more than 1, 2, 3, or 4 month intervals. In some embodiments of the invention, a single dose of the pharmaceutical compositions of the invention is administered about once per month. In other embodiments of the invention, a single dose of the pharmaceutical compositions of the invention is administered quarterly (i.e., about every three months). In other embodiments of the invention, a single dose of the pharmaceutical compositions of the invention is administered twice per year (i.e., about once every six months).

The skilled artisan will appreciate that certain factors can influence the dosage and timing required to effectively treat a subject, including but not limited to mutations present in the subject, previous treatments, the general health or age of the subject, and other diseases present. Moreover, treatment of a subject with a prophylactically or therapeutically effective amount, as appropriate, of a composition can include a single treatment or a series of treatments.

The iRNA can be delivered in a manner to target a particular tissue (e.g., hepatocytes).

Pharmaceutical compositions of the present invention include, but are not limited to, solutions, emulsions, and liposome-containing formulations. These compositions can be generated from a variety of components that include, but are not limited to, preformed liquids, self-emulsifying solids, and self-emulsifying semisolids. Formulations include those that target the liver.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers.

A. Additional Formulations
i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution either in the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic, and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives, and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

The application of emulsion formulations via dermatological, oral, and parenteral routes, and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

ii. Microemulsions

In one embodiment of the present invention, the compositions of iRNAs and nucleic acids are formulated as microemulsions. A microemulsion can be defined as a system of water, oil, and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215).

iii. Microparticles

An iRNA of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers and their use in manufacture of pharmaceutical compositions and delivery of pharmaceutical agents are well known in the art.

v. Excipients

In contrast to a carrier compound, a "pharmaceutical carrier" or "excipient" is a pharmaceutically acceptable solvent, suspending agent, or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Such agent are well known in the art.

vi. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings, or aromatic substances, and the like which do not deleteriously interact with the nucleic acid(s) of the formulation.

Aqueous suspensions can contain substances which increase the viscosity of the suspension including, for example, sodium carboxymethylcellulose, sorbitol, or dextran. The suspension can also contain stabilizers.

In some embodiments, pharmaceutical compositions featured in the invention include (a) one or more iRNA and (b) one or more agents which function by a non-iRNA mechanism and which are useful in treating an apolipoprotein C3-associated disorder, e.g., hypertriglyceridemia.

Toxicity and prophylactic efficacy of such compounds can be determined by standard pharmaceutical procedures in cell cultures or experimental animals, e.g., for determining the LD50 (the dose lethal to 50% of the population) and the ED50 (the dose prophylactically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50, preferably an ED80 or ED90, with little or no toxicity. The dosage can vary within this range depending upon the dosage form employed and the route of administration utilized. For any compound used in the methods featured in the invention, the prophylactically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) or higher levels of inhibition as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents used for the prevention or treatment of an apolipoprotein C3-associated disorder, e.g., hypertriglyceridemia. In any event, the administering physician can adjust the amount and timing of iRNA administration on the basis of results observed using standard measures of efficacy known in the art or described herein.

VI. Methods for Inhibiting Apolipoprotein C3 Expression

The present invention also provides methods of inhibiting expression of an APOC3 gene in a cell. The methods include contacting a cell with an RNAi agent, e.g., double stranded RNA agent, in an amount effective to inhibit expression of APOC3 in the cell, thereby inhibiting expression of APOC3 in the cell.

Contacting of a cell with an iRNA, e.g., a double stranded RNA agent, may be done in vitro or in vivo. Contacting a cell in vivo with the iRNA includes contacting a cell or group of cells within a subject, e.g., a human subject, with the iRNA. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest.

The term "inhibiting," as used herein, is used interchangeably with "reducing," "silencing," "downregulating", "suppressing", and other similar terms, and includes any level of inhibition.

The phrase "inhibiting expression of a apolipoprotein C3" is intended to refer to inhibition of expression of any apolipoprotein C3 gene (such as, e.g., a mouse apolipoprotein C3 gene, a rat apolipoprotein C3 gene, a monkey apolipoprotein C3 gene, or a human apolipoprotein C3 gene) as well as variants or mutants of an apolipoprotein C3 gene. Thus, the apolipoprotein C3 gene may be a wild-type apolipoprotein C3 gene, a mutant apolipoprotein C3 gene, or a transgenic apolipoprotein C3 gene in the context of a genetically manipulated cell, group of cells, or organism.

"Inhibiting expression of an apolipoprotein C3 gene" includes any level of inhibition of an apolipoprotein C3 gene, e.g., at least partial suppression of the expression of an apolipoprotein C3 gene. The expression of the apolipoprotein C3 gene may be assessed based on the level, or the change in the level, of any variable associated with apolipoprotein C3 gene expression, e.g., apolipoprotein C3 mRNA level or apolipoprotein C3 protein level. This level may be assessed in an individual cell or in a group of cells, including, for example, a sample derived from a subject. It is understood that apolipoprotein C3 is expressed predominantly in the liver, but also in the brain, gall bladder, heart, and kidney, and is present in circulation.

Inhibition may be assessed by a decrease in an absolute or relative level of one or more variables that are associated with apolipoprotein C3 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of an apolipoprotein C3 gene is inhibited by at least 50%, 55%, 60%, 65%, 70%, 75%, 80%, 85%, 90%, or 95%, or to below the level of detection of the assay. In preferred embodiments, expression of an apolipoprotein C3 gene is inhibited by at least 70%. It is further understood that inhibition of apolipoprotein C3 expression in certain tissues, e.g., in liver, without a significant inhibition of expression in other tissues, e.g., brain, may be desirable. In preferred embodiments, expression level is determined using the assay method provided in Example 2 with a 10 nM siRNA concentration in the appropriate species matched cell line.

In certain embodiments, inhibition of expression in vivo is determined by knockdown of the human gene in a rodent expressing the human gene, e.g., an AAV-infected mouse expressing the human target gene (i.e., apolipoprotein C3), e.g., when administered as a single dose, e.g., at 3 mg/kg at the nadir of RNA expression. Knockdown of expression of an endogenous gene in a model animal system can also be determined, e.g., after administration of a single dose at, e.g., 3 mg/kg at the nadir of RNA expression. Such systems are useful when the nucleic acid sequence of the human gene and the model animal gene are sufficiently close such that the human iRNA provides effective knockdown of the model animal gene. RNA expression in liver is determined using the PCR methods provided in Example 2.

Inhibition of the expression of an apolipoprotein C3 gene may be manifested by a reduction of the amount of mRNA expressed by a first cell or group of cells (such cells may be present, for example, in a sample derived from a subject) in which an apolipoprotein C3 gene is transcribed and which has or have been treated (e.g., by contacting the cell or cells with an iRNA of the invention, or by administering an iRNA of the invention to a subject in which the cells are or were present) such that the expression of an apolipoprotein C3 gene is inhibited, as compared to a second cell or group of cells substantially identical to the first cell or group of cells but which has not or have not been so treated (control cell(s) not treated with an iRNA or not treated with an iRNA targeted to the gene of interest). In preferred embodiments, the inhibition is assessed by the method provided in Example 2 using a 10 nM siRNA concentration in the species matched cell line and expressing the level of mRNA in treated cells as a percentage of the level of mRNA in control cells, using the following formula:

$$\frac{(\text{mRNA in control cells}) - (\text{mRNA in treated cells})}{(\text{mRNA in control cells})} \cdot 100\%$$

In other embodiments, inhibition of the expression of an apolipoprotein C3 gene may be assessed in terms of a reduction of a parameter that is functionally linked to apolipoprotein C3 gene expression, e.g., apolipoprotein C3 protein level in blood or serum from a subject. Apolipoprotein C3 gene silencing may be determined in any cell expressing apolipoprotein C3, either endogenous or heterologous from an expression construct, and by any assay known in the art.

Inhibition of the expression of an apolipoprotein C3 protein may be manifested by a reduction in the level of the apolipoprotein C3 protein that is expressed by a cell or group of cells or in a subject sample (e.g., the level of protein in a blood sample derived from a subject). As explained above, for the assessment of mRNA suppression, the inhibition of protein expression levels in a treated cell or group of cells may similarly be expressed as a percentage of the level of protein in a control cell or group of cells, or the change in the level of protein in a subject sample, e.g., blood or serum derived therefrom.

A control cell, a group of cells, or subject sample that may be used to assess the inhibition of the expression of an apolipoprotein C3 gene includes a cell, group of cells, or subject sample that has not yet been contacted with an RNAi agent of the invention. For example, the control cell, group of cells, or subject sample may be derived from an individual subject (e.g., a human or animal subject) prior to treatment of the subject with an RNAi agent or an appropriately matched population control.

The level of apolipoprotein C3 mRNA that is expressed by a cell or group of cells may be determined using any method known in the art for assessing mRNA expression. In one embodiment, the level of expression of apolipoprotein C3 in a sample is determined by detecting a transcribed polynucleotide, or portion thereof, e.g., mRNA of the apolipoprotein C3 gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene™ (PreAnalytix™, Switzerland). Typical assay formats utilizing ribonucleic acid hybridization include nuclear run-on assays, RT-PCR, RNase protection assays, northern blotting, in situ hybridization, and microarray analysis.

In some embodiments, the level of expression of apolipoprotein C3 is determined using a nucleic acid probe. The term "probe", as used herein, refers to any molecule that is capable of selectively binding to a specific apolipoprotein C3. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to apolipoprotein C3 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of apolipoprotein C3 mRNA.

An alternative method for determining the level of expression of apolipoprotein C3 in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of APOC3 is determined by quantitative fluorogenic RT-PCR (i.e., the TaqMan™ System). In preferred embodiments, expression level is determined by the method provided in Example 2 using, e.g., a 10 nM siRNA concentration, in the species matched cell line.

The expression levels of apolipoprotein C3 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of apolipoprotein C3 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein. In preferred embodiments, expression level is determined by the method provided in Example 2 using a 10 nM siRNA concentration in the species matched cell line.

The level of APOC3 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

In some embodiments, the efficacy of the methods of the invention are assessed by a decrease in C3 mRNA or protein level (e.g., in a liver biopsy).

In some embodiments of the methods of the invention, the iRNA is administered to a subject such that the iRNA is delivered to a specific site within the subject. The inhibition of expression of apolipoprotein C3 may be assessed using measurements of the level or change in the level of apolipoprotein C3 mRNA or apolipoprotein C3 protein in a sample derived from fluid or tissue from the specific site within the subject (e.g., liver or blood).

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

VII. Prophylactic and Treatment Methods of the Invention

The present invention also provides methods of using an iRNA of the invention or a composition containing an iRNA of the invention to inhibit expression of apolipoprotein C3, thereby preventing or treating an apolipoprotein C3-associated disorder, e.g., hypertriglyceridemia, non-alcoholic fatty liver disease, non-alcoholic steatohepatitis, polycystic ovary syndrome, kidney disease, obesity, type 2 diabetes mellitus (insulin resistance); hypertension; cardiovascular disorders, e.g., artherosclerosis; and pancreatitis, e.g., acute pancreatitis. In the methods of the invention the cell may be contacted with the siRNA in vitro or in vivo, i.e., the cell may be within a subject.

A cell suitable for treatment using the methods of the invention may be any cell that expresses an apolipoprotein C3 gene, e.g., a liver cell, a brain cell, a gall bladder cell, a heart cell, or a kidney cell, but preferably a liver cell. A cell suitable for use in the methods of the invention may be a mammalian cell, e.g., a primate cell (such as a human cell, including human cell in a chimeric non-human animal, or a non-human primate cell, e.g., a monkey cell or a chimpanzee cell), or a non-primate cell. In certain embodiments, the cell is a human cell, e.g., a human liver cell. In the methods of the invention, apolipoprotein C3 expression is inhibited in the cell by at least 50, 55, 60, 65, 70, 75, 80, 85, 90, or 95, or to a level below the level of detection of the assay.

The in vivo methods of the invention may include administering to a subject a composition containing an iRNA, where the iRNA includes a nucleotide sequence that is complementary to at least a part of an RNA transcript of the apolipoprotein C3 gene of the mammal to which the RNAi agent is to be administered. The composition can be administered by any means known in the art including, but not limited to oral, intraperitoneal, or parenteral routes, including intracranial (e.g., intraventricular, intraparenchymal, and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intramuscular injection.

In one aspect, the present invention also provides methods for inhibiting the expression of an apolipoprotein C3 gene in a mammal. The methods include administering to the mammal a composition comprising a dsRNA that targets an apolipoprotein C3 gene in a cell of the mammal and maintaining the mammal for a time sufficient to obtain degradation of the mRNA transcript of the apolipoprotein C3 gene, thereby inhibiting expression of the apolipoprotein C3 gene in the cell. Reduction in gene expression can be assessed by any methods known in the art and by methods, e.g. qRT-PCR, described herein, e.g., in Example 2. Reduction in protein production can be assessed by any methods known it the art, e.g. ELISA. In certain embodiments, a puncture liver biopsy sample serves as the tissue material for monitoring the reduction in the apolipoprotein C3 gene or protein expression. In other embodiments, a blood sample serves as the subject sample for monitoring the reduction in the apolipoprotein C3 protein expression.

The present invention further provides methods of treatment in a subject in need thereof, e.g., a subject diagnosed with an apolipoprotein C3-associated disorder, such as, hypertriglyceridemia, non-alcoholic fatty liver disease, non-alcoholic steatohepatitis, polycystic ovary syndrome, kidney disease, obesity, type 2 diabetes mellitus (insulin resistance); hypertension; cardiovascular disorders, e.g., artherosclerosis; and pancreatitis, e.g., acute pancreatitis.

The present invention further provides methods of prophylaxis in a subject in need thereof. The treatment methods of the invention include administering an iRNA of the invention to a subject, e.g., a subject that would benefit from a reduction of apolipoprotein C3 expression, in a prophylactically effective amount of an iRNA targeting an apolipoprotein C3 gene or a pharmaceutical composition comprising an iRNA targeting an apolipoprotein C3 gene.

In one embodiment, an apolipoprotein C3-associated disease is selected from the group consisting of hypertriglyceridemia, non-alcoholic fatty liver disease, non-alcoholic steatohepatitis, polycystic ovary syndrome, kidney disease, obesity, type 2 diabetes mellitus (insulin resistance); hypertension; cardiovascular disorders, e.g., artherosclerosis; and pancreatitis, e.g., acute pancreatitis.

In one embodiment, an APOC3-associated disease is hypertriglyceridemia, or a high triglyceride levels. The levels of triglycerides in a serum of a subject, e.g., a human subject, that may be indicative of hypertriglyceridemia are described in Oh, R. C. et al., (2007) *American Family Physician,* 75(9):1366-1371. Specifically, hypertriglyceridemia may be associated with "borderline-high serum triglyceride levels" (i.e., 150 to 199 mg per dL or 1.70 to 2.25 mmol per L); "high serum triglyceride levels" (i.e., 200 to 499 mg per dL or 2.26 to 5.64 mmol per L); or "very high triglyceride levels" (i.e., 500 mg per dL or higher (or 5.65 mmol per L or higher)

In one embodiment, an APOC3-associated disease is primary hypertriglyceridemia. "Primary triglyceridemia" results from environmental or genetic causes (e.g., a result of no obvious underlying medical cause). Exemplary diseases characterized as primary hypertriglyceridemias include, but are not limited to, familial chylomicronemia (hyperlipoproteinemia type I), primary mixed hyperlipidemia (type 5), familial hypertriglyceridemia (hyperlipoproteinemia type 4), familial combined hyperlipoproteinemia (type 2B) and familial dysbetalipoproteinemia (hyperlipoproteinemia type 3).

In another embodiment, an APOC3-associated disease is secondary hypertriglyceridemia. "Secondary triglyceridemia" is caused by, or be associated with, other underlying disorders and conditions. Such disorders and/or conditions include, e.g., obesity, metabolic syndrome, diabetes, fatty liver, alcohol use, renal disease, pregnancy, nonalcoholic fatty liver disorder, hypothyroidism, paraproteinemias (such as hypergammaglobulinemia in macroglobulinemia, myeloma, lymphoma and lymphocytic leukemias), autoimmune disorders (such as systemic lupus erythematosis), intake of medications (such as antiretroviral drugs, including ritonavir and lopinavir, and antipsychotic medications, including clozapine and olanzapine), see G. Yuan et al., (2007) *Canadian Medical Association Journal,* 176(8): 1113-1120.

Any disorder that may be a cause of hypertriglyceridemia (e.g., secondary hypertriglyceridemia) or that may be a consequence of hypertriglyceridemia (e.g., primary or secondary hypertriglyceridemia) is encompassed by the term "APOC3-associated disease". Non-limiting examples of APOC3-associated diseases include metabolic disorders, e.g., non-alcoholic fatty liver disease, non-alcoholic steatohepatitis, polycystic ovary syndrome, kidney disease, obesity, type 2 diabetes mellitus (insulin resistance); hypertension; cardiovascular disorders, e.g., artherosclerosis; and pancreatitis, e.g., acute pancreatitis.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from an inhibition of APOC3 gene expression are subjects susceptible to or diagnosed with an APOC3-associated disorder, such as hypertriglyceridemia, non-alcoholic fatty liver disease, non-alcoholic steatohepatitis, polycystic ovary syndrome, kidney disease, obesity, type 2 diabetes mellitus (insulin resistance); hypertension; cardiovascular disorders, e.g., artherosclerosis; and pancreatitis, e.g., acute pancreatitis.

In an embodiment, the method includes administering a composition featured herein such that expression of the target apolipoprotein C3 gene is decreased, such as for about 1, 2, 3, 4, 5, 6, 1-6, 1-3, or 3-6 months per dose. In certain embodiments, the composition is administered once every 3-6 months.

Preferably, the iRNAs useful for the methods and compositions featured herein specifically target RNAs (primary or processed) of the target apolipoprotein C3 gene. Compositions and methods for inhibiting the expression of these genes using iRNAs can be prepared and performed as described herein.

Administration of the iRNA according to the methods of the invention may result prevention or treatment of an apolipoprotein C3-associated disorder, e.g., hypertriglyceridemia, non-alcoholic fatty liver disease, non-alcoholic steatohepatitis, polycystic ovary syndrome, kidney disease, obesity, type 2 diabetes mellitus (insulin resistance); hypertension; cardiovascular disorders, e.g., artherosclerosis; and pancreatitis, e.g., acute pancreatitis.

Subjects can be administered a therapeutic amount of iRNA, such as about 0.01 mg/kg to about 200 mg/kg.

The iRNA is preferably administered subcutaneously, i.e., by subcutaneous injection. One or more injections may be used to deliver the desired dose of iRNA to a subject. The injections may be repeated over a period of time.

The administration may be repeated on a regular basis. In certain embodiments, after an initial treatment regimen, the treatments can be administered on a less frequent basis. A repeat-dose regimen may include administration of a therapeutic amount of iRNA on a regular basis, such as once per month to once a year. In certain embodiments, the iRNA is administered about once per month to about once every three months, or about once every three months to about once every six months.

The invention further provides methods and uses of an iRNA agent or a pharmaceutical composition thereof for treating a subject that would benefit from reduction and/or inhibition of APOC3 gene expression, e.g., a subject having an APOC3-associated disease, in combination with other pharmaceuticals and/or other therapeutic methods, e.g., with known pharmaceuticals and/or known therapeutic methods, such as, for example, those which are currently employed for treating these disorders.

Accordingly, in some aspects of the invention, the methods which include either a single iRNA agent of the invention, further include administering to the subject one or more additional therapeutic agents.

The iRNA agent and an additional therapeutic agent and/or treatment may be administered at the same time and/or in the same combination, e.g., parenterally, or the additional therapeutic agent can be administered as part of a separate composition or at separate times and/or by another method known in the art or described herein.

Examples of additional therapeutic agents include those known to treat hypertriglyceridemia and other diseases that are caused by, associated with or are a consequence of hypertriglyceridemia. For example, an iRNA featured in the invention can be administered with, e.g., a PCSK9 inhibitor (e.g., an anti-PCSK9 monoclonal antibody, e.g., evolocumab (Repatha®) and alirocumab (Praluent®), a dsRNA agent targeting PCSK9 (e.g., Inclisran)), an HMG-CoA reductase inhibitor (e.g., a statin), a fibrate, a bile acid sequestrant, niacin, an antiplatelet agent, an angiotensin converting enzyme inhibitor, an angiotensin II receptor antagonist (e.g., losartan potassium, such as Merck & Co.'s Cozaar®), an acylCoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR) agonist, a gene-based therapy, a composite vascular protectant (e.g., AGI-1067, from Atherogenics), a glycoprotein IIb/IIIa inhibitor, aspirin or an aspirin-like compound, an IBAT inhibitor (e.g., S-8921, from Shionogi), a squalene synthase inhibitor, a monocyte chemoattractant protein (MCP)-I inhibitor, or fish oil. Exemplary HMG-CoA reductase inhibitors include atorvastatin (Pfizer's Lipitor®/Tahor/Sortis/Torvast/Cardyl), pravastatin (Bristol-Myers Squibb's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis). Exemplary fibrates include, e.g., bezafibrate (e.g., Roche's Befizal®/Cedur®/Bezalip®, Kissei's Bezatol), clofibrate (e.g., Wyeth's Atromid-S®), fenofibrate (e.g., Fournier's Lipidil/Lipantil, Abbott's Tricor®, Takeda's Lipantil, generics), gemfibrozil (e.g., Pfizer's Lopid/Lipur) and ciprofibrate (Sanofi-Synthelabo's Modalim®). Exemplary bile acid sequestrants include, e.g., cholestyramine (Bristol-Myers Squibb's Questran® and Questran Light™) colestipol (e.g., Pharmacia's Colestid), and colesevelam (Genzyme/Sankyo's WelChol™). Exemplary niacin therapies include, e.g., immediate release formulations, such as Aventis' Nicobid, Upsher-Smith's Niacor, Aventis' Nicolar, and Sanwakagaku's Perycit. Niacin extended release formulations include, e.g., Kos Pharmaceuticals' Niaspan and Upsher-Smith's SIo-Niacin. Exemplary antiplatelet agents include, e.g., aspirin (e.g., Bayer's aspirin), clopidogrel (Sanofi-Synthelabo/Bristol-Myers Squibb's Plavix), and ticlopidine (e.g., Sanofi-Synthelabo's Ticlid and Daiichi's Panaldine). Other aspirin-like compounds useful in combination with a dsRNA targeting APOC3 include, e.g., Asacard (slow-release aspirin, by Pharmacia) and Pamicogrel (Kanebo/Angelini Ricerche/CEPA). Exemplary angiotensin-converting enzyme inhibitors include, e.g., ramipril (e.g., Aventis' Altace) and enalapril (e.g., Merck & Co.'s Vasotec). Exemplary acyl CoA cholesterol acetyltransferase (ACAT) inhibitors include, e.g., avasimibe (Pfizer), eflucimibe (BioMsrieux Pierre Fabre/Eli Lilly), CS-505 (Sankyo and Kyoto), and SMP-797 (Sumito). Exemplary cholesterol absorption inhibitors include, e.g., ezetimibe (Merck/Schering-Plough Pharmaceuticals Zetia®) and Pamaqueside (Pfizer). Exemplary CETP inhibitors include, e.g., Torcetrapib (also called CP-529414, Pfizer), JTT-705 (Japan Tobacco), and CETi-I (Avant Immunotherapeutics). Exemplary microsomal triglyceride transfer protein (MTTP) inhibitors include, e.g., implitapide (Bayer), R-103757 (Janssen), and CP-346086 (Pfizer). Other exemplary cholesterol modulators include, e.g., NO—1886 (Otsuka/TAP Pharmaceutical), CI—1027 (Pfizer), and WAY—135433 (Wyeth-Ayerst).

Exemplary bile acid modulators include, e.g., HBS-107 (Hisamitsu/Banyu), Btg-511 (British Technology Group), BARI-1453 (Aventis), S-8921 (Shionogi), SD-5613 (Pfizer), and AZD—7806 (AstraZeneca). Exemplary peroxisome proliferation activated receptor (PPAR) agonists include, e.g., tesaglitazar (AZ-242) (AstraZeneca), Netoglitazone (MCC-555) (Mitsubishi/Johnson & Johnson), GW-409544 (Ligand Pharniaceuticals/GlaxoSmithKline), GW-501516 (Ligand Pharmaceuticals/GlaxoSmithKline), LY-929 (Ligand Pharmaceuticals and Eli Lilly), LY-465608 (Ligand Pharmaceuticals and Eli Lilly), LY-518674 (Ligand Pharmaceuticals and Eli Lilly), and MK-767 (Merck and Kyorin). Exemplary gene-based therapies include, e.g., AdGWEGF 121.10 (GenVec), ApoA1 (UCB Pharma/ Groupe Fournier), EG-004 (Trinam) (Ark Therapeutics), and ATP-binding cassette transporter-A1 (ABCA1) (CV Therapeutics/Incyte, Aventis, Xenon). Exemplary Glycoprotein IIb/IIIa inhibitors include, e.g., roxifiban (also called DMP754, Bristol-Myers Squibb), Gantofiban (Merck KGaA/Yamanouchi), and Cromafiban (Millennium Pharmaceuticals). Exemplary squalene synthase inhibitors include, e.g., BMS-1884941 (Bristol-Myers Squibb), CP-210172 (Pfizer), CP-295697 (Pfizer), CP-294838 (Pfizer), and TAK-475 (Takeda). An exemplary MCP-I inhibitor is, e.g., RS-504393 (Roche Bioscience). The anti-atherosclerotic agent BO—653 (Chugai Pharmaceuticals), and the nicotinic acid derivative Nyclin (Yamanouchi Pharmacuticals) are also appropriate for administering in combination with a dsRNA featured in the invention. Exemplary combination therapies suitable for administration with a dsRNA targeting APOC3 include, e.g., advicor (Niacin/lovastatin from Kos Pharmaceuticals), amlodipine/atorvastatin (Pfizer), and ezetimibe/simvastatin (e.g., Vytorin® 10/10, 10/20, 10/40, and 10/80 tablets by Merck/Schering-Plough Pharmaceuticals). Agents for treating hypertriglyceridemia, and suitable for administration in combination with a dsRNA targeting APOC3 include, e.g., lovastatin, niacin Altoprev® Extended-Release Tablets (Andrx Labs), lovastatin Caduet® Tablets (Pfizer), amlodipine besylate, atorvastatin calcium Crestor® Tablets (AstraZeneca), rosuvastatin calcium Lescol® Capsules (Novartis), fluvastatin sodium Lescol® (Reliant, Novartis), fluvastatin sodium Lipitor® Tablets (Parke-Davis), atorvastatin calcium Lofibra® Capsules (Gate), Niaspan Extended-Release Tablets (Kos), niacin Pravachol Tablets (Bristol-Myers Squibb), pravastatin sodium TriCor® Tablets (Abbott), fenofibrate Vytorin® 10/10 Tablets (Merck/Schering-Plough Pharmaceuticals), ezetimibe, simvastatin WelChol™ Tablets (Sankyo), colesevelam hydrochloride Zetia® Tablets (Schering), ezetimibe Zetia® Tablets (Merck/Schering-Plough Pharmaceuticals), and ezetimibe Zocor® Tablets (Merck).

In one embodiment, an iRNA agent is administered in combination with a PCSK9 inhibitor. In one embodiment, the PCSK9 inhibitor is an anti-PCSK9 monoclonal antibody, e.g., evolocumab (Repatha®) and alirocumab (Praluent®). In another embodiment, the PCSK9 inhibitor is a dsRNA agent targeting PCSK9, e.g., Inclisiran. In one embodiment, the iRNA agent is administered to the patient, and then the additional therapeutic agent is administered to the patient (or vice versa). In another embodiment, the iRNA agent and the additional therapeutic agent are administered at the same time.

In one embodiment, an iRNA agent is administered in combination with ezetimibe/simvastatin combination (e.g., Vytorin® (Merck/Schering-Plough Pharmaceuticals)). In one embodiment, the iRNA agent is administered to the patient, and then the additional therapeutic agent is administered to the patient (or vice versa). In another embodiment, the iRNA agent and the additional therapeutic agent are administered at the same time.

The iRNA agent and an additional therapeutic agent and/or treatment may be administered at the same time and/or in the same combination, e.g., parenterally, or the additional therapeutic agent can be administered as part of a separate composition or at separate times and/or by another method known in the art or described herein.

VIII. Kits

In certain aspects, the instant disclosure provides kits that include a suitable container containing a pharmaceutical formulation of a siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof).

Such kits include one or more dsRNA agent(s) and instructions for use, e.g., instructions for administering a prophylactically or therapeutically effective amount of a dsRNA agent(s). The dsRNA agent may be in a vial or a pre-filled syringe. The kits may optionally further comprise means for administering the dsRNA agent (e.g., an injection device, such as a pre-filled syringe), or means for measuring the inhibition of APOC3 (e.g., means for measuring the inhibition of APOC3 mRNA, APOC3 protein, and/or APOC3 activity). Such means for measuring the inhibition of APOC3 may comprise a means for obtaining a sample from a subject, such as, e.g., a plasma sample. The kits of the invention may optionally further comprise means for determining the therapeutically effective or prophylactically effective amount.

In certain embodiments the individual components of the pharmaceutical formulation may be provided in one container, e.g., a vial or a pre-filled syringe. Alternatively, it may be desirable to provide the components of the pharmaceutical formulation separately in two or more containers, e.g., one container for a siRNA compound preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

This invention is further illustrated by the following examples which should not be construed as limiting. The entire contents of all references, patents and published patent applications cited throughout this application, as well as the informal Sequence Listing and Figures, are hereby incorporated herein by reference.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

siRNA Design siRNAs targeting the human Apolipoprotein C3 (APOC3) gene (human: NCBI refseqID NM_000040.3; NCBI GeneID: 345) were designed using custom R and Python scripts. The human NM_000040.3 REFSEQ mRNA, has a length of 535 bases.

Detailed lists of the unmodified APOC3 sense and antisense strand nucleotide sequences are shown in Tables 2 and 4. Detailed lists of the modified apolipoprotein C3 sense and antisense strand nucleotide sequences are shown in Tables 3 and 5.

It is to be understood that, throughout the application, a duplex name without a decimal is equivalent to a duplex name with a decimal which merely references the batch number of the duplex. For example, AD-959917 is equivalent to AD-959917.1.

siRNA Synthesis siRNAs were synthesized and annealed using routine methods known in the art.

Briefly, siRNA sequences were synthesized on a 1 μmol scale using a Mermade 192 synthesizer (BioAutomation) with phosphoramidite chemistry on solid supports. The solid support was controlled pore glass (500-1000 Å) loaded with a custom GalNAc ligand (3'-GalNAc conjugates), universal solid support (AM Chemicals), or the first nucleotide of interest. Ancillary synthesis reagents and standard 2-cyanoethyl phosphoramidite monomers (2'-deoxy-2'-fluoro, 2'-O-methyl, RNA, DNA) were obtained from Thermo-Fisher (Milwaukee, Wis.), Hongene (China), or Chemgenes (Wilmington, Mass., USA). Additional phosphoramidite monomers were procured from commercial suppliers, prepared in-house, or procured using custom synthesis from various CMOs. Phosphoramidites were prepared at a concentration of 100 mM in either acetonitrile or 9:1 acetonitrile:DMF and were coupled using 5-Ethylthio-1H-tetrazole (ETT, 0.25 M in acetonitrile) with a reaction time of 400 s. Phosphorothioate linkages were generated using a 100 mM solution of 3-((Dimethylamino-methylidene) amino)-3H-1,2,4-dithiazole-3-thione (DDTT, obtained from Chemgenes (Wilmington, Mass., USA)) in anhydrous acetonitrile/pyridine (9:1 v/v). Oxidation time was 5 minutes. All sequences were synthesized with final removal of the DMT group ("DMT-Off").

Upon completion of the solid phase synthesis, solid-supported oligoribonucleotides were treated with 300 μL of Methylamine (40% aqueous) at room temperature in 96 well plates for approximately 2 hours to afford cleavage from the solid support and subsequent removal of all additional base-labile protecting groups. For sequences containing any natural ribonucleotide linkages (2'-OH) protected with a tert-butyl dimethyl silyl (TBDMS) group, a second deprotection step was performed using TEA.3HF (triethylamine trihydrofluoride). To each oligonucleotide solution in aqueous methylamine was added 200 μL of dimethyl sulfoxide (DMSO) and 300 μL TEA.3HF and the solution was incubated for approximately 30 mins at 60° C. After incubation, the plate was allowed to come to room temperature and crude oligonucleotides were precipitated by the addition of 1 mL of 9:1 acetontrile:ethanol or 1:1 ethanol:isopropanol. The plates were then centrifuged at 4° C. for 45 mins and the supernatant carefully decanted with the aid of a multichannel pipette. The oligonucleotide pellet was resuspended in 20 mM NaOAc and subsequently desalted using a HiTrap size exclusion column (5 mL, GE Healthcare) on an Agilent LC system equipped with an autosampler, UV detector, conductivity meter, and fraction collector. Desalted samples were collected in 96 well plates and then analyzed by LC-MS and UV spectrometry to confirm identity and quantify the amount of material, respectively.

Duplexing of single strands was performed on a Tecan liquid handling robot. Sense and antisense single strands were combined in an equimolar ratio to a final concentration of 10 μM in 1× PBS in 96 well plates, the plate sealed, incubated at 100° C. for 10 minutes, and subsequently allowed to return slowly to room temperature over a period of 2-3 hours. The concentration and identity of each duplex was confirmed and then subsequently utilized for in vitro screening assays.

Example 2. In Vitro Screening Methods

Cell Culture and 384-Well Transfections

Hep3b cells (ATCC, Manassas, Va.) were grown to near confluence at 37° C. in an atmosphere of 5% $CO_2$ in Eagle's Minimum Essential Medium (Gibco) supplemented with 10% FBS (ATCC) before being released from the plate by trypsinization. Transfection was carried out by adding 14.8 μl of Opti-MEM plus 0.2 μl of Lipofectamine RNAiMax per well (Invitrogen, Carlsbad Calif. cat #13778-150) to 5 μl of each siRNA duplex to an individual well in a 96-well plate. The mixture was then incubated at room temperature for 15 minutes. Eighty μl of complete growth media without antibiotic containing ~$2 \times 10^4$ Hep3B cells were then added to the siRNA mixture. Cells were incubated for 24 hours prior to RNA purification. Single dose experiments were performed at 10 nM and 0.1 nM final duplex concentration and dose response experiments were done using 8×5-fold serial dilutions over the range of 10 nM to 128 pM.

Total RNA Isolation Using DYNABEADS mRNA Isolation Kit (Invitrogen™, Part #: 610-12)

Cells were lysed in 75 μl of Lysis/Binding Buffer containing 3 μL of beads per well and mixed for 10 minutes on an electrostatic shaker. The washing steps were automated on a Biotek EL406, using a magnetic plate support. Beads were washed (in 90 μL) once in Buffer A, once in Buffer B, and twice in Buffer E, with aspiration steps in between. Following a final aspiration, complete 10 μL RT mixture was added to each well, as described below.

cDNA Synthesis Using ABI High Capacity cDNA Reverse Transcription Kit (Applied Biosystems, Foster City, Calif., Cat #4368813)

A master mix of 1 μl 10× Buffer, 0.4 μl 25×dNTPs, 1 μl Random primers, 0.5 μl Reverse Transcriptase, 0.5 μl RNase inhibitor and 6.6 μl of $H_2O$ per reaction were added per well. Plates were sealed, agitated for 10 minutes on an electrostatic shaker, and then incubated at 37 degrees C. for 2 hours. Following this, the plates were agitated at 80 degrees C. for 8 minutes.

Real Time PCR

Two microlitre (μl) of cDNA were added to a master mix containing 0.5 μl of human GAPDH TaqMan Probe (4326317E), 0.5 μl human APOC3, 41 nuclease-free water and 5 μl Lightcycler 480 probe master mix (Roche Cat #04887301001) per well in a 384 well plates (Roche cat

04887301001). Real time PCR was done in a LightCycler480 Real Time PCR system (Roche).

To calculate relative fold change, data were analyzed using the ΔΔCt method and normalized to assays performed with cells transfected with 10 nM AD-1955, or mock transfected cells. $IC_{50}$s were calculated using a 4 parameter fit model using XLFit and normalized to cells transfected with AD-1955 or mock-transfected. The sense and antisense sequences of AD-1955 are: sense: cuuAcGcuGAGuAcuucGAdTsdT (SEQ ID NO:22) and antisense UCGAAGuACUcAGCGuAAGdTsdT (SEQ ID NO:23).

The results of the screening of the dsRNA agents listed in Tables 3 and 5 in Hep3B cells are shown in Tables 6 and 7, respectively.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine -3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L10 | N-(cholesterylcarboxamidocaproyl)-4-hydroxyprolinol (Hyp-C6-Chol) |
| L96 | N-[tris(GalNAc-alkyl)-amidodecanoyl)]-4-hydroxyprolinol (Hyp-(GalNAc-alkyl)3) |
| Y34 | 2-hydroxymethyl-tetrahydrofurane-4-methoxy-3-phosphate (abasic 2'-OMe furanose) |
| Y44 | inverted abasic DNA (2-hydroxymethyl-tetrahydrofurane-5-phosphate) |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |
| (Tgn) | Thymidine-glycol nucleic acid (GNA) S-Isomer |
| P | Phosphate |
| VP | Vinyl-phosphonate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |
| (C2p) | cytidine-2'-phosphate |
| (G2p) | guanosine-2'-phosphate |
| (U2p) | uridine-2'-phosphate |
| (A2p) | adenosine-2'-phosphate |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| (Chd) | 2'-O-hexadecyl-cytidine-3'-phosphate |
| (Ahd) | 2'-O-hexadecyl-adenosine-3'-phosphate |
| (Ghd) | 2'-O-hexadecyl-guanosine-3'-phosphate |
| (Uhd) | 2'-O-hexadecyl-uridine-3'-phosphate |
| i | 2'-O-methylionsine-3'-phosphate |

TABLE 2

Unmodified Sense and Antisense Strand Sequences of Apolipoprotein C3 dsRNA Agents

| Duplex ID | Sense Sequence 5' to 3' | SEQ ID NO: | Source Name | Range | Antisense Sequence 5' to 3' | SEQ ID NO: | Source Name | Range |
|---|---|---|---|---|---|---|---|---|
| AD-959917.1 | CUUCAGUUCCCUGAAAGACUU | 24 | NM_000040.3_245-265_A21U_s | 245-265 | AAGUCUUUCAGGGAACUGAAGCC | 25 | NM_000040.3_243-265_U1A_as | 243-265 |
| AD-959918.1 | UUCAGUCCCUGAAAGACUAU | 26 | NM_000040.3_246-266_C21U_s | 246-266 | AUAGUCUUUCAGGGAACUGAAGC | 27 | NM_000040.3_244-266_U1A_as | 244-266 |
| AD-960096.1 | CCAAUAAAGCUGGACAAGAAU | 28 | NM_000040.3_506-526_G21U_s | 506-526 | AUUCUUGUCCAGCUUUAUUGGGA | 29 | NM_000040.3_504-526_C1A_as | 504-526 |
| AD-960064.1 | AAAAGGGACAGUAUUCUCAGU | 30 | NM_000040.3_435-455_s | 435-455 | ACUGAGAAUACUGUCCCUUUUAA | 31 | NM_000040.3_433-455_as | 433-455 |
| AD-959914.1 | AUGGCUUCAGUUCCCUGAAAU | 32 | NM_000040.3_241-261_G21U_s | 241-261 | AUUUCAGGGAACUGAAGCCAUCG | 33 | NM_000040.3_239-261_C_1A_as | 239-261 |
| AD-959941.1 | AGCACCUUAAGGACAAGUUU | 34 | NM_000040.3_270-290_C21U_s | 270-290 | AAACUGUCCUUAACGGUGCUCC | 35 | NM_000040.3_268-290_G1A_as | 268-290 |
| AD-960031.1 | UAAAAGGGACAGUAUUCUCAU | 36 | NM_000040.3_434-454_G21U_s | 434-454 | AUGAGAAUACUGUCCCUUUUAAG | 37 | NM_000040.3_432-454_G1A_as | 432-454 |
| AD-959910.1 | ACCGAUGGCUUCAGUUCCCU | 38 | NM_000040.3_237-257_G21U_s | 237-257 | AAGGGAACUGAAGCCAUCGGUCA | 39 | NM_000040.3_235-257_C1A_as | 235-257 |
| AD-960063.1 | UAAAAGGGACAGUAUAUU | 40 | NM_000040.3_433-453_A21U_s | 433-453 | AGAGAAUACUGUCCCUUUUAAGC | 41 | NM_000040.3_431-453_U1A_as | 431-453 |
| AD-959916.1 | GCUCUCAGUUCCCUGAAAGACU | 42 | NM_000040.3_244-264_s | 244-264 | AGUCUUUCAGGGAACUGAAGCCA | 43 | NM_000040.3_242-264_as | 242-264 |
| AD-959913.1 | GAUGGCUUCAGUUCCCUU | 44 | NM_000040.3_240-260_A21U_s | 240-260 | AUCAGGGAACUGAAGCCAUCGG | 45 | NM_000040.3_238-260_U1A_as | 238-260 |
| AD-960066.1 | AAGGGACAGUAUUCUCAGUGU | 46 | NM_000040.3_437-457_C21U_s | 437-457 | ACACUGAGAAUACUGUCCCUUU | 47 | NM_000040.3_435-457_G1A_as | 435-457 |
| AD-960062.1 | CUUAAAAGGGACAGUAUUCUU | 48 | NM_000040.3_432-452_C21U_s | 432-452 | AAGAAUACUGUCCCUUUUAAGCA | 49 | NM_000040.3_430-452_G1A_as | 430-452 |
| AD-960093.1 | CUCCCAGUAAAGCUGGACAAU | 50 | NM_000040.3_503-523_G21U_s | 503-523 | AUUGUCCAGCUUUAUUGGGAGGC | 51 | NM_000040.3_501-523_C1A_as | 501-523 |
| AD-960061.1 | UGCUUAAAAGGGACAGUAGU | 52 | NM_000040.3_430-450_C21U_s | 430-450 | AAAUACUGUCCCUUUUAAGCAAC | 53 | NM_000040.3_428-450_G1A_as | 428-450 |
| AD-960092.1 | CCUCCCAUAAAGCUGGACAU | 54 | NM_000040.3_502-522_A21U_s | 502-522 | AUGUCCAGCUUUAUUGGGAGGCC | 55 | NM_000040.3_500-522_U1A_as | 500-522 |
| AD-960030.1 | GCUUAAAAGGGACAGUAUCU | 56 | NM_000040.3_431-451_s | 431-451 | AGAAUACUGUCCCUUUUAAGCAA | 57 | NM_000040.1_428-450_as | 429-451 |
| AD-80794.6 | CUUAAAAGGGACAGUAUUCUA | 13 | NM_000040.1_H433-452_C21A_s | 433-452 | UAGAAUACUGUCCCUUUUAAGCA | 58 | NM_000040.1_H433-452_C21A_s | 433-452 |
| AD-960095.1 | CCCAAUAAAGCUGGACAAGAU | 59 | NM_000040.3_505-525_A21U_s | 505-525 | AUCUUGUCCAGCUUUAUUGGGAG | 60 | NM_000040.3_503-525_U1A_as | 503-525 |
| AD-959938.1 | CUGGAGCACCGUUAAGGACAU | 61 | NM_000040.3_266-286_A21U_s | 266-286 | AUGUCCUUAACGGUGCUCCAGUA | 62 | NM_000040.3_264-286_U1A_as | 264-286 |
| AD-960065.1 | AAAAGGGACAGUAUUCUCAGU | 63 | NM_000040.3_436-456_A21U_s | 436-456 | AACUGAGAAUACUGUCCCUUUUA | 64 | NM_000040.3_434-456_U1A_as | 434-456 |
| AD-959907.1 | GUGACCGAUGGCUUCAU | 65 | NM_000040.3_234-254_G21U_s | 234-254 | AGAACUGAAGCCAUCGGUCACCC | 66 | NM_000040.3_232-254_C1A_as | 232-254 |
| AD-960094.1 | UCCCAAUAAAGCUGGACAGU | 67 | NM_000040.3_504-524_A21U_s | 504-524 | ACUUGUCCAGCUUUAUUGGGAGG | 68 | NM_000040.3_502-524_U1A_as | 502-524 |

TABLE 2-continued

Unmodified Sense and Antisense Strand Sequences of Apolipoprotein C3 dsRNA Agents

| Duplex ID | Sense Sequence 5' to 3' | SEQ ID NO: | Source Name | Range | Antisense Sequence 5' to 3' | SEQ ID NO: | Source Name | Range |
|---|---|---|---|---|---|---|---|---|
| AD-960060.1 | GGUUGCUUAAAAGGGACAGUU | 69 | NM_000040.3_427-447_A21U_s | 427-447 | AACUGUCCCUUUUAAGCAACUA | 70 | NM_000040.3_425-447_U1A_as | 425-447 |
| AD-959919.1 | UCAGUCCCUGAAAGACUACU | 71 | NM_000040.3_247-267_s | 247-267 | AGUAGUCUUUCAGGGAACUGAAG | 72 | NM_000040.3_245-267_as | 245-267 |
| AD-959932.1 | AGACUACUGGAGCACCGUUAU | 73 | NM_000040.3_260-280_A21U_s | 260-280 | AUAACGGUGCUCCAGUAGUCUUU | 74 | NM_000040.3_258-280_U1A_as | 258-280 |
| AD-959859.1 | CCACCAAGACCGCCAAGGAUU | 75 | NM_000040.3_163-183_G21U_s | 163-183 | AAUCCUUGGCGGUCUUGGUGGCG | 76 | NM_000040.3_161-183_C1A_as | 161-183 |
| AD-959908.1 | UGACCGAUGGCUUCAGUUCCU | 77 | NM_000040.3_235-255_C21U_s | 235-255 | AGGAACUGAAGCCAUCGGUCACC | 78 | NM_000040.3_233-255_G1A_as | 233-255 |
| AD-959903.1 | CUGGGUGACCGAUGGCUUCAU | 79 | NM_000040.3_230-250_G21U_s | 230-250 | AUGAAGCCAUCGGUCACCCAGCC | 80 | NM_000040.3_228-250_C1A_as | 228-250 |
| AD-960097.1 | CAAUAAAGCUGGACAAGAAGU | 81 | NM_000040.3_507-527_C21U_s | 507-527 | ACUUCUUGUCCAGCUUUAUUGGG | 82 | NM_000040.3_505-527_G1A_as | 505-527 |
| AD-959912.1 | CGAUGGCUUCAGUUCCCUGAU | 83 | NM_000040.3_239-259_A21U_s | 239-259 | AUCAGGGAACUGAAGCCAUCGGU | 84 | NM_000040.3_237-259_U1A_as | 237-259 |
| AD-960067.1 | AGGGACAGUAUUCUCAGUGCU | 85 | NM_000040.3_438-458_s | 438-458 | AGCACUGAGAAUACUGUCCCUUU | 86 | NM_000040.3_436-458_as | 436-458 |
| AD-959927.1 | AUAAAGCUGGACAAGAACACU | 87 | NM_000040.3_255-275_C21U_s | 255-275 | AGUGCUUCCAGUAGUCUUUCAGGG | 88 | NM_000040.3_253-275_G1A_as | 253-275 |
| AD-960099.1 | AAGCUGGACAAGAAGCACCGCUU | 89 | NM_000040.3_509-529_G21U_s | 509-529 | AAGCUUCUUGUCCAGCUUAUUGG | 90 | NM_000040.3_507-529_C1A_as | 507-529 |
| AD-959931.1 | AAGACUACUGGAGCACCGUUU | 91 | NM_000040.3_259-279_A21U_s | 259-279 | AAACGGUGCUCCAGUAGUCUUUA | 92 | NM_000040.3_257-279_U1A_as | 257-279 |
| AD-959879.1 | UGGCUUCAGUUCCCUGAAAGU | 93 | NM_000040.3_242-262_A21U_s | 242-262 | ACUUUCAGGGAACUGAAGCCAUC | 94 | | |
| AD-960091.1 | GCCUCCAAUAAAGCUGGACU | 95 | NM_000040.3_501-521_A21U_s | 501-521 | AGUCCAGCUUUAUUGGGAGGCCA | 96 | NM_000040.3_499-521_U1A_as | 499-521 |
| AD-959921.1 | AGUUCCCUGAAAGACUACUA | 97 | NM_000040.3_249-269_C21U_s | 249-269 | ACAGUAGUCUUUCAGGGAACUGA | 98 | NM_000040.3_247-269_C1A_as | 247-269 |
| AD-960102.1 | AAGCUGGACAAGAAGCUGCUU | 99 | NM_000040.3_512-532_A21U_s | 512-532 | AAGCAGCUUCUUGUCCAGCUUUA | 100 | NM_000040.3_510-532_U1A_as | 510-532 |
| AD-80793.6 | GCUGGACAAGAAGCUGCUAUA | 101 | NM_000040.11_515-534_G21A_s | 515-534 | UAUAGCAGCUUCUUGUCCAGCUU | 102 | NM_000040.11_513-534_G21A_as | 513-534 |
| AD-959925.1 | CCCUGAAAGACUACUGGAGCU | 103 | NM_000040.3_253-273 | 253-273 | AGCUCCAGUAGUCUUUCAGGGAA | 104 | NM_000040.3_251-273_U1A_as | 251-273 |
| AD-960098.1 | AAUAAAGCUGGACAAGAAGCU | 105 | NM_000040.3_508-528_s | 508-528 | AGCUUCUUGUCCAGCUUUAUUGG | 106 | NM_000040.3_506-528_as | 506-528 |
| AD-959901.1 | GUUGGUGGACCGAUGGCUUU | 107 | NM_000040.3_228-248_C21U_s | 228-248 | AAAGCCAUCGGUCACCAGCC | 108 | NM_000040.3_226-248_G1A_as | 226-248 |
| AD-959920.1 | CAGUUCCCUGAAAGACUACU | 109 | NM_000040.3_248-268_C21U_s | 248-268 | AAGUAGUCUUUCAGGGAACUGAA | 110 | NM_000040.3_246-268_G1A_as | 246-268 |
| AD-959926.1 | CCUGAAAGACUACUGGAGCAU | 111 | NM_000040.3_254-274_C21U_s | 254-274 | AUGCUCCAGUAGUCUUUCAGGGA | 112 | NM_000040.3_252-274_G1A_as | 252-274 |
| AD-959737.1 | CAUCCCUAGAGGCAGCUGCUU | 113 | NM_000040.3_11-31_C21U_s | 11-31 | AAGCAGCUGCCUCUAGGGAUGAA | 114 | NM_000040.3_9-31_G1A_as | 9-31 |
| AD-960011.1 | CUGCCCUGAGACCUUCAAUACCU | 115 | NM_000040.3_340-360_C21U_s | 340-360 | AGGUAUUGAGGUUCAGGCAGCC | 116 | NM_000040.3_338-360_G1A_as | 338-360 |

TABLE 2-continued

Unmodified Sense and Antisense Strand Sequences of Apolipoprotein C3 dsRNA Agents

| Duplex ID | Sense Sequence 5' to 3' | SEQ ID NO: | Source Name | Range | Antisense Sequence 5' to 3' | SEQ ID NO: | Source Name | Range |
|---|---|---|---|---|---|---|---|---|
| AD-960101.1 | AAAGCUGGACAAGAAGCUGCU | 117 | NM_000040.3_511-531_s | 511-531 | AGCAGCUUCUUGUCCAGCUUUAU | 118 | NM_000040.3_509-531_as | 509-531 |
| AD-959923.1 | UUCCCUGAAAGACUACUGGAU | 119 | NM_000040.3_251-271_G21U_s | 251-271 | AUCCAGUAGUCUUUCAGGGAACU | 120 | NM_000040.3_249-271_C_1A_as | 249-271 |
| AD-960058.1 | UAGGUUGCUUAAAAGGGACAU | 121 | NM_000040.3_425-445_G21U_s | 425-445 | AUGUCCCUUUUAAGCAACCUACA | 122 | NM_000040.3_423-445_C1A_as | 423-445 |
| AD-959860.1 | CACCAAGACCGCCAAGGAUGU | 123 | NM_000040.3_164-184_G21U_s | 164-184 | ACAUCCUUGGCGGUCUUGGUGGC | 124 | NM_000040.3_162-184_G1A_as | 162-184 |
| AD-960059.1 | AGGUUGCUUAAAAGGGACAGU | 125 | NM_000040.3_426-446_s | 426-446 | ACUGUCCCUUUUAAGCAACCUAC | 126 | NM_000040.3_424-446_as | 424-446 |
| AD-960103.1 | AGCAGGACAAGAAGCUGCUAU | 127 | NM_000040.3_513-533_s | 513-533 | AUAGCAGCUUCUUGUCCAGCUUU | 128 | NM_000040.3_511-533_as | 511-533 |
| AD-959740.1 | CCCUAGAGGCAGCUGCUCCAU | 129 | NM_000040.3_14-34_s | 14-34 | AUGGAGCAGCUGCCUCUAGGGAU | 130 | NM_000040.3_12-34_as | 12-34 |
| AD-959939.1 | UGGAGCACCGUUAAGGACAAU | 131 | NM_000040.3_267-287_G21U_s | 267-287 | AUUGUCCUUAACGGUGCUCCAGU | 132 | NM_000040.3_265-287_C1A_as | 265-287 |
| AD-959865.1 | GACCGCCAAGGAUGCACUGAU | 133 | NM_000040.3_170-190_G21U_s | 170-190 | AUCAGUGCAUCCUUGGCGGUCUU | 134 | NM_000040.3_168-190_C1A_as | 168-190 |
| AD-960100.1 | UAAAGCUGGACAAGAAGCUGU | 135 | NM_000040.3_510-530_G21U_s | 510-530 | ACAGCUUCUUGUCCAGCUUUAUU | 136 | NM_000040.3_508-530_G1A_as | 508-530 |
| AD-959924.1 | UCCCUGAAAGACUACUGGAGU | 137 | NM_000040.3_252-272_G21U_s | 252-272 | ACUCCAGUAGUCUUUCAGGGAAC | 138 | NM_000040.3_250-272_G1A_as | 250-272 |
| AD-959909.1 | GACCGAUGGCUUCAGUUCCCU | 139 | NM_000040.3_236-256_s | 236-256 | AGGGAACUGAAGCCAUCGGUCAC | 140 | NM_000040.3_234-256_as | 234-256 |
| AD-959739.1 | UCCCUAGAGGCAGCUGCUCCU | 141 | NM_000040.3_13-33_s | 13-33 | AGGAGCAGCUGCCUCUAGGGAUG | 142 | NM_000040.3_11-33_as | 11-33 |
| AD-959911.1 | CCGAUGGCUUCAGUUCCCUGU | 143 | NM_000040.3_238-258_A21U_s | 238-258 | ACAGGGAACUGAAGCCAUCGGUC | 144 | NM_000040.3_236-258_as | 236-258 |
| AD-960057.1 | GUAGGUUGCUUAAAAGGGACU | 145 | NM_000040.3_424-444_A21U_s | 424-444 | AGUCCCUUUUAAGCAACCUACAG | 146 | NM_000040.3_422-444_U1A_as | 422-444 |
| AD-959741.1 | CCUAGAGGCAGCUGCUCCAGU | 147 | NM_000040.3_15-35_G21U_s | 15-35 | ACUGGAGCAGCUGCCUCUAGGGA | 148 | NM_000040.3_13-35_U1A_as | 13-35 |
| AD-960056.1 | UGUAGGUUGCUUAAAAAGGAU | 149 | NM_000040.3_423-443_C1U_s | 423-443 | AUCCCUUUUAAGCAACCUACAGG | 150 | NM_000040.3_421-443_G1A_as | 421-443 |
| AD-959930.1 | AAAGACUACUGGAGCACCGUU | 151 | NM_000040.3_258-278_A21U_s | 258-278 | AACGGUGCUCCAGUAGUCUUUCA | 152 | NM_000040.3_256-278_as | 256-278 |
| AD-959746.1 | AGGCAGCUGCUCCAGGAACAU | 153 | NM_000040.3_20-40_G21U_s | 20-40 | AUGUUCCUGGAGCAGCUGCCUCU | 154 | NM_000040.3_18-40_U1A_as | 18-40 |
| AD-959748.1 | CAGCCUGCUCCAGGAACAGU | 155 | NM_000040.3_22-42_G21U_s | 22-42 | AUCUGUUCCUGGAGCAGCUGCCU | 156 | NM_000040.3_20-42_C1A_as | 20-42 |
| AD-959857.1 | CGCCACCAAGACCGCCAGGU | 157 | NM_000040.3_161-181_A21U_s | 161-181 | ACCUUGGCGGUCUUGGUGGCGGU | 158 | NM_000040.3_159-181_U1A_as | 159-181 |
| AD-959935.1 | CUACUGGAGCACCGUUAAGGU | 159 | NM_000040.3_263-283_A21U_s | 263-283 | ACCUUAACGGUGCUCCAGUAGUC | 160 | NM_000040.3_261-283_U1A_as | 261-283 |
| AD-960008.1 | UGGCUGCCUGAGACCUCAAUU | 161 | NM_000040.3_337-357_A21U_s | 337-357 | AAUUGAGGUCUCAGGCAGCCACG | 162 | NM_000040.3_335-357_U1A_as | 335-357 |
| AD-959915.1 | GCUUCAGUUCCCUGAAAGAU | 163 | NM_000040.3_243-263_C21U_s | 243-263 | AUCUUUCAGGGAACUGAAGCCAU | 164 | NM_000040.3_241-263_G1A_as | 241-263 |

TABLE 2-continued

Unmodified Sense and Antisense Strand Sequences of Apolipoprotein C3 dsRNA Agents

| Duplex ID | Sense Sequence 5' to 3' | SEQ ID NO: | Source Name | Range | Antisense Sequence 5' to 3' | SEQ ID NO: | Source Name | Range |
|---|---|---|---|---|---|---|---|---|
| AD-959738.1 | AUCCCUAGAGGCAGCUGCUCU | 165 | NM_000040.3_12-32_C21U_s | 12-32 | AGAGCAGCUGCCUCUAGGGAUGA | 166 | NM_000040.3_10-32_G1A_as | 08-32 |
| AD-959928.1 | UGAAAGACUACUGGAGCACCU | 167 | NM_000040.3_256-276_G21U_s | 256-276 | AGGUGCUCCAGUAGUCUUUCAGG | 168 | NM_000040.3_254-276_C1A_as | 254-276 |
| AD-959863.1 | AAGACCGCCAAGGAUGCACUU | 169 | NM_000040.3_168-188_G21U_s | 168-188 | AAGUGCAUCCUUGGCGGUCUUGG | 170 | NM_000040.3_166-188_C1A_as | 166-188 |
| AD-960010.1 | GCUGCCUGAGACCUCAAUACU | 171 | NM_000040.3_339-359_C21U_s | 339-359 | AGUAUUGAGGUCUCAGGCAGCCA | 172 | NM_000040.3_337-359_G1A_as | 337-359 |
| AD-960090.1 | GGCCUCCCAAUUAAAGCUGGAU | 173 | NM_000040.3_500-520_C21U_s | 500-520 | AUCCAGCUUUAUUGGGAGGCCAG | 174 | NM_000040.3_498-520_G1A_as | 498-520 |
| AD-959732.1 | CAGUCAUCCCUAGAGGCAGU | 175 | NM_000040.3_6-26_C21U_s | 6-26 | ACUGCCUCUAGGGAUGAACUGAG | 176 | NM_000040.3_4-26_G1A_as | 4-26 |
| AD-960009.1 | GGCUGCCUGAGACCUCAAUAU | 177 | NM_000040.3_338-358_C21U_s | 338-358 | AUAUUGAGGUCUCAGGCAGCCAC | 178 | NM_000040.3_336-358_G1A_as | 336-358 |
| AD-959929.1 | GAAAGACUACUGGAGCACCGU | 179 | NM_000040.3_257-277_s | 257-277 | ACGUGCUCCAGUAGUCUUUCAG | 180 | NM_000040.3_255-277_as | 255-277 |
| AD-959745.1 | GAGGCAGCUGCCUCUAGGAACU | 181 | NM_000040.3_19-39_A21U_s | 19-39 | AGUUCCUGAGGCAGCUGCCCUA | 182 | NM_000040.3_17-39_U1A_as | 17-39 |
| AD-960007.1 | GUGGCUGCCUGAGACCUCAAU | 183 | NM_000040.3_336-356_s | 336-356 | AUUGAGGUCUCAGGCAGCCACCGG | 184 | NM_000040.3_334-356_as | 334-356 |
| AD-959902.1 | GCUGGGCUGACCGAUGGCCUCU | 185 | NM_000040.3_229-249_s | 229-249 | AGAAGCCAUCGGUCACCCAGCCC | 186 | NM_000040.3_227-249_as | 227-249 |
| AD-959940.1 | GGAGCACCGUUAAGGACAAGU | 187 | NM_000040.3_268-288_s | 268-288 | ACUUGUCCUUAACGGUGCUCCAG | 188 | NM_000040.3_266-288_as | 266-288 |
| AD-960055.1 | CUGUAGGUUGCCUUAAAAGGGU | 189 | NM_000040.3_422-442_A21U_s | 422-442 | ACCCUUUAAGCAACCUACAGGG | 190 | NM_000040.3_420-442_U1A_as | 420-442 |
| AD-959922.1 | GUUCCCGAAAGACUACUGG | 191 | NM_000040.3_250-270_A21U_s | 250-270 | ACCAGUAGUCUUUCUUCAGGGAACUG | 192 | NM_000040.3_248-270_U1A_as | 248-270 |
| AD-959900.1 | GGGCUGGGUGACCGAUGGCUU | 193 | NM_000040.3_227-247_s | 227-247 | AAGCCAUCGGUCACCCAGCCCCU | 194 | NM_000040.3_225-247_as | 225-247 |
| AD-959858.1 | GCCACCAAGACCGCCAAGGAU | 195 | NM_000040.3_162-182_s | 162-182 | AUCCUUGGCGGUCUUGGUGGCGU | 196 | NM_000040.3_160-182_as | 160-182 |
| AD-959744.1 | AGAGGCAGCUGCCUCCAGGAAU | 197 | NM_000040.3_18-38_C21U_s | 18-38 | AUUCCUGGAGCAGCUGCCUCUAG | 198 | NM_000040.3_16-38_G1A_as | 16-38 |
| AD-959736.1 | UCAUCCCUAGAGGCAGCUGCU | 199 | NM_000040.3_10-30_s | 10-30 | AGCAGCUGCCUCUAGGGAUGAAC | 200 | NM_000040.3_8-30_as | 08-30 |
| AD-959735.1 | UUCAUCCCUAGAGGCAGCAG | 201 | NM_000040.3_9-29_s | 9-29 | ACAGCUGCCUCUAGGGAUGAACU | 202 | NM_000040.3_7-29_as | 29-Jul |
| AD-960039.1 | CGAGCUCCUUGGGUCCUCUGU | 203 | NM_000040.3_386-406_C21U_s | 386-406 | AUGCAGGACCCAAGGACUCCGCA | 204 | NM_000040.3_384-406_G1A_as | 384-406 |
| AD-959747.1 | GGCAGCUGCCUCCAGGAACAGU | 205 | NM_000040.3_21-41_A21U_s | 21-41 | ACUGUUCCUGGAGCAGCUGCCUC | 206 | NM_000040.3_19-41_U1A_as | 19-41 |
| AD-959862.1 | CCAAGACCGCCAAGGAUGCAU | 207 | NM_000040.3_166-186_C21U_s | 166-186 | AUGCAUCCUUGGCGGUCUUGGUG | 208 | NM_000040.3_164-186_G1A_as | 164-186 |
| AD-959933.1 | GACUACUGGAGCACCGUUAAU | 209 | NM_000040.3_261-281_G21U_s | 261-281 | AUUAACGGUGCUCCAGUAGUCU | 210 | NM_000040.3_259-281_C1A_as | 259-281 |
| AD-959733.1 | AGUUCAUCCCUAGAGGCAGCU | 211 | NM_000040.3_7-27_s | 7-27 | AGCUGCCUCUAGGGAUGAACUGA | 212 | NM_000040.3_5-27_as | 5-28 |

TABLE 2-continued

Unmodified Sense and Antisense Strand Sequences of Apolipoprotein C3 dsRNA Agents

| Duplex ID | Sense Sequence 5' to 3' | SEQ ID NO: | Source Name | Range | Antisense Sequence 5' to 3' | SEQ ID NO: | Source Name | Range |
|---|---|---|---|---|---|---|---|---|
| AD-959937.1 | ACUGGAGCACCGUUAAGGACU | 213 | NM_000040.3_265-285_A21U_s | 265-285 | AGUCCUUAACGGUGCUC CAGUAG | 214 | NM_000040.3_263-285_U1A_as | 263-285 |
| AD-959904.1 | UGGGUGACCGAUGGCUUCAGU | 215 | NM_000040.3_231-251_s | 231-251 | ACUGAAGCCAUCGGUCA CCCAGC | 216 | NM_000040.3_229-251_as | 229-251 |
| AD-959797.1 | CCGAGCUUCAGAGGCCGAGGU | 217 | NM_000040.3_101-121_A21U_s | 101-121 | ACCUCGGCCUCUGAAGC UCGGGC | 218 | NM_000040.3_99-121_U1A_as | 99-121 |
| AD-959861.1 | ACCAAGACCGCCAAGGAUGCU | 219 | NM_000040.3_165-185_A21U_s | 165-185 | AGCAUCCUUGGCGGUCU UGGUGG | 220 | NM_000040.3_163-185_U1A_as | 163-185 |
| AD-959743.1 | UAGAGGCAGCUGCUCCAGGAU | 221 | NM_000040.3_17-37_A21U_s | 17-37 | AUCCUGGAGCAGCUGCC UCUAGG | 222 | NM_000040.3_15-37_U1A_as | 15-37 |
| AD-959905.1 | GGGUGACCGAUGGCUUCAGUU | 223 | NM_000040.3_232-252_s | 232-252 | AACUGAAGCCAUCGGUC ACCCAG | 224 | NM_000040.3_230-252_as | 230-252 |
| AD-959734.1 | GUUCAUCCCUAGAGGCAGCUU | 225 | NM_000040.3_8-28_s | 8-28 | AAGCUGCCUCUAGGGAU GAACUG | 226 | NM_000040.3_6-28_as | 6-28 |
| AD-959934.1 | ACUACUGGAGCACCGUUAAGU | 227 | NM_000040.3_262-282_G21U_s | 262-282 | ACUUAACGGUGCUCCAG UAGUCU | 228 | NM_000040.3_260-282_as | 260-282 |
| AD-959749.1 | CAGCUGCUCCAGGAACAGAGU | 229 | NM_000040.3_23-43_G21U_s | 23-43 | ACUCUGUUCCUGGAGCA GCUGCC | 230 | NM_000040.3_21-43_as | 21-43 |
| AD-959798.1 | CGAGCUUCAGAGGCCGAGGAU | 231 | NM_000040.3_102-122_G21U_s | 102-122 | AUCCUCGGCCUCUGAAG CUCGGG | 232 | NM_000040.3_100-122_as | 100-122 |
| AD-959742.1 | CUAGAGGCAGCUGCUCCAGGU | 233 | NM_000040.3_16-36_A21U_s | 16-36 | ACCUGGAGCAGCUGCCU CUAGGG | 234 | NM_000040.3_14-36_as | 14-36 |
| AD-959897.1 | GAGUCCCAGGUGGGCCCAGCU | 235 | NM_000040.3_201-221_G21U_s | 201-221 | AUGCUGGGCCCACCUGGG ACUCCU | 236 | NM_000040.3_199-221_as | 199-221 |
| AD-959864.1 | AGACCGCCAAGGAUGCAGUUU | 237 | NM_000040.3_169-189_G21U_s | 169-189 | AACAGCAUCCUUGGCGG UCUUGG | 238 | NM_000040.3_167-189_U1A_as | 167-189 |
| AD-959899.1 | CCAGGUGGGCCCAGCAGGCAU | 239 | NM_000040.3_206-226_G21U_s | 206-226 | AUGCCUGCUGGGCCCAC CUGGGA | 240 | NM_000040.3_204-226_as | 204-226 |
| AD-959856.1 | ACGCCACCCAAGACCGCCAAGU | 241 | NM_000040.3_160-180_G21U_s | 160-180 | ACUUGGCGGUCUUGGUG GCGUGC | 242 | NM_000040.3_158-180_C1A_as | 158-180 |
| AD-959906.1 | GGUGACCGAUGGCUUCAGUUU | 243 | NM_000040.3_233-253_C21U_s | 233-253 | AAACUGAAGCCAUCGGU CACCCA | 244 | NM_000040.3_231-253_G1A_as | 231-253 |
| AD-959936.1 | UACUGGAGCACCGUUAAGGAU | 245 | NM_000040.3_264-284_C21U_s | 264-284 | AUCCUUAACGGUGCUCC AGUAGU | 246 | NM_000040.3_262-284_G1A_as | 262-284 |
| AD-959896.1 | GGAGUCCCAGGUGGGCCCAGU | 247 | NM_000040.3_200-220_A21U_s | 200-220 | AGUGGGCCCACCUGGGA CUCCUG | 248 | NM_000040.3_198-220_U1A_as | 198-220 |
| AD-959893.1 | GCAGGAGUCCCAGGUGGGCCU | 249 | NM_000040.3_197-217_A21U_s | 197-217 | AGGGCCACCUGGGACUC CUGCAC | 250 | NM_000040.3_195-217_U1A_as | 195-217 |
| AD-959892.1 | UGCAGGAGUCCCAGGUGGGCU | 251 | NM_000040.3_196-216_C21U_s | 196-216 | AGGCCACCUGGGACUCC UGCACG | 252 | NM_000040.3_194-216_G1A_as | 194-216 |
| AD-959894.1 | CAGGAGUCCCAGGUGGGCCCU | 253 | NM_000040.3_198-218_C21U_s | 198-218 | AUGGGCCACCUGGGACU CCUGCA | 254 | NM_000040.3_196-218_G1A_as | 196-218 |
| AD-959750.1 | AGCUGCUCCAGGAACAGAGGU | 255 | NM_000040.3_24-44_s | 24-44 | ACCUCUGUUCCUGGAGC AGCUGC | 256 | NM_000040.3_22-44_as | 22-44 |

TABLE 2-continued

Unmodified Sense and Antisense Strand Sequences of Apolipoprotein C3 dsRNA Agents

| Duplex ID | Sense Sequence 5' to 3' | SEQ ID NO: | Source Name | Range | Antisense Sequence 5' to 3' | SEQ ID NO: | Source Name | Range |
|---|---|---|---|---|---|---|---|---|
| AD-959898.1 | AGUCCCAGGUGGCCCAGCAGU | 257 | NM_000040.3_202-222_G21U_s | 202-222 | ACUGCUGGGCCACCUGGGACUCC | 258 | NM_000040.3_200-222_C1A_as | 200-222 |
| AD-959895.1 | AGGAGUCCCAGGUGGCCCAGU | 259 | NM_000040.3_199-219_C21U_s | 199-219 | ACUGGGCCACCUGGGACUCCUGC | 260 | NM_000040.3_197-219_G1A_as | 197-219 |

TABLE 3

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-959917.1 | csusucagUfuCfCfCfctugaaagacuuL96 | 341 | asAfsgucUfuUfCfcaggAfaCfctugaagscsc | 342 | GGCUUCAGUUCCCUGAAAGACUA | 343 |
| AD-959918.1 | ususcagUfcCfCfCfuUfgaaagacuauL96 | 344 | asUfsaguCfuUTUfcaggGfaAfcugaasgsc | 345 | GCUUCAGUUCCCUGAAAGACUAC | 346 |
| AD-960096.1 | cscsaauaAfaGfCfUfggacaagaauL96 | 347 | asUfsucuUfguCfcagcUfUfauuggsgsa | 348 | UCCCAAUAAAGCUGGACAAGAAG | 349 |
| AD-960064.1 | asaaaaggGfaCfAfGfUfuauucucaguL96 | 350 | asCfsugaGfaAfUfacugUfcCfcuuuusasa | 351 | UUAAAAGGGACAGUAUUCUCAGU | 352 |
| AD-959914.1 | asusggcuUfcAfGfUfuccccugaaauL96 | 353 | asUfsuucAfgGfGfAfcaacGfaAfgccauscsg | 354 | CGAUGGCUUCAGUUCCCUGAAAG | 355 |
| AD-959941.1 | asgcaccCfuUfAfAfGfgacaaguuuL96 | 356 | asAfsacuUfgUfCfcuuaAfcGfgugcuscsc | 357 | GGAGCACCGUUAAGGACAAGUUC | 358 |
| AD-960031.1 | usasaaagGfgAfCfAfgUfauaucucauL96 | 359 | asUfsgagAfaUfAfcuguCfcCfuuuasasg | 360 | CUUAAAAGGGACAGUAUUCUCAG | 361 |
| AD-959910.1 | asccgaugGfcCfUfUfCfaguccccuuL96 | 362 | asAfsgggaAfaCfUfggaagCfcAfucggucsa | 363 | UGACCGAUGGCUUCAGUUCCCUG | 364 |
| AD-960063.1 | ususaaaaGfgGfaCfUfAfcaguauucucuL96 | 365 | asGfsagaAfuAfcUfguccCfcUfuuuaasgsc | 366 | GCUUAAAAGGGACAGUAUUCUCA | 367 |
| AD-959916.1 | gscsuucaGfuUfCfCfCfugaaagacuuL96 | 368 | asGfsucuUfuCfAfgggaAfcUfgaagcscsa | 369 | UGGCUUCAGUUCCCUGAAAGACU | 370 |
| AD-959913.1 | gsasuggCfuUfCfAfGfUfuucccugaauL96 | 371 | asUfsucaGfgGfAfacugUfuCfccaucsgsg | 372 | CCGAUGGCUUCAGUUCCCUGAAA | 373 |
| AD-960066.1 | asasggggaCfaGfUfAfauucucaguguL96 | 374 | asCfsacuGfaGfAfauacUfgUfcccuususu | 375 | AAAAGGGACAGUAUUCUCAGUGC | 376 |
| AD-960062.1 | csusuaaaAfgGfGfAfcagauaucuuL96 | 377 | asGfsgaaUfaCfUfguccCfuUfuaagcscsa | 378 | UGCUUAAAAGGGACAGUAUUCUC | 379 |
| AD-960093.1 | csuscccaAfuAfAfAfgcuggacaauL96 | 380 | asUfsugucCfcAfgCfcuuuAfuUfgggagsgsc | 381 | GCUCCCAAUAAAGCUGGACAAG | 382 |
| AD-960061.1 | usggcuuaAfaAfGfGfgacaguauuL96 | 383 | asAfsauaCfuGfUfccccUfuUfuaagcasasc | 384 | GUUGCUUAAAAGGGACAGUAUUC | 385 |
| AD-960092.1 | cscsuccAfaUfAfAfAfagcuggacaauL96 | 386 | asUfsguCfCfaGfCfcuuuaUfuGfggaggscsc | 387 | GGCCUCCCAAUAAAGCUGGACAA | 388 |
| AD-960030.1 | gscsuuaaAfaGfGfGfacaguauucuL96 | 389 | asGfsaaaAfcUfGfuccCfUfuUfuaagcsasa | 390 | UUGCUUAAAAGGGACAGUAUUCU | 391 |
| AD-80794.6 | csusuaaaAfgGfGfAfCfaguauucuaL96 | 17 | usAfsgaaUfaCfUfgucCfuUfuuaagscsa | 392 | CUUAAAAGGGACAGUAUUCUA | 393 |
| AD-960095.1 | cscscaauAfaAfAfGfCfuggacaagauL96 | 394 | asUfscuuGfuCfCfagcuUfuAfuugggsasg | 395 | CUCCCAAUAAAGCUGGACAAGAA | 396 |
| AD-959938.1 | csusggagCfaCfCfGfUfuaaggacauL96 | 397 | asUfsgucCfuUfAfacgGfgCfuccagsusa | 398 | UACUGGAGCACCGUUAAGGACAA | 399 |
| AD-960065.1 | asaaaggGfaCfAfGfUfauucucaguL96 | 400 | asCfsugaAfgAfAfuacuGfuCfccuuususa | 401 | UAAAAGGGACAGUAUUCUCAGUG | 402 |
| AD-959907.1 | gsusgaccGfaUfGfGfCfcuucaguucuL96 | 403 | asGfsaacUfgAfAfgccaUfcGfgucaccscsc | 404 | GGGUGCCGAUGGCUUCAGUUCC | 405 |
| AD-960094.1 | uscscccaaUfaAfAfAfGfcuggacaaguL96 | 406 | asCfsuugUfcCfAfgcuuUfaUfuggasgsg | 407 | CCUCCCAAUAAAGCUGGACAAGA | 408 |
| AD-960060.1 | gsggsuugcUfuAfAfAfaagggacaguuL96 | 409 | asAfscugUfcCfCfuuuuAfaGfcaaccsusa | 410 | UAGGUUGCUUAAAAGGGACAGUA | 411 |

TABLE 3-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-959919.1 | uscsaguuCfcCfUfGfaaagacuacuL96 | 412 | asGfsuagUfcUfUfucagGfgAfacugasasg | 413 | CUUCAGUUCCCUGAAAGACUACU | 414 |
| AD-959932.1 | asggsacuaCfuGfGfAfgcaccguuauL96 | 415 | asUfsaacGfgUfGfcuccAfgUfagucususu | 416 | AAAGACUACUGGAGCACCGUUAA | 417 |
| AD-959859.1 | cscssaccaAfgAfCfCfcgccaaggauuL96 | 418 | asAfsuccUfuGfGfcgguCfuUfggugscsg | 419 | CGCCACCAAGACCGCCAAGGAUG | 420 |
| AD-959908.1 | usgsaccgAfuGfGfGfCfuucaguuccuL96 | 421 | asGfsgaaCfuGfAfagcCfAfuCfggucascsc | 422 | GGUGACCCGAUGGCUUCAGUCCC | 423 |
| AD-959903.1 | csusggggUfaCfCfGfauggcuucauL96 | 424 | asUfsgaaGfcCfAfucgGfucAfcccagscsc | 425 | GGCUGGGUGACCCGAUGGCUUCAG | 426 |
| AD-960097.1 | csasauaaAfgCfUfGfGfgacaagaguL96 | 427 | asCfsuucUfuGfUfccagCfuUfuauugsgsg | 428 | CCCAAUAAAGCUGGACAAGAAGC | 429 |
| AD-959912.1 | csgsauggCfufUfCfAfguucccgauL96 | 430 | asUfscagGfgAfAfcugaAfgCfcaucgsgsu | 431 | ACCGAUGGCUUCAGUUCCCUGAA | 432 |
| AD-960067.1 | asgggaCfAfgGfGfAfUfucucagugcuL96 | 433 | asGfscacUfgAfGfaauaCfuGfuccususu | 434 | AAAGGGACAGUAUUCUCAGUGCU | 435 |
| AD-959927.1 | csusgaaaGfaCfuUfAfcuggagcacuL96 | 436 | asGfsugcUfcCfAfguagUfcUfuucagsgsg | 437 | CCCUGAAAGACUACUGGAGCACC | 438 |
| AD-960099.1 | asuaaaaGfcUfGfGfAfcaagaaguL96 | 439 | asAfsgcuUfcUfUfguccAfgCfuuuaususg | 440 | CAAUAAAGCUGGACAAGAAGCUG | 441 |
| AD-959931.1 | asasgacuAfcUfGfGfAfagcaccguuuL96 | 442 | asAfsacgGfuGfCfuuccAfgUfaAfgucuusususc | 443 | GAAAGACUACUGGAGCACCGUUA | 444 |
| AD-959879.1 | ugsgcuucCfaGfUfUfcccugaaagaL96 | 445 | asCfsuuucCfaGfGfgaacUfgGfaagcasusuc | 446 | GAUGGCUUCAGUUCCCUGAAAGA | 447 |
| AD-960091.1 | gcscuccCfaAfAfUfAfaagcuggacuL96 | 448 | asGfsuccAfgCfUfuuauUfgGfgaggcscsa | 449 | UGGCCCUCCCAAUAAAGCUGGACA | 450 |
| AD-959921.1 | asgguccCfuGfAfAfAfagacuacuguL96 | 451 | asCfsaguaAfgUfCfuuucAfgGfgaacusgsa | 452 | UCAGUCCCUGAAAGACUACUGG | 453 |
| AD-960102.1 | asasgcugGfaCfAfAfgaagcugcuuL96 | 454 | asAfsgcadUfcCfUfUfcuugUfcCfagcuususa | 455 | UAAAGCUGGACAAGAAGCUGCUA | 456 |
| AD-80793.6 | gcsuggaCfaAfGfAfAfagcugcuauaL96 | 457 | usAfsuagCfaGfCfuuucUfgUfccagcsusu | 458 | GCUGGACAAGAAGCUGCUAUAUA | 459 |
| AD-959925.1 | cscscugaAfaGfAfCfUfacuggagcaL96 | 460 | asGfscucCfcaGfUfagucUfuUfcagggsasa | 461 | UUCCCUGAAAGACUACUGGAGCA | 462 |
| AD-960098.1 | asasuaaaGfcUfGfGfGfacaagaaguL96 | 463 | asGfscucCfuUfGfuccaGfcUfiuauusgsg | 464 | CCAAUAAAGCUGGACAAGAAGCU | 465 |
| AD-959901.1 | gggscuggCfuGfUfGfAfcccgauggcuuL96 | 466 | asAfsgccCfaUfCfgguCfAfccCfcagccsc | 467 | GGGGCUGGGUGACCCGAUGGCUUC | 468 |
| AD-959920.1 | csasguuCfcCfUfGfAfaagacuacuL96 | 469 | asGfsuagUfuCfUfuucaGfgAfaacugsasa | 470 | UUCCCUGAAAGACUACUACUG | 471 |
| AD-959926.1 | cscsugaaAfgAfCfUfAfcuggagcauL96 | 472 | asUfsgcuCfcAfGfuaguCfuUfucagggsa | 473 | UCCCUGAAAGACUACUGGAGCAC | 474 |
| AD-959737.1 | csasuccCfuGfAfGfGfcccuCfuaGfcagcugcuL96 | 475 | asAfsgcaGfcUfGfCfccuCfuaGfggaugsasa | 476 | UUCAUCCCUAGAGGCCAGCUGCUC | 477 |
| AD-960011.1 | csusgccuGfaGfAfCfIfcucaauaccuL96 | 478 | asGfsguaUfuGfAfggucCfuCfAfggcagsc | 479 | GGCUGCCUGAGACCUUCAAUACCC | 480 |
| AD-960101.1 | asasagcugCfuAfCfCfAfagaagcugcuL96 | 481 | asGfscagCfuUfCfuuguCfcAfgcuuuasu | 482 | AUAAAGCUGGACAAGAAGCUGCU | 483 |

TABLE 3-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-959923.1 | ususcccuGfaAfAfGfAfGfacuacuggauL96 | 484 | asUfsccaGfuAfGfucuuUfcAfgggaascsu | 485 | AGUCCCUGAAAGACUACUGGAG | 486 |
| AD-960058.1 | usasgguuGfcUfUfAfAfAfaagggacauL96 | 487 | asUfsguCfcUfUfuuaaGfcAfaccuascsa | 488 | UGUAGGUUGCUUAAAAGGGACAG | 489 |
| AD-959860.1 | csasccaGfacCfCfGfCfccaaggaugsuL96 | 490 | asCfsauccfuUfGfcgguUfcUfuggusgsgsc | 491 | GCCACCAAGACCGCCAAGGAUGC | 492 |
| AD-960059.1 | agsguugCfuUfAfAfAfaagggacagsuL96 | 493 | asCfsugugUfccCfUfuuuaAfgCfaaccusasc | 494 | GUAGGUUGCUUAAAAGGGACAGU | 495 |
| AD-960103.1 | agscuggAfcAfAfGfAfagcuguacuauL96 | 496 | asUfsagcAfgCfUfucuuGfuCfcagcucsusu | 497 | AAAGCUGACAAGAAGCUGCUAU | 498 |
| AD-959740.1 | cscscuagAfgGfCfAfgfcugcuccauL96 | 499 | asUfsggaGfcAfGfcugcCfuCfiaggggsasu | 500 | AUCCCUAGAGGCAGCUGCUCCAG | 501 |
| AD-959939.1 | ugsggacAfccCfGfUfuaaggacaauL96 | 502 | asUfsguguCfcUfUfaacgGfuGfcuccasgsu | 503 | ACUGGAGCACCGUUAAGGACAAG | 504 |
| AD-959865.1 | gsasccgcCfaAfGfGfGfaugcacugaUL96 | 505 | asUfscagUfgCfAfuccuUfgGfcggucsusu | 506 | AAGACCGCCAAGGAUGCACUGAG | 507 |
| AD-960100.1 | usasaagcUfgGfAfCfAfaagaagcuguL96 | 508 | asCfsagcUfuCfUfuguCfCfaGfcuuuasusu | 509 | AAUAAAGCUGGACAAGAAGCUGC | 510 |
| AD-959924.1 | uscscugaAfgAfAfGfAfcuacuggaguL96 | 511 | asCfscuuCfAfgUfucuUfcUfaggggasasc | 512 | GUUCCCUGAAAGACUACUGGAGC | 513 |
| AD-959909.1 | gsasccgaAfcUfGfGfCfcUfucaguucccuL96 | 514 | asGfsggaAfcUfGfaagcCfaUfcggucsasc | 515 | GUGACCGAUGGCUUCAGUCCCU | 516 |
| AD-959739.1 | uscscuuaGfaGfCfcagctgccucuL96 | 517 | asCfscagfcTaGfCfugcCfUfaggasugs | 518 | CAUCCUAGAGGCAGCUGCUCCA | 519 |
| AD-959911.1 | cscsgaugGfcUfCfUfaguccgugul96 | 520 | asCfsaggGfaAfCfugaAfGfcfaucgsusc | 521 | GACCGAUGGCUUCAGUCCCUGA | 522 |
| AD-960057.1 | gsusagguUfgCfUfUfaaaagggactL96 | 523 | asCfsuccCfUfUfuaagCfaAfcuacsasg | 524 | CUGUAGGUUGCUUAAAAGGGACA | 525 |
| AD-959741.1 | cscsuagaGfgCfAfgfcuguccaguL96 | 526 | asCfsuggaAfgCfAfgucgCfcUfcuaggsgsa | 527 | UCCCUAGAGGCAGCUGCUCCAGG | 528 |
| AD-960056.1 | ugsuaggUfuGfCfUfUfuaaagggauL96 | 529 | asUfscccUfuUfUfaagcAfaCfcuacasgsg | 530 | CCUGUAGGUUGCUUAAAAGGGAC | 531 |
| AD-959930.1 | asasagaCfuAfcUfUfGfgagcaccguuL96 | 532 | asAfscgUfgCfUfccagUfaGfucuuuscsa | 533 | UGAAAGACUACUGGAGCACCGUU | 534 |
| AD-959746.1 | agsgsgcagCfuGfCfUfUfccaggaacauL96 | 535 | asUfsguuCfcUfGfgagcAfgCfugccucsusu | 536 | AGAGGCAGCUGCUCCAGGAACAG | 537 |
| AD-959748.1 | gscsagcugCfuCfCfCfaggaacagauL96 | 538 | asUfscugUfucfCfuggaGfcAfgcugcsccsu | 539 | AGGCAGCUGCUCCAGGAACAGAG | 540 |
| AD-959857.1 | csgscscaCfaaGfAfCfCfgcaaggauL96 | 541 | asCfscuuGfgCfGfgucUfgGfuggcgsusg | 542 | CACGCCACCAAGACCGCCAAGGA | 543 |
| AD-959935.1 | csusacugGfaGfCfAfcgucsuaaaagguL96 | 544 | asCfscuuAfacfGfgugcUfcCfaguagsusc | 545 | GACUACUGGAGCACCGUUAAGGA | 546 |
| AD-960008.1 | usgsgcuuCfcUfAfGfaccucaauuL96 | 547 | asAfsuugAfgGfUfcuaGfgfcagcascsg | 548 | CGUGGCUGCCUGAGACCUUCAAUA | 549 |
| AD-959915.1 | gsgscuucAfgGfUfCfccugaaagauL96 | 550 | asUfscuUfUfCfAfGfggaaCfuGfaagccsasu | 551 | AUGGCUUCAGUCCCUGAAAGAC | 552 |
| AD-959738.1 | asuscccuAfgGfCfGfcagcugcucuL96 | 553 | asGfsagcAfgCfUfgccucfCfuAfgggausga | 554 | UCAUCCCUAGGCGCAGCUGCUCC | 555 |
| AD-959928.1 | ugsgaaagAfcUfAfCfuggagcaccuL96 | 556 | asGfsgugCfucCfCfagtuaGfuCfuuucasgsg | 557 | CCUGAAAGACUACUGGAGCACCG | 558 |

TABLE 3-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-959863.1 | asasgaccGfcCfAfAfggaugcacuLl96 | 559 | asAfsgugCfaUfCfcuugGfcGfgucuusgsg | 560 | CCAAGACCGCCAAGGAUGCACUG | 561 |
| AD-960010.1 | gscsugcCfugAfGfAfccucaauacuLl96 | 562 | asGfsuauUfgAfGfgucucUfaGfgcagcscsa | 563 | UGGCUGCCUGAGACCUCAAUACC | 564 |
| AD-960090.1 | gggscccucCfcAfAfUfaaagcuggauLl96 | 565 | asUfsccaGfcUfUfuauuGfgGfaggccsasg | 566 | CUGGCCUCCCAAUAAAGCUGGAC | 567 |
| AD-959732.1 | csasguucAfucCfcUfCfcuaggagcaguLl96 | 568 | asUfsgcCfuCfUfaggAfuGfaacugasasg | 569 | CUCAGUUCAUCCCUAGAGGCAGC | 570 |
| AD-960009.1 | gggscugCfugGfAfGfaccucaauauLl96 | 571 | asUfsauuGfaGfGfucucAfgGfcagccsasc | 572 | GUGGCUGCCUGAGACCUCAAUAC | 573 |
| AD-959929.1 | gsasaagaCfuAfCfUfUfggagcaccguLl96 | 574 | asCfsgguGfcUfCfcaguAfgUfcuuucsasg | 575 | CUGAAAGACUACUGGAGCACCGU | 576 |
| AD-959745.1 | gsasggcaGfcUfCfUfGfCfuccaggaacuLl96 | 577 | asGfsuucCfuGfGfagcacfcUfgcccusus | 578 | UAGAGGCAGCUGCCUGGAGGAACA | 579 |
| AD-960007.1 | gsusggcuGfcCfUfCfGfagaccucaauLl96 | 580 | asUfsugaGfgUfCfucagGfcAfgccacgsg | 581 | CCCUGGCUGCCUGAGACCUCAAU | 582 |
| AD-959902.1 | gscsugggUfgAfCfCfGfUfugaugcuuLl96 | 583 | asGfsaagCfcAfUfcgguCfaCfccagccsc | 584 | GGGCUGGGUGACCGAUGGCUUCA | 585 |
| AD-959940.1 | gsgsagcacCfcGfUfUfaaggacaaguLl96 | 586 | asCfsuugcCfuCfUfuaacCfgUfgcccasg | 587 | CUGGAGCACCGUUAAGGACAAGU | 588 |
| AD-960055.1 | csusugaCfcUfuGfGfCfuuaaaagggLl96 | 589 | asCfsccuUfuUfAfagcaFfcFtacagsgsg | 590 | CCCUGUAGGUUGCUUAAAAGGGA | 591 |
| AD-959922.1 | gsusuccCfugGfAfAfAfgacuacuggcuLl96 | 592 | asCfscaguUfaGfUfcuuucCfaGfgaacsusg | 593 | CAGUCCCUGGAAAGACUACUGGA | 594 |
| AD-959900.1 | gsgsgcugCfugGfgfgfAfAfccgaugcuLl96 | 595 | asAfsgcCfaUfCfggucaCfccCfagcccsc | 596 | AGGGGCUGGGUGACCGAUGGCUU | 597 |
| AD-959858.1 | gscscaccAfagAfCfCfgccaaggauLl96 | 598 | asUfsccUfgGfCfgguCfcUfGfuggcsgsu | 599 | ACGCCACCAAGACCGCCAAGGAU | 600 |
| AD-959744.1 | asgsaggcAfgcCfUfGfCfucucaggaauLl96 | 601 | asUfsuccCfuGfAfGfcagCfuGfccucusasg | 602 | CUAGAGGCAGCUGCUCCAGGAAC | 603 |
| AD-959736.1 | uscsauccCfuAfGfAfgcCfugcaguLl96 | 604 | asGfscagCfuGfCfcucuAfgGfgaugasasc | 605 | GUUCAUCCCUAGAGGCAGCUGCU | 606 |
| AD-959735.1 | ususcaucCfcUfAfGfaggcagcuguLl96 | 607 | asCfsagcUfgCfCfucuaGfgGfaugaascsu | 608 | AGUUCAUCCCUAGAGGCAGCUGC | 609 |
| AD-960039.1 | csgsagcuCfcUfUfGfGfgucCfuGfcaaLl96 | 610 | asUfsgcaGfgAfCfcaaGfgAfgcucgscsa | 611 | UGCCGAGCUCCUUGGGUCCUGCAA | 612 |
| AD-959747.1 | gggscagCfugCfUfCfcaggaacaGfaLl96 | 613 | asCfsuguUfcCfUfggaGfcAfgcugccsusc | 614 | GAGGCAGCUGCUCCAGGAACAGA | 615 |
| AD-959862.1 | cscsaagaCfcGfCfCfAfaaggauGfcauLl96 | 616 | asUfsgcaUfccUfUfggcGfgUfcuuggsusg | 617 | CACCAAGACCGCCAAGGAUGCAC | 618 |
| AD-959933.1 | gsasuacUfggAfGfCfaccguuaauLl96 | 619 | asUfsuaaCfgGfUfgcucCfaGfuagucsusu | 620 | AAGACUACUGGAGCACCGUUAAG | 621 |
| AD-959736.1 | asgsuucaUfcCfCfUfafagaggcaguLl96 | 622 | asGfscugCfcUfCfuaggGfaUfgaacusgsa | 623 | UCAGUUCAUCCCUAGAGGCAGCU | 624 |
| AD-959937.1 | ascsuggaGfcAfCfCfGfuuaaggacuLl96 | 625 | asGfsuccUfuAfAfcgguCfUfccagusasg | 626 | CUACUGGAGCACCGUUAAGGACA | 627 |
| AD-959904.1 | uagsgggUfgAfcCfGfaUfuggcuucaguLl96 | 628 | asCfsugaAfgCfCfaucgGfuCffaccasgsc | 629 | GCUGGGUGACCGAUGGCUUCAGU | 630 |

TABLE 3-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-959797.1 | cscsgagcUfucfAfGfaggccgagguL96 | 631 | asCfscucGfgCfcfucugAfaGfcucgsgsc | 632 | GCCCGAGCUUCAGAGGCCGAGGA | 633 |
| AD-959861.1 | ascscaagaAfcCfGfCfcaaggaugcuL96 | 634 | asGfscauCfcUfUfggcgGfcUfiuggusgsg | 635 | CCACCAAGACCGCCAAGGAUGCA | 636 |
| AD-959743.1 | uasgsaggCfaGfCfUfUfgcuccaggauL96 | 637 | asUfsccuGfaGfCfcagcUfgCfcucuasgsg | 638 | CCUAGAGGCAGCUGCUCCAGGAA | 639 |
| AD-959905.1 | gsgsgugaCfcGfAfUfggcuucaguguL96 | 640 | asAfscugAfaGfCfcaucGfgUfcacccsasg | 641 | CUGGGUGACCGAUGGCUUCAGUU | 642 |
| AD-959734.1 | gsusucauCfccUfUfAfgaggcagcuuL96 | 643 | asAfsgcuGfcCfUfcuagGfgAfugaacsusg | 644 | CAGUUCAUCCCUAGAGGCAGCUG | 645 |
| AD-959934.1 | ascsuacuGfgAfGfCfcaccguuaaguL96 | 646 | asCfsuuaAfcGfGfugcuCfcAfguaguscsu | 647 | AGACUACUGGAGCACCGUUAAGG | 648 |
| AD-959749.1 | csasgcugCfucCfCfAfggaacagaguL96 | 649 | asCfsucuGfuUfCfcuggAfgCfagcugcsc | 650 | GGCAGCUGCUCCAGGAACAGAGG | 651 |
| AD-959798.1 | csgsagcuUfcAfGfAfAfggccgaggauL96 | 652 | asUfsccuCfgGfCfcucuGfaAfgcugsgsg | 653 | CCCGAGCUUCAGAGGCCGAGGAU | 654 |
| AD-959742.1 | csusagaGfgCfAfGfCfUfgcuccaggauL96 | 655 | asCfscugUfaGfCfagcuGfcCfucuagsgsg | 656 | CCCUAGAGGCAGCUGCUCCAGGA | 657 |
| AD-959897.1 | gsasguccCfaGfGfUfGfgcccagcauL96 | 658 | asUfsgcuGfgGfCfcaccUfgGfgacucscsu | 659 | AGGAGUCCCAGGUGGCCCAGCAG | 660 |
| AD-959864.1 | asgsaccgCfcAfAfGfAfGfgaugcacuguL96 | 661 | asCfsaguGfcAfUfccuuGfgCfggucususg | 662 | CAAGACCGCCAAGGAUGCACUGA | 663 |
| AD-959899.1 | cscsagguUfgGfCfCfCfagcaggccauL96 | 664 | asUfsggcCfugGfCfugggCfcAfccuggsa | 665 | UCCCAGGUGGCCCAGCAGGCCAG | 666 |
| AD-959856.1 | ascsgccaCfcAfAfGfAfccgccaaguL96 | 667 | asCfsuugGfcGfUfuccuuGfgUfggcgusgc | 668 | GCACGCCACCAAGACCGCCAAGG | 669 |
| AD-959906.1 | gsgsgugaCfgAfUfGfGfcuucaguuuL96 | 670 | asAfsacuGfaAfGfccaucGfUfucaccscsa | 671 | UGGGUGACCGAUGGCUUCAGUUC | 672 |
| AD-959936.1 | usascsuggAfgCfAfCfcguuaaggauL96 | 673 | asUfscccUfaAfCfggugCfuCfcaguasgsu | 674 | ACUACUGGAGCACCGUUAAGGAC | 675 |
| AD-959896.1 | gsgsaguCfcAfGfGfuggcccagcuL96 | 676 | asGfscugGfcCfCfaccuGfgAfcucusg | 677 | CAGGAGUCCCAGGUGGCCCAGCA | 678 |
| AD-959893.1 | gscsaggaGfucCfCfCfaggugccccuL96 | 679 | asGfsggcCfaCfCfugggAfcUfccugcsasc | 680 | GUGCAGGAGUCCCAGGUGGCCCA | 681 |
| AD-959892.1 | usgscsagAfgUfCfCfCfaggugccuL96 | 682 | asGfsgccAfcCfUfgggaCfuCfucgcascsg | 683 | CGUGCAGGAGUCCCAGGUGGCCC | 684 |
| AD-959894.1 | csasggagUfccCfAfGfgugggcccauL96 | 685 | asUfgggGfCfcAfCfcuggGfaCfuccugcsa | 686 | UGCAGGAGUCCCAGGUGGCCCAG | 687 |
| AD-959750.1 | asgscugGfcCfAfGfaacagagguL96 | 688 | asCfscucUfgUfUfccugGfaGfcagcugsc | 689 | GCAGCUGCUCCAGGAACAGAGGU | 690 |
| AD-959898.1 | asgsuccaAfgGfUfGfGfcccagcaguL96 | 691 | asCfsugcUfgGfGfccacCfuGfggacucsc | 692 | GGAGUCCCAGGUGGCCCAGCAGG | 693 |
| AD-959895.1 | asgsgaguCfccCfAfGfGfuggcccaguL96 | 694 | asCfsuggGfcCfAfccuggCfgAfcuccusgc | 695 | GCAGGAGUCCCAGGUGGCCCAGC | 696 |

TABLE 4

Unmodified Sense and Antisense Strand Sequences of Apolipoprotein C3 dsRNA Agents

| Duplex Name | Sense Sequence 5 to 3' | SEQ ID NO: | Range in NM_000040.3 | Antisense Sequence 5' to 3' | SEQ ID NO: | Range in NM_000040.3 |
|---|---|---|---|---|---|---|
| AD-960293.1 | CUUCAGUUCCCUGAAAGACUU | 24 | 245-265 | AAGUCUUCAGGGAACUGAAGCC | 261 | 243-265 |
| AD-960288.1 | GAUGGCUUCAGUUCCCUGAAU | 44 | 240-260 | AUUCAGGGAACUGAAGCCAUCGG | 45 | 238-260 |
| AD-960445.1 | AAGGGACAGUAUUCUCAGUGU | 46 | 437-457 | ACACUGAGAAUACUGUCCCUUUU | 47 | 435-457 |
| AD-960292.1 | GCUUCAGUUCCCUGAAAGACU | 42 | 244-264 | AGUCUUCAGGGAACUGAAGCCA | 262 | 242-264 |
| AD-960475.1 | CCAAUAAAGCUGGACAAGAAU | 28 | 506-526 | AUUCUUGUCCAGCUUUAUUGGGA | 29 | 504-526 |
| AD-960442.1 | UAAAAGGGACAGUAUUCUCAU | 36 | 434-454 | AUGAGAAUACUGUCCCUUUUAAG | 37 | 432-454 |
| AD-960470.1 | GCCUCCCAAUAAAGCUGGACU | 95 | 501-521 | AGUCCAGCUUUAUUGGGAGGCCA | 96 | 499-521 |
| AD-960436.1 | GUUGCUUAAAAGGGACAGUAU | 263 | 428-448 | AUACUGUCCCUUUUAAGCAACCU | 264 | 426-448 |
| AD-960446.1 | AGGGACAGUAUUCUCAGUGCU | 85 | 438-458 | AGCACUGAGAAUACUGUCCCUUU | 86 | 436-458 |
| AD-960474.1 | CCCAAUAAAGCUGGACAAGAU | 59 | 505-525 | AUCUUGUCCAGCUUUAUUGGGAG | 265 | 503-525 |
| AD-960294.1 | UUCAGUUCCCUGAAAGACUAU | 26 | 246-266 | AUAGUCUUCAGGGAACUGAAGC | 266 | 244-266 |
| AD-960471.1 | CCUCCCAAUAAAGCUGGACAU | 54 | 502-522 | AUGUCCAGCUUUAUUGGGAGGCC | 55 | 500-522 |
| AD-960314.1 | CUGGAGCACCGUUAAGGACAU | 61 | 266-286 | AUGUCCUAACGGUGCUCCAGUA | 267 | 264-286 |
| AD-960443.1 | AAAAGGGACAGUAUUCUCAGU | 30 | 435-455 | ACUGAGAAUACUGUCCCUUUUAA | 31 | 433-455 |
| AD-960282.1 | GUGACCGAUGGCUUCAGUUCU | 65 | 234-254 | AGAACUGAAGCCAUCGGUCACCC | 66 | 232-254 |
| AD-960283.1 | UGACCGAUGGCUUCAGUUCCU | 77 | 235-255 | AGGAACTGAAGCCAUCGGUCACC | 268 | 233-255 |
| AD-80794.7 | CUUAAAAGGGACAGUAUUCUA | 13 | 432-450 | UAGAAUACUGUCCCUUUUAAGCA | 58 | 430-450 |
| AD-960295.1 | UCAGUUCCCUGAAAGACUACU | 71 | 247-267 | AGUAGUCUUCAGGGAACUGAAG | 72 | 245-267 |
| AD-960478.1 | AUAAAGCUGGACAAGAAGCUU | 89 | 509-529 | AAGCUUCUUGUCCAGCUUUAUUG | 90 | 507-529 |
| AD-960289.1 | AUGGCUUCAGUUCCCUGAAAU | 32 | 241-261 | AUUUCAGGGAACUGAAGCCAUCG | 33 | 239-261 |
| AD-960481.1 | AAGCUGGACAAGAAGCUGCUU | 99 | 512-532 | AAGCAGCUUCUUGUCCAGCUUUA | 100 | 510-532 |
| AD-960318.1 | AGCACCGUUAAGGACAAGUUU | 34 | 270-290 | AAACUUGUCCUUAACGGUGCUCC | 35 | 268-290 |
| AD-960297.1 | AGUUCCCUGAAAGACUACUGU | 97 | 249-269 | ACAGUAGUCUUUCAGGGAACUGA | 98 | 247-269 |
| AD-960477.1 | AAUAAAGCUGGACAAGAAGCU | 105 | 508-528 | AGCUUCUGUCCAGCUUUAUUGG | 269 | 506-528 |
| AD-960317.1 | GAGCACCGUUAAGGACAAGUU | 270 | 269-289 | AACUUGUCCUUAACGGUGCUCCA | 271 | 267-289 |
| AD-960476.1 | CAAUAAAGCUGGACAAGAAGU | 81 | 507-527 | ACUUCUGUCCAGCUUUAUUGGG | 272 | 505-527 |
| AD-960241.1 | GACCGCCAAGGAUGCACUGAU | 133 | 170-190 | AUCAGUGCAUCCUUGGCGGUCUU | 134 | 168-190 |
| AD-960480.1 | AAAGCUGGACAAGAAGCUGCU | 117 | 511-531 | AGCAGCUUCUUGUCCAGCUUUAU | 273 | 509-531 |
| AD-960482.1 | AGCUGGACAAGAAGCUGCUAU | 127 | 513-533 | AUAGCAGCUUCUUGUCCAGCUUU | 128 | 511-533 |
| AD-80793.7 | GCUGGACAAGAAGCUGCUAUA | 101 | 514-533 | UAUAGCAGCUUCUUGUCCAGCUU | 102 | 512-533 |
| AD-960107.1 | CAGUUCAUCCCUAGAGGCAGU | 175 | 6-26 | ACUGCCUCUAGGGAUGAACUGAG | 274 | 6-26 |
| AD-960308.1 | AGACUACUGGAGCACCGUUAU | 73 | 260-280 | AUAACGGUGCUCCAGUAGUCUUU | 74 | 258-280 |
| AD-960121.1 | AGGCAGCUGCUCCAGGAACAU | 153 | 20-40 | AUGUUCCUGGAGCAGCUGCCUCU | 154 | 18-40 |
| AD-960287.1 | CGAUGGCUUCAGUUCCCUGAU | 83 | 239-259 | AUCAGGGAACUGAAGCCAUCGGU | 84 | 237-259 |
| AD-960473.1 | UCCCAAUAAAGCUGGACAAGU | 67 | 504-524 | ACUUGUCCAGCUUUAUUGGGAGG | 68 | 502-524 |
| AD-960479.1 | UAAAGCUGGACAAGAAGCUGU | 135 | 510-530 | ACAGCUCUUGUCCAGCUUUAUU | 275 | 508-530 |
| AD-960278.1 | CUGGGUGACCGAUGGCUUCAU | 79 | 230-250 | AUGAAGCCAUCGGUCACCCAGCC | 80 | 228-250 |

TABLE 4-continued

Unmodified Sense and Antisense Strand Sequences of Apolipoprotein C3 dsRNA Agents

| Duplex Name | Sense Sequence 5 to 3' | SEQ ID NO: | Range in NM_000040.3 | Antisense Sequence 5' to 3' | SEQ ID NO: | Range in NM_000040.3 |
|---|---|---|---|---|---|---|
| AD-960113.1 | AUCCCUAGAGGCAGCUGCUCU | 165 | 12-32 | AGAGCAGCUGCCUCUAGGGAUGA | 166 | 10-32 |
| AD-960472.1 | CUCCCAAUAAAGCUGGACAAU | 50 | 503-523 | AUUGUCCAGCUUUAUUGGGAGGC | 51 | 501-523 |
| AD-960444.1 | AAAGGGACAGUAUUCUCAGUU | 63 | 436-456 | AACUGAGAAUACUGUCCCUUUUA | 64 | 434-456 |
| AD-960303.1 | CUGAAAGACUACUGGAGCACU | 87 | 255-275 | AGUGCUCCAGUAGUCUUUCAGGG | 88 | 253-275 |
| AD-960438.1 | UGCUUAAAAGGGACAGUAUUU | 52 | 430-450 | AAAUACTGUCCCUUUUAAGCAAC | 276 | 428-450 |
| AD-960290.1 | UGGCUUCAGUUCCCUGAAAGU | 93 | 242-262 | ACUUUCAGGGAACUGAAGCCAUC | 94 | 240-262 |
| AD-960304.1 | UGAAAGACUACUGGAGCACCU | 167 | 256-276 | AGGUGCUCCAGUAGUCUUUCAGG | 277 | 254-276 |
| AD-960388.1 | CUGCCUGAGACCUCAAUACCU | 115 | 340-360 | AGGUAUGAGGUCUCAGGCAGCC | 278 | 338-360 |
| AD-960233.1 | GCCACCAAGACCGCCAAGGAU | 195 | 162-182 | AUCCUUGGCGGUCUUGGUGGCGU | 196 | 160-182 |
| AD-960234.1 | CCACCAAGACCGCCAAGGAUU | 75 | 163-183 | AAUCCUGGCGGUCUUGGUGGCG | 279 | 161-183 |
| AD-960114.1 | UCCCUAGAGGCAGCUGCUCCU | 141 | 13-33 | AGGAGCAGCUGCCUCUAGGGAUG | 142 | 11-33 |
| AD-960296.1 | CAGUUCCCUGAAAGACUACUU | 109 | 248-268 | AAGUAGTCUUUCAGGGAACUGAA | 280 | 246-268 |
| AD-960431.1 | UGUAGGUUGCUUAAAAGGGAU | 149 | 423-443 | AUCCCUUUUAAGCAACCUACAGG | 281 | 421-443 |
| AD-960316.1 | GGAGCACCGUUAAGGACAAGU | 187 | 268-288 | ACUUGUCCUUAACGGUGCUCCAG | 188 | 266-288 |
| AD-960307.1 | AAGACUACUGGAGCACCGUUU | 91 | 259-279 | AAACGGTGCUCCAGUAGUCUUUC | 282 | 257-279 |
| AD-960120.1 | GAGGCAGCUGCUCCAGGAACU | 181 | 19-39 | AGUUCCUGGAGCAGCUGCCUCUA | 283 | 17-39 |
| AD-960238.1 | CAAGACCGCCAAGGAUGCACU | 284 | 167-187 | AGUGCAUCCUUGGCGGUCUUGGU | 285 | 165-187 |
| AD-960301.1 | CCCUGAAAGACUACUGGAGCU | 103 | 253-273 | AGCUCCAGUAGUCUUUCAGGGAA | 104 | 251-273 |
| AD-960235.1 | CACCAAGACCGCCAAGGAUGU | 123 | 164-184 | ACAUCCUGGCGGUCUUGGUGGC | 286 | 162-184 |
| AD-960123.1 | GCAGCUGCUCCAGGAACAGAU | 155 | 22-42 | AUCUGUCCUGGAGCAGCUGCCU | 287 | 20-42 |
| AD-960300.1 | UCCCUGAAAGACUACUGGAGU | 137 | 252-272 | ACUCCAGUAGUCUUUCAGGGAAC | 138 | 250-272 |
| AD-960285.1 | ACCGAUGGCUUCAGUUCCCUU | 38 | 237-257 | AAGGGAACUGAAGCCAUCGGUCA | 39 | 235-257 |
| AD-960469.1 | GGCCUCCCAAUAAAGCUGGAU | 173 | 500-520 | AUCCAGCUUUAUUGGGAGGCCAG | 174 | 498-520 |
| AD-960387.1 | GCUGCCUGAGACCUCAUACU | 171 | 339-359 | AGUAUUGAGGUCUCAGGCAGCCA | 172 | 337-359 |
| AD-960384.1 | GUGGCUGCCUGAGACCUCAAU | 183 | 336-356 | AUUGAGGUCUCAGGCAGCCACGG | 184 | 334-356 |
| AD-960109.1 | GUUCAUCCCUAGAGGCAGCUU | 225 | 10-28 | AAGCUGCCUCUAGGGAUGAACUG | 226 | 6-28 |
| AD-960112.1 | CAUCCCUAGAGGCAGCUGCUU | 113 | 11-31 | AAGCAGCUGCCUCUAGGGAUGAA | 114 | 9-31 |
| AD-960386.1 | GGCUGCCUGAGACCUCAAUAU | 177 | 338-358 | AUAUUGAGGUCUCAGGCAGCCAC | 178 | 336-358 |
| AD-960302.1 | CCUGAAAGACUACUGGAGCAU | 111 | 254-274 | AUGCUCCAGUAGUCUUUCAGGGA | 112 | 252-274 |
| AD-960118.1 | UAGAGGCAGCUGCUCCAGGAU | 221 | 17-37 | AUCCUGGAGCAGCUGCCUCUAGG | 222 | 15-37 |
| AD-960111.1 | UCAUCCCUAGAGGCAGCUGCU | 199 | 10-30 | AGCAGCUGCCUCUAGGGAUGAAC | 288 | 8-30 |
| AD-960299.1 | UUCCCUGAAAGACUACUGGAU | 119 | 251-271 | AUCCAGTAGUCUUUCAGGGAACU | 289 | 249-271 |
| AD-960115.1 | CCCUAGAGGCAGCUGCUCCAU | 129 | 14-34 | AUGGAGCAGCUGCCUCUAGGGAU | 130 | 12-34 |
| AD-960439.1 | GCUUAAAAGGGACAGUAUUCU | 56 | 431-451 | AGAAUACUGUCCCUUUUAAGCAA | 57 | 429-451 |
| AD-960441.1 | UUAAAAGGGACAGUAUUCUCU | 40 | 433-453 | AGAGAATACUGUCCCUUUUAAGC | 290 | 431-453 |
| AD-960232.1 | CGCCACCAAGACCGCCAAGGU | 157 | 161-181 | ACCUUGGCGGUCUUGGUGGCGUG | 158 | 159-181 |

TABLE 4-continued

Unmodified Sense and Antisense Strand Sequences of Apolipoprotein C3 dsRNA Agents

| Duplex Name | Sense Sequence 5 to 3' | SEQ ID NO: | Range in NM_000040.3 | Antisense Sequence 5' to 3' | SEQ ID NO: | Range in NM_000040.3 |
|---|---|---|---|---|---|---|
| AD-960276.1 | GGCUGGGUGACCGAUGGCUUU | 107 | 228-248 | AAAGCCAUCGGUCACCCAGCCCC | 108 | 226-248 |
| AD-960435.1 | GGUUGCUUAAAAGGGACAGUU | 69 | 427-447 | AACUGUCCCUUUUAAGCAACCUA | 70 | 425-447 |
| AD-960306.1 | AAAGACUACUGGAGCACCGUU | 151 | 258-278 | AACGGUGCUCCAGUAGUCUUUCA | 152 | 256-278 |
| AD-960172.1 | CCGAGCUUCAGAGGCCGAGGU | 217 | 101-121 | ACCUCGGCCUCUGAAGCUCGGGC | 218 | 99-121 |
| AD-960385.1 | UGGCUGCCUGAGACCUCAAUU | 161 | 337-357 | AAUUGAGGUCUCAGGCAGCCACG | 162 | 335-357 |
| AD-960110.1 | UUCAUCCCUAGAGGCAGCUGU | 201 | 9-29 | ACAGCUGCCUCUAGGGAUGAACU | 202 | 7-29 |
| AD-960116.1 | CCUAGAGGCAGCUGCUCCAGU | 147 | 15-35 | ACUGGAGCAGCUGCCUCUAGGGA | 148 | 13-35 |
| AD-960434.1 | AGGUUGCUUAAAAGGGACAGU | 125 | 426-446 | ACUGUCCCUUUUAAGCAACCUAC | 126 | 424-446 |
| AD-960430.1 | CUGUAGGUUGCUUAAAAGGGU | 189 | 422-442 | ACCCUUUAAGCAACCUACAGGG | 291 | 420-442 |
| AD-960305.1 | GAAAGACUACUGGAGCACCGU | 179 | 257-277 | ACGGUGCUCCAGUAGUCUUUCAG | 180 | 255-277 |
| AD-960279.1 | UGGGUGACCGAUGGCUUCAGU | 215 | 231-251 | ACUGAAGCCAUCGGUCACCCAGC | 216 | 229-251 |
| AD-960298.1 | GUUCCCUGAAAGACUACUGGU | 191 | 250-270 | ACCAGUAGUCUUUCAGGGAACUG | 192 | 248-270 |
| AD-960284.1 | GACCGAUGGCUUCAGUUCCCU | 139 | 236-256 | AGGGAACUGAAGCCAUCGGUCAC | 140 | 234-256 |
| AD-960313.1 | ACUGGAGCACCGUUAAGGACU | 213 | 265-285 | AGUCCUAACGGUGCUCCAGUAG | 292 | 263-285 |
| AD-960432.1 | GUAGGUUGCUUAAAAGGGACU | 145 | 424-444 | AGUCCCUUUUAAGCAACCUACAG | 293 | 422-444 |
| AD-960124.1 | CAGCUGCUCCAGGAACAGAGU | 229 | 23-43 | ACUCUGUCCUGGAGCAGCUGCC | 294 | 21-43 |
| AD-960119.1 | AGAGGCAGCUGCUCCAGGAAU | 197 | 18-38 | AUUCCUGGAGCAGCUGCCUCUAG | 198 | 16-38 |
| AD-960437.1 | UUGCUUAAAAGGGACAGUAUU | 295 | 429-449 | AAUACUGUCCCUUUUAAGCAACC | 296 | 427-449 |
| AD-960315.1 | UGGAGCACCGUUAAGGACAAU | 131 | 267-287 | AUUGUCCUUAACGGUGCUCCAGU | 132 | 265-287 |
| AD-960117.1 | CUAGAGGCAGCUGCUCCAGGU | 233 | 16-36 | ACCUGGAGCAGCUGCCUCUAGGG | 234 | 14-36 |
| AD-960311.1 | CUACUGGAGCACCGUUAAGGU | 159 | 263-283 | ACCUUAACGGUGCUCCAGUAGUC | 160 | 261-283 |
| AD-960272.1 | GAGUCCCAGGUGGCCCAGCAU | 235 | 201-221 | AUGCUGGGCCACCUGGGACUCCU | 236 | 199-221 |
| AD-960414.1 | CGAGCUCCUUGGGUCCUGCAU | 203 | 386-406 | AUGCAGGACCCAAGGAGCUCGCA | 204 | 384-406 |
| AD-960240.1 | AGACCGCCAAGGAUGCACUGU | 237 | 169-189 | ACAGUGCAUCCUUGGCGGUCUUG | 238 | 167-189 |
| AD-960286.1 | CCGAUGGCUUCAGUUCCCUGU | 143 | 238-258 | ACAGGGAACUGAAGCCAUCGGUC | 144 | 236-258 |
| AD-960281.1 | GGUGACCGAUGGCUUCAGUUU | 243 | 233-253 | AAACUGAAGCCAUCGGUCACCCA | 244 | 231-253 |
| AD-960277.1 | GCUGGGUGACCGAUGGCUUCU | 185 | 229-249 | AGAAGCCAUCGGUCACCCAGCCC | 186 | 227-249 |
| AD-960274.1 | CCAGGUGGCCCAGCAGGCCAU | 239 | 206-226 | AUGGCCTGCUGGGCCACCUGGGA | 297 | 204-226 |
| AD-960108.1 | AGUUCAUCCCUAGAGGCAGCU | 211 | 11-27 | AGCUGCCUCUAGGGAUGAACUGA | 212 | 11-27 |
| AD-960239.1 | AAGACCGCCAAGGAUGCACUU | 169 | 168-188 | AAGUGCAUCCUUGGCGGUCUUGG | 170 | 166-188 |
| AD-960122.1 | GGCAGCUGCUCCAGGAACAGU | 205 | 21-41 | ACUGUUCCUGGAGCAGCUGCCUC | 206 | 19-41 |
| AD-960291.1 | GGCUUCAGUUCCCUGAAAGAU | 163 | 243-263 | AUCUUUCAGGGAACUGAAGCCAU | 164 | 241-263 |
| AD-960125.1 | AGCUGCUCCAGGAACAGAGGU | 255 | 24-44 | ACCUCUGUUCCUGGAGCAGCUGC | 256 | 22-44 |
| AD-960231.1 | ACGCCACCAAGACCGCCAAGU | 241 | 160-180 | ACUUGGCGGUCUUGGUGGCGUGC | 242 | 158-180 |
| AD-960275.1 | GGGCUGGGUGACCGAUGGCUU | 193 | 227-247 | AAGCCATCGGUCACCCAGCCCU | 298 | 225-247 |
| AD-960173.1 | CGAGCUUCAGAGGCCGAGGAU | 231 | 102-122 | AUCCUCGGCCUCUGAAGCUCGGG | 232 | 100-122 |
| AD-960271.1 | GGAGUCCCAGGUGGCCCAGCU | 247 | 200-220 | AGCUGGGCCACCUGGGACUCCUG | 248 | 198-220 |

TABLE 4-continued

Unmodified Sense and Antisense Strand Sequences of Apolipoprotein C3 dsRNA Agents

| Duplex Name | Sense Sequence 5 to 3' | SEQ ID NO: | Range in NM_000040.3 | Antisense Sequence 5' to 3' | SEQ ID NO: | Range in NM_000040.3 |
|---|---|---|---|---|---|---|
| AD-960433.1 | UAGGUUGCUUAAAAGGGACAU | 121 | 425-445 | AUGUCCCUUUUAAGCAACCUACA | 122 | 423-445 |
| AD-960267.1 | UGCAGGAGUCCCAGGUGGCCU | 251 | 196-216 | AGGCCACCUGGGACUCCUGCACG | 252 | 194-216 |
| AD-960236.1 | ACCAAGACCGCCAAGGAUGCU | 219 | 165-185 | AGCAUCCUUGGCGGUCUUGGUGG | 220 | 163-185 |
| AD-960310.1 | ACUACUGGAGCACCGUUAAGU | 227 | 262-282 | ACUUAACGGUGCUCCAGUAGUCU | 228 | 260-282 |
| AD-960312.1 | UACUGGAGCACCGUUAAGGAU | 245 | 264-284 | AUCCUUAACGGUGCUCCAGUAGU | 246 | 262-284 |
| AD-960309.1 | GACUACUGGAGCACCGUUAAU | 209 | 261-281 | AUUAACGGUGCUCCAGUAGUCUU | 210 | 259-281 |
| AD-960440.1 | CUUAAAAGGGACAGUAUUCUU | 48 | 432-452 | AAGAAUACUGUCCCUUUUAAGCA | 49 | 430-452 |
| AD-960237.1 | CCAAGACCGCCAAGGAUGCAU | 207 | 166-186 | AUGCAUCCUUGGCGGUCUUGGUG | 208 | 164-186 |
| AD-960268.1 | GCAGGAGUCCCAGGUGGCCCU | 249 | 197-217 | AGGGCCACCUGGGACUCCUGCAC | 250 | 195-217 |
| AD-960269.1 | CAGGAGUCCCAGGUGGCCCAU | 253 | 198-218 | AUGGGCCACCUGGGACUCCUGCA | 254 | 196-218 |
| AD-960280.1 | GGGUGACCGAUGGCUUCAGUU | 223 | 232-252 | AACUGAAGCCAUCGGUCACCCAG | 224 | 230-252 |
| AD-960270.1 | AGGAGUCCCAGGUGGCCCAGU | 259 | 199-219 | ACUGGGCCACCUGGGACUCCUGC | 260 | 197-219 |
| AD-960273.1 | AGUCCCAGGUGGCCCAGCAGU | 257 | 202-222 | ACUGCUGGGCCACCUGGGACUCC | 258 | 200-222 |

TABLE 5

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-960293.1 | csusucagUfuCfCfCfctugaaagacuuL96 | 341 | asAfsgucu(Tgn)ucagggAfaCfugaagsgsc | 697 | GGCUUCAGUUCCCUGAAAGACUA | 343 |
| AD-960288.1 | ususcaguUfcCfCfCfUfgaaagacuauL96 | 344 | asUfsucag(Ggn)gaacugAfaGfccaucsgsg | 698 | CCGAUGGCUUCAGUUCCCUGAAA | 373 |
| AD-960445.1 | cscsaauaAfaGfCfUfggacaagaauL96 | 347 | asCfsacug(Agn)gaauacUfgUfcccuususu | 699 | AAAAGGGACAGUAUUCCAGUGC | 376 |
| AD-960292.1 | asasaaagGfacCfAfGfUfuauucucaguL96 | 350 | asGfsucuu(Tgn)cagggaAfcUfgaagcscsa | 700 | UGGCUUCAGUAUUCCCUGAAAGACU | 370 |
| AD-960475.1 | asusggcuUfcAfGfUfuccuugaaauL96 | 353 | asUfsucuu(Ggn)uccagcUfiuUfauugssga | 701 | UCCCAAUAAAGCUGGACAAGAAG | 349 |
| AD-960442.1 | asgcaccCfuUfAfAfAfggacaaguuuL96 | 356 | asUfsgaga(Agn)uacuguCfcCfuuuuasasg | 702 | CUUAAAAGGGACAGUAUUCUCAG | 361 |
| AD-960470.1 | usasaaagGfgAfCfUfAfguauucauL96 | 359 | asGfsucca(Ggn)cuuuauUfgGfgaggcssa | 703 | UGGCUCCCAAUAAAGCUGGACA | 450 |
| AD-960436.1 | ascscgauGfgCfUfUfcaguaccculL96 | 362 | asUfsacug(Tgn)cccuuuUfaAfgcaacsccu | 704 | AGGUUGCUUAAAAGGGACAGUAU | 705 |
| AD-960446.1 | ususuaaaGfgGfAfCfAfguauucucuL96 | 365 | asGfscacu(Ggn)agaauaCfuGfuccusususu | 706 | AAAGGGACAGUAUUCCAGUGCU | 435 |
| AD-960474.1 | gscsuucaGfguUfCfCfcugaaagacuL96 | 368 | asUfscuug(Tgn)ccagcuUfaUfuugggsasg | 707 | CUCCCAAUAAAGCUGGACAAGAA | 396 |
| AD-960294.1 | gsasuggcUfucCfAfGfUfuccccugaauL96 | 371 | asUfsaguc(Tgn)uucaggGfaAfcugaasgsc | 708 | GCUUCAGUCCCUGAAAGACUAC | 346 |
| AD-960471.1 | asasgggaCfaGfUfAfUfucucagugUL96 | 374 | asUfsgucc(Afgn)gcuuuaUfuGfgaggsgsc | 709 | GGCCUCCAAUAAAGCUGGACAA | 388 |
| AD-960314.1 | csusuaaaGfgGfAfCfAfcaguauucuL96 | 377 | asCfsaguc(Tgn)uaacggUfgCfuccagsusa | 710 | UACUGGAGCACCGUUAAGGACAA | 399 |
| AD-960443.1 | csusucccAfuAfAfAfGfCfuggacaauL96 | 380 | asCfsugag(Agn)auacugUfcCfcuuuusasa | 711 | UUAAAAGGGACAGUAUUCUCAGU | 352 |
| AD-960282.1 | usgscuuaAfaFfAfGfgacaguauuL96 | 383 | asGfsaacu(Ggn)aagccaUfcGfgucascsc | 712 | GGGUGACCGAUGGCUUCAGUUCC | 405 |
| AD-960283.1 | cscsuccaAfaUfAfAfAfaguuggacuuccuL96 | 386 | asGfsgaac(Tgn)gaagccAfuCfggucascsc | 713 | GGGUGACCGAUGGCUUCAGUUCC | 423 |
| AD-80794.7 | gscsuuaaAfaFfaGfCfUfgucccCfuUfuuaagscsa | 389 | usAfsgaaUfaCfUfgucccCfuUfuuaagscsa | 392 | UAGAAUACUGUCCCUUUAAGCA | 714 |
| AD-960295.1 | csusucagUfuCfCfCfctugaaagacuuL96 | 341 | asGfsuagu(Cgn)uuucagGfgAfacugasasg | 715 | CUUCAGUUCCCUGAAAGACUACU | 414 |
| AD-960478.1 | gsasuggCfUfaGfUfuccccugaauL96 | 371 | asGfsgcuu(Cgn)uugcccAfgCfuuuaususg | 716 | CAAUAAAGCUGGACAAGAAGCUG | 441 |
| AD-960289.1 | asasgggaCfaGfuAfAfuccccaguaL96 | 374 | asUfsuuca(Ggn)ggaacuGfaAfgccauscsg | 717 | CGAUGGCUUCAGUCCCUGAAAG | 355 |
| AD-960481.1 | gscsuucaGfuuFfCfCfcugaaagacuL96 | 368 | asAfsgcag(Cgn)uucuugUfcCfagcuususa | 718 | UAAAGCUGGACAAGAAGCUGCUA | 456 |
| AD-960318.1 | cscsaauaAfaGfCfUfGfgacaagaauL96 | 347 | asAfsacuu(Ggn)uccuuaAfcGfgugcuscsc | 719 | GGAGCACCGUUAAGGACAAGUUC | 358 |
| AD-960297.1 | usasaaagGfgAfCfAfAfguauucauL96 | 359 | asCfsagua(Ggn)ucuuucAfgGfgaacugsa | 720 | UCAGUCCCUGAAAGACUACUGG | 453 |
| AD-960477.1 | gscscuccCfaaUfAfAfaagcuggacuL96 | 448 | asGfscuuc(Tgn)ugccaGfcUfuauuusgsg | 721 | CCAAUAAAGCUGGACAAGAAGCU | 465 |

TABLE 5-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-960317.1 | gsusugcuUfaAfAfAfAfggacaguauL96 | 722 | asAfscuug(Tgn)ccuuaaCfgGfugcucscsa | 723 | UGGAGCACCGUUAAGGACAAGUU | 724 |
| AD-960476.1 | asgsggacAfgUfAfUfucucagugcuL96 | 433 | asCfsuucu(Tgn)guccagCfuUfuauugsgsg | 725 | CCCAAUAAAGCUGGACAAGAAGC | 429 |
| AD-960241.1 | cscscaauAfaAfGfCfuggacaagauL96 | 394 | asUfscagu(Ggn)cauccuUfgGfcgucsusu | 726 | AAGACCGCCAAGGAUGCACUGAG | 507 |
| AD-960480.1 | ususcaguUfcCfCfUfgaaagacuauL96 | 344 | asGfscagc(Tgn)ucuuguCfcAfgcuuuasu | 727 | AUAAAGCUGGACAAGAAGCUGCU | 483 |
| AD-960482.1 | cscsuccaAfaUfAfAfAfagcuggacauL96 | 386 | asUfsagca(Ggn)cuucuuGfuCfcagcususu | 728 | AAAGCUGGACAAGAAGCUGCUAU | 498 |
| AD-80793.7 | csusgggaCfacCfCfGfuuaaggacauL96 | 397 | usAfsuagCfaGfCfuucuUfgUfccagcsusu | 458 | UAUAGCAGCUUCUUGUCCAGCUU | 729 |
| AD-960107.1 | asasaaagCfacCfAfGfuauucucaguL96 | 350 | asCfsugcc(Tgn)cuagggAfuGfaacugsasg | 730 | CUCAGUUCAUCCCUAGAGGCAGC | 570 |
| AD-960308.1 | gsusgaccCfaUfGfGfcuucaguucuL96 | 403 | asUfsaacg(Ggn)ugcccAfgUfagucususu | 731 | AAAGACUACUGGAGCACCGUUAA | 417 |
| AD-960121.1 | usgsaccgAfuGfGfCfuucaguucccuL96 | 421 | asUfsguuc(Cgn)uggagcAfgCfugccuscsu | 732 | AGAGGCAGCUGCUCCAGGAACAG | 537 |
| AD-960287.1 | csusuaaaAfgGfGfAfcaguauucuaL96 | 17 | asUfscagg(Ggn)aacugaAfgCfcaucgsgsu | 733 | ACCGAUGGCUUCAGUUCCCUGAA | 432 |
| AD-960473.1 | uscsaguuCfccCfUfGfaaagacuacuL96 | 412 | asCfsuugu(Cgn)cagcuuUfaUfuggasgsg | 734 | CCUUCCAAUAAAGCUGGACAAGA | 408 |
| AD-960479.1 | asusaaagCfuGfGfAfcaagaagcuL96 | 439 | asCfsagcu(Tgn)cuuguCfaGfcuuuasusu | 735 | AAUAAAGCUGGACAAGAAGCUGC | 510 |
| AD-960278.1 | asusggcuUfcAfGfUfucccugaaauL96 | 353 | asUfsgaag(Cgn)caucggUfcAfcccagscsc | 736 | GGCUGGUGACCGAUGGCUUCAG | 426 |
| AD-960113.1 | asasgcuggAfcAfAfGfaagcugcuuL96 | 454 | asGfsagca(Ggn)cugccuCfuAfgggausga | 737 | UCAUCCCUAGAGGCAGCUGCUCC | 555 |
| AD-960472.1 | asgscaccGfuUfAfAfAfggacaaguL96 | 356 | asUfsuguc(Cgn)agcuuuAfuUfgggagsgsc | 738 | GCCUCCCAAUAAAGCUGGACAAG | 382 |
| AD-960444.1 | asgsuuccCfuGfAfAfAfagacuacuguL96 | 451 | asAfscuga(Ggn)aauacuGfuCfccuuususa | 739 | UAAAAGGGACAGUAUUCUCAGUG | 402 |
| AD-960303.1 | asasuaaaGfcUfGfGfacaagaagcuL96 | 463 | asGfsugcu(Cgn)caguagUfcUfuucagsgsg | 740 | CCCUGAAAGACUACUGGAGCACC | 438 |
| AD-960438.1 | gsasgcacCfgUfUfAfAfgggacaaguL96 | 741 | asAfsauac(Tgn)guccuUfiUfaagcasasc | 742 | GUUGCUUAAAGGGACAGUAUUC | 385 |
| AD-960290.1 | csaaatuaAfgCfUfGfGfgacaagaaguL96 | 427 | asCfsuuuc(Agn)gggaacUfgAfagccasusc | 743 | GAUGGCUUCAGUUCCCUGAAAGA | 447 |
| AD-960304.1 | gsasccgCfaAfGfGfGfaugcacugauL96 | 505 | asGfsgugc(Tgn)ccaguaGfucUfuuucasgsg | 744 | CCUGAAAGACUACUGGAGCACCG | 558 |
| AD-960388.1 | asasagcuGfgAfCfAfAfgaagcugcuL96 | 481 | asGfsguau(Tgn)gaggucUfcAfggcagscsc | 745 | GGCUGCCUGAGACCCUCAUACCC | 480 |
| AD-960233.1 | asgscuggAfcAfAfGfAfaagcugcuauL96 | 496 | asUfsccuu(Ggn)gcgucUfuGfguggcsgsu | 746 | ACGCCACCAAGACCGCCAAGGAU | 600 |
| AD-960234.1 | gscsuggaCfaAfGfAfAfgcugcuauL96 | 457 | asAfsuccu(Tgn)ggcgguCfuUfggggscsg | 747 | CGCCACCAAGACCGCCAAGGAUG | 420 |
| AD-960114.1 | csasguucCfaAfGfGfAfcaagaaguL96 | 568 | asGfsgagc(Agn)gcugccUfcAfaggasusg | 748 | CAUCCCUAGAGGCAGCUGCUCCA | 519 |

TABLE 5-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-960296.1 | agsgsactuaCfuGfGfAfgcaccguuauL96 | 415 | asAfsguag(Tgn)cuuucaGfgGfaacugsasa | 749 | UUCAGUCCCUGAAAGACUACUG | 471 |
| AD-960431.1 | asgsgcagCfuGfCfUfccaggaacauL96 | 535 | asUfscccu(Tgn)uuaagcAfaCfcuacasgsg | 750 | CCUGUAGUUGCUUAAAGGGAC | 531 |
| AD-960316.1 | csgsauggCfuUfCfAfguuccugauL96 | 430 | asCfsuugu(Cgn)cuuaacGfgUfgcuccsasg | 751 | CUGGAGCACCGUUAAGGACAAGU | 588 |
| AD-960307.1 | uscsccaaUfaAfAfGfcuggacaaguL96 | 406 | asAfsacgg(Tgn)gcuccaGfuAfgucuuusuc | 752 | GAAAGACUACUGGAGCACCGUUA | 444 |
| AD-960120.1 | usasaagCfUfgGfAfCfaagaagcugdL96 | 508 | asGfsuucc(Tgn)ggagcaGfcUfgccucsusa | 753 | UAGAGGCAGCUGCUCCAGGAACA | 579 |
| AD-960238.1 | csusggguGfaCfCfGfauggcuucauL96 | 424 | asGfsugca(Tgn)ccuuggCfgGfucuugsgsu | 754 | ACCAAGACCGCCAAGGAUGCACU | 755 |
| AD-960301.1 | asusccccuAfgAfGfGfcagcugcucuL96 | 553 | asGfscucc(Agn)guaguCfUfUfcagggasa | 756 | UUCCCUGAAAGACUACUGGAGCA | 462 |
| AD-960235.1 | csusccCaAfuAfAfAfgcuggacaauL96 | 380 | asCfsaucc(Tgn)uggcggUfcUfuggugsgsc | 757 | GCCACCAAGACCGCCAAGGAUGC | 492 |
| AD-960123.1 | asasasagggAfcAfGfUfauucucaguuL96 | 400 | asUfscugu(Tgn)ccuggaGfcAfgcugcscsu | 758 | AGGCAGCUGCUCCAGGAACAGAG | 540 |
| AD-960300.1 | csusgaaaGfaCfUfAfAfCfuggagcacuL96 | 436 | asCfsucca(Ggn)uagucuUfuCfaggasasc | 759 | GUUCCCUGAAAGACUACUGGAGC | 513 |
| AD-960285.1 | usgscuuaAfaAfAfAfGfGfgacaguauuL96 | 383 | asAfsggga(Agn)cugaagCfcAfucgguscsa | 760 | UGACCGAUGGCUUCAGUCCCUG | 364 |
| AD-960469.1 | ugsgscuuCfaGfCfUfUfCfcccugaaaguL96 | 445 | asUfsccag(Agn)uuuauuGfgGfaggccsasa | 761 | CUGGCUCCCCCAAUAAAGCUGGAC | 567 |
| AD-960387.1 | uasgsaaagAfcUfAfAfCfUfcuggagcacuL96 | 556 | asGfsuauu(Ggn)aggucuAfGfcagcscsa | 762 | UGGCUGCUGCCCUGAGACCUCAAU | 564 |
| AD-960384.1 | csusgccgUfGfaFfCfAfCfCfucaauaaccuL96 | 478 | asUfsugag(Ggn)ucucagGfcAfgcacgsgg | 763 | CCGUGCUGCCCUGAGACCUCAAU | 582 |
| AD-960109.1 | gscscaccAfaGfAfCfCfgccaaggauuL96 | 598 | asAfsgcug(Cgn)cucuagGfgAfugaacsusg | 764 | CAGUCAUCCCUUAGAGGCAGCUG | 645 |
| AD-960112.1 | cscsaccaAfgAfCfCfCfgcaaggauuL96 | 418 | asUfsauug(Agn)ggucucAfgGfcagcssasc | 765 | UUCAUCCCUUAGAGGCAGCUCUC | 477 |
| AD-960386.1 | uscsccuaGfaGfGfCfagcugccacuL96 | 517 | asUfsgcuc(Cgn)aguaguCfuUfucaggsgsa | 766 | GUGGCUGCCUGAGACCUCAAUAC | 573 |
| AD-960302.1 | csasguucCfcUfGfAfAfagacuacuL96 | 469 | asUfsgcuc(Cgn)agcagcUfgCfcucuasgsg | 767 | UCCCUGAAAGACUACUGGAGCAC | 474 |
| AD-960118.1 | usgsguagGfUfluGfCfUfUfuaaaaggauL96 | 529 | asGfsccug(Ggn)agcagcUfgCfcucuasgasc | 768 | CCUAGAGGCAGCUGCUCCAGGAA | 639 |
| AD-960111.1 | gsgsagcaCfcGfUfUfaaggaCaaguL96 | 586 | asUfsccagc(Tgn)gcucuaAfgGfgauasasc | 769 | GUUCAUCCCUAGAGGCAGCUGCU | 606 |
| AD-960299.1 | asasagacuAfcUfGfGfagcaccguuuL96 | 442 | asUfsccag(Tgn)agucuuUfcAfgggaascsu | 770 | AGUCCCUGAAAGACUACUGGAG | 486 |
| AD-960115.1 | gsasgggcaCfgCfCfAfaggaugcacuL96 | 577 | asUfsggag(Cgn)agcugcCfcUfuaagcsasa | 771 | AUCCCUAGAGGCAGCUGCUCCAG | 501 |
| AD-960439.1 | csasagaCfgCfCfAfAfggaugCfacuL96 | 772 | asGfsaaua(Cgn)ugcccUfUfuaagCfsasa | 773 | UUGCUUAAAAGGGACAGUAUUCU | 391 |
| AD-960441.1 | cscscugaAfaGfAfCfuaCfuggagcuL96 | 460 | asGfsagaa(Tgn)acugccCfcUfuuuaasgsc | 774 | GCUUAAAAGGGACAGUAUUCUCA | 367 |
| AD-960232.1 | csasccagCfaCfCfGfccaaggauguL96 | 490 | asCfscuug(Ggn)cggucuUfgGfuggcgsusg | 775 | CACGCCACCAAGACCGCCAAGGA | 543 |

TABLE 5-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-960276.1 | gscsagcuGfcUfCfCfaggaacagauL96 | 538 | asAfsagcc(Agn)ucggucAfcCfcagccscsc | 776 | GGGGCUGGGUGACCGAUGGCUUC | 468 |
| AD-960435.1 | uscsccugAfaAfGfGfAfcuacuggaguL96 | 511 | asAfscugu(Cgn)ccuuuuAfaGfcaaccsusa | 777 | UAGGUUGCUUAAAGGGACCAGUA | 411 |
| AD-960306.1 | ascscgauGfgCfUfUfcaguuccuuL96 | 362 | asAfscggu(Ggn)cuccagUfaGfucuuuscsa | 778 | UGAAAGACUACUGGAGCACCGUU | 534 |
| AD-960172.1 | gsgsccucCfcAfAfAfUfaaagcuggauL96 | 565 | asCfscucg(Ggn)cccugaAfaGfcucggsgsc | 779 | GCCCGAGCUUGCAGAGGCCGAGGA | 633 |
| AD-960385.1 | gsusgcCfUfgAfGfGfAfAfcccuaauacuL96 | 562 | asAfsuuga(Ggn)gucucaGfgCfagccascsg | 780 | CGUGGCUGCCUGAGACCUUCAAUA | 549 |
| AD-960110.1 | gsusggcugCfcCfUfGfagaccuccaauL96 | 580 | asCfsagcu(Ggn)ccucuaGfgGfaugaascsu | 781 | AGUUCAUCCCUAGAGGCAGCUGC | 609 |
| AD-960116.1 | gsusucaucCfcCfUfAfgaggcaguuL96 | 643 | asCfsugga(Ggn)cagcugCfcUfcuaggsgsa | 782 | UCCCUAGAGGCAGCUGCUUCCAGG | 528 |
| AD-960434.1 | csasuccCfuAfGfAfGfGfcagcugcuuL96 | 475 | asCfsuguc(Cgn)cuuuuaAfgCfcaaccusasc | 783 | GUAGGUUGCUUAAAGGGACAGU | 495 |
| AD-960430.1 | gsgscugCfuGfAfGfCfUfacccuacaauauL96 | 571 | asCfscuu(Tgn)uaagcaAfcCfcuacagsgsg | 784 | CCCUGUAGGUUGCUUAAAGGGA | 591 |
| AD-960305.1 | cscsaugaaAfgCfCfUfacuggagcauL96 | 637 | asCfsugaa(Ggn)ccaucgGfuCfaccasgsc | 785 | CUGAAAGACUACUGGAGCACCGU | 576 |
| AD-960279.1 | usasgaggCfaGfCfUfGfAfAfggcagcuggauL96 | 604 | asCfscagu(Agn)gucuuuCfaGfggaacsugc | 786 | GCUGGGCCUGAAAGACUACUGGA | 630 |
| AD-960298.1 | uscsauccCfuAfGfAfAfGfAfuacuacuggauL96 | 484 | asCfscagu(Cgn)ugaagcCfaUfcgguscsac | 787 | CAGUCCCUGAGAAGACUACUGGA | 594 |
| AD-960284.1 | cscscuagAfgGfCfUfAfgcucuccaauL96 | 499 | asGfsuccu(Tgn) aacgguGfcUfccagusaac | 788 | GUGACCUGAGCACCGUUAAGGACU | 516 |
| AD-960313.1 | gscsuuaaAfaGfGfGfacagauucucuL96 | 389 | asGfsuccc(Tgn)uuuaagCfaAfcuacsasg | 789 | CUACUGGAGCACCGUUAAGGACA | 627 |
| AD-960432.1 | ususaaaaGfgGfAfAfCfaguauucucuL96 | 365 | asCfsucug(Tgn)uccuggAfgCfagcugscsc | 790 | CUGUAGGUUGCUUAAAGGGACA | 525 |
| AD-960124.1 | csgscccacCfaAfGfAfCfcgccaagguL96 | 541 | asUfsuccu(Ggn)gagcagCfuGfccucusasg | 791 | GGCAGCUGCUCCAGGACACAGAGG | 651 |
| AD-960119.1 | gsgsucggGfuAfAfCfcgauggcuuuL96 | 466 | asAfsuacu(Ggn)uccuuUfuAfgcaaascsc | 792 | CUAGAGGCAGCUGCUCCAGGAAC | 603 |
| AD-960437.1 | gsgsuugCfUfuAfAfAfgggacaccguL96 | 409 | asUfsuguc(Cgn)uuaacgGfuGfuccasgsu | 793 | GGUUGCUUAAAGGGACAGUAUU | 794 |
| AD-960315.1 | asasagaCfaCfUfGfGfagcaccguL96 | 532 | asCfscugg(Agn)gcagcuGfcCfucuagsgg | 795 | ACUGGAGCACCGUUAAGGACAAG | 504 |
| AD-960117.1 | cscsgagcUfUfcAfGfGfaggcgaggnuL96 | 631 | asCfscuua(Agn)cggugcUfcCfaguagsusc | 796 | CCCUAGAGGCAGCUGCUCCAGGA | 657 |
| AD-960311.1 | usgsgcuGfcUfAfGfGfAfgaccucaauuL96 | 547 | asUfsgcug(Ggn)gccaccUfgGfgacucssu | 797 | GACUACUGGAGCACCGUUAAGGA | 546 |
| AD-960272.1 | ususcaucCfcUfAfAfGfaggcagcuguL96 | 607 | asUfsgcag(Ggn)acccaaGfgAfgcucgscsa | 798 | AGGAGUCCAGUGGCCCAGCAG | 660 |
| AD-960414.1 | cscsuagaGfgCfAfGfCfugcuccagruL96 | 526 | asCfsagug(Cgn)auccuuGfcGfggucsusug | 799 | UGCCAGCUCCUUGGGUCCUGCAA | 612 |
| AD-960240.1 | cscsuagaGfgCfAfGfCfugcuccaguL96 | 526 | asCfsagug(Cgn)auccugUfcGfggucsusug | 800 | CAAGACCGCCAAGGAUGCACUGA | 663 |

TABLE 5-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-960286.1 | asgsguugCfuUfAfAfaaggdacagauL96 | 493 | asCfsaggg(Agn)acugaaGfcCfaucggsusc | 801 | GACCGAUGGCUUCAGUCCCUGA | 522 |
| AD-960281.1 | csusguagGfuUfGfCfuuaaaagggUuL96 | 589 | asAfsacug(Agn)agccaucUfgGfucacsscsa | 802 | UGGGUGACCGAUGGCUUCAGUUC | 672 |
| AD-960277.1 | gsasaagaCfuAfCfUfUfggagcaccguL96 | 574 | asGfsaagc(Cgn)aucgguaCfccagcsgcsc | 803 | GGGCUGGGUGACCGAUGGCUUCA | 585 |
| AD-960274.1 | usgsggugAfcCfGfAfaUfggcuucaguL96 | 628 | asUfsggcc(Tgn)gcugggCfcAfccuggsgsa | 804 | UCCCAGUGGGCCCAGCAGGCCAG | 666 |
| AD-960108.1 | gsusucccUfgAfAfAfagacuacuggUuL96 | 592 | asGfscugc(Cgn)ucuaggGfaUfgaacusgsa | 805 | UCAGUCAUCCUAGAGAGCAGCU | 624 |
| AD-960239.1 | gsasccgaUfgGfCfUfucaguuccccUuL96 | 514 | asGfsgugu(Agn)uccuugGfcGfgucuuusgg | 806 | CCAAGACCGCCAAGGAUGCACUG | 561 |
| AD-960122.1 | ascsuggaGfcAfCfCfCfguuaaggacuL96 | 625 | asCfsuguu(Cgn)cuggagCfaGfcugccsusc | 807 | GAGGCAGCUGCUCCAGGAACAGA | 615 |
| AD-960291.1 | gsusagguUfgAfCfUfUfaaaagggacuL96 | 523 | asUfscuuu(Cgn)agggaaCfuGfaagccsasu | 808 | AUGGCUUCAGUCCCUGAAAGAC | 552 |
| AD-960125.1 | csasgcugCfucCfCfAfggaacagaguL96 | 649 | asCfscucu(Ggn)uuccugGfaGfcagcusgsc | 809 | GCAGCUGCUCCAGGAACAGAGGU | 690 |
| AD-960231.1 | asgsaggcAfgCfUfGfCfuccaggaauL96 | 601 | asCfsuugg(Cgn)ggucuuGfgUfgcgusgsc | 810 | GCACGCCACCAAGACCGCCAAGG | 669 |
| AD-960275.1 | ususgcuuAfaAfAfGfGfacuaagguL96 | 811 | asAfsgcca(Tgn)cggucaCfcCfagccscsu | 812 | AGGGGCUGGGUGACCGAUGGCUU | 597 |
| AD-960173.1 | usgsgagaGfaCfcGfGfUfuaaggacaauL96 | 502 | asUfsccuc(Ggn)gccucuGfaAfgcucgsgg | 813 | CCCGAGCUUCAGGAGGCCGAGGAU | 654 |
| AD-960271.1 | csusagagGfcAfGfCfUfugcuccaggUuL96 | 655 | asGfscugg(Ggn)ccaccuGfgAfcuccsusg | 814 | CAGGAGUCCCAGGAGGCCCAGCA | 678 |
| AD-960433.1 | csusacugGfaGfCfUfAfcccguuaagguL96 | 544 | asUfsgucc(Cgn)uuuuaaGfcAfaccuascsa | 815 | UGUAGGUUGCUUAAAAGGGACAG | 489 |
| AD-960267.1 | gsasagucCfuAfGfGfUfuggccagcauL96 | 658 | asGfsgcca(Cgn)cuggaCfuCfcugcascsg | 816 | CGUGCAGGAGUCCCAGGUGGCCC | 684 |
| AD-960236.1 | csgsagucUfCfCfUfUfGfgguccugcauL96 | 610 | asGfscauc(Cgn)uuggcgGfuCfuuggusgg | 817 | CCACCAAGACCGCCAAGGAUGCA | 636 |
| AD-960310.1 | asgsaccgCfcAfAfGfgaugcacuguL96 | 661 | asCfsuuaa(Cgn)ggugcuCfcAfguaguscu | 818 | AGACUACUGGAGCACCGUUAAGG | 648 |
| AD-960312.1 | cscsgaugCfcUfUfCfaguuccccuguL96 | 520 | asUfsccuu(Agn)acggugCfuCfaguasgsu | 819 | ACUACUGGAGCACCGUUAAGGAC | 675 |
| AD-960309.1 | gsgsgugaCfgFfAfUfGfcuucaguuUuL96 | 670 | asUfsuaac(Ggn)gugcucCfaGfuagucsusu | 820 | AAGACUACUGGAGCACCGUUAAG | 621 |
| AD-960440.1 | gscssugGfufAfCfCfcfgauggcuucuL96 | 583 | asAfsgaau(Agn)cuguccCfuUfuuaagscsa | 821 | UGCUUAAAAGGGACAGUAUUCUC | 379 |
| AD-960237.1 | cscssaggUfgCfCfCfcagcagccauL96 | 664 | asUfsgcau(Cgn)cuuggcGfgUfcuuggsug | 822 | CACCAAGACCGCCAAGGAUGCAC | 618 |
| AD-960268.1 | asgsuucaUfcCfCfAfAfggaugcacuuL96 | 622 | asGfsggcc(Agn)ccugggAfcUfcugcsasc | 823 | GUGCAGGAGUCCCAGGUGGCCCA | 681 |
| AD-960269.1 | asasagaccGfcCfAfAfggaugcacuuL96 | 559 | asUfsgggc(Cgn)accuggGfaCfuccugscsa | 824 | UGCAGGAGUCCCAGGUGGCCCAG | 687 |

TABLE 5-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-960280.1 | gsgscagcUfgCfUfCfcaggaacaguL96 | 613 | asAfscuga(Agn)gccaucGfgUfcacccsasg | 825 | CUGGGUGACCGAUGGCUUCAGUU | 642 |
| AD-960270.1 | gsgscuucAfgUfUfCfcccugaaagauL96 | 550 | asCfsuggg(Cgn)caccugGfgAfcuccusgsc | 826 | GCAGGAGUCCCAGGUGGCCCAGC | 696 |
| AD-960273.1 | asggscugcUfcCfAfGfgaacagaggguL96 | 688 | asCfsugcu(Ggn)ggccacCfuGfggacuscsc | 827 | GGAGUCCCAGGUGGCCCAGCAGG | 693 |

TABLE 6

APOC3 Single Dose Screens in Hep3B cells

| Duplex | 50 nM Dose | | 10 nM Dose | | 1.0 nM Dose | | 0.1 nM Dose | |
| --- | --- | --- | --- | --- | --- | --- | --- | --- |
| | Avg % APOC3 mRNA Remaining | SD | Avg % APOC3 mRNA Remaining | SD | Avg % APOC3 mRNA Remaining | SD | Avg % APOC3 mRNA Remaining | SD |
| AD-959917.1 | 4.2 | 1.8 | 5.1 | 1.6 | 17.7 | 3.8 | 53.5 | 5.1 |
| AD-959918.1 | 5.1 | 0.8 | 5.6 | 2.2 | 34.5 | 13.4 | 52.1 | 10.0 |
| AD-960096.1 | 7.8 | 4.6 | 7.3 | 2.2 | 24.3 | 2.1 | 88.2 | 6.8 |
| AD-960064.1 | 3.7 | 0.4 | 8.2 | 1.0 | 22.1 | 6.2 | 40.1 | 7.3 |
| AD-959914.1 | 5.9 | 1.1 | 9.8 | 2.4 | 39.4 | 4.2 | 70.4 | 17.8 |
| AD-959941.1 | 11.5 | 6.1 | 9.9 | 1.7 | 33.7 | 2.9 | 75.4 | 4.8 |
| AD-960031.1 | 6.5 | 2.2 | 9.9 | 3.0 | 18.8 | 3.4 | 47.6 | 2.7 |
| AD-959910.1 | 5.5 | 0.9 | 10.5 | 1.6 | 28.4 | 7.3 | 60.4 | 5.8 |
| AD-960063.1 | 8.5 | 3.1 | 11.1 | 2.4 | 29.7 | 7.1 | 79.4 | 10.0 |
| AD-67781.7 | 6.1 | 1.5 | 11.2 | 2.5 | 45.7 | 2.2 | 61.4 | 3.7 |
| AD-67782.2 | 6.3 | 1.0 | 12.4 | 5.6 | 38.0 | 2.3 | 68.4 | 8.5 |
| AD-959916.1 | 5.3 | 0.7 | 12.5 | 2.8 | 45.6 | 5.9 | 58.5 | 2.0 |
| AD-959913.1 | 6.2 | 0.3 | 12.7 | 1.1 | 32.2 | 5.9 | 67.0 | 10.0 |
| AD-960066.1 | 7.7 | 1.1 | 13.2 | 1.6 | 42.3 | 3.7 | 94.7 | 27.8 |
| AD-960062.1 | 8.8 | 1.2 | 13.7 | 1.8 | 48.8 | 4.7 | 73.1 | 16.8 |
| AD-960093.1 | 12.5 | 1.8 | 13.7 | 3.0 | 37.4 | 12.5 | 64.0 | 17.2 |
| AD-960061.1 | 7.3 | 0.4 | 13.9 | 1.3 | 42.4 | 7.9 | 69.2 | 10.6 |
| AD-960092.1 | 16.2 | 10.7 | 14.2 | 2.0 | 53.1 | 13.9 | 95.0 | 13.2 |
| AD-960030.1 | 14.8 | 5.6 | 14.7 | 1.2 | 40.7 | 8.2 | 94.2 | 9.5 |
| AD-80794.6 | 15.2 | 6.5 | 15.5 | 1.7 | 41.3 | 5.3 | 84.6 | 1.8 |
| AD-960095.1 | 12.6 | 1.6 | 16.0 | 1.9 | 55.4 | 9.0 | 86.4 | 2.9 |
| AD-959938.1 | 14.9 | 8.3 | 16.5 | 3.4 | 59.9 | 12.6 | 83.8 | 4.5 |
| AD-960065.1 | 12.6 | 3.5 | 17.1 | 3.8 | 51.7 | 7.4 | 79.1 | 10.3 |
| AD-959907.1 | 10.7 | 5.0 | 17.4 | 6.4 | 51.1 | 3.5 | 89.4 | 10.9 |
| AD-960094.1 | 12.4 | 3.7 | 18.8 | 5.3 | 76.5 | 17.2 | 131.2 | 4.0 |
| AD-960060.1 | 12.9 | 2.6 | 19.3 | 3.7 | 77.8 | 5.5 | 69.6 | 5.8 |
| AD-959919.1 | 14.1 | 3.1 | 19.8 | 2.0 | 72.6 | 13.4 | 105.9 | 9.6 |
| AD-959932.1 | 11.8 | 5.9 | 20.1 | 8.9 | 47.1 | 9.8 | 102.2 | 4.3 |
| AD-959859.1 | 20.6 | 8.2 | 20.5 | 6.8 | 93.5 | 12.1 | 161.4 | 40.6 |
| AD-959908.1 | 9.6 | 2.2 | 20.8 | 2.5 | 48.7 | 4.7 | 78.8 | 18.0 |
| AD-959903.1 | 12.9 | 5.5 | 20.9 | 3.1 | 58.0 | 14.2 | 96.2 | 12.5 |
| AD-960097.1 | 19.1 | 6.5 | 21.0 | 4.9 | 77.5 | 11.3 | 78.4 | 3.8 |
| AD-959912.1 | 12.0 | 1.3 | 21.1 | 1.3 | 75.3 | 10.6 | 108.4 | 26.5 |
| AD-960067.1 | 19.9 | 4.6 | 21.2 | 3.6 | 81.4 | 11.3 | 85.8 | 9.3 |
| AD-959927.1 | 16.1 | 2.6 | 21.3 | 6.3 | 68.8 | 13.0 | 102.7 | 17.7 |
| AD-960099.1 | 13.4 | 3.0 | 21.9 | 3.6 | 46.1 | 8.7 | 76.3 | 4.2 |
| AD-959931.1 | 20.4 | 5.4 | 22.6 | 7.6 | 58.7 | 5.0 | 105.7 | 12.0 |
| AD-959879.1 | 12.6 | 5.1 | 22.8 | 6.0 | 89.8 | 10.4 | 78.1 | 2.3 |
| AD-960091.1 | 29.8 | 7.8 | 23.2 | 6.8 | 84.3 | 16.5 | 159.8 | 73.0 |
| AD-959921.1 | 14.9 | 5.1 | 23.2 | 6.6 | 64.2 | 8.3 | 71.0 | 7.7 |
| AD-960102.1 | 19.2 | 3.9 | 23.3 | 10.3 | 43.4 | 12.0 | 75.9 | 13.5 |
| AD-80793.6 | 21.8 | 3.6 | 24.3 | 3.9 | 51.8 | 12.8 | 90.4 | 7.2 |
| AD-959925.1 | 13.0 | 1.5 | 25.2 | 3.3 | 75.6 | 10.3 | 87.4 | 21.4 |
| AD-960098.1 | 31.3 | 4.6 | 26.8 | 6.1 | 103.2 | 15.8 | 93.3 | 4.5 |
| AD-959901.1 | 23.6 | 8.4 | 27.1 | 6.8 | 97.7 | 8.5 | 162.1 | 29.0 |
| AD-959920.1 | 21.7 | 0.4 | 28.1 | 4.4 | 83.1 | 11.3 | 101.1 | 20.9 |
| AD-959926.1 | 21.6 | 6.1 | 29.3 | 8.9 | 98.8 | 21.6 | 113.8 | 18.8 |
| AD-959737.1 | 33.0 | 9.7 | 30.3 | 7.5 | 78.6 | 12.9 | 95.6 | 8.4 |
| AD-960011.1 | 14.5 | 4.9 | 33.2 | 5.1 | 104.7 | 19.0 | 101.2 | 12.7 |
| AD-960101.1 | 24.7 | 4.0 | 33.2 | 10.2 | 82.8 | 7.0 | 159.8 | 73.4 |
| AD-959923.1 | 14.1 | 3.3 | 33.2 | 2.8 | 74.7 | 12.0 | 78.8 | 4.9 |
| AD-68107.2 | 21.1 | 5.4 | 33.3 | 5.5 | 67.1 | 11.7 | 113.1 | 10.0 |
| AD-960058.1 | 35.5 | 4.4 | 33.7 | 6.2 | 98.2 | 19.6 | 138.9 | 18.2 |
| AD-68103.2 | 27.9 | 6.5 | 34.1 | 11.0 | 69.9 | 2.5 | 105.4 | 14.6 |
| AD-959860.1 | 27.6 | 6.2 | 35.5 | 11.2 | 98.2 | 16.5 | 164.2 | 15.9 |
| AD-960059.1 | 17.1 | 2.1 | 38.7 | 5.3 | 131.1 | 18.8 | 119.6 | 59.9 |
| AD-960103.1 | 40.3 | 3.0 | 39.4 | 5.8 | 69.9 | 4.1 | 95.8 | 2.3 |
| AD-959740.1 | 37.2 | 4.1 | 39.5 | 5.8 | 97.8 | 27.9 | 96.4 | 7.4 |
| AD-959939.1 | 31.1 | 2.2 | 40.4 | 6.6 | 94.9 | 12.6 | 104.9 | 21.0 |
| AD-959865.1 | 35.7 | 8.5 | 41.0 | 2.8 | 92.9 | 11.8 | 111.2 | 7.3 |
| AD-960100.1 | 31.6 | 3.3 | 43.2 | 10.9 | 75.7 | 11.1 | 103.8 | 17.7 |
| AD-959924.1 | 21.9 | 4.3 | 43.2 | 8.2 | 102.8 | 20.3 | 96.8 | 10.7 |
| AD-959909.1 | 24.2 | 3.5 | 45.1 | 3.1 | 92.8 | 7.8 | 79.7 | 3.7 |
| AD-959739.1 | 38.8 | 2.4 | 46.4 | 7.9 | 101.5 | 5.6 | 108.4 | 4.3 |
| AD-959911.1 | 21.5 | 3.8 | 46.9 | 9.1 | 90.4 | 13.1 | 104.5 | 9.5 |
| AD-960057.1 | 32.9 | 2.5 | 47.8 | 3.1 | 95.1 | 7.8 | 79.8 | 12.4 |
| AD-959741.1 | 42.5 | 1.7 | 48.5 | 6.4 | 89.5 | 14.3 | 117.1 | 10.4 |
| AD-960056.1 | 24.9 | 0.9 | 48.6 | 6.1 | 87.6 | 15.6 | 85.7 | 6.9 |
| AD-959930.1 | 52.4 | 8.4 | 49.4 | 9.3 | 86.6 | 17.9 | 118.5 | 15.0 |
| AD-959746.1 | 41.4 | 5.4 | 49.6 | 2.4 | 62.0 | 7.8 | 111.9 | 15.6 |
| AD-959748.1 | 40.9 | 5.9 | 50.1 | 15.5 | 89.4 | 14.7 | 100.3 | 10.6 |

TABLE 6-continued

APOC3 Single Dose Screens in Hep3B cells

| Duplex | 50 nM Dose | | 10 nM Dose | | 1.0 nM Dose | | 0.1 nM Dose | |
| --- | --- | --- | --- | --- | --- | --- | --- | --- |
| | Avg % APOC3 mRNA Remaining | SD | Avg % APOC3 mRNA Remaining | SD | Avg % APOC3 mRNA Remaining | SD | Avg % APOC3 mRNA Remaining | SD |
| AD-959857.1 | 41.9 | 19.2 | 51.7 | 3.9 | 106.7 | 11.7 | 105.0 | 14.0 |
| AD-959935.1 | 35.3 | 2.3 | 54.1 | 13.2 | 126.1 | 24.7 | 188.1 | 72.0 |
| AD-960008.1 | 56.3 | 9.9 | 54.4 | 5.8 | 92.2 | 7.7 | 109.6 | 19.1 |
| AD-959915.1 | 30.3 | 5.8 | 57.3 | 3.7 | 104.2 | 15.9 | 82.1 | 7.3 |
| AD-959738.1 | 52.6 | 10.0 | 58.6 | 9.4 | 94.3 | 14.0 | 100.5 | 22.3 |
| AD-959928.1 | 42.3 | 6.1 | 60.0 | 7.6 | 85.3 | 11.8 | 123.3 | 14.2 |
| AD-959863.1 | 58.7 | 4.0 | 60.1 | 9.5 | 81.4 | 4.9 | 119.4 | 8.8 |
| AD-960010.1 | 58.6 | 8.9 | 60.3 | 11.8 | 115.5 | 18.5 | 105.5 | 13.5 |
| AD-960090.1 | 73.2 | 10.7 | 60.5 | 16.0 | 102.0 | 14.8 | 95.3 | 11.5 |
| AD-959732.1 | 45.4 | 6.7 | 63.0 | 6.1 | 101.4 | 14.6 | 118.0 | 11.4 |
| AD-960009.1 | 50.6 | 5.9 | 63.1 | 17.5 | 106.1 | 10.9 | 109.4 | 19.6 |
| AD-959929.1 | 72.2 | 10.3 | 66.2 | 15.5 | 140.7 | 47.3 | 108.3 | 18.1 |
| AD-959745.1 | 48.8 | 7.7 | 66.8 | 15.0 | 104.7 | 17.4 | 125.3 | 7.3 |
| AD-960007.1 | 64.1 | 8.4 | 67.0 | 13.1 | 86.3 | 8.9 | 104.1 | 7.6 |
| AD-959902.1 | 41.4 | 9.8 | 68.2 | 4.7 | 98.8 | 18.0 | 132.1 | 37.4 |
| AD-959940.1 | 50.8 | 9.8 | 69.0 | 9.1 | 105.0 | 18.3 | 96.8 | 13.0 |
| AD-960055.1 | 52.7 | 8.5 | 70.1 | 5.7 | 101.4 | 20.6 | 115.3 | 18.2 |
| AD-959922.1 | 54.7 | 6.2 | 70.1 | 6.4 | 113.6 | 16.0 | 93.0 | 7.3 |
| AD-959900.1 | 65.2 | 7.0 | 70.6 | 5.3 | 102.9 | 11.3 | 179.9 | 77.2 |
| AD-959858.1 | 72.9 | 18.5 | 71.4 | 17.7 | 103.4 | 11.1 | 116.6 | 6.1 |
| AD-959744.1 | 56.0 | 11.2 | 71.6 | 22.1 | 106.2 | 18.3 | 127.0 | 21.8 |
| AD-959736.1 | 67.3 | 8.2 | 72.6 | 10.6 | 100.5 | 15.8 | 108.3 | 15.6 |
| AD-959735.1 | 68.8 | 14.9 | 75.5 | 15.3 | 112.0 | 26.5 | 116.0 | 19.0 |
| AD-960039.1 | 94.8 | 13.8 | 75.5 | 15.3 | 112.7 | 8.6 | 138.0 | 14.7 |
| AD-959747.1 | 75.4 | 8.4 | 76.0 | 10.3 | 121.7 | 13.3 | 100.0 | 5.8 |
| AD-959862.1 | 79.3 | 3.4 | 77.9 | 25.8 | 103.2 | 7.9 | 118.8 | 12.4 |
| AD-959933.1 | 66.7 | 12.1 | 79.0 | 10.7 | 121.8 | 16.7 | 142.3 | 29.2 |
| AD-959733.1 | 60.8 | 10.8 | 81.7 | 15.8 | 95.7 | 15.4 | 114.2 | 9.7 |
| AD-959937.1 | 65.7 | 6.0 | 85.2 | 13.6 | 120.8 | 17.1 | 101.8 | 3.2 |
| AD-959904.1 | 52.7 | 7.6 | 86.9 | 6.4 | 130.2 | 24.2 | 124.9 | 16.7 |
| AD-959797.1 | 85.6 | 3.9 | 87.2 | 16.3 | 102.0 | 5.9 | 129.5 | 24.1 |
| AD-959861.1 | 63.0 | 14.0 | 88.4 | 16.5 | 109.2 | 7.3 | 140.1 | 25.0 |
| AD-959743.1 | 56.2 | 4.8 | 89.3 | 9.4 | 100.1 | 5.8 | 143.9 | 25.4 |
| AD-959905.1 | 55.9 | 20.6 | 91.7 | 11.8 | 110.6 | 16.2 | 122.3 | 33.1 |
| AD-959734.1 | 67.0 | 10.9 | 93.5 | 18.4 | 100.7 | 19.0 | 128.9 | 13.4 |
| AD-959934.1 | 82.1 | 17.1 | 95.1 | 24.1 | 109.8 | 7.7 | 115.6 | 12.4 |
| AD-959749.1 | 74.1 | 15.9 | 95.7 | 13.1 | 111.2 | 15.8 | 129.2 | 16.1 |
| AD-959798.1 | 111.9 | 18.4 | 96.6 | 20.7 | 134.4 | 42.1 | 124.5 | 40.5 |
| AD-959742.1 | 79.3 | 6.8 | 104.1 | 18.5 | 117.5 | 14.2 | 167.7 | 48.7 |
| AD-959897.1 | 114.4 | 14.2 | 104.7 | 20.1 | 95.8 | 14.8 | 103.7 | 11.1 |
| AD-959864.1 | 139.0 | 7.4 | 108.7 | 19.7 | 121.8 | 8.3 | 134.4 | 34.1 |
| AD-959899.1 | 111.2 | 12.3 | 109.0 | 17.8 | 99.4 | 6.6 | 114.9 | 19.1 |
| AD-959856.1 | 120.8 | 10.0 | 112.1 | 6.2 | 142.0 | 30.4 | 86.1 | 4.2 |
| AD-959906.1 | 87.2 | 12.3 | 112.3 | 15.7 | 119.5 | 3.6 | 123.0 | 9.0 |
| AD-959936.1 | 95.8 | 11.2 | 112.6 | 17.9 | 108.7 | 12.1 | 133.5 | 20.9 |
| AD-959896.1 | 86.2 | 10.8 | 114.9 | 9.7 | 104.9 | 12.0 | 111.6 | 13.5 |
| AD-959893.1 | 110.4 | 6.1 | 115.5 | 23.1 | 102.0 | 14.7 | 112.9 | 9.6 |
| AD-959892.1 | 97.9 | 20.0 | 118.4 | 10.8 | 97.9 | 9.2 | 114.0 | 14.5 |
| AD-959894.1 | 118.2 | 10.8 | 132.2 | 25.9 | 103.5 | 3.9 | 134.0 | 17.1 |
| AD-959750.1 | 150.2 | 3.6 | 136.5 | 12.9 | 113.4 | 7.3 | 135.5 | 21.5 |
| AD-959898.1 | 129.1 | 11.8 | 139.1 | 29.1 | 125.4 | 12.1 | 137.4 | 13.5 |
| AD-959895.1 | 107.1 | 12.9 | 158.5 | 27.8 | 116.8 | 12.8 | 133.9 | 13.1 |

TABLE 7

APOC3 Single Dose Screens in Hep3B cells

| Duplex | 50 nM Dose | | 10 nM Dose | | 1.0 nM Dose | | 0.1 nM Dose | |
| --- | --- | --- | --- | --- | --- | --- | --- | --- |
| | Avg % APOC3 mRNA Remaining | SD | Avg % APOC3 mRNA Remaining | SD | Avg % APOC3 mRNA Remaining | SD | Avg % APOC3 mRNA Remaining | SD |
| AD-960293.1 | 5.3 | 1.1 | 4.4 | 0.9 | 12.7 | 3.6 | 49.3 | 8.8 |
| AD-960288.1 | 7.1 | 1.1 | 4.5 | 0.3 | 16.4 | 2.8 | 60.9 | 3.2 |
| AD-960445.1 | 7.2 | 2.3 | 4.6 | 0.9 | 24.9 | 4.1 | 67.0 | 11.2 |
| AD-960292.1 | 8.4 | 2.7 | 6.1 | 1.8 | 35.0 | 3.6 | 89.3 | 13.2 |

TABLE 7-continued

APOC3 Single Dose Screens in Hep3B cells

| | 50 nM Dose | | 10 nM Dose | | 1.0 nM Dose | | 0.1 nM Dose | |
|---|---|---|---|---|---|---|---|---|
| Duplex | Avg % APOC3 mRNA Remaining | SD | Avg % APOC3 mRNA Remaining | SD | Avg % APOC3 mRNA Remaining | SD | Avg % APOC3 mRNA Remaining | SD |
| AD-960475.1 | 9.5 | 1.8 | 6.2 | 1.5 | 20.0 | 7.7 | 79.7 | 7.4 |
| AD-960442.1 | 12.1 | 1.5 | 6.5 | 1.7 | 21.5 | 1.3 | 79.3 | 18.3 |
| AD-960470.1 | 11.8 | 1.9 | 7.1 | 0.6 | 40.0 | 10.6 | 78.1 | 5.5 |
| AD-960436.1 | 11.3 | 3.2 | 7.9 | 2.0 | 31.6 | 3.0 | 86.2 | 7.7 |
| AD-960446.1 | 8.3 | 1.8 | 8.4 | 1.6 | 43.0 | 10.6 | 77.2 | 4.3 |
| AD-960474.1 | 11.6 | 1.8 | 8.4 | 0.9 | 39.4 | 5.9 | 103.2 | 18.7 |
| AD-960294.1 | 14.0 | 1.7 | 8.5 | 1.6 | 32.8 | 9.1 | 74.7 | 5.8 |
| AD-960471.1 | 12.2 | 1.5 | 8.5 | 0.8 | 28.8 | 7.5 | 81.1 | 16.8 |
| AD-960314.1 | 11.0 | 0.4 | 9.3 | 1.1 | 41.2 | 9.8 | 79.2 | 4.3 |
| AD-960443.1 | 17.7 | 6.1 | 9.9 | 2.6 | 33.4 | 5.5 | 95.7 | 15.2 |
| AD-960282.1 | 12.2 | 1.9 | 10.0 | 2.4 | 51.8 | 13.2 | 106.4 | 30.6 |
| AD-960283.1 | 13.2 | 0.9 | 10.0 | 1.3 | 50.3 | 6.3 | 101.6 | 8.4 |
| AD-80794.7 | 9.5 | 1.4 | 10.8 | 2.5 | 34.9 | 9.1 | 78.4 | 7.5 |
| AD-960295.1 | 25.0 | 4.9 | 11.4 | 4.0 | 43.9 | 2.4 | 82.2 | 10.5 |
| AD-960478.1 | 15.1 | 1.9 | 11.8 | 3.4 | 17.7 | 2.1 | 62.6 | 9.7 |
| AD-960289.1 | 14.9 | 0.7 | 11.8 | 1.4 | 44.7 | 4.4 | 97.2 | 16.6 |
| AD-960481.1 | 17.1 | 2.8 | 12.8 | 2.3 | 25.9 | 6.9 | 56.2 | 2.0 |
| AD-960318.1 | 21.0 | 5.6 | 13.3 | 2.4 | 43.2 | 2.3 | 83.6 | 11.4 |
| AD-960297.1 | 21.5 | 2.5 | 14.1 | 1.8 | 49.0 | 5.0 | 103.4 | 9.0 |
| AD-960477.1 | 13.6 | 5.0 | 14.1 | 3.1 | 29.8 | 6.1 | 89.6 | 17.5 |
| AD-960317.1 | 20.9 | 5.7 | 14.3 | 3.9 | 48.5 | 19.9 | 101.0 | 28.8 |
| AD-960476.1 | 14.2 | 1.5 | 16.3 | 1.0 | 41.1 | 7.5 | 92.0 | 4.5 |
| AD-960241.1 | 15.6 | 2.3 | 17.1 | 1.4 | 68.4 | 8.4 | 103.7 | 27.4 |
| AD-960480.1 | 20.1 | 1.0 | 18.0 | 2.5 | 62.0 | 10.9 | 91.8 | 12.4 |
| AD-960482.1 | 25.5 | 6.0 | 19.8 | 2.8 | 37.2 | 3.5 | 60.8 | 11.6 |
| AD-80793.7 | 16.6 | 3.1 | 20.2 | 3.5 | 43.8 | 5.9 | 64.1 | 5.9 |
| AD-960107.1 | 30.1 | 1.1 | 20.6 | 3.8 | 61.2 | 8.7 | 95.4 | 14.3 |
| AD-960308.1 | 31.9 | 3.3 | 23.3 | 2.2 | 48.0 | 5.8 | 90.2 | 4.9 |
| AD-960121.1 | 25.3 | 4.5 | 24.7 | 4.5 | 65.9 | 7.8 | 87.0 | 12.5 |
| AD-960287.1 | 37.5 | 6.9 | 24.8 | 10.3 | 90.3 | 22.4 | 82.9 | 5.2 |
| AD-960473.1 | 22.4 | 5.3 | 25.1 | 3.4 | 98.0 | 19.4 | 104.8 | 24.8 |
| AD-960479.1 | 28.3 | 4.1 | 25.4 | 8.2 | 72.6 | 18.2 | 90.5 | 8.2 |
| AD-960278.1 | 22.8 | 5.6 | 25.6 | 5.4 | 71.9 | 8.8 | 105.8 | 15.8 |
| AD-960113.1 | 26.5 | 4.8 | 25.7 | 7.0 | 59.0 | 5.7 | 114.0 | 17.3 |
| AD-960472.1 | 38.2 | 8.0 | 26.5 | 8.2 | 56.0 | 8.7 | 107.3 | 28.4 |
| AD-960444.1 | 26.5 | 4.8 | 27.3 | 3.0 | 72.4 | 12.5 | 127.2 | 16.8 |
| AD-960303.1 | 30.6 | 4.3 | 28.4 | 6.1 | 82.0 | 15.0 | 104.9 | 20.2 |
| AD-960438.1 | 31.3 | 4.4 | 28.6 | 6.0 | 59.2 | 6.1 | 90.3 | 14.4 |
| AD-960290.1 | 29.8 | 5.6 | 30.3 | 3.9 | 80.8 | 4.3 | 107.1 | 12.4 |
| AD-960304.1 | 32.6 | 7.7 | 30.4 | 3.0 | 86.3 | 9.9 | 100.4 | 15.6 |
| AD-960388.1 | 29.6 | 2.0 | 30.7 | 2.2 | 71.8 | 11.7 | 102.8 | 27.2 |
| AD-960233.1 | 28.4 | 4.7 | 31.5 | 5.7 | 96.7 | 11.8 | 99.0 | 17.2 |
| AD-960234.1 | 46.3 | 7.2 | 33.1 | 8.5 | 93.3 | 10.2 | 97.3 | 14.5 |
| AD-960114.1 | 15.9 | 2.5 | 33.2 | 4.3 | 58.9 | 4.5 | 93.9 | 11.3 |
| AD-960296.1 | 49.5 | 5.3 | 34.5 | 9.2 | 70.8 | 7.0 | 93.6 | 8.3 |
| AD-960431.1 | 40.7 | 8.8 | 35.1 | 1.1 | 87.2 | 3.7 | 108.8 | 8.6 |
| AD-960316.1 | 35.5 | 2.6 | 37.2 | 8.2 | 78.9 | 14.8 | 93.4 | 15.1 |
| AD-960307.1 | 25.4 | 1.3 | 37.4 | 4.6 | 90.9 | 7.7 | 99.5 | 10.8 |
| AD-960120.1 | 21.4 | 1.7 | 37.8 | 5.6 | 86.5 | 12.6 | 107.1 | 16.1 |
| AD-960238.1 | 20.5 | 2.9 | 37.9 | 9.9 | 79.7 | 22.5 | 128.8 | 11.2 |
| AD-960301.1 | 35.6 | 6.4 | 38.2 | 7.4 | 75.6 | 9.0 | 101.6 | 21.1 |
| AD-960235.1 | 32.1 | 6.1 | 39.4 | 12.7 | 107.9 | 8.9 | 167.9 | 37.6 |
| AD-960123.1 | 29.3 | 3.4 | 42.8 | 3.8 | 85.3 | 7.9 | 101.2 | 19.9 |
| AD-960300.1 | 24.4 | 3.1 | 45.3 | 13.1 | 77.9 | 12.3 | 101.2 | 15.3 |
| AD-960285.1 | 64.5 | 4.8 | 46.0 | 6.9 | 86.7 | 12.6 | 98.6 | 9.4 |
| AD-960469.1 | 43.0 | 6.1 | 46.3 | 6.8 | 72.4 | 12.5 | 96.4 | 20.8 |
| AD-960387.1 | 40.5 | 2.6 | 46.6 | 16.0 | 94.0 | 8.6 | 99.9 | 6.8 |
| AD-960384.1 | 42.8 | 2.9 | 47.1 | 2.9 | 103.6 | 9.9 | 103.2 | 13.1 |
| AD-960109.1 | 41.1 | 5.7 | 48.6 | 6.8 | 66.1 | 7.0 | 81.6 | 10.0 |
| AD-960112.1 | 44.6 | 2.4 | 48.8 | 5.3 | 69.0 | 17.5 | 103.7 | 12.3 |
| AD-960386.1 | 59.3 | 4.9 | 49.2 | 10.1 | 100.5 | 20.4 | 106.1 | 13.2 |
| AD-960302.1 | 69.2 | 12.5 | 49.4 | 10.1 | 82.4 | 14.5 | 106.2 | 14.6 |
| AD-960118.1 | 44.1 | 5.1 | 49.7 | 10.8 | 98.1 | 23.5 | 136.2 | 29.0 |
| AD-960111.1 | 43.3 | 6.9 | 50.0 | 4.5 | 93.6 | 9.3 | 107.0 | 20.0 |
| AD-960299.1 | 44.7 | 5.2 | 51.2 | 4.0 | 105.0 | 11.8 | 114.8 | 7.7 |
| AD-960115.1 | 42.3 | 6.0 | 52.1 | 2.6 | 82.4 | 12.1 | 85.4 | 15.0 |
| AD-960439.1 | 51.3 | 16.3 | 52.8 | 1.8 | 92.2 | 13.9 | 98.5 | 12.5 |
| AD-960441.1 | 74.3 | 9.3 | 53.2 | 5.7 | 98.1 | 21.9 | 102.2 | 20.2 |
| AD-960232.1 | 43.3 | 6.8 | 54.7 | 4.6 | 105.5 | 8.5 | 109.6 | 5.2 |
| AD-960276.1 | 39.7 | 10.0 | 54.9 | 21.4 | 101.5 | 29.8 | 107.1 | 22.3 |
| AD-960435.1 | 64.2 | 1.1 | 57.2 | 4.9 | 85.5 | 12.3 | 109.9 | 13.3 |

TABLE 7-continued

APOC3 Single Dose Screens in Hep3B cells

| | 50 nM Dose | | 10 nM Dose | | 1.0 nM Dose | | 0.1 nM Dose | |
| --- | --- | --- | --- | --- | --- | --- | --- | --- |
| Duplex | Avg % APOC3 mRNA Remaining | SD | Avg % APOC3 mRNA Remaining | SD | Avg % APOC3 mRNA Remaining | SD | Avg % APOC3 mRNA Remaining | SD |
| AD-960306.1 | 57.8 | 4.6 | 57.8 | 3.7 | 74.1 | 15.0 | 91.4 | 10.5 |
| AD-960172.1 | 39.5 | 1.4 | 57.8 | 3.6 | 117.6 | 27.7 | 115.2 | 36.2 |
| AD-960385.1 | 89.3 | 7.4 | 59.2 | 19.5 | 124.6 | 37.9 | 107.8 | 16.4 |
| AD-960110.1 | 36.5 | 2.7 | 62.2 | 15.6 | 64.7 | 6.4 | 82.5 | 12.4 |
| AD-960116.1 | 26.8 | 3.5 | 62.4 | 10.8 | 78.8 | 10.9 | 81.0 | 12.9 |
| AD-960434.1 | 64.8 | 7.8 | 63.1 | 19.2 | 79.0 | 6.8 | 111.8 | 14.9 |
| AD-960430.1 | 75.9 | 11.5 | 67.0 | 8.7 | 111.9 | 8.6 | 103.9 | 4.9 |
| AD-960305.1 | 54.3 | 7.1 | 68.7 | 18.0 | 83.3 | 9.3 | 106.2 | 24.0 |
| AD-960279.1 | 97.3 | 25.7 | 69.3 | 1.5 | 138.6 | 43.7 | 108.2 | 17.4 |
| AD-960298.1 | 82.1 | 2.0 | 72.0 | 18.4 | 81.0 | 18.2 | 97.0 | 22.4 |
| AD-960284.1 | 91.4 | 20.3 | 74.0 | 11.1 | 103.5 | 15.0 | 115.2 | 20.0 |
| AD-960313.1 | 88.5 | 3.6 | 74.6 | 18.9 | 116.9 | 17.3 | 96.1 | 8.5 |
| AD-960432.1 | 77.1 | 6.5 | 76.4 | 8.3 | 94.7 | 20.2 | 103.7 | 10.5 |
| AD-960124.1 | 62.0 | 6.5 | 76.7 | 9.3 | 110.4 | 22.7 | 115.3 | 9.8 |
| AD-960119.1 | 78.8 | 6.0 | 77.7 | 6.6 | 106.5 | 24.1 | 140.7 | 8.0 |
| AD-960437.1 | 101.3 | 8.8 | 77.7 | 11.6 | 98.4 | 23.9 | 116.1 | 21.1 |
| AD-960315.1 | 84.1 | 10.8 | 79.6 | 8.0 | 107.5 | 13.0 | 103.5 | 4.3 |
| AD-960117.1 | 82.4 | 28.4 | 81.8 | 8.8 | 126.7 | 10.4 | 118.9 | 17.6 |
| AD-960311.1 | 82.6 | 12.2 | 82.3 | 8.7 | 138.1 | 20.4 | 112.0 | 24.6 |
| AD-960272.1 | 90.8 | 17.5 | 84.1 | 4.2 | 114.7 | 13.2 | 90.1 | 4.8 |
| AD-960414.1 | 105.6 | 23.4 | 84.5 | 4.9 | 117.2 | 13.8 | 113.6 | 24.8 |
| AD-960240.1 | 81.0 | 9.2 | 85.6 | 14.5 | 98.0 | 5.1 | 95.5 | 27.7 |
| AD-960286.1 | 87.4 | 6.6 | 85.8 | 11.8 | 122.0 | 17.0 | 101.7 | 2.6 |
| AD-960281.1 | 119.9 | 27.1 | 86.6 | 23.2 | 120.5 | 17.4 | 112.4 | 6.8 |
| AD-960277.1 | 126.8 | 14.6 | 94.8 | 21.3 | 166.0 | 68.5 | 99.9 | 13.6 |
| AD-960274.1 | 120.6 | 27.3 | 95.6 | 17.5 | 128.4 | 17.1 | 123.9 | 27.1 |
| AD-960108.1 | 79.8 | 6.1 | 95.8 | 17.5 | 103.7 | 9.4 | 96.7 | 11.4 |
| AD-960239.1 | 106.5 | 19.7 | 95.9 | 13.8 | 112.7 | 16.0 | 109.3 | 10.7 |
| AD-960122.1 | 100.1 | 10.3 | 96.3 | 3.1 | 132.0 | 3.7 | 117.6 | 8.3 |
| AD-960291.1 | 111.5 | 17.5 | 96.3 | 18.2 | 99.9 | 18.0 | 125.3 | 23.6 |
| AD-960125.1 | 134.2 | 17.5 | 98.0 | 12.3 | 122.9 | 17.1 | 100.1 | 12.4 |
| AD-960231.1 | 95.9 | 17.6 | 99.4 | 23.7 | 99.8 | 27.2 | 99.9 | 23.1 |
| AD-960275.1 | 69.0 | 6.8 | 99.7 | 7.9 | 93.7 | 14.8 | 137.6 | 22.2 |
| AD-960173.1 | 81.3 | 13.7 | 99.8 | 30.0 | 96.3 | 19.1 | 104.6 | 28.9 |
| AD-960271.1 | 94.3 | 8.3 | 100.1 | 5.2 | 106.7 | 13.0 | 101.9 | 14.3 |
| AD-960433.1 | 165.5 | 10.3 | 101.1 | 10.9 | 145.3 | 26.4 | 101.8 | 9.0 |
| AD-960267.1 | 114.1 | 6.1 | 101.4 | 8.4 | 105.4 | 23.3 | 112.1 | 4.1 |
| AD-960236.1 | 95.8 | 5.7 | 101.8 | 10.5 | 106.6 | 25.8 | 110.3 | 13.0 |
| AD-960310.1 | 112.9 | 9.5 | 103.5 | 13.1 | 106.6 | 16.8 | 112.8 | 19.0 |
| AD-960312.1 | 106.2 | 3.8 | 103.8 | 17.4 | 147.1 | 31.1 | 107.2 | 8.8 |
| AD-960309.1 | 91.5 | 6.4 | 107.7 | 14.0 | 104.1 | 14.2 | 100.7 | 23.9 |
| AD-960440.1 | 106.8 | 12.6 | 110.3 | 15.5 | 89.7 | 23.6 | 108.7 | 17.4 |
| AD-960237.1 | 129.8 | 8.4 | 113.2 | 15.2 | 101.1 | 18.6 | 127.7 | 5.6 |
| AD-960268.1 | 100.0 | 8.7 | 114.3 | 5.7 | 97.1 | 5.1 | 89.3 | 16.4 |
| AD-960269.1 | 134.7 | 14.3 | 118.2 | 10.1 | 107.5 | 21.8 | 131.1 | 22.3 |
| AD-960280.1 | 83.9 | 4.5 | 121.9 | 23.0 | 116.0 | 20.5 | 118.5 | 41.7 |
| AD-960270.1 | 122.8 | 11.5 | 122.1 | 13.0 | 102.7 | 15.9 | 114.3 | 16.2 |
| AD-960273.1 | 149.2 | 4.7 | 142.6 | 33.3 | 107.4 | 10.5 | 145.7 | 16.6 |

Example 3. In Vivo Screening of dsRNA Duplexes in Mice

Duplexes of interest, identified from the above in vitro studies, were evaluated in vivo. In particular, at pre-dose day −14 wild-type mice (C57BL/6) were transduced by retrorbital administration of $2\times10^{10}$ viral particles of an adeno-associated virus 8 (AAV8) vector encoding human APOC3. In particular, mice were administered an AAV8 encoding the human APOC3 mRNA, referred to as AAV8-TBG-PI-APOC3.

At day 0, groups of three mice were subcutaneously administered a single 3 mg/kg dose of the agents of interest or PBS control. Table 8 provides the treatment groups and Table 9 provides the modifided nucleotide sequences of the sense and antisense strands of the duplexes of interest. At day 7 or day 14 post-dose animals were sacrificed, liver samples were collected and snap-frozen in liquid nitrogen. Liver mRNA was extracted and analyzed by the RT-QPCR method.

Human APOC3 mRNA levels were compared to a housekeeping gene, GAPDH. The values were then normalized to the average of PBS vehicle control group. The data were expressed as percent of baseline value, and presented as mean plus standard deviation. The results, listed in Table 10 and shown in FIG. 1, demonstrate that the exemplary duplex agents tested effectively reduce the level of the human APOC3 messenger RNA in vivo.

TABLE 8

Treatment Groups

| Group # | Animal # | Treatment | Dose | Timepoint |
|---|---|---|---|---|
| 1 | 1 | PBS | n/a | D 0, D 7, D 14 |
|   | 2 |   |   |   |
|   | 3 |   |   |   |
| 2 | 4 | Naïve | n/a |   |
|   | 5 |   |   |   |
|   | 6 |   |   |   |
| 3 | 7 | AD-959917.1 | 3 mpk |   |
|   | 8 |   |   |   |
|   | 9 |   |   |   |
| 4 | 10 | AD-960064.1 |   |   |
|   | 11 |   |   |   |
|   | 12 |   |   |   |
| 5 | 13 | AD-960293.1 |   |   |
|   | 14 |   |   |   |
|   | 15 |   |   |   |
| 6 | 16 | AD-960288.1 |   |   |
|   | 17 |   |   |   |
|   | 18 |   |   |   |
| 7 | 19 | AD-960445.1 |   |   |
|   | 20 |   |   |   |
|   | 21 |   |   |   |
| 8 | 22 | AD-960292.1 |   |   |
|   | 23 |   |   |   |
|   | 24 |   |   |   |
| 9 | 25 | AD-960475.1 |   |   |
|   | 26 |   |   |   |
|   | 27 |   |   |   |
| 10 | 28 | AD-960442.1 |   |   |
|   | 29 |   |   |   |
|   | 30 |   |   |   |
| 11 | 31 | AD-960470.1 |   |   |
|   | 32 |   |   |   |
|   | 33 |   |   |   |
| 12 | 34 | AD-960446.1 |   |   |
|   | 35 |   |   |   |
|   | 36 |   |   |   |
| 13 | 37 | AD-960436.1 |   |   |
|   | 38 |   |   |   |
|   | 39 |   |   |   |
| 14 | 40 | AD-960443.1 |   |   |
|   | 41 |   |   |   |
|   | 42 |   |   |   |
| 15 | 43 | AD-960063.1 |   |   |
|   | 44 |   |   |   |
|   | 45 |   |   |   |
| 16 | 46 | AD-960031.1 |   |   |
|   | 47 |   |   |   |
|   | 48 |   |   |   |
| 17 | 49 | AD-959910.1 |   |   |
|   | 50 |   |   |   |
|   | 51 |   |   |   |
| 18 | 52 | AD-960096.1 |   |   |
|   | 53 |   |   |   |
|   | 54 |   |   |   |
| 19 | 55 | AD-959918.1 |   |   |
|   | 56 |   |   |   |
|   | 57 |   |   |   |
| 20 | 58 | AD-80794.7 |   |   |
|   | 59 |   |   |   |
|   | 60 |   |   |   |

TABLE 9

Duplexes of Interest

| Duplex ID | Range in NM-000040.3 |
|---|---|
| AD-959917.1 | 243-265 |
| AD-960064.1 | 433-455 |
| AD-960031.1 | 431-453 |
| AD-960063.1 | 431-453 |
| AD-960293.1 | 243-265 |
| AD-960288.1 | 238-260 |
| AD-960445.1 | 435-457 |
| AD-960292.1 | 242-264 |
| AD-960475.1 | 504-526 |
| AD-960442.1 | 432-454 |
| AD-960470.1 | 499-521 |
| AD-960436.1 | 426-448 |
| AD-960446.1 | 436-458 |
| AD-960474.1 | 503-525 |
| AD-960294.1 | 244-266 |
| AD-960443.1 | 433-455 |
| AD-80794.7 | 430-450 |
| AD-959910.1 | 235-257 |

TABLE 10

| | D 14 | | | |
|---|---|---|---|---|
| | Liver RTqPCR | | | |
| | % Message | | ELISA | |
| Duplex | Remaining | SD | Avg | SEM |
| PBS | 100.56 | 10.81 | 173.05 | 34.36 |
| Naïve | 105.57 | 1.84 | 125.40 | 46.86 |
| AD-959917.1 | 38.42 | 16.51 | 63.57 | 13.65 |
| AD-960064.1 | 16.01 | 2.36 | 36.97 | 15.66 |
| AD-960293.1 | 60.82 | 17.10 | 119.00 | 12.04 |
| AD-960288.1 | 75.24 | 14.48 | 99.64 | 12.46 |
| AD-960445.1 | 19.60 | 7.46 | 61.84 | 1.26 |
| AD-960292.1 | 91.68 | 22.51 | 78.59 | 3.24 |
| AD-960475.1 | 61.18 | 20.12 | 73.65 | 14.56 |
| AD-960442.1 | 55.63 | 17.52 | 91.45 | 8.10 |
| AD-960470.1 | 31.48 | 9.94 | 87.10 | 13.53 |
| AD-960446.1 | 34.44 | 5.34 | 62.84 | 11.40 |

TABLE 10-continued

| | D 14 | | | |
|---|---|---|---|---|
| | Liver RTqPCR | | ELISA | |
| Duplex | % Message Remaining | SD | Avg | SEM |
| AD-960436.1 | 35.50 | 9.98 | 68.61 | 17.47 |
| AD-960443.1 | 60.00 | 3.61 | 88.72 | 8.31 |
| AD-960063.1 | 14.64 | 7.30 | 42.19 | 2.84 |
| AD-960031.1 | 11.45 | 5.18 | 20.57 | 5.87 |
| AD-959910.1 | 67.13 | 13.87 | 59.45 | 0.75 |
| AD-960096.1 | 22.96 | 8.58 | 13.15 | 3.40 |
| AD-959918.1 | 76.69 | 7.97 | 51.37 | 3.33 |
| AD-80794.7 | 23.00 | 15.59 | 17.38 | 3.01 |

Additional duplexes of interest, identified from the above in vitro studies, were also evaluated in vivo. In particular, at pre-dose day −14 wild-type mice (C57BL/6) were transduced by retrorbital administration of $2 \times 10^{10}$ viral particles of an adeno-associated virus 8 (AAV8) vector encoding human APOC3. In particular, mice were administered an AAV8 encoding the human APOC3 mRNA, referred to as AAV8-TBG-PI-APOC3.

At day 0, groups of three mice were subcutaneously administered a single 3 mg/kg dose of the agents of interest or PBS control. Table 11 provides the treatment groups and Table 12 provides the modified nucleotide sequences of the sense and antisense strands of the duplexes of interest. At day 7 or day 14 post-dose animals were sacrificed, liver samples were collected and snap-frozen in liquid nitrogen. Liver mRNA was extracted and analyzed by the RT-QPCR method.

Figure 2:
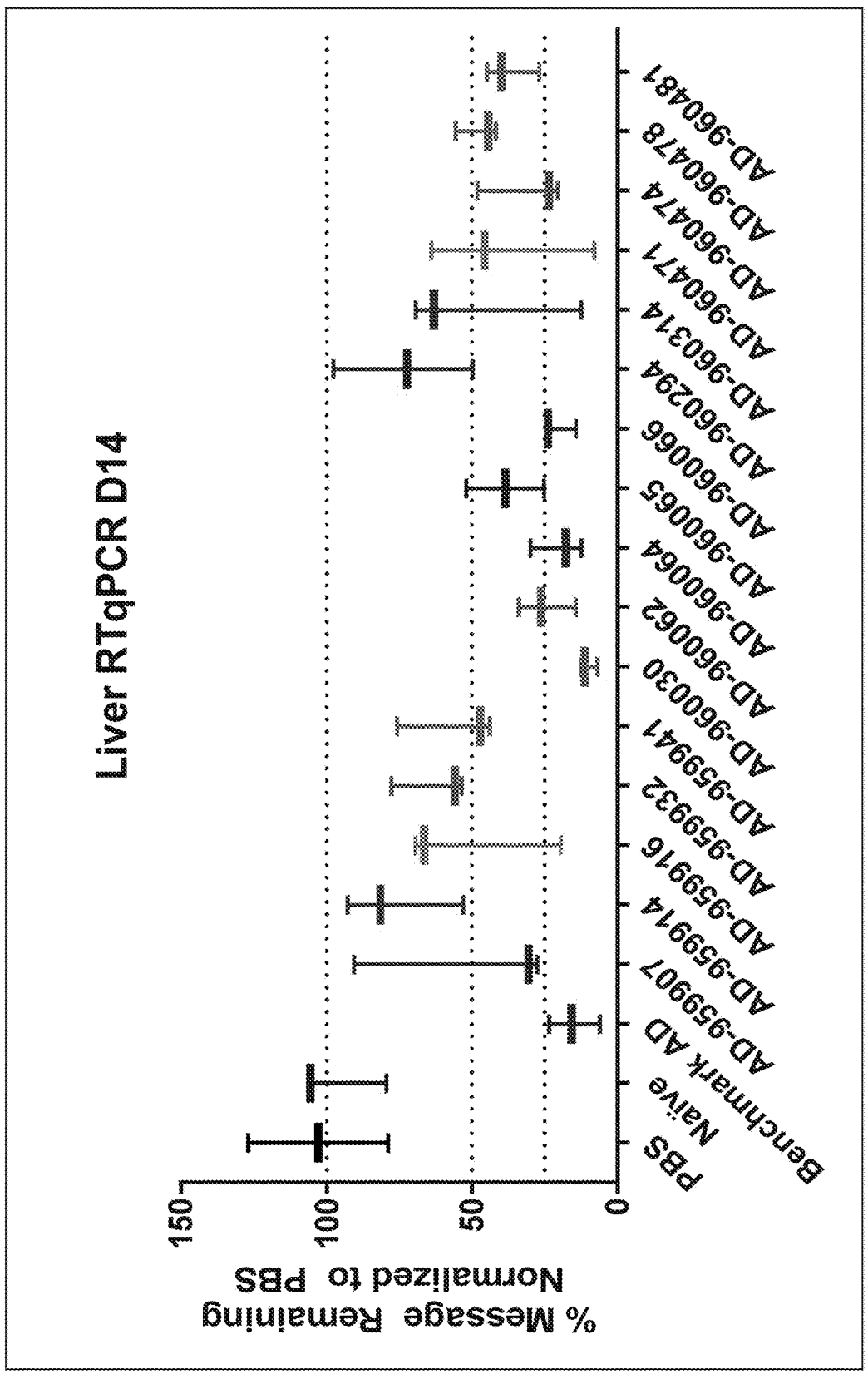
FIG. 2 is a graph showing human APOC3 mRNA levels in mice (n=3 per group) subcutaneously administered a single 3 mg/kg dose of the indicated dsRNA duplexes, on day14 post-dose. Human APOC3 mRNA levels are shown relative to control levels detected with PBS treatment.

Human APOC3 mRNA levels were compared to a housekeeping gene, GAPDH. The values were then normalized to the average of PBS vehicle control group. The data were expressed as percent of baseline value, and presented as mean plus standard deviation. The results, listed in Table 13 and shown in FIG. 2, demonstrate that the exemplary duplex agents tested effectively reduce the level of the human APOC3 messenger RNA in vivo.

TABLE 11

Treatment Groups

| Group # | Animal # | Treatment | Dose | Timepoint |
|---|---|---|---|---|
| 1 | 1 | PBS | n/a | D 0, D 7, D 14 |
| | 2 | | | |
| | 3 | | | |
| 2 | 4 | Naïve | n/a | |
| | 5 | | | |
| | 6 | | | |
| 3 | 7 | AD-80794 | 3 mpk | |
| | 8 | | | |
| | 9 | | | |
| 4 | 10 | AD-959907 | | |
| | 11 | | | |
| | 12 | | | |
| 5 | 13 | AD-959914 | | |
| | 14 | | | |
| | 15 | | | |
| 6 | 16 | AD-959916 | | |
| | 17 | | | |
| | 18 | | | |
| 7 | 19 | AD-959932 | | |
| | 20 | | | |
| | 21 | | | |
| 8 | 22 | AD-959941 | | |
| | 23 | | | |
| | 24 | | | |
| 9 | 25 | AD-960030 | | |
| | 26 | | | |
| | 27 | | | |
| 10 | 28 | AD-960062 | | |
| | 29 | | | |
| | 30 | | | |
| 11 | 31 | AD-960064 | | |
| | 32 | | | |
| | 33 | | | |
| 12 | 34 | AD-960065 | | |
| | 35 | | | |
| | 36 | | | |
| 13 | 37 | AD-960066 | | |
| | 38 | | | |
| | 39 | | | |
| 14 | 40 | AD-960294 | | |
| | 41 | | | |
| | 42 | | | |
| 15 | 43 | AD-960314 | | |
| | 44 | | | |
| | 45 | | | |
| 16 | 46 | AD-960471 | | |
| | 47 | | | |
| | 48 | | | |
| 17 | 49 | AD-960474 | | |
| | 50 | | | |
| | 51 | | | |
| 18 | 52 | AD-960478 | | |
| | 53 | | | |
| | 54 | | | |
| 19 | 55 | AD-960481 | | |
| | 56 | | | |
| | 57 | | | |

TABLE 12

Additional Duplexes of Interest

| Duplex ID | Range in NM-000040.3 |
|---|---|
| AD-80794.8 | 430-450 |
| AD-959907.2 | 232-254 |
| AD-959914.2 | 239-261 |
| AD-959916.2 | 242-264 |
| AD-959932.2 | 258-280 |
| AD-960314.2 | 264-286 |
| AD-959941.2 | 268-290 |
| AD-960030.2 | 429-451 |
| AD-960062.2 | 430-452 |
| AD-960064.2 | 433-455 |
| AD-960065.2 | 434-456 |
| AD-960066.2 | 435-457 |
| AD-960294.2 | 244-266 |
| AD-960471.2 | 500-522 |
| AD-960474.2 | 503-525 |
| AD-960478.2 | 507-529 |
| AD-960481.2 | 510-532 |

TABLE 13

| Duplex | % Message Remaining | SD |
|---|---|---|
| PBS | 102.94 | 34.16 |
| Naïve | 97.12 | 15.32 |
| AD-80794 | 15.17 | 8.74 |

TABLE 13-continued

| Duplex | % Message Remaining | SD |
|---|---|---|
| AD-959907 | 49.60 | 35.60 |
| AD-959914 | 75.84 | 20.55 |
| AD-959916 | 51.81 | 27.99 |
| AD-959932 | 62.36 | 13.32 |
| AD-959941 | 55.60 | 17.44 |
| AD-960030 | 10.26 | 2.93 |
| AD-960062 | 24.91 | 9.81 |
| AD-960064 | 20.04 | 8.94 |
| AD-960065 | 38.62 | 18.89 |
| AD-960066 | 20.93 | 5.78 |
| AD-960294 | 73.30 | 24.03 |
| AD-960314 | 48.32 | 31.10 |
| AD-960471 | 39.24 | 28.51 |
| AD-960474 | 30.81 | 15.15 |
| AD-960478 | 47.27 | 7.36 |
| AD-960481 | 37.22 | 9.27 |

Example 4. Structure-Activity Relationship Analyses

Based on the in vitro analyses in Example 2 and the in vivo analyses in Example 4, structure-active relationship (SAR) analyses were performed. In particular, additional duplexes were designed, synthesized, and assayed in vitro and in vivo. The additional agents were designed to target within nucleotides 429-455 or nucleotides 504-532 of NM_000040.3.

siRNAs were synthesized and annealed using routine methods known in the art and described above.

Detailed lists of the unmodified APOC3 sense and antisense strand nucleotide sequences are shown in Table 14. Detailed lists of the modified apolipoprotein C3 sense and antisense strand nucleotide sequences are shown in Table 15.

For free uptake, experiments were performed by adding 2.5 µl of siRNA duplexes in PBS per well into a 96 well plate. Complete growth media (47.5 µl) containing about 1.5×10$^4$ Hep3B cells was then added to the siRNA. Cells were incubated for 48 hours prior to RNA purification and RT-qPCR, as described above. Single dose experiments were performed at 500 nM, 100 nM, 10 nM, and 1 nM final duplex concentration.

For transfections, Hep3b cells (ATCC, Manassas, Va.) were grown to near confluence at 37° C. in an atmosphere of 5% $CO_2$ in Eagle's Minimum Essential Medium (Gibco) supplemented with 10% FBS (ATCC) before being released from the plate by trypsinization. Transfection was carried out by adding 7.5 µl of Opti-MEM plus 0.1 µl of Lipofectamine RNAiMax per well (Invitrogen, Carlsbad Calif. cat #13778-150) to 2.5 µl of each siRNA duplex to an individual well in a 384-well plate. The mixture was then incubated at room temperature for 15 minutes. Forty µl of complete growth media without antibiotic containing ~1.5× 10$^4$ Hep3B cells were then added to the siRNA mixture. Cells were incubated for 24 hours prior to RNA purification. Single dose experiments were performed at 50, nM, 10 nM, 1 nM, and 0.1 nM final duplex concentration.

Total RNA isolation was performed using DYNABEADS. Briefly, cells were lysed in 10 µl of Lysis/Binding Buffer containing 3 µL of beads per well and mixed for 10 minutes on an electrostatic shaker. The washing steps were automated on a Biotek EL406, using a magnetic plate support. Beads were washed (in 3 µL) once in Buffer A, once in Buffer B, and twice in Buffer E, with aspiration steps in between. Following a final aspiration, complete 12 µL RT mixture was added to each well, as described below.

For cDNA synthesis, a master mix of 1.5 µl 10× Buffer, 0.6 µl 10× dNTPs, 1.5 µl Random primers, 0.75 µl Reverse Transcriptase, 0.75 µl RNase inhibitor and 9.9 µl of $H_2O$ per reaction were added per well. Plates were sealed, agitated for 10 minutes on an electrostatic shaker, and then incubated at 37 degrees C. for 2 hours. Following this, the plates were agitated at 80 degrees C. for 8 minutes.

RT-qPCR was performed as described above and relative fold change was calculated as described above.

The results of the free uptake experiments of the dsRNA agents listed in Tables 14 and 15 are shown in Table 16 and the results of the transfection assays of the dsRNA agents listed in Tables 14 and 15 in Hep3B cells are shown in Table 17.

TABLE 14

Unmodified Sense and Antisense Strand Sequences of Apolipoprotein C3 dsRNA Agents

| Duplex Name | Sense Sequence 5' to 3' | SEQ ID NO: | Range in NM_000040.3 | Antisense Sequence 5' to 3' | SEQ ID NO: | Range in NM_000040.3 |
|---|---|---|---|---|---|---|
| AD-80794.10 | CUUAAAAGGGACAGUAUUCUA | 13 | 434-452 | UAGAAUACUGUCCCUUUUAAGCA | 58 | 432-452 |
| AD-1143240.1 | CUUAAAAGGGACAGUAUUCUA | 13 | 434-452 | UAGAAUACUGUCCCUUUUAAGCA | 58 | 432-452 |
| AD-1143241.1 | CUUAAAAGGGACAGUAUUCUA | 13 | 434-452 | UAGAAUACUGUCCCUUUUAAGCA | 58 | 432-452 |
| AD-1143242.1 | CUUAAAAGGGACAGUAUUCUA | 13 | 434-452 | UAGAAUACUGUCCCUUUUAAGCC | 14 | 432-452 |
| AD-1143243.1 | CUUAAAAGGGACAGUAUUCUA | 13 | 434-452 | UAGAAUACUGUCCCUUUUAAGCC | 14 | 432-452 |
| AD-1143244.1 | UAAAAGGGACAGUAUUCUA | 299 | 434-452 | UAGAAUACUGUCCCUUUUAAG | 300 | 432-452 |
| AD-1143245.1 | UAAAAGGGACAGUAUUCUA | 299 | 434-452 | UAGAAUACUGUCCCUUUUAAG | 300 | 432-452 |
| AD-1143246.1 | CUUAAAAGGGACAGUAUUCUA | 13 | 432-452 | UAGAAUACUGUCCCUUUUAAGCC | 14 | 430-452 |
| AD-1143247.1 | CUUAAAAGGGACAGUAUUCUA | 13 | 432-452 | UAGAAUACUGUCCCUUUUAAGCC | 14 | 430-452 |
| AD-1143248.1 | CUUAAAAGGGACAGUAUUCUA | 13 | 432-452 | UAGAAUACUGUCCCUUUUAAGCC | 14 | 430-452 |
| AD-1143249.1 | CUUAAAAGGGACAGUAUUCUA | 13 | 432-452 | UAGAAUACUGUCCCUUUUAAGCC | 14 | 430-452 |

TABLE 14-continued

Unmodified Sense and Antisense Strand Sequences of Apolipoprotein C3 dsRNA Agents

| Duplex Name | Sense Sequence 5' to 3' | SEQ ID NO: | Range in NM_000040.3 | Antisense Sequence 5' to 3' | SEQ ID NO: | Range in NM_000040.3 |
|---|---|---|---|---|---|---|
| AD-960030.3 | GCUUAAAAGGGACAGUAUUCU | 56 | 431-451 | AGAAUACUGUCCCUUUUAAGCAA | 57 | 429-451 |
| AD-1143250.1 | GCUUAAAAGGGACAGUAUUCU | 56 | 431-451 | AGAAUACUGUCCCUUUUAAGCAA | 57 | 429-451 |
| AD-1143251.1 | GCUUAAAAGGGACAGUAUUCU | 56 | 431-451 | AGAAUACUGUCCCUUUUAAGCAA | 57 | 429-451 |
| AD-1143252.1 | GCUUAAAAGGGACAGUAUUCU | 56 | 431-451 | AGAATACUGUCCCUUUUAAGCAA | 301 | 429-451 |
| AD-1143253.1 | GCUUAAAAGGGACAGUAUUCU | 56 | 431-451 | AGAAUACUGUCCCUUUUAAGCGC | 302 | 429-451 |
| AD-1143254.1 | GCUUAAAAGGGACAGUAUUCU | 56 | 431-451 | AGAATACUGUCCCUUUUAAGCGC | 303 | 429-451 |
| AD-1143255.1 | UUAAAAGGGACAGUAUUCU | 304 | 433-451 | AGAAUACUGUCCCUUUUAAGC | 305 | 431-451 |
| AD-1143256.1 | UUAAAAGGGACAGUAUUCU | 304 | 433-451 | AGAATACUGUCCCUUUUAAGC | 306 | 431-451 |
| AD-1143257.1 | GCUUAAAAGGGACAGUAUUCU | 56 | 431-451 | AGAAUACUGUCCCUUUUAAGCGC | 302 | 429-451 |
| AD-1143258.1 | GCUUAAAAGGGACAGUAUUCU | 56 | 431-451 | AGAATACUGUCCCUUUUAAGCGC | 303 | 429-451 |
| AD-1143259.1 | GCUUAAAAGGGACAGUAUUCU | 56 | 431-451 | AGAAUACUGUCCCUUUUAAGCGC | 302 | 429-451 |
| AD-1143260.1 | GCUUAAAAGGGACAGUAUUCU | 56 | 431-451 | AGAATACUGUCCCUUUUAAGCGC | 303 | 429-451 |
| AD-960031.3 | UAAAAGGGACAGUAUUCUCAU | 36 | 434-454 | AUGAGAAUACUGUCCCUUUUAAG | 37 | 432-454 |
| AD-1143261.1 | UAAAAGGGACAGUAUUUCAU | 307 | 434-454 | AUGAAAAUACUGUCCCUUUUAAG | 308 | 432-454 |
| AD-1143262.1 | UAAAAGGGACAGUAUUCUCAU | 36 | 434-454 | AUGAGAAUACUGUCCCUUUUAAG | 37 | 432-454 |
| AD-1143263.1 | UAAAAGGGACAGUAUUCUCAU | 36 | 434-454 | AUGAGAAUACUGUCCCUUUUAAG | 37 | 432-454 |
| AD-1143264.1 | UAAAAGGGACAGUAUUCUCAU | 36 | 434-454 | AUGAGAAUACUGUCCCUUUUACC | 309 | 432-454 |
| AD-1143265.1 | UAAAAGGGACAGUAUUCUCAU | 36 | 434-454 | AUGAGAAUACUGUCCCUUUUACC | 309 | 432-454 |
| AD-1143266.1 | AAAGGGACAGUAUUCUCAU | 310 | 436-454 | AUGAGAAUACUGUCCCUUUUG | 311 | 434-454 |
| AD-1143267.1 | AAAGGGACAGUAUUCUCAU | 310 | 436-454 | AUGAGAAUACUGUCCCUUUUG | 311 | 434-454 |
| AD-1143268.1 | UAAAAGGGACAGUAUUCUCAU | 36 | 434-454 | AUGAGAAUACUGUCCCUUUUACC | 309 | 432-454 |
| AD-1143269.1 | AAAAGGGACAGUAUUCUCAU | 312 | 434-454 | AUGAGAAUACUGUCCCUUUUGCC | 313 | 432-454 |
| AD-1143270.1 | UAAAAGGGACAGUAUUCUCAU | 36 | 434-454 | AUGAGAAUACUGUCCCUUUUACC | 309 | 432-454 |
| AD-1143271.1 | UAAAAGGGACAGTAUUCUCAU | 314 | 434-454 | AUGAGAAUACUGUCCCUUUUACC | 309 | 432-454 |
| AD-1143272.1 | UAAAAGGGACAGTAUUCUCAU | 314 | 434-454 | AUGAGAAUACUGUCCCUUUUACC | 309 | 432-454 |
| AD-1143273.1 | UAAAAGGGACAGUAUUCUCAU | 36 | 434-454 | AUGAGAAUACUGUCCCUUUUAAG | 37 | 432-454 |
| AD-1143274.1 | UAAAAGGGACAGTAUUCUCAU | 314 | 434-454 | AUGAGAAUACUGUCCCUUUUAAG | 37 | 432-454 |
| AD-960062.3 | CUUAAAAGGGACAGUAUUCUU | 48 | 432-452 | AAGAAUACUGUCCCUUUUAAGCA | 49 | 430-452 |
| AD-1143275.1 | CUUAAAAGGGACAGUAUUCUU | 48 | 432-452 | AAGAAUACUGUCCCUUUUAAGCA | 49 | 430-452 |
| AD-1143276.1 | CUUAAAAGGGACAGUAUUCUU | 48 | 432-452 | AAGAAUACUGUCCCUUUUAAGCA | 49 | 430-452 |
| AD-1143277.1 | CUUAAAAGGGACAGUAUUCUU | 48 | 432-452 | AAGAAUACUGUCCCUUUUAAGCC | 315 | 430-452 |
| AD-1143278.1 | CUUAAAAGGGACAGUAUUCUU | 48 | 432-452 | AAGAAUACUGUCCCUUUUAAGCC | 315 | 430-452 |
| AD-1143279.1 | UAAAAGGGACAGUAUUCUU | 316 | 434-452 | AAGAAUACUGUCCCUUUUAAG | 317 | 432-452 |
| AD-1143280.1 | UAAAAGGGACAGUAUUCUU | 316 | 434-452 | AAGAAUACUGUCCCUUUUAAG | 317 | 432-452 |
| AD-1143281.1 | CUUAAAAGGGACAGUAUUCUU | 48 | 432-452 | AAGAAUACUGUCCCUUUUAAGCC | 315 | 430-452 |
| AD-1143282.1 | CUUAAAAGGGACAGUAUUCUU | 48 | 432-452 | AAGAAUACUGUCCCUUUUAAGCC | 315 | 430-452 |

TABLE 14-continued

Unmodified Sense and Antisense Strand Sequences of Apolipoprotein C3 dsRNA Agents

| Duplex Name | Sense Sequence 5' to 3' | SEQ ID NO: | Range in NM_000040.3 | Antisense Sequence 5' to 3' | SEQ ID NO: | Range in NM_000040.3 |
|---|---|---|---|---|---|---|
| AD-1143283.1 | CUUAAAAGGGACAGUAUUCUU | 48 | 432-452 | AAGAAUACUGUCCCUUUUAAGCC | 315 | 430-452 |
| AD-1143284.1 | CUUAAAAGGGACAGUAUUCUU | 48 | 432-452 | AAGAAUACUGUCCCUUUUAAGCC | 315 | 430-452 |
| AD-960064.3 | AAAAGGGACAGUAUUCUCAGU | 30 | 435-455 | ACUGAGAAUACUGUCCCUUUUAA | 31 | 433-455 |
| AD-1143285.1 | AAAAGGGACAGUAUUCUCAGU | 30 | 435-455 | ACUGAGAAUACUGUCCCUUUUAA | 31 | 433-455 |
| AD-1143286.1 | AAAAGGGACAGUAUUCUCAGU | 30 | 435-455 | ACUGAGAAUACUGUCCCUUUUAA | 31 | 433-455 |
| AD-1143287.1 | AAAAGGGACAGUAUUCUCAGU | 30 | 435-455 | ACUGAGAAUACUGUCCCUUUUGC | 318 | 433-455 |
| AD-1143288.1 | AAAAGGGACAGUAUUCUCAGU | 30 | 435-455 | ACUGAGAAUACUGUCCCUUUUCC | 319 | 433-455 |
| AD-1143289.1 | AAGGGACAGUAUUCUCAGU | 320 | 437-455 | ACUGAGAAUACUGUCCCUUUU | 321 | 435-455 |
| AD-1143290.1 | AAAAGGGACAGUAUUCUCAGU | 30 | 435-455 | ACUGAGAAUACUGUCCCUUUUGC | 318 | 433-455 |
| AD-1143291.1 | AAAAGGGACAGUAUUCUCAGU | 30 | 435-455 | ACUGAGAAUACUGUCCCUUUUCC | 319 | 433-455 |
| AD-1143292.1 | AAAAGGGACAGUAUUUUCAGU | 322 | 435-455 | ACUGAAAAUACUGUCCCUUUUGC | 323 | 433-455 |
| AD-1143293.1 | AAAAGGGACAGUAUUCUCAGU | 30 | 435-455 | ACUGAGAAUACUGUCCCUUUUGC | 318 | 433-455 |
| AD-1143294.1 | AAAAGGGACAGUAUUCUCAGU | 30 | 435-455 | ACUGAGAAUACUGUCCCUUUUCC | 319 | 433-455 |
| AD-1143295.1 | AAAAGGGACAGUAUUCUCAGU | 30 | 435-455 | ACUGAGAAUACUGUCCCUUUUGC | 318 | 433-455 |
| AD-1143296.1 | AAAAGGGACAGUAUUCUCAGU | 30 | 435-455 | ACUGAGAAUACUGUCCCUUUUCC | 319 | 433-455 |
| AD-960096.3 | CCAAUAAAGCUGGACAAGAAU | 28 | 506-526 | AUUCUUGUCCAGCUUUAUUGGGA | 29 | 504-526 |
| AD-1143297.1 | CCAAUAAAGCUGGAUAAGAAU | 324 | 506-526 | AUUCUUAUCCAGCUUUAUUGGGA | 325 | 504-526 |
| AD-1143298.1 | CCAAUAAAGCUGGACAAGAAU | 28 | 506-526 | AUUCTUGUCCAGCUUUAUUGGGA | 326 | 504-526 |
| AD-1143299.1 | CCAAUAAAGCUGGACAAGAAU | 28 | 506-526 | AUUCTUGUCCAGCUUUAUUGGGC | 327 | 504-526 |
| AD-1143300.1 | AAUAAAGCUGGACAAGAAU | 328 | 508-526 | AUUCTUGUCCAGCUUUAUUGG | 329 | 506-526 |
| AD-1143301.1 | AAUAAAGCUGGACAAGAAU | 328 | 508-526 | AUUCTUGUCCAGCUUUAUUCC | 330 | 506-526 |
| AD-1143302.1 | CCAAUAAAGCUGGACAAGAAU | 28 | 506-526 | AUUCTUGUCCAGCUUUAUUGGGC | 327 | 504-526 |
| AD-1143303.1 | CCAAUAAAGCUGGACAAGAAU | 28 | 506-526 | AUUCTUGUCCAGCUUUAUUGG | 329 | 506-526 |
| AD-1143304.1 | CCAAUAAAGCUGGACAAGAAU | 28 | 506-526 | AUUCTUGUCCAGCUUUAUUGGGC | 327 | 504-526 |
| AD-1143305.1 | CCAAUAAAGCUGGACAAGAAU | 28 | 506-526 | AUUCTUGUCCAGCUUUAUUGG | 329 | 506-526 |
| AD-1143306.1 | CCAAUAAAGCUGGACAAGAAU | 28 | 506-526 | AUUCUUGUCCAGCUUUAUUGGGA | 29 | 504-526 |
| AD-1143307.1 | CCAAUAAAGCUGGACAAGAAU | 28 | 506-526 | AUUCUUGUCCAGCUUUAUUGGGA | 29 | 504-526 |
| AD-960481.3 | AAGCUGGACAAGAAGCUGCUU | 99 | 512-532 | AAGCAGCUUCUUGUCCAGCUUUA | 100 | 510-532 |
| AD-1143308.1 | AAGCUGGACAAGAAGCUGCUU | 99 | 512-532 | AAGCAGCUUCUUGUCCAGCUUUA | 100 | 510-532 |
| AD-1143309.1 | AAGCUGGACAAGAAGCUGCUU | 99 | 512-532 | AAGCAGCUUCUUGUCCAGCUUUA | 100 | 510-532 |
| AD-1143310.1 | AAGCUGGACAAGAAGCUGCUU | 99 | 512-532 | AAGCAGCUUCUUGUCCAGCUUUA | 100 | 510-532 |
| AD-1143311.1 | AAGCUGGACAAGAAGCUGCUU | 99 | 512-532 | AAGCAGCUUCUUGUCCAGCUUUC | 331 | 510-532 |
| AD-1143312.1 | AAGCUGGACAAGAAGCUGCUU | 99 | 512-532 | AAGCAGCUUCUUGUCCAGCUUUC | 331 | 510-532 |
| AD-1143313.1 | AAGCUGGACAAGAAGCUGCUU | 99 | 512-532 | AAGCAGCUUCUUGUCCAGCUUCC | 332 | 510-532 |
| AD-1143314.1 | AAGCUGGACAAGAAGCUGCUU | 99 | 512-532 | AAGCAGCUUCUUGUCCAGCUUCC | 332 | 510-532 |
| AD-1143315.1 | GCUGGACAAGAAGCUGCUU | 333 | 514-532 | AAGCAGCUUCUUGUCCAGCUU | 334 | 512-532 |
| AD-1143316.1 | GCUGGACAAGAAGCUGCUU | 333 | 514-532 | AAGCAGCUUCUUGUCCAGCUU | 334 | 512-532 |

TABLE 14-continued

Unmodified Sense and Antisense Strand Sequences of Apolipoprotein C3 dsRNA Agents

| Duplex Name | Sense Sequence 5' to 3' | SEQ ID NO: | Range in NM_000040.3 | Antisense Sequence 5' to 3' | SEQ ID NO: | Range in NM_000040.3 |
|---|---|---|---|---|---|---|
| AD-1143317.1 | AAGCUGGACAAGAAGCUGCUU | 99 | 512-532 | AAGCAGCUUCUUGUCCAGCUUCC | 332 | 510-532 |
| AD-1143318.1 | AAGCUGGACAAGAAGCUGCUU | 99 | 512-532 | AAGCAGCUUCUUGUCCAGCUUCC | 332 | 510-532 |
| AD-1143319.1 | AAGCUGGACAAGAAGCUGCUU | 99 | 512-532 | AAGCAGCUUCUUGUCCAGCUUCC | 332 | 510-532 |
| AD-1143320.1 | AAGCUGGACAAGAAGCUGCUU | 99 | 512-532 | AAGCAGCUUCUUGUCCAGCUUCC | 332 | 510-532 |
| AD-1143321.1 | AAGCUGGACAAGAAGCUACUU | 335 | 512-532 | AAGUAGCUUCUUGUCCAGCUUCC | 336 | 510-532 |
| AD-1143322.1 | AAGCUGGACAAGAAGUUGCUU | 337 | 512-532 | AAGCAACUUCUUGUCCAGCUUCC | 338 | 510-532 |
| AD-1183925 | AAGCUGGACAAGAAGCUGCUU | 99 | 512-532 | AAGCAGCUUCUUGUCCAGCUUUC | 331 | 510-532 |
| AD-1183926 | GCUGGACAAGAAGCUGCUU | 333 | 514-532 | AAGCAGCUUCUUGUCCAGCUU | 334 | 512-532 |
| AD-1019001 | ACGGGACAGUAUUCUCAGUA | 339 | 437-456 | UCACUGAGAAUACUGUCCCGU | 340 | 437-457 |

TABLE 15

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-80794.10 | csusuaaaAfgGfGfAfcaguauucuaL96 | 17 | usAfsgaaUfacCfUfgucCfuFfuuaagscsa | 392 | CUUAAAAGGGACAGUAUUCUC | 828 |
| AD-1143240.1 | csusuaaaAfgGfGfAfcaguauucuaL96 | 17 | usAfsgaaUfacuguccCfuUfuuaagscsa | 829 | CUUAAAAGGGACAGUAUUCUC | 828 |
| AD-1143241.1 | csusuaaaAfgGfGfAfcaguauucuaL96 | 17 | usdAsgaaUfacuguccCfuUfuuaagscsa | 830 | CUUAAAAGGGACAGUAUUCUC | 828 |
| AD-1143242.1 | csusuaaaAfgGfGfAfcaguauucuaL96 | 17 | usAfsgaaUfacuguccCfuUfuuaagscsc | 831 | CUUAAAAGGGACAGUAUUCUC | 828 |
| AD-1143243.1 | csusuaaaAfgGfGfAfcaguauucuaL96 | 17 | usdAsgadAudAcuguccCfuUfuuasasg | 832 | CUUAAAAGGGACAGUAUUCUC | 828 |
| AD-1143244.1 | usasasaAfgGfGfAfc aguauucuaL96 | 832 | usAfsgaaUfacuguccCfuUfuuasasg | 833 | CUUAAAAGGGACAGUAUUCUC | 828 |
| AD-1143245.1 | usasasaAfgGfGfAfc aguauucuaL96 | 832 | usdAsgadAudAcuguccCfuUfuuasasg | 834 | CUUAAAAGGGACAGUAUUCUC | 828 |
| AD-1143246.1 | csusuaaaagdGgdAcaguauucuaL96 | 835 | usAfsgaaUfacuguccCfuUfuuaagscsc | 831 | UGCUUAAAGGGACAGUAUUCUC | 379 |
| AD-1143247.1 | csusuaaaagdGgdAcaguauucuaL96 | 835 | usdAsgadAudAcuguccCfuUfuuaagscsc | 16 | UGCUUAAAGGGACAGUAUUCUC | 379 |
| AD-1143248.1 | csusuaaaagdGgdAcfaguauucuaL96 | 836 | usAfsgaaUfacuguccCfuUfuuaagscsc | 831 | UGCUUAAAGGGACAGUAUUCUC | 379 |
| AD-1143249.1 | csusuaaaagdGgdAcfaguauucuaL96 | 836 | usdAsgadAudAcuguccCfuUfuuaagscsc | 16 | UGCUUAAAGGGACAGUAUUCUC | 379 |
| AD-960030.3 | gscsuuaaaAfaGfGfGfacaguauucuL96 | 389 | asGfsaauAfcUfGfuccCfUfGfuuccCfUfuaagcsasa | 390 | UUGCUUAAAGGGACAGUAUUCU | 391 |
| AD-1143250.1 | gscsuuaaaAfaGfGfGfacaguauucuL96 | 389 | asGfsaauAfcuguccCfUfUfuaagcsasa | 837 | UUGCUUAAAGGGACAGUAUUCU | 391 |
| AD-1143251.1 | gscsuuaaaAfaGfGfGfacaguauucuL96 | 389 | asdGsaauAfcuguccUfuUfuaagcsasa | 838 | UUGCUUAAAGGGACAGUAUUCU | 391 |
| AD-1143252.1 | gscsuuaaaAfaGfGfGfacaguauucuL96 | 389 | asdGsaadTadCuguccUfuUfuaagcsasa | 839 | UUGCUUAAAGGGACAGUAUUCU | 391 |
| AD-1143253.1 | gscsuuaaaAfaGfGfGfacaguauucuL96 | 389 | asdGsaauAfcuguccUfuUfuaagcsgsc | 840 | UUGCUUAAAGGGACAGUAUUCU | 391 |
| AD-1143254.1 | gscsuuaaaAfaGfGfGfacaguauucuL96 | 389 | asdGsaadTadCuguccUfuUfuaagcsgsc | 841 | UUGCUUAAAGGGACAGUAUUCU | 391 |

TABLE 15-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1143255.1 | ususaaAfaGfGfGfacaguauucuL96 | 842 | asdGsaauAfcuguccUfuUfuaasgsc | 843 | GCUUAAAGGGACAGUAUUCU | 844 |
| AD-1143256.1 | ususaaAfaGfGfGfcacaguauucuL96 | 842 | asdGsaadTadCuguccUfuUfuaasgsc | 845 | GCUUAAAGGGACAGUAUUCU | 844 |
| AD-1143257.1 | gscsuuaaaaGdGgdGacaguauucuL96 | 846 | asdGsaauAfcuguccUfuUfuaagcsgsc | 840 | UUGCUUAAAGGGACAGUAUUCU | 391 |
| AD-1143258.1 | gscsuuaaaaGdGgdGacaguauucuL96 | 846 | asdGsaadTadCuguccUfuUfuaagcsgsc | 841 | UUGCUUAAAGGGACAGUAUUCU | 391 |
| AD-1143259.1 | gscsuuaaaaGdGgdGadCaguauucuL96 | 847 | asdGsaauAfcuguccUfuUfuaagcsgsc | 840 | UUGCUUAAAGGGACAGUAUUCU | 391 |
| AD-1143260.1 | gscsuuaaaaGdGgdGadCaguauucuL96 | 847 | asdGsaadTadCuguccUfuUfuaagcsgsc | 841 | UUGCUUAAAGGGACAGUAUUCU | 391 |
| AD-960031.3 | usasaaagGfgAfCfAfguauuucucaL96 | 359 | asUfsgagAfaUfAfcuguCfcCfuuuuasasg | 360 | CUUAAAAGGGACAGUAUUCUCAG | 361 |
| AD-1143261.1 | usasaaagGfgAfCfAfguauuucucaL96 | 359 | asUfsgaaAfaUfAfcuguCfcCfuuuuasasg | 849 | CUUAAAAGGGACAGUAUUCUCAG | 361 |
| AD-1143262.1 | usasaaagGfgAfCfAfguauuucucaL96 | 359 | asUfsgadGa(Agn)uacuguCfcCfuuuuasasg | 850 | CUUAAAAGGGACAGUAUUCUCAG | 361 |
| AD-1143263.1 | usasaaagGfgAfCfAfguauuucucaL96 | 359 | asUfsgadGa(A2p)uacuguCfcCfuuuuasasg | 851 | CUUAAAAGGGACAGUAUUCUCAG | 361 |
| AD-1143264.1 | usasaaagGfgAfCfAfguauuucucaL96 | 359 | asUfsgadGa(Agn)uacuguCfcCfuuuuascsc | 852 | CUUAAAAGGGACAGUAUUCUCAG | 361 |
| AD-1143265.1 | usasaaagGfgAfCfAfguauuucucaL96 | 359 | asUfsgadGa(A2p)uacuguCfcCfuuuuascsc | 853 | CUUAAAAGGGACAGUAUUCUCAG | 361 |
| AD-1143266.1 | asasagGfgAfCfAfguauuccucaL96 | 854 | asUfsgadGa(Agn)uacuguCfcCfuuuususg | 855 | UAAAAGGGACAGUAUUCUCAG | 856 |
| AD-1143267.1 | asasagGfgAfCfAfguauuccucaL96 | 854 | asUfsgadGa(A2p)uacuguCfcCfuuuususg | 857 | UAAAAGGACAGUAUUCUCAG | 856 |
| AD-1143268.1 | usasaaagggdAcdAguauuccucauL96 | 858 | asUfsgadGa(Agn)uacuguCfcCfuuuuugcsc | 852 | CUUAAAAGGGACAGUAUUCUCAG | 361 |
| AD-1143269.1 | asasaaagggdAcdAguauuccucauL96 | 859 | asUfsgadGa(Agn)uacuguCfcCfuuuugcsc | 860 | CUUAAAAGGACAGUAUUCUCAG | 361 |
| AD-1143270.1 | usasaaagggdAcdAguauuccucauL96 | 858 | asUfsgadGa(A2p)uacuguCfcCfuuuuascsc | 853 | CUUAAAAGGGACAGUAUUCUCAG | 361 |

TABLE 15-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1143271.1 | usasaaagggdAcdAgdTauucucauL96 | 861 | asUfsgadGa(Agn)uacuguCfccfuuuuascsc | 852 | CUUAAAAGGGACAGUAUUCUCAG | 361 |
| AD-1143272.1 | usasaaagggdAcdAgdTauucucauL96 | 861 | asUfsgadGa(A2p)uacuguCfccfuuuuascsc | 853 | CUUAAAAGGGACAGUAUUCUCAG | 361 |
| AD-1143273.1 | usasaaagggdAcdAguauucucauL96 | 858 | asUfsgadGaAuacuguCfcCfuuuuasasg | 862 | CUUAAAAGGGACAGUAUUCUCAG | 361 |
| AD-1143274.1 | usasaaagggdAcdAgdTauucucauL96 | 861 | asUfsgadGaAuacuguCfcCfuuuuasasg | 862 | CUUAAAAGGGACAGUAUUCUCAG | 361 |
| AD-960062.3 | csusuaaaAfgGfGfAfcaguauucuuL96 | 377 | asAfsgaaUfaCfUfguccCfuUfuuaagscsa | 378 | UGCUUAAAAGGGACAGUAUUCUC | 379 |
| AD-1143275.1 | csusuaaaAfgGfGfAfcaguauucuuL96 | 377 | asAfsgaaUfacuguccCfuUfuuaagscsa | 863 | UGCUUAAAAGGGACAGUAUUCUC | 379 |
| AD-1143276.1 | csusuaaaAfgGfGfAfcaguauucuuL96 | 377 | asdAsgaaUfacuguccCfuUfuuaagscsa | 864 | UGCUUAAAAGGGACAGUAUUCUC | 379 |
| AD-1143277.1 | csusuaaaAfgGfGfAfcaguauucuuL96 | 377 | asdAsgaaUfacuguccCfuUfuuaagscsc | 865 | UGCUUAAAAGGGACAGUAUUCUC | 379 |
| AD-1143278.1 | csusuaaaAfgGfGfAfcaguauucuuL96 | 377 | asdAsgadAudAcuguccCfuUfuuaagscsc | 866 | UGCUUAAAAGGGACAGUAUUCUC | 379 |
| AD-1143279.1 | usasaaaAfgGfGfAfcaguauucuuL96 | 867 | asdAsgaaUfacuguccCfuUfuuaasasg | 868 | CUUAAAAGGGACAGUAUUCUC | 828 |
| AD-1143280.1 | usasuaaaAfgGfGfAfcaguauucuuL96 | 867 | asdAsgadAudAcuguccCfuUfuuaagscsa | 869 | CUUAAAAGGGACAGUAUUCUC | 828 |
| AD-1143281.1 | csusuaaaagdGfAcaguauucuuL96 | 870 | asdAsgaaUfacuguccCfuUfuuaagscsc | 865 | UGCUUAAAAGGGACAGUAUUCUC | 379 |
| AD-1143282.1 | csusuaaaagdGgdAcaguauucuuL96 | 870 | asdAsgadAudAcuguccCfuUfuuaagscsc | 866 | UGCUUAAAAGGGACAGUAUUCUC | 379 |
| AD-1143283.1 | csusuaaaagdGgdAcdAguauucuuL96 | 871 | asdAsgaaUfacuguccCfuUfuuaagscsc | 865 | UGCUUAAAAGGGACAGUAUUCUC | 379 |
| AD-1143284.1 | csusuaaaagdGgdAcdAguauucuuL96 | 871 | asdAsgadAudAcuguccCfuUfuuaagscsc | 866 | UGCUUAAAAGGGACAGUAUUCUC | 379 |
| AD-960064.3 | asasaaggGfaCfAfGfuauucucaguL96 | 350 | asCfsugaGfaAfUfacugUfcCfcuuuusasa | 351 | UUAAAAGGGACAGUAUUCUCAGU | 352 |
| AD-1143285.1 | asasaaggGfaCfAfGfuauacucaguL96 | 350 | asCfsugaGfaauacugUfcCfcuuuusasa | 872 | UUAAAAGGGACAGUAUUCUCAGU | 352 |

TABLE 15-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1143286.1 | asasaaggGfaCfAfGfuauucucaguL96 | 350 | asCfsugdAgdAauacugUfcCfcuuuusasa | 873 | UUAAAAGGGACAGUAUUCUCAGU | 352 |
| AD-1143287.1 | asasaaggGfaCfAfGfuauucucaguL96 | 350 | asCfsugdAgdAauacugUfcCfcuuuusgsc | 874 | UUAAAAGGGACAGUAUUCUCAGU | 352 |
| AD-1143288.1 | asasaaggGfaCfAfGfuauucucaguL96 | 350 | asCfsugdAgdAauacugUfcCfcuuuuscsc | 875 | UUAAAAGGGACAGUAUUCUCAGU | 352 |
| AD-1143289.1 | asasggGfaCfAfGfuauucucaguL96 | 876 | asCfsugdAgdAauacugUfcCfcususu | 877 | AAAAGGGACAGUAUUCUCAGU | 878 |
| AD-1143290.1 | asasaagggaCfadGuauucucaguL96 | 879 | asCfsugdAgdAaauacugUfcCfcuuuusgc | 874 | UUAAAAGGGACAGUAUUCUCAGU | 352 |
| AD-1143291.1 | asasaagggaCfadGuauuuucaguL96 | 879 | asCfsugdAgdAaauacugUfcCfcuuuuscsc | 875 | UUAAAAGGGACAGUAUUCUCAGU | 352 |
| AD-1143292.1 | asasaagggadCadGuauucucaguL96 | 880 | asCfsugdAgdAaauacugUfcCfcuuuusgc | 881 | UUAAAAGGGACAGUAUUCUCAGU | 352 |
| AD-1143293.1 | asasaagggadCadGuauucucaguL96 | 882 | asCfsugdAgdAaauacugUfcCfcuuuuscsc | 874 | UUAAAAGGGACAGUAUUCUCAGU | 352 |
| AD-1143294.1 | asasaagggadCadGUfauucucaguL96 | 882 | asCfsugdAgdAaauacugUfcCfcuuuusgc | 875 | UUAAAAGGGACAGUAUUCUCAGU | 352 |
| AD-1143295.1 | asasaagggadCadGUfauucucaguL96 | 883 | asCfsugdAgdAaauacugUfcCfcuuuuscsc | 874 | UUAAAAGGGACAGUAUUCUCAGU | 352 |
| AD-1143296.1 | cscsaauaaAfaGfCfUfggacaagaauL96 | 883 | asUfsucuUfgUfCfcagcUfuUfauuggsgsa | 875 | UCCCAUAAAGCUGGACAAGAAG | 352 |
| AD-960096.3 | cscsaauaAfaGfCfUfggauaagaauL96 | 347 | asUfsucuUfauccagcUfuUfauuggsgsa | 348 | UCCCAUAAAGCUGGACAAGAAG | 349 |
| AD-1143297.1 | cscsaauaAfaGfCfUfggauaagaauL96 | 884 | asUfsucuUfauccagcUfuUfauuggsgsa | 885 | UCCCAUAAAGCUGGACAAGAAG | 349 |
| AD-1143298.1 | cscsaauaAfaGfCfUfggacaagaauL96 | 347 | asUfsucdTu(G2p)uccagcUfuUfauuggsgsa | 886 | UCCCAUAAAGCUGGACAAGAAG | 349 |
| AD-1143299.1 | cscsaauaAfaGfCfUfggacaagaauL96 | 347 | asUfsucdTu(G2p)uccagcUfuUfauuggsgsc | 887 | UCCCAUAAAGCUGGACAAGAAG | 349 |
| AD-1143300.1 | asasuaAfaGfCfUfggacaagaauL96 | 888 | asUfsucdTu(G2p)uccagcUfuUfauusgsg | 889 | CCAAUAAAGCUGGACAAGAAG | 890 |

TABLE 15-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1143301.1 | asasuaAfaGfCfUfggacaagaauL96 | 888 | asUfsucdTu(G2p)uccagcUfuUfauuscsc | 891 | CCAAUAAAGCUGGACAAGAAG | 890 |
| AD-1143302.1 | cscsaauaaagCfUfggacaagaauL96 | 892 | asUfsucdTu(G2p)uccagcUfuUfauuggsgsc | 887 | UCCCAUAAAGCUGGACAAGAAG | 349 |
| AD-1143303.1 | cscsaauaaagCfUfggacaagaauL96 | 892 | asUfsucdTu(G2p)uccagcUfuUfauusgsg | 889 | CCAAUAAAGCUGGACAAGAAG | 890 |
| AD-1143304.1 | cscsaauadAagCfUfggacaagaauL96 | 893 | asUfsucdTu(G2p)uccagcUfuUfauuggsgsc | 887 | UCCCAUAAAGCUGGACAAGAAG | 349 |
| AD-1143305.1 | cscsaauadAagCfUfggacaagaauL96 | 893 | asUfsucdTu(G2p)uccagcUfuUfauusgg | 889 | CCAAUAAAGCUGGACAAGAAG | 890 |
| AD-1143306.1 | cscsaauauaaagCfUfggacaagaauL96 | 892 | asUfsucuUfguccagcUfuUfauuggsgsa | 894 | UCCCAUAAAGCUGGACAAGAAG | 349 |
| AD-1143307.1 | cscsaauadAagCfUfggacaagaauL96 | 893 | asUfsucuUfguccagcUfuUfauuggsgsa | 894 | UCCCAUAAAGCUGGACAAGAAG | 349 |
| AD-960481.3 | asasgcugGfaCfAfAfgaagcugcuuL96 | 454 | asAfsgcag(Cgn)uucuugUfcCfagcuusususa | 718 | UAAAGCUGGACAAGAGCUGCUA | 456 |
| AD-1143308.1 | asasgcugGfaCfAfAfgaagcugcuuL96 | 454 | asAfsgcdAg(Cgn)uucuugUfcCfagcuususa | 895 | UAAAGCUGGACAAGAGCUGCUA | 456 |
| AD-1143309.1 | asasgcugGfaCfAfAfgaagcugcuuL96 | 454 | asdAsgcdAg(Cgn)uucuugUfcCfagcuususa | 896 | UAAAGCUGGACAAGAGCUGCUA | 456 |
| AD-1143310.1 | asasgcugGfaCfAfAfgaagcugcuuL96 | 454 | asdAsgcdAg(C2p)uucuugUfcCfagcuususa | 897 | UAAAGCUGGACAAGAGCUGCUA | 456 |
| AD-1143311.1 | asasgcugGfaCfAfAfgaagcugcuuL96 | 454 | asdAsgcdAg(Cgn)uucuugUfcCfagcuususc | 898 | UAAAGCUGGACAAGAGCUGCUA | 456 |
| AD-1143312.1 | asasgcugGfaCfAfAfgaagcugcuuL96 | 454 | asdAsgcdAg(Cgn)uucuugUfcCfagcuususa | 899 | UAAAGCUGGACAAGAGCUGCUA | 456 |
| AD-1143313.1 | asasgcugGfaCfAfAfgaagcugcuuL96 | 454 | asdAsgcdAg(Cgn)uucuugUfcCfagcuuscsc | 900 | UAAAGCUGGACAAGAGCUGCUA | 456 |
| AD-1143314.1 | asasgcugGfaCfAfAfgaagcugcuuL96 | 454 | asdAsgcdAg(C2p)uucuugUfcCfagcuuscsc | 901 | UAAAGCUGGACAAGAGCUGCUA | 456 |
| AD-1143315.1 | gscsugGfaCfAfAfgaagcugcuuL96 | 902 | asdAsgcdAg(Cgn)uucuugUfcCfagcsusu | 903 | AAGCUGGACAAGAGCUGCUA | 904 |

TABLE 15-continued

Modified Sense and Antisense Strand Sequences of Apolipoprotein C3 dsRNA Agents

| Duplex Name | Sense Sequence 5' to 3' | SEQ ID NO: | Antisense Sequence 5' to 3' | SEQ ID NO: | mRNA target sequence | SEQ ID NO: |
|---|---|---|---|---|---|---|
| AD-1143316.1 | gscsugGfaCfAfAfgaagcugcuuL96 | 902 | asdAsgcdAg(C2p)uucuugUfcCfagcsusu | 905 | AAGCUGGACAAGAAGCUGCUA | 904 |
| AD-1143317.1 | asasgcuggaCfadAgaagcugcuuL96 | 906 | asdAsgcdAg(Cgn)uucuugUfcCfagcuuscsc | 900 | UAAAGCUGGACAAGAAGCUGCUA | 456 |
| AD-1143318.1 | asasgcuggaCfadAgaagcugcuuL96 | 906 | asdAsgcdAg(C2p)uucuugUfcCfagcuuscsc | 901 | UAAAGCUGGACAAGAAGCUGCUA | 456 |
| AD-1143319.1 | asasgcuggaCfadAgdAagcugcuuL96 | 907 | asdAsgcdAg(Cgn)uucuugUfcCfagcuuscsc | 900 | UAAAGCUGGACAAGAAGCUGCUA | 456 |
| AD-1143320.1 | asasgcuggaCfadAgdAagcugcuuL96 | 907 | asdAsgcdAg(C2p)uucuugUfcCfagcuuscsc | 901 | UAAAGCUGGACAAGAAGCUGCUA | 456 |
| AD-1143321.1 | asasgcuggaCfadAgaagcugcuacuuL96 | 908 | asdAsgudAg(C2p)uucuugUfcCfagcuuscsc | 909 | UAAAGCUGGACAAGAAGCUGCUA | 456 |
| AD-1143322.1 | asasgcuggaCfadAgaagcugcuuL96 | 910 | asdAsgcdAa(C2p)uucuugUfcCfagcuuscsc | 911 | UAAAGCUGGACAAGAAGCUGCUA | 456 |
| AD-1183925 | asasgcuggaCfAfAfgaagcugcuuL96 | 912 | asdAsgcdAg(C2p)uucuugUfcCfagcuusuc | 899 | UAAAGCUGGACAAGAAGCUGCUA | 456 |
| AD-1183926 | gscsuggaCfAfAfgaagcugcuuL96 | 913 | asdAsgcdAg(C2p)uucuugUfcCfagcsusu | 905 | AAGCUGGACAAGAAGCUGCUA | 904 |
| AD-1019001 | Y44sacgggacaGfUfAfuuucucaguiasY44 | 914 | usCfsasCfuGfagaauAfcUfgUfcCfcGfsu | 915 | AAGGGACAGUAUUCUCAGUGC | 916 |

TABLE 16

Single Dose Free Uptake Screens in Hep3B cells

| Duplex Name | 500 nM Avg | SD | 100 nM Avg | SD | 10 nM Avg | SD | 1 nM Avg | SD |
|---|---|---|---|---|---|---|---|---|
| AD-80794.10 | 50.01 | 2.91 | 57.23 | 3.03 | 73.67 | 4.07 | 92.13 | 2.45 |
| AD-1143240.1 | 59.83 | 5.91 | 62.99 | 4.12 | 75.71 | 3.36 | 90.44 | 4.01 |
| AD-1143241.1 | 46.00 | 2.20 | 51.40 | 2.74 | 70.00 | 5.07 | 87.46 | 2.15 |
| AD-1143242.1 | 46.98 | 2.67 | 57.58 | 4.13 | 74.48 | 4.89 | 85.07 | 2.08 |
| AD-1143243.1 | 32.17 | 2.39 | 37.22 | 2.97 | 62.41 | 5.86 | 83.22 | 3.83 |
| AD-1143244.1 | 61.26 | 3.79 | 65.51 | 3.33 | 70.95 | 4.64 | 86.55 | 1.88 |
| AD-1143245.1 | 29.99 | 2.62 | 38.17 | 2.32 | 57.74 | 5.64 | 81.92 | 3.13 |
| AD-1143246.1 | 104.48 | 22.29 | 76.68 | 3.36 | 84.88 | 3.76 | 91.31 | 6.20 |
| AD-1143247.1 | 49.96 | 1.22 | 57.75 | 3.51 | 76.50 | 6.15 | 86.40 | 1.72 |
| AD-1143248.1 | 76.38 | 2.07 | 81.24 | 4.83 | 90.92 | 6.41 | 91.34 | 2.56 |
| AD-1143249.1 | 47.94 | 1.92 | 53.80 | 3.52 | 74.14 | 2.76 | 89.48 | 3.45 |
| AD-960030.3 | 41.64 | 0.96 | 49.21 | 2.30 | 70.81 | 4.30 | 90.77 | 7.86 |
| AD-1143250.1 | 43.66 | 1.99 | 50.06 | 2.06 | 71.09 | 1.41 | 88.52 | 1.54 |
| AD-1143251.1 | 44.46 | 2.85 | 53.43 | 0.48 | 70.58 | 4.73 | 87.93 | 2.59 |
| AD-1143252.1 | 35.28 | 4.47 | 39.27 | 3.04 | 63.45 | 2.88 | 84.67 | 3.62 |
| AD-1143253.1 | 45.97 | 4.59 | 48.91 | 3.12 | 72.50 | 3.30 | 85.82 | 2.60 |
| AD-1143254.1 | 33.14 | 1.27 | 39.94 | 2.86 | 67.59 | 4.55 | 85.51 | 1.63 |
| AD-1143255.1 | 22.44 | 3.31 | 33.91 | 6.67 | 53.15 | 3.97 | 80.09 | 3.20 |
| AD-1143256.1 | 12.09 | 1.29 | 18.11 | 1.50 | 54.06 | 9.34 | 75.50 | 2.77 |
| AD-1143257.1 | 108.85 | 5.61 | 93.98 | 5.84 | 92.13 | 5.41 | 93.92 | 3.11 |
| AD-1143258.1 | 84.74 | 1.55 | 82.30 | 2.97 | 85.54 | 5.46 | 93.59 | 2.95 |
| AD-1143259.1 | 84.03 | 3.05 | 88.74 | 1.41 | 85.29 | 2.51 | 100.73 | 15.35 |
| AD-1143260.1 | 87.46 | 3.43 | 78.59 | 4.36 | 83.55 | 2.88 | 91.04 | 3.38 |
| AD-960031.3 | 29.38 | 3.85 | 41.40 | 6.94 | 62.15 | 5.10 | 83.65 | 3.72 |
| AD-1143261.1 | 96.26 | 12.69 | 97.98 | 11.29 | 88.10 | 5.65 | 94.22 | 4.29 |
| AD-1143262.1 | 76.29 | 3.64 | 75.61 | 2.89 | 90.82 | 7.38 | 95.42 | 4.11 |
| AD-1143263.1 | 48.38 | 9.73 | 61.04 | 5.42 | 81.86 | 3.97 | 92.05 | 5.07 |
| AD-1143264.1 | 66.67 | 3.82 | 76.51 | 1.92 | 84.98 | 1.39 | 91.16 | 1.37 |
| AD-1143265.1 | 68.17 | 13.37 | 77.06 | 12.29 | 81.83 | 3.04 | 92.15 | 6.59 |
| AD-1143266.1 | 74.35 | 11.32 | 68.43 | 4.30 | 82.16 | 4.30 | 96.14 | 13.04 |
| AD-1143267.1 | 44.99 | 5.20 | 64.81 | 10.27 | 78.18 | 9.28 | 89.68 | 4.66 |
| AD-1143268.1 | 75.66 | 8.75 | 91.75 | 14.39 | 89.63 | 5.81 | 100.77 | 5.48 |
| AD-1143269.1 | 70.81 | 3.28 | 84.12 | 5.28 | 95.03 | 5.00 | 97.24 | 7.30 |
| AD-1143270.1 | 71.74 | 4.79 | 78.83 | 3.42 | 92.89 | 4.17 | 95.82 | 5.96 |
| AD-1143271.1 | 71.77 | 5.30 | 76.02 | 3.43 | 91.08 | 9.11 | 95.56 | 3.23 |
| AD-1143272.1 | 69.18 | 1.04 | 77.97 | 1.16 | 91.30 | 7.61 | 90.72 | 2.88 |
| AD-1143273.1 | 46.11 | 5.48 | 58.47 | 5.63 | 79.00 | 5.34 | 86.46 | 2.44 |
| AD-1143274.1 | 57.35 | 7.81 | 59.49 | 3.88 | 82.43 | 4.08 | 94.65 | 5.38 |
| AD-960062.3 | 42.21 | 6.42 | 58.97 | 13.39 | 76.38 | 11.22 | 100.56 | 15.42 |
| AD-1143275.1 | 54.25 | 10.60 | 67.40 | 11.53 | 80.59 | 6.62 | 108.48 | 13.17 |
| AD-1143276.1 | 57.96 | 3.63 | 64.19 | 4.11 | 80.40 | 1.72 | 91.66 | 2.79 |
| AD-1143277.1 | 60.46 | 6.29 | 73.08 | 8.35 | 114.87 | Dia | 95.41 | 7.44 |
| AD-1143278.1 | 30.74 | 2.87 | 46.93 | 7.31 | 75.59 | 3.54 | 90.06 | 12.78 |
| AD-1143279.1 | 46.16 | 2.13 | 63.91 | 11.43 | 84.18 | 4.57 | 89.02 | 3.39 |
| AD-1143280.1 | 26.65 | 6.19 | 39.95 | 8.20 | 71.49 | 2.71 | 84.48 | 2.10 |
| AD-1143281.1 | 83.25 | 5.26 | 97.82 | 9.56 | 87.57 | 5.49 | 95.78 | 5.34 |
| AD-1143282.1 | 62.39 | 5.01 | 70.93 | 12.74 | 77.38 | 0.93 | 92.25 | 3.23 |
| AD-1143283.1 | 74.72 | 3.35 | 81.27 | 5.49 | 92.84 | 2.43 | 100.14 | 3.42 |
| AD-1143284.1 | 53.26 | 1.19 | 63.20 | 4.02 | 83.55 | 3.21 | 95.11 | 4.68 |
| AD-960064.3 | 35.24 | 4.68 | 45.96 | 3.22 | 73.26 | 3.33 | 88.25 | 3.26 |
| AD-1143285.1 | 26.79 | 2.81 | 34.47 | 4.00 | 77.33 | 6.80 | 86.04 | 9.70 |
| AD-1143286.1 | 19.35 | 3.41 | 29.77 | 4.83 | 67.58 | 14.28 | 88.54 | 12.85 |
| AD-1143287.1 | 36.62 | 2.41 | 40.55 | 10.58 | 64.21 | 2.67 | 88.54 | 12.76 |
| AD-1143288.1 | 45.07 | 9.60 | 50.93 | 11.36 | 74.56 | 9.65 | 87.44 | 7.30 |
| AD-1143289.1 | 18.55 | 4.13 | 26.32 | 5.27 | 59.92 | 6.61 | 85.97 | 12.38 |
| AD-1143290.1 | 66.75 | 2.91 | 75.76 | 4.76 | 89.92 | 10.03 | 103.24 | 6.45 |
| AD-1143291.1 | 61.61 | 1.41 | 74.92 | 7.37 | 96.58 | 6.23 | 92.67 | 4.65 |
| AD-1143292.1 | 103.71 | 13.87 | 96.00 | 6.82 | 102.08 | 18.11 | 89.10 | 2.78 |
| AD-1143293.1 | 64.75 | 7.70 | 70.52 | 5.16 | 82.76 | 2.30 | 88.53 | 6.30 |
| AD-1143294.1 | 66.74 | 10.80 | 69.22 | 11.38 | 80.55 | 4.13 | 100.67 | 14.77 |
| AD-1143295.1 | 62.66 | 9.65 | 62.74 | 10.64 | 89.92 | 20.11 | 99.75 | 17.24 |
| AD-1143296.1 | 68.47 | 8.32 | 74.41 | 5.35 | 89.72 | 15.96 | 102.45 | 15.29 |
| AD-960096.3 | 62.06 | 9.14 | 62.82 | 3.97 | 73.10 | 3.78 | 98.71 | 13.86 |
| AD-1143297.1 | 63.46 | 2.13 | 64.77 | 0.99 | 94.66 | 15.45 | 87.45 | 1.11 |
| AD-1143298.1 | 36.30 | 4.11 | 45.39 | 2.87 | 77.72 | 6.66 | 88.99 | 6.44 |
| AD-1143299.1 | 63.33 | 7.70 | 60.86 | 4.26 | 84.28 | 16.31 | 83.82 | 4.27 |
| AD-1143300.1 | 31.00 | 5.52 | 36.78 | 5.31 | 75.23 | 10.17 | 89.41 | 15.09 |
| AD-1143301.1 | 63.14 | 13.06 | 51.90 | 3.83 | 83.74 | 24.11 | 97.24 | 14.28 |
| AD-1143302.1 | 65.92 | 4.89 | 72.42 | 3.43 | 82.76 | 5.03 | 94.16 | 5.49 |
| AD-1143303.1 | 72.20 | 8.33 | 70.63 | 2.96 | 89.97 | 10.86 | 101.84 | 15.93 |
| AD-1143304.1 | 55.09 | 2.79 | 63.03 | 4.77 | 78.29 | 1.36 | 82.37 | 3.89 |
| AD-1143305.1 | 56.12 | 9.04 | 58.35 | 3.55 | 85.76 | 6.85 | 95.38 | 7.01 |
| AD-1143306.1 | 95.15 | 16.35 | 87.12 | 1.78 | 94.75 | 12.83 | 93.02 | 5.19 |
| AD-1143307.1 | 101.10 | 14.18 | 89.16 | 9.67 | 98.12 | 17.65 | 97.60 | 10.55 |
| AD-960481.3 | 76.27 | 13.63 | 63.55 | 6.29 | 94.32 | 27.33 | 96.57 | 14.20 |

TABLE 16-continued

Single Dose Free Uptake Screens in Hep3B cells

| Duplex Name | 500 nM Avg | SD | 100 nM Avg | SD | 10 nM Avg | SD | 1 nM Avg | SD |
|---|---|---|---|---|---|---|---|---|
| AD-1143308.1 | 53.08 | 3.84 | 60.34 | 1.74 | 73.24 | 2.55 | 89.76 | 1.87 |
| AD-1143309.1 | 65.24 | 6.58 | 68.94 | 9.69 | 87.87 | 12.46 | 89.04 | 4.03 |
| AD-1143310.1 | 60.98 | 1.83 | 65.14 | 2.41 | 80.93 | 11.19 | 86.62 | 7.35 |
| AD-1143311.1 | 61.07 | 0.91 | 61.76 | 3.10 | 91.14 | 13.28 | 87.45 | 1.73 |
| AD-1143312.1 | 61.85 | 14.18 | 53.82 | 1.28 | 85.58 | 8.53 | 83.02 | 5.64 |
| AD-1143313.1 | 79.09 | 10.91 | 68.96 | 8.44 | 114.58 | 9.72 | 84.57 | 5.14 |
| AD-1143314.1 | 65.98 | 14.04 | 54.39 | 4.13 | 97.29 | 9.49 | 85.95 | 15.06 |
| AD-1143315.1 | 69.73 | 9.31 | 56.52 | 4.43 | 89.23 | 19.66 | 87.97 | 11.47 |
| AD-1143316.1 | 37.58 | 9.74 | 45.48 | 4.36 | 67.15 | 13.63 | 86.39 | 8.46 |
| AD-1143317.1 | 75.31 | 5.07 | 77.89 | 3.77 | 79.47 | 3.23 | 89.32 | 2.95 |
| AD-1143318.1 | 88.04 | 2.18 | 85.20 | 2.80 | 84.34 | 4.84 | 92.15 | 3.21 |
| AD-1143319.1 | 78.11 | 1.03 | 78.66 | 1.90 | 85.48 | 3.98 | 87.83 | 4.39 |
| AD-1143320.1 | 72.96 | 4.16 | 76.75 | 5.12 | 83.72 | 3.86 | 86.10 | 1.86 |
| AD-1143321.1 | 88.56 | 4.22 | 87.05 | 4.63 | 92.98 | 16.13 | 86.86 | 2.20 |
| AD-1143322.1 | 96.56 | 8.01 | 87.69 | 5.49 | 94.48 | 14.95 | 90.38 | 1.88 |

TABLE 17

APOC3 Single Dose Screens in Hep3B cells

| Duplex Name | 50 nM Avg | SD | 10 nM Avg | SD | 1 nM Avg | SD | 0.1 nM Avg | SD |
|---|---|---|---|---|---|---|---|---|
| AD-80794.10 | 5.7 | 1.1 | 9.95 | 0.48 | 32.69 | 7.14 | 64.32 | 3.18 |
| AD-1143240.1 | 7.1 | 1.2 | 15.92 | 1.88 | 38.52 | 6.25 | 69.61 | 5.09 |
| AD-1143241.1 | 5.7 | 0.4 | 10.24 | 0.34 | 25.95 | 2.96 | 57.20 | 3.42 |
| AD-1143242.1 | 6.4 | 0.9 | 13.22 | 1.13 | 34.61 | 3.94 | 61.90 | 6.43 |
| AD-1143243.1 | 3.6 | 1.2 | 4.93 | 1.44 | 11.97 | 2.19 | 41.16 | 3.87 |
| AD-1143244.1 | 6.1 | 0.6 | 14.76 | 2.30 | 35.03 | 5.30 | 63.06 | 1.15 |
| AD-1143245.1 | 3.2 | 1.0 | 4.79 | 0.38 | 13.05 | 3.50 | 35.33 | 4.64 |
| AD-1143246.1 | 23.5 | 2.7 | 48.43 | 3.38 | 51.77 | 11.43 | 62.50 | 8.17 |
| AD-1143247.1 | 8.2 | 1.5 | 15.58 | 1.25 | 33.36 | 3.62 | 67.35 | 1.28 |
| AD-1143248.1 | 30.0 | 7.8 | 42.16 | 4.87 | 71.78 | 8.67 | 90.87 | 8.70 |
| AD-1143249.1 | 6.7 | 1.3 | 10.12 | 1.10 | 30.61 | 2.16 | 73.82 | 12.68 |
| AD-960030.3 | 6.3 | 1.2 | 10.86 | 0.88 | 33.81 | 1.58 | 78.29 | 7.19 |
| AD-1143250.1 | 7.3 | 2.6 | 11.13 | 3.32 | 38.58 | 5.25 | 74.13 | 15.33 |
| AD-1143251.1 | 5.7 | 0.4 | 11.28 | 2.82 | 26.55 | 4.13 | 73.77 | 9.73 |
| AD-1143252.1 | 3.6 | 0.8 | 7.27 | 1.30 | 14.89 | 2.35 | 60.85 | 12.26 |
| AD-1143253.1 | 3.7 | 0.9 | 9.57 | 2.15 | 24.55 | 4.12 | 66.79 | 6.79 |
| AD-1143254.1 | 3.4 | 0.7 | 5.32 | 2.07 | 14.73 | 2.96 | 53.26 | 5.75 |
| AD-1143255.1 | 4.6 | 1.3 | 5.67 | 1.06 | 21.00 | 4.11 | 71.94 | 13.73 |
| AD-1143256.1 | 3.3 | 0.6 | 4.51 | 0.83 | 11.84 | 1.22 | 44.47 | 5.74 |
| AD-1143257.1 | 42.1 | 5.6 | 66.28 | 4.64 | 77.50 | 16.10 | 85.21 | 5.60 |
| AD-1143258.1 | 14.8 | 2.8 | 30.73 | 2.64 | 50.53 | 2.24 | 76.78 | 4.31 |
| AD-1143259.1 | 39.3 | 10.8 | 62.34 | 10.95 | 58.31 | 9.70 | 92.23 | 23.63 |
| AD-1143260.1 | 10.3 | 4.1 | 27.71 | 4.89 | 46.07 | 6.70 | 76.35 | 6.59 |
| AD-960031.3 | 4.1 | 0.5 | 6.33 | 1.49 | 13.71 | 3.98 | 52.14 | 2.03 |
| AD-1143261.1 | 30.0 | 7.0 | 45.40 | 7.52 | 76.11 | 11.73 | 96.35 | 13.51 |
| AD-1143262.1 | 8.7 | 0.6 | 12.67 | 2.42 | 33.93 | 4.28 | 80.72 | 10.76 |
| AD-1143263.1 | 7.0 | 1.9 | 8.59 | 1.53 | 24.97 | 4.76 | 70.04 | 3.98 |
| AD-1143264.1 | 10.5 | 2.6 | 15.57 | 2.68 | 36.20 | 4.20 | 69.58 | 4.36 |
| AD-1143265.1 | 7.0 | 1.1 | 14.90 | 4.74 | 29.19 | 7.67 | 68.07 | 6.60 |
| AD-1143266.1 | 7.4 | 3.6 | 14.06 | 3.79 | 36.54 | 10.79 | 69.23 | 16.16 |
| AD-1143267.1 | 6.4 | 2.8 | 10.39 | 4.74 | 27.85 | 9.35 | 77.07 | 14.58 |
| AD-1143268.1 | 18.4 | 5.3 | 30.21 | 7.20 | 64.69 | 15.99 | 87.24 | 6.39 |
| AD-1143269.1 | 12.7 | 1.0 | 23.02 | 5.11 | 48.27 | 3.18 | 89.49 | 12.32 |
| AD-1143270.1 | 11.9 | 1.8 | 23.75 | 6.38 | 48.58 | 8.61 | 85.30 | 6.72 |
| AD-1143271.1 | 15.6 | 2.4 | 22.50 | 4.14 | 51.50 | 15.12 | 75.61 | 4.59 |
| AD-1143272.1 | 13.6 | 0.7 | 23.31 | 5.30 | 48.00 | 6.30 | 79.88 | 3.87 |
| AD-1143273.1 | 6.5 | 1.7 | 10.62 | 2.32 | 30.43 | 12.95 | 59.42 | 3.85 |
| AD-1143274.1 | 5.9 | 1.9 | 9.74 | 2.72 | 20.44 | 5.25 | 59.55 | 8.94 |
| AD-960062.3 | 6.0 | 1.1 | 14.90 | 3.08 | 38.29 | 5.48 | 78.23 | 11.31 |
| AD-1143275.1 | 21.9 | 20.0 | 20.20 | 4.71 | 58.80 | 19.25 | 87.53 | 3.36 |
| AD-1143276.1 | 13.5 | 4.1 | 17.22 | 1.37 | 45.40 | 5.79 | 81.50 | 8.12 |
| AD-1143277.1 | 11.2 | 2.2 | 17.51 | 2.37 | 42.03 | 6.65 | 81.04 | 9.28 |
| AD-1143278.1 | 5.0 | 1.4 | 6.79 | 0.82 | 15.99 | 2.77 | 58.30 | 14.40 |
| AD-1143279.1 | 7.6 | 2.0 | 11.26 | 1.68 | 32.37 | 4.56 | 62.14 | 3.43 |
| AD-1143280.1 | 4.8 | 3.0 | 5.89 | 0.52 | 13.05 | 3.98 | 41.79 | 5.31 |
| AD-1143281.1 | 45.7 | 5.9 | 59.48 | 7.68 | 70.38 | 3.75 | 77.63 | 7.52 |
| AD-1143282.1 | 16.3 | 2.4 | 24.29 | 6.42 | 56.76 | 5.55 | 80.93 | 3.65 |
| AD-1143283.1 | 25.8 | 1.5 | 44.82 | 11.38 | 72.55 | 14.90 | 94.36 | 5.31 |
| AD-1143284.1 | 10.4 | 2.8 | 16.97 | 2.34 | 42.91 | 5.08 | 79.91 | 4.59 |

TABLE 17-continued

APOC3 Single Dose Screens in Hep3B cells

| Duplex Name | 50 nM Avg | SD | 10 nM Avg | SD | 1 nM Avg | SD | 0.1 nM Avg | SD |
|---|---|---|---|---|---|---|---|---|
| AD-960064.3 | 4.2 | 0.6 | 7.37 | 3.78 | 19.17 | 4.36 | 49.10 | 5.66 |
| AD-1143285.1 | 5.4 | 1.4 | 7.86 | 1.22 | 17.89 | 1.37 | 54.59 | 14.15 |
| AD-1143286.1 | 4.0 | 1.4 | 5.02 | 1.00 | 14.71 | 4.90 | 39.71 | 1.47 |
| AD-1143287.1 | 4.7 | 1.9 | 5.59 | 2.40 | 15.79 | 4.39 | 48.62 | 13.52 |
| AD-1143288.1 | 6.7 | 1.6 | 6.50 | 0.81 | 21.80 | 8.36 | 64.64 | 18.78 |
| AD-1143289.1 | 4.8 | 0.7 | 7.27 | 1.89 | 19.96 | 2.45 | 72.86 | 11.19 |
| AD-1143290.1 | 13.1 | 3.0 | 21.10 | 3.85 | 56.96 | 2.68 | 84.38 | 17.46 |
| AD-1143291.1 | 11.3 | 0.7 | 20.46 | 3.83 | 57.48 | 7.36 | 83.09 | 13.09 |
| AD-1143292.1 | 73.7 | 6.0 | 76.74 | 12.40 | 85.93 | 13.10 | 85.38 | 4.81 |
| AD-1143293.1 | 9.3 | 1.3 | 20.27 | 4.53 | 42.95 | 5.74 | 73.75 | 2.06 |
| AD-1143294.1 | 12.1 | 1.4 | 25.36 | 7.70 | 49.62 | 7.18 | 86.00 | 5.63 |
| AD-1143295.1 | 8.3 | 2.3 | 12.41 | 2.06 | 36.35 | 1.40 | 58.61 | 9.02 |
| AD-1143296.1 | 9.8 | 1.2 | 18.77 | 6.23 | 47.68 | 14.59 | 85.91 | 4.26 |
| AD-960096.3 | 8.5 | 1.9 | 10.64 | 2.21 | 28.32 | 4.33 | 69.12 | 1.44 |
| AD-1143297.1 | 8.7 | 0.7 | 14.90 | 2.16 | 51.05 | 16.48 | 90.58 | 15.04 |
| AD-1143298.1 | 4.9 | 0.3 | 6.62 | 0.97 | 18.55 | 4.52 | 65.95 | 17.11 |
| AD-1143299.1 | 5.5 | 1.2 | 7.73 | 1.65 | 22.91 | 1.45 | 59.57 | 8.18 |
| AD-1143300.1 | 4.9 | 1.2 | 8.31 | 3.19 | 22.19 | 11.16 | 52.43 | 7.83 |
| AD-1143301.1 | 6.3 | 0.9 | 10.75 | 1.98 | 28.49 | 7.31 | 70.30 | 10.58 |
| AD-1143302.1 | 7.9 | 1.5 | 11.19 | 3.20 | 38.83 | 14.98 | 87.33 | 15.21 |
| AD-1143303.1 | 8.6 | 1.3 | 12.40 | 2.65 | 48.46 | 1.79 | 98.13 | 17.19 |
| AD-1143304.1 | 9.7 | 2.5 | 11.07 | 1.79 | 35.65 | 3.16 | 93.11 | 17.36 |
| AD-1143305.1 | 9.1 | 4.3 | 10.51 | 2.17 | 36.75 | 4.73 | 75.09 | 5.82 |
| AD-1143306.1 | 41.1 | 6.7 | 58.50 | 7.88 | 85.88 | 16.83 | 85.51 | 2.76 |
| AD-1143307.1 | 37.6 | 4.0 | 48.21 | 1.96 | 90.07 | 19.23 | 99.33 | 19.17 |
| AD-960481.3 | 14.3 | 3.0 | 16.70 | 1.93 | 24.93 | 4.18 | 58.59 | 12.39 |
| AD-1143308.1 | 10.4 | 0.9 | 11.43 | 0.75 | 20.45 | 6.28 | 55.52 | 9.39 |
| AD-1143309.1 | 15.5 | 1.4 | 16.40 | 2.68 | 34.69 | 2.64 | 67.90 | 12.70 |
| AD-1143310.1 | 13.8 | 1.0 | 15.28 | 1.15 | 30.24 | 5.65 | 68.82 | 8.91 |
| AD-1143311.1 | 15.4 | 2.4 | 17.79 | 2.39 | 34.59 | 7.22 | 65.86 | 10.52 |
| AD-1143312.1 | 14.5 | 1.6 | 15.72 | 3.57 | 31.73 | 11.40 | 57.08 | 6.92 |
| AD-1143313.1 | 20.8 | 3.4 | 27.95 | 14.33 | 42.27 | 7.42 | 75.75 | 8.10 |
| AD-1143314.1 | 17.1 | 2.1 | 19.52 | 2.15 | 37.72 | 8.99 | 72.95 | 22.77 |
| AD-1143315.1 | 12.7 | 3.7 | 17.40 | 3.53 | 31.01 | 8.81 | 76.52 | 15.22 |
| AD-1143316.1 | 11.8 | 0.8 | 14.83 | 1.86 | 30.60 | 5.14 | 67.90 | 8.60 |
| AD-1143317.1 | 18.8 | 2.0 | 22.92 | 3.28 | 44.93 | 5.70 | 70.55 | 6.43 |
| AD-1143318.1 | 35.6 | 2.2 | 34.82 | 2.89 | 59.98 | 8.35 | 75.30 | 3.45 |
| AD-1143319.1 | 15.9 | 1.3 | 21.27 | 3.79 | 41.72 | 6.38 | 70.74 | 12.44 |
| AD-1143320.1 | 23.8 | 1.4 | 33.05 | 5.65 | 59.79 | 7.71 | 68.64 | 11.31 |
| AD-1143321.1 | 52.4 | 6.7 | 60.14 | 7.06 | 73.20 | 5.57 | 71.89 | 1.25 |
| AD-1143322.1 | 51.0 | 3.8 | 62.29 | 7.70 | 67.07 | 7.38 | 78.84 | 15.84 |

Duplexes of interest, identified from the above in vitro SAR studies, were evaluated in vivo. In particular, at pre-dose day −14 wild-type mice (C57BL/6) were transduced by retrorbital administration of $2\times10^{10}$ viral particles of an adeno-associated virus 8 (AAV8) vector encoding human APOC3. In particular, mice were administered an AAV8 encoding the human APOC3 mRNA, referred to as AAV8-TBG-PI-APOC3.

At day 0, groups of three mice were subcutaneously administered a single 3 mg/kg dose of the agents of interest or PBS control. Table 18 provides the treatment groups and Table 19 provides the duplexes of interest. At day 7 or day 14 post-dose animals were sacrificed, liver samples were collected and snap-frozen in liquid nitrogen. Liver mRNA was extracted and analyzed by the RT-QPCR method.

Figure 3:
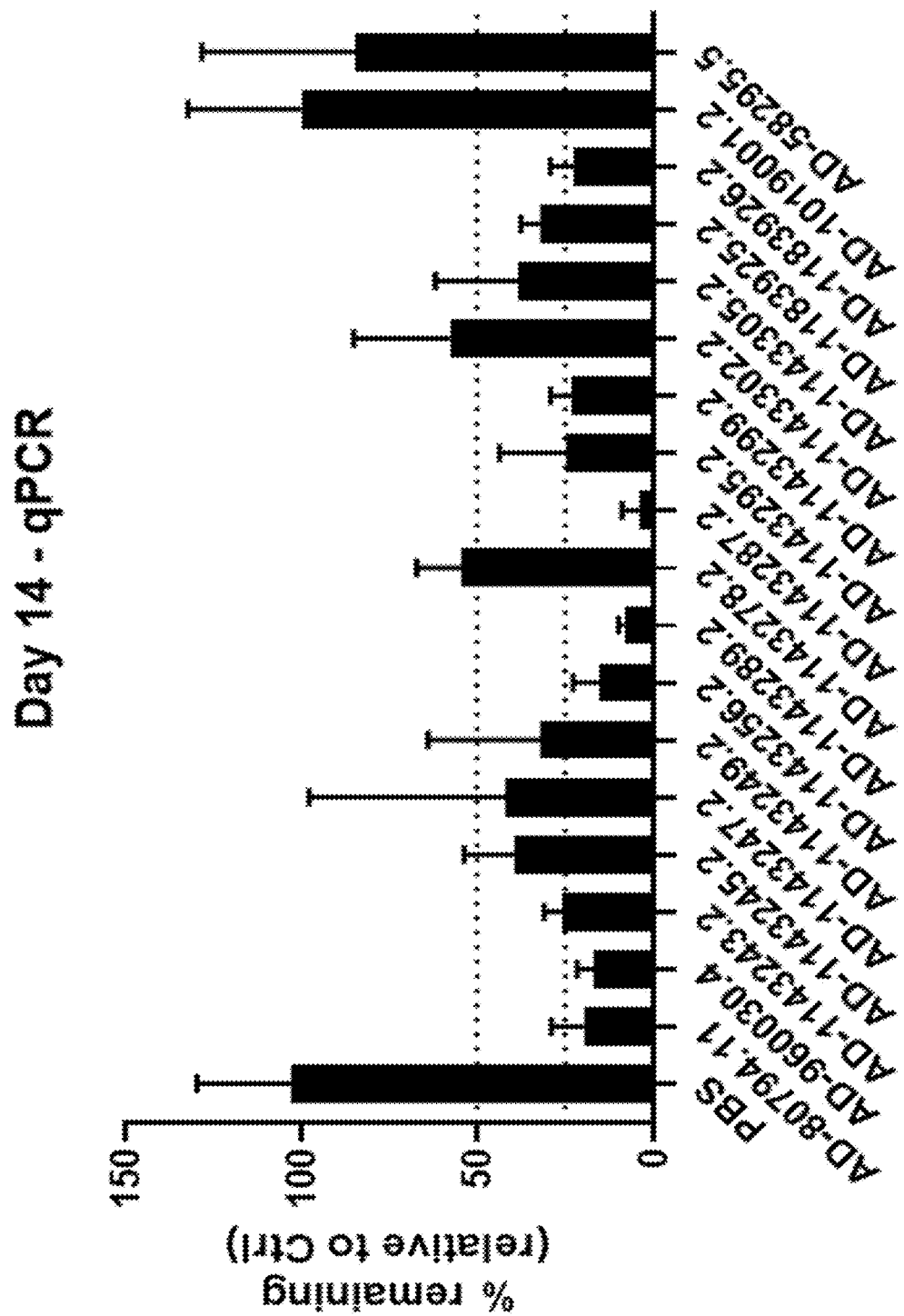
FIG. 3 is a graph showing human APOC3 mRNA levels in mice (n=3 per group) subcutaneously administered a single 3 mg/kg dose of the indicated dsRNA duplexes, on day14 post-dose. Human APOC3 mRNA levels are shown relative to control levels detected with PBS treatment.

Human APOC3 mRNA levels were compared to a housekeeping gene, GAPDH. The values were then normalized to the average of PBS vehicle control group. The data were expressed as percent of baseline value, and presented as mean plus standard deviation. The results, listed in Table 20 and shown in FIG. 3, demonstrate that the exemplary duplex agents tested effectively reduce the level of the human APOC3 messenger RNA in vivo.

TABLE 18

Treatment Groups

| Group # | Animal # | Treatment | Dose | Timepoint |
|---|---|---|---|---|
| 1 | 1 | PBS | n/a | D 0, D 7, D 14 |
|  | 2 |  |  |  |
|  | 3 |  |  |  |
| 2 | 4 | Naïve | n/a |  |
|  | 5 | (AAV only) |  |  |
|  | 6 |  |  |  |
| 3 | 7 | AD-80794 | 3 mpk |  |
|  | 8 | (Benchmark) |  |  |
|  | 9 |  |  |  |
| 4 | 10 | AD-960030 |  |  |
|  | 11 |  |  |  |
|  | 12 |  |  |  |
| 5 | 13 | AD-1143243 |  |  |
|  | 14 |  |  |  |
|  | 15 |  |  |  |
| 6 | 16 | AD-1143245 |  |  |
|  | 17 |  |  |  |
|  | 18 |  |  |  |
| 7 | 19 | AD-1143247 |  |  |
|  | 20 |  |  |  |
|  | 21 |  |  |  |

TABLE 18-continued

Treatment Groups

| Group # | Animal # | Treatment | Dose | Timepoint |
|---|---|---|---|---|
| 8 | 22 | AD-1143249 | | |
|  | 23 | | | |
|  | 24 | | | |
| 9 | 25 | AD-1143256 | | |
|  | 26 | | | |
|  | 27 | | | |
| 10 | 28 | AD-1143289 | | |
|  | 29 | | | |
|  | 30 | | | |
| 11 | 31 | AD-1143278 | | |
|  | 32 | | | |
|  | 33 | | | |
| 12 | 34 | AD-1143287 | | |
|  | 35 | | | |
|  | 36 | | | |
| 13 | 37 | AD-1143295 | | |
|  | 38 | | | |
|  | 39 | | | |
| 14 | 40 | AD-1143299 | | |
|  | 41 | | | |
|  | 42 | | | |
| 15 | 43 | AD-1143302 | | |
|  | 44 | | | |
|  | 45 | | | |
| 16 | 46 | AD-1143305 | | |
|  | 47 | | | |
|  | 48 | | | |
| 17 | 49 | AD-1183925 | | |
|  | 50 | | | |
|  | 51 | | | |
| 18 | 52 | AD-1183926 | | |
|  | 53 | | | |
|  | 54 | | | |
| 19 | 55 | AD-1019001 (Arrowhead) | | |
|  | 56 | | | |
|  | 57 | | | |
| 20 | 58 | AD-58295 | | |
|  | 59 | | | |
|  | 60 | | | |

TABLE 19

Duplexes of Interest

| DuplexID | Range in NM-000040.3 |
|---|---|
| AD-960030 | 429-451 |
| AD-1143243 | 432-452 |
| AD-1143245 | 432-452 |
| AD-1143247 | 430-452 |
| AD-1143249 | 430-452 |
| AD-1143256 | 431-451 |
| AD-1143260 | 429-451 |
| AD-1143278 | 430-452 |
| AD-1143287 | 433-455 |
| AD-1143295 | 433-455 |
| AD-1143299 | 504-526 |
| AD-1143302 | 504-526 |
| AD-1143305 | 506-526 |
| AD-1183925 | 510-532 |
| AD-1183926 | 512-532 |
| AD-58295 | Negative Control |

TABLE 20

| Duplex | % Message Remaining | SD |
|---|---|---|
| PBS | 102.64 | 27.23 |
| AD-80794.11 | 19.86 | 9.05 |
| AD-960030.4 | 16.99 | 4.69 |
| AD-1143243.2 | 25.98 | 5.12 |
| AD-1143245.2 | 39.13 | 14.55 |
| AD-1143247.2 | 41.77 | 56.07 |
| AD-1143249.2 | 31.91 | 32.10 |
| AD-1143256.2 | 15.43 | 7.40 |
| AD-1143289.2 | 8.27 | 1.73 |
| AD-1143278.2 | 54.31 | 12.95 |
| AD-1143287.2 | 4.00 | 4.94 |
| AD-1143295.2 | 24.85 | 18.86 |
| AD-1143299.2 | 23.37 | 5.80 |
| AD-1143302.2 | 57.80 | 27.34 |
| AD-1143305.2 | 38.33 | 23.55 |
| AD-1183925.2 | 31.91 | 5.66 |
| AD-1183926.2 | 22.87 | 6.44 |
| AD-1019001.2 | 99.93 | 32.38 |
| AD-58295.5 | 84.59 | 43.87 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A double stranded ribonucleic acid (dsRNA) agent for inhibiting expression of apolipoprotein C3 in a cell,
    wherein the dsRNA agent comprises a sense strand and an antisense strand forming a double stranded region,
    wherein the sense strand comprises at least 15 contiguous nucleotides differing by no more than 3 nucleotides from the nucleotide sequence of 5'-CUUAAAAGGGACAGUAUUCUA-3' (SEQ ID NO:13), and the antisense strand comprises at least 15 contiguous nucleotides from the nucleotide sequence of 5'-UAGAAUACUGUCCCUUUUAAGCC-3' (SEQ ID NO:14),
    wherein all of the nucleotides of the sense strand and all of the nucleotides of the antisense strand comprise a modification selected from the group consisting of a 2'-O-methyl modification, a 2'-fluoro modification, and a deoxy-modification,
    wherein the sense strand comprises 4 2'-fluoro modified nucleotides at nucleotides 7 and 9-11, counting from the 5'-end, and the antisense strand comprises 2 2'-fluoro modified nucleotides at nucleotides 14 and 16, counting from the 5'-end, and 3 2'-deoxy-modified nucleotides at nucleotides 2, 5, and 7, counting from the 5'-end,
    wherein both the sense strand and the antisense strand independently further comprise at least one phosphorothioate or methylphosphonate internucleotide linkage, and
    wherein at least one strand is conjugated to a ligand.

2. The dsRNA agent of claim 1, wherein the sense strand comprises two phosphorothioate or methylphosphonate internucleotide linkages at the 5'-terminus.

3. The dsRNA agent of claim 1, wherein the antisense strand comprises two phosphorothioate or methylphosphonate internucleotide linkages at both the 5'- and the 3'-terminus.

4. The dsRNA agent of claim 1, wherein the sense strand comprises two phosphorothioate or methylphosphonate internucleotide linkages at the 5'-terminus and the antisense strand comprises two phosphorothioate or methylphosphonate internucleotide linkages at both the 5'- and the 3'-terminus.

5. The dsRNA agent of claim 1, wherein the ligand is conjugated to the 3'-end of the sense strand.

6. The dsRNA agent of claim 1, wherein the ligand is an N-acetylgalactosamine (GalNAc) derivative.

7. The dsRNA agent of claim 6, wherein the ligand is one or more GalNAc derivatives attached through a monovalent, bivalent, or trivalent branched linker.

8. The dsRNA agent of claim 7, wherein the ligand is

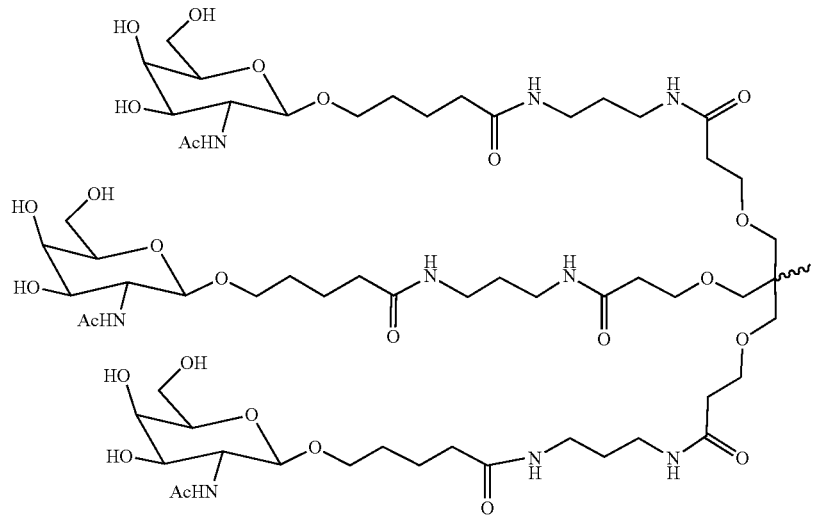

9. The dsRNA agent of claim 8, wherein the dsRNA agent is conjugated to the ligand as shown in the following schematic

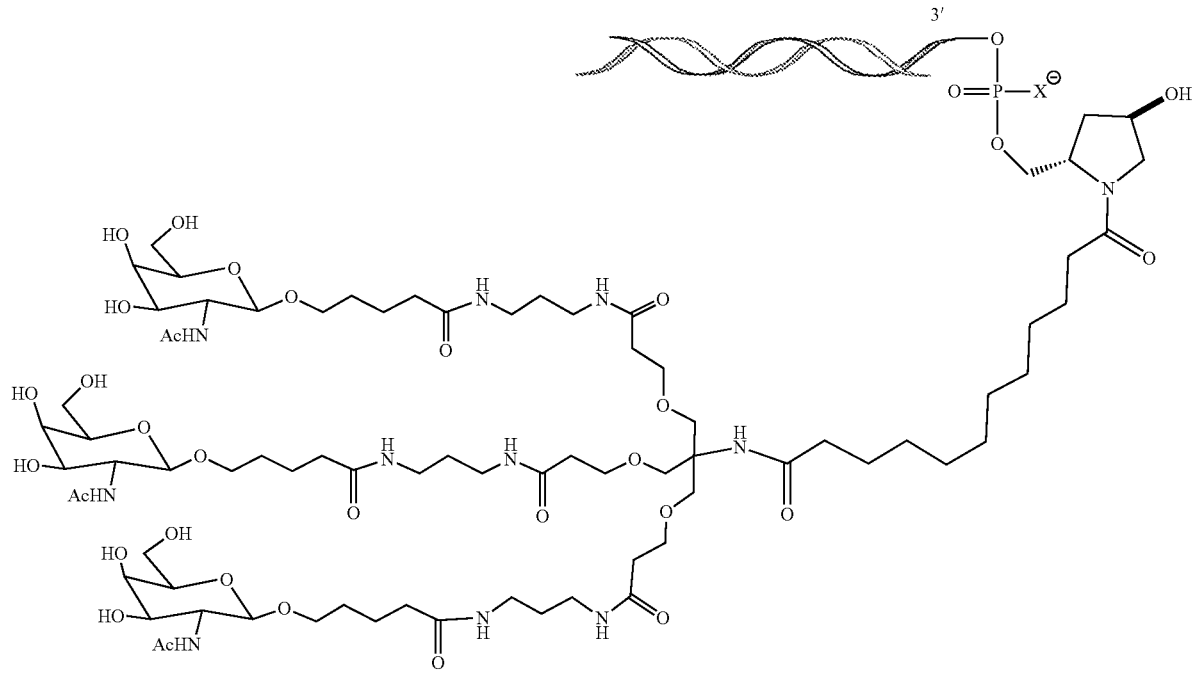

and, wherein X is O.

10. A double stranded ribonucleic acid (dsRNA) agent for inhibiting expression of apolipoprotein C3 in a cell,
wherein the dsRNA agent comprises a sense strand and an antisense strand forming a double stranded region, wherein the sense strand differs by no more than 3 modified nucleotides from the nucleotide sequence of 5'-csusuaaaAfgGfGfAfcaguauucua-3' (SEQ ID NO: 15) and wherein the antisense strand differs by no more than 3 modified nucleotides from the nucleotide sequence of 5'-usdAsgadAudAcuguccCfuUfuuaagscsc-3' (SEQ ID NO:16), wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

11. The dsRNA agent of claim 10, wherein the sense strand differs by no more than 2 modified nucleotides from the nucleotide sequence of 5'-csusuaaaAfgGfGfAfc-aguauucua-3' (SEQ ID NO: 15) and wherein the antisense strand differs by no more than 2 modified nucleotides from the nucleotide sequence of 5'-usdAsgadAudAcuguccCfuUfuuaagscsc-3' (SEQ ID NO:16).

12. The dsRNA agent of claim 10, wherein the sense strand differs by no more than 1 modified nucleotide from the nucleotide sequence of 5'-csusuaaaAfgGfGfAfc-aguauucua-3' (SEQ ID NO: 15) and wherein the antisense strand differs by no more than 1 modified nucleotides from the nucleotide sequence of 5'-usdAsgadAudAcuguccCfuUfuuaagscsc-3' (SEQ ID NO:16).

13. The dsRNA agent of claim 10, wherein the dsRNA agent is conjugated to the ligand as shown in the following schematic

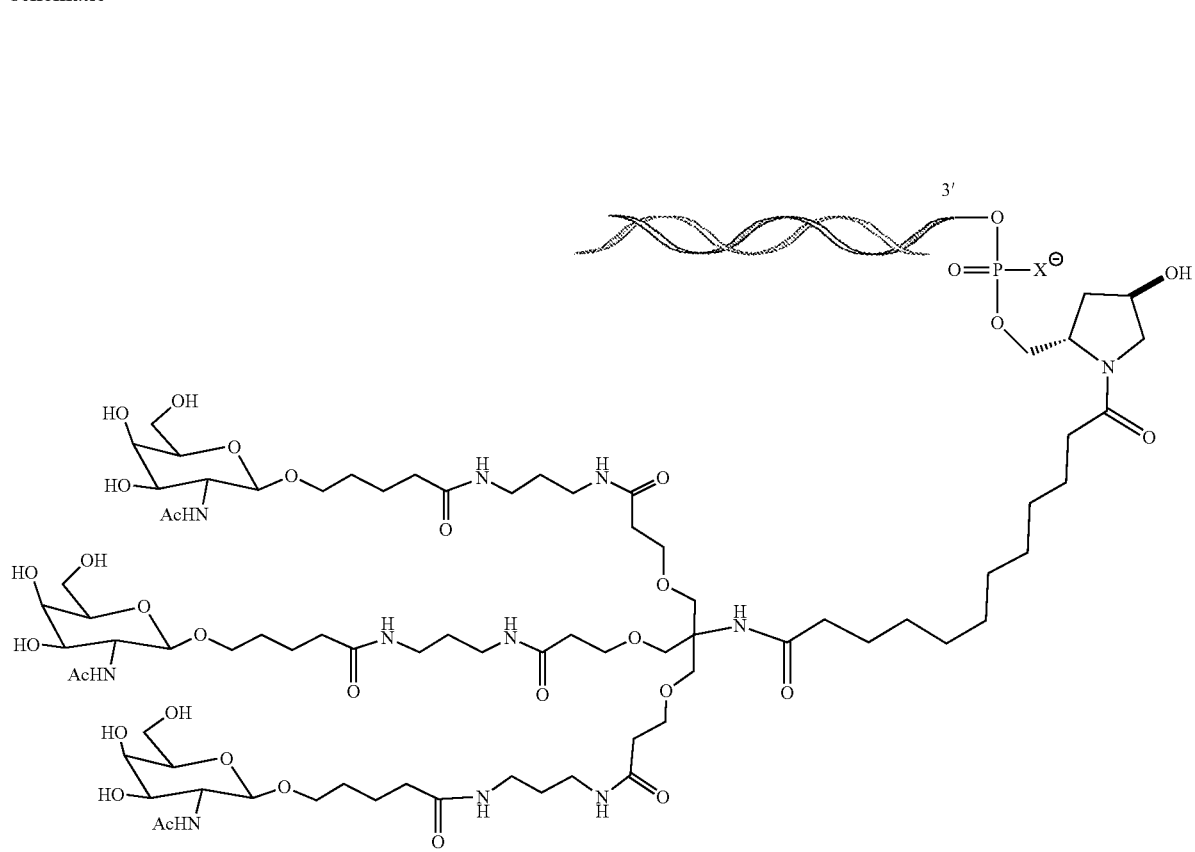

and, wherein X is O.

14. A double stranded ribonucleic acid (dsRNA) agent for inhibiting expression of apolipoprotein C3 in a cell,
wherein the dsRNA agent comprises a sense strand and an antisense strand forming a double stranded region,
wherein the sense strand comprises the nucleotide sequence of 5'-csusuaaaAfgGfGfAfcaguauucua-3' (SEQ ID NO: 15) and the antisense strand comprises the nucleotide sequence of 5'-usdAsgadAudAcuguccCfuUfuuaagscsc-3' (SEQ ID NO:16),
wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage.

15. The dsRNA agent of claim 14, wherein the sense strand comprises the nucleotide sequence of 5'-csusuaaaAfgGfGfAfcaguauucuaL96-3' (SEQ ID NO: 17) and the antisense strand comprises the nucleotide sequence of 5'-usdAsgadAudAcuguccCfuUfuuaagscsc-3' (SEQ ID NO:16),
wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; s is a phosphorothioate linkage, and L96 is N-[tris(GalNAc-alkyl)-amidodecanoyl)]-4-hydroxyprolinol.

16. The dsRNA agent of claim 14, wherein the sense strand comprises the nucleotide sequence of 5'-csusuaaaAfgGfGfAfcaguauucua-3' (SEQ ID NO: 15) and the antisense strand comprises the nucleotide sequence of 5'-usdAsgadAudAcuguccCfuUfuuaagscsc-3' (SEQ ID NO:16),
wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage; and wherein the 3'-end of the sense strand is conjugated to a ligand as shown in the following schematic:

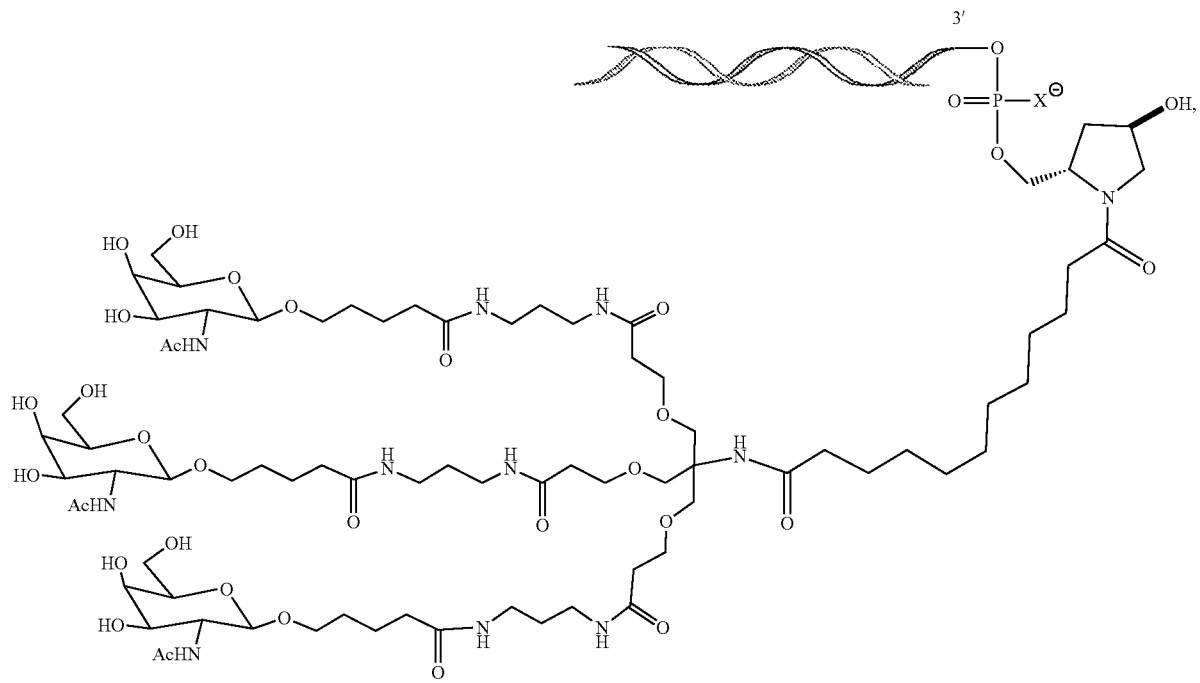

wherein X is O.

17. A double stranded ribonucleic acid (dsRNA) agent for inhibiting expression of apolipoprotein C3 in a cell,
wherein the dsRNA agent comprises a sense strand and an antisense strand forming a double stranded region,
wherein the sense strand consists of the nucleotide sequence of 5'-csusuaaaAfgGfGfAfcaguauucua-3' (SEQ ID NO: 15) and the antisense strand consists of the nucleotide sequence of 5'-usdAsgadAudAcugu-ccCfuUfuuaagscsc-3' (SEQ ID NO:16),
wherein a, g, c and u are 2'-O-methyl (2'-OMe) A, G, C, and U respectively; Af, Gf, Cf and Uf are 2'-fluoro A, G, C and U respectively; dA is a 2'-deoxyadenosine-3'-phosphate nucleotide; and s is a phosphorothioate linkage; and
wherein the 3'-end of the sense strand is conjugated to a ligand as shown in the following schematic:

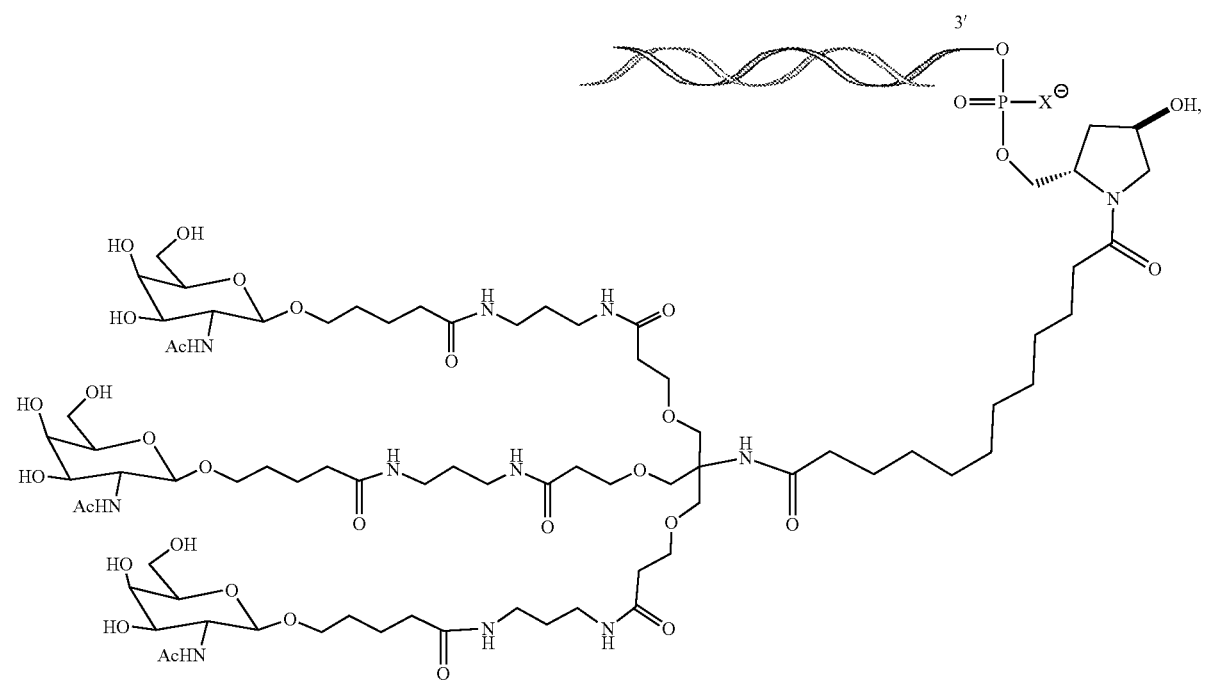

wherein X is O.

18. A pharmaceutical composition for inhibiting expression of a gene encoding apolipoprotein C3 (APOC3) comprising the dsRNA agent of claim 1.

19. The pharmaceutical composition of claim 18, wherein dsRNA agent is in an unbuffered solution.

20. The pharmaceutical composition of claim 19, wherein the unbuffered solution is saline or water.

21. The pharmaceutical composition of claim 18, wherein said dsRNA agent is in a buffer solution.

22. The pharmaceutical composition of claim 21, wherein the buffer solution comprises acetate, citrate, prolamine, carbonate, or phosphate or any combination thereof.

23. The pharmaceutical composition of claim 22, wherein the buffer solution is phosphate buffered saline (PBS).

\* \* \* \* \*